(12) United States Patent
Niculescu

(10) Patent No.: US 11,608,532 B2
(45) Date of Patent: Mar. 21, 2023

(54) PRECISION MEDICINE FOR TREATING AND PREVENTING SUICIDALITY

(71) Applicants: Indiana University Research and Technology Corporation, Indianapolis, IN (US); United States Government as Represented by the Department of Veterans Affairs, Washington, DC (US)

(72) Inventor: Alexander Bogdan Niculescu, Indianapolis, IN (US)

(73) Assignees: Indiana University Research and Technology Corporation, Bloomington, IN (US); The United States Government as Reprecented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/677,414

(22) Filed: Nov. 7, 2019

(65) Prior Publication Data
US 2020/0318188 A1    Oct. 8, 2020

Related U.S. Application Data

(63) Continuation-in-part of application No. PCT/US2018/032540, filed on May 14, 2018.

(60) Provisional application No. 62/505,197, filed on May 12, 2017.

(51) Int. Cl.
| | |
|---|---|
| *C12Q 1/6883* | (2018.01) |
| *G16H 10/60* | (2018.01) |
| *G16H 50/20* | (2018.01) |
| *G16B 50/30* | (2019.01) |
| *A61K 45/06* | (2006.01) |

(52) U.S. Cl.
CPC ........... *C12Q 1/6883* (2013.01); *G16B 50/30* (2019.02); *G16H 10/60* (2018.01); *G16H 50/20* (2018.01); *A61K 45/06* (2013.01); *C12Q 2600/158* (2013.01); *G01N 2800/52* (2013.01); *G01N 2800/60* (2013.01)

(58) Field of Classification Search
CPC ...... C12Q 1/6883; G16B 50/30; G16H 50/20; G01N 2800/60
See application file for complete search history.

(56) References Cited

U.S. PATENT DOCUMENTS

| | | |
|---|---|---|
| 8,401,801 B2 | 3/2013 | Mrazek et al. |
| 8,688,385 B2 | 4/2014 | Mrazek et al. |
| 10,196,693 B2 | 2/2019 | Peterson et al. |
| 2005/0282911 A1 | 12/2005 | Hakkarainen et al. |
| 2012/0041911 A1 | 2/2012 | Pestian et al. |
| 2012/0269906 A1 | 10/2012 | Sheehan et al. |
| 2013/0142776 A1 | 6/2013 | Blumenfeld |
| 2013/0330429 A1 | 12/2013 | Vuckovic |
| 2014/0235663 A1 | 8/2014 | Yovell |
| 2014/0243211 A1 | 8/2014 | Niculescu |

(Continued)

FOREIGN PATENT DOCUMENTS

| | | |
|---|---|---|
| WO | 2015/006645 A1 | 1/2015 |
| WO | 2016/201299 A1 | 12/2016 |

OTHER PUBLICATIONS

Asellus et al., J. Affective Disorders, 2016, 190:132-142.*

(Continued)

*Primary Examiner* — Olga N Chernyshev
(74) *Attorney, Agent, or Firm* — Faegre Drinker Biddle & Reath LLP

(57) ABSTRACT

The present disclosure relates generally to discovery of novel compounds involved in the treatment and prevention of suicidality by bioinformatics drug repurposing using novel genes expression biomarkers involved in suicidality. Disclosed are methods for assessing severity, determining future risk, matching with a drug treatment, and measuring response to treatment, for suicidality. Also disclosed are new methods of use for drugs and natural compounds repurposed for use in preventing and treating suicidality. These methods include computer-assisted methods analyzing the expression of panels of genes, clinical measures, and drug databases. Detailed herein are methods using a universal approach, in everybody, as well as personalized approaches by gender, and by diagnosis. The discovery describes compounds for use in everybody (universal), as well as personalized by gender (males, females), diagnosis (bipolar, depression), gender and diagnosis combined (male bipolar, male depression), male PTSD, male SZ/SZA), and subtypes of suicidality (high anxiety, low mood, combined (affective), and high psychosis (non-affective). Also disclosed are methods for identifying which subjects should be receiving which treatment, using genes expression biomarkers for patient stratification and measuring response to treatment. The disclosure also relates to algorithms, universal and personalized by gender and diagnosis. The algorithms combine biomarkers as well as clinical measures for suicidality and for mental state, in order to identify subjects who are at risk of committing suicide, as well as to track responses to treatments. The disclosure further relates to determining subtypes of suicidality. Such subtypes may delineate groups of individuals that are more homogenous in terms of biology, behavior, and response to treatment.

7 Claims, 42 Drawing Sheets

(7 of 42 Drawing Sheet(s) Filed in Color)

(56) References Cited

U.S. PATENT DOCUMENTS

| | | |
|---|---|---|
| 2016/0153044 A1 | 6/2016 | Kaminsky et al. |
| 2016/0215346 A1 | 7/2016 | Niculescu |
| 2018/0181701 A1 | 6/2018 | Niculescu |
| 2020/0312425 A1 | 10/2020 | Niculescu |

OTHER PUBLICATIONS

Hwang et al., Dementia and geriatric cognitive disorders, 2006, 22(4):334-8.*

Niculescu et al., "Effects of p21Cip1/Waf1 at Both the G1/S and the G2/M Cell Cycle Transitions: pRb Is a Critical Determinant in Blocking DNA Replication and in Preventing Endoreduplication," Molecular and cellular biology, (1998), 18(1):629-643.

Niculescu et al., Psychiatric blood biomarkers: avoiding jumping to premature negative or positive conclusions, Mol. Psychiatry, (2015), 20(3):286-288.

Niculescu et al., "Understanding and predicting suicidality using a combined genomic and clinical risk assessment approach," Molecular Psychiatry, (2015), 20:1266-1285.

Niculescu et al., Precision medicine for suicidality: from universality to subtypes and personalization, Molecular Psychiatry, (2017), 22:1250-1273.

Niculescu, A. B. and H. Le-Niculescu (2010). "Convergent Functional Genomics: what we have learned and can learn about genes, pathways, and mechanisms." Neuropsychopharmacology 35(1): 355-356.

Niculescu, A. B., 3rd, D.S. Segal, et al. (2000). "Identifying a series of candidate genes for mania and psychosis: a convergent functional genomics approach." Physiological genomics 4(1): 83-91.

Niculescu, et al., PhenoChipping of psychotic disorders: a novel approach for deconstructing and quantitating psychiatric phenotypes. American Journal of Medical Genetics. Part B, Neuropsychiatric genetics: the official publication of the International Society of Psychiatric Genetics 141B, 653-662, doi:10.1002/ajmg.b.30404 (2006).

Nock, M. K., G. Borges, et al. (2008). "Suicide and suicidal behavior." Epidemiol Rev 30: 133-154.

Ogden, C. A., M. E. Rich, et at. (2004). "Candidate genes, pathways and mechanisms for bipolar (manic-depressive) and related disorders: an expanded convergent functional genomics approach." Molecular psychiatry 9(11): 1007-1029.

Oquendo et al., "Toward a Biosignature for Suicide," Am. J. Psychiatry, (2014) 171(12):1259-1277.

Oquendo, M.A., D. Currier, et al. (2010). "Increased risk for suicidal behavior in comorbid bipolar disorder and alcohol use disorders: results from the National Epidemiologic Survey on Alcohol and Related Conditions (NESARC)." The Journal of clinical psychiatry 71(7): 902-909.

Owens, Predictors of suicidal behavior found in blood, Nature, doi:10.1038/nature.2013.13570; Aug. 20, 2013. Available at http://www.nature.com/news/predictors-of-suicidal-behaviour-found-in-blood-1.13570.

Pandey, G. N., H. S. Rizavi, et al. (2012). "Proinflammatory cytokines in the prefrontal cortex of teenage suicide victims." J Psychiatr Res 46(1): 57-63.

Pandey, G. N., Y. Dwivedi, et al. (2003). "Altered expression and phosphorylation of myristoylated alanine-rich C kinase substrate (MARCKS) in postmortem brain of suicide victims with or without depression." J Psychiatr Res 37(5):421-432.

Patel S.D. et al., "Coming to grips with complex disorders: genetic risk prediction in bipolar disorder using panels of genes identified through convergence functional genomics," American Journal of Medical Genetics Part b, Neuropsychiatric genetics: the official publication of the International Society of Psychiatric genetics 153B, 850-877, doi:10.1pp2/ajmg.b.31087 (2010).

Pietila et al., Activation of polyamine catabolism profoundly alters tissue polyamine pools and affects hair growth and female fertility in transgenic mice overexpressing spermidine/spermine N1-acetyltransferase. J Biol. Chem. 272, 18746-18751 (1997).

Sequeira A. et al., Gene expression changes in the prefrontal cortex, anterior cingulate cortex and nucleus accumbens of mood disorders subjects that committed suicide, PioS one 7, e35367, doi:10,1371/journal.pone.0035367 (2012).

Sequeira, A., F. Mamdani, et al. (2009). "Global brain gene expression analysis links glutamatergic and GABAergic alterations to suicide and major depression." PLoS One 4(8): e6585 (2010).

Sequeira, A., T. Klempan, et al. (2007). "Patterns of gene expression in the limbic system of suicides with and without major depression." Mol Psychiatry 12(7): 640-655.

Sequeira. A., F. G. Gwadry, et al. (2006). "Implication of SSAT by gene expression and genetic variation in suicide and major depression." Arch Gen Psychiatry 63(1): 35-48.

Stopkova, et al. "Identification of PIK3C3 Promoter Variant Associated with Bipolar Disorder and Schizophrenia. Biological Psychiatry", May 15, 2004; vol. 55, No. 10; pp. 981-988.

Sublette M. et al., "Omega-3 polyunsaturated essential fatty acid status as a predictor of future suicide risk," Am J Psychiatry 163, 1100-1102, doi:10.1176/appi.ajp.163.6.110 (2006).

Supplementary European search report dated Jan. 21, 2019 for EP Application No. 16808423.

Tsai et al., "Bcl-2 associated with positive symptoms of schizophrenic patients in an acute phase", Psychiatry Research vol. 210, Issue 3, Dec. 30, 2013, pp. 735-738.

Underwood, A blood test for suicide?, https://www.sciencemag.org/news/2013/08/blood-test-suicide.

Ayalew M. et al., "Convergent functional genomics of schizophrenia: from comprehensive understanding to genetic risk prediction," Molecular Psychiatry 17, 887-905, doi:10.1038/mp.2012.37 (2012).

Belzeaux et al. (2010) "Clinical variations modulate patterns of gene expression and define blood biomarkers in major depression" Journal of Psychiatric Research 44(16): 1205-1213.

Benedetti et al., Opposite effects of suicidality and lithium on gray matter volumes in bipolar depression. J Affect Disord 135, 139-147, doi:10.1016/j.jad.2011.07.006 (2011).

Berngruber, T. W., S. Lion, et al., "Evolution of suicide as a defence strategy against pathogens in a spatially structured environment." Ecol Lett (2013).

Bertone-Johnson et al., Vitamin D and the Occurrence of Depression: Casual Associate or Circumstantial Evidence?; Nutr Ref. Aug. 2009, vol. 67, No. 8, pp. 481-492.

Brent et al., Pharmacogenomics of Suicidal events; Pharmacogenomics, 2010, vol. 11, No. 6, pp. 793-807.

Brucker et al., "Assessing Risk of Future Suicidality in Emergency Department Patients," Acad. Emerg Med., (2019), 26(4):376-383.

Chen, G. G., L. M. Fiori, et al. "Evidence of altered polyamine concentrations in cerebral cortex of suicide completers." Neuropsychopharmacology 35(7): 1477-1484 (2010).

Duckworth C.A. et al., "CD24 is expressed in gastric parietal cells and regulates apoptosis and the response to Helicobacter felis infection in the murine stomach," American Journal of Physiology, Gastrointestinal and Liver Physiology 303, G915-926, doi:10.1152/ajpgi.00068.2012 (2012).

Dwivedi, Y., H. S. Rizavi, et al. "Modulation in activation and expression of phosphatase and tensin homolog on chromosome ten, Aktl, and 3-phosphoinositide-dependent kinase 1: further evidence demonstrating altered phosphoinositide 3-kinase signaling in post-mortem brain of suicide subjects." Biol Psychiatry 67(11): 1017-1025 (2010).

Falcone et al. (2010) "Serum S1OOB: A Potential Biomarker for Suicidality in Adolescents?" PLoS ONE 5(6): e11089.

Fiori et al., Global gene expression profiling of the polyamine system in suicide completers. Int. J. Neuropsychopharmacol. 14, 595-605, doi:10.1017/S1461145710001574 (2011).

Fiori, L. M., H. Zouk, et al. (2011). "X chromosome and suicide." Mol Psychiatry 16(2): 216-226.

Fiori, L. M., N. Mechawar, et al. "Identification and characterization of spermidine/spermine N1-acetyltransferase promoter variants in suicide completers." Biol Psychiatry 66(5): 460-467 (2009).

Fiori. L. M. and G. Turecki "Epigenetic regulation of spermidinelspermine N acetyltransferase (SATI) in suicide." J Psychiatr Res 45(9): 1229-1235 (2011).

(56) References Cited

OTHER PUBLICATIONS

Fiori. L. M.. B. Wanner, et al. "Association of polyaminergic loci with anxiety, mood disorders, and attempted suicide." PLoS One 5(11): e15146 (2010).

Gaiteri C, Guilloux JP, Lewis DA, Sibille E. Altered gene synchrony suggests a combined hormone-mediated dysregulated state in major depression. PLoS One; 5(4): e9970.

Galfalvy, H., G. Zalsman, et al. (2013). "A pilot genome wide association and gene expression array study of suicide with and without major depression." World J Biol Psychiatry.

Guipponi, M., S. Deutsch, et al. (2008). "Genetic and epigenetic analysis of SSAT gene dysregulation in suicidal behavior." Am J Med Genet B Neuropsychiatr Genet 150B(6): 799-807.

Hakak Y, Walker JR, Li C, Wong WH, Davis KL, Buxbaum JD et al. Genome-wide expression analysis reveals dysregulation of myelination-related genes in chronic schizophrenia. Proc Natl Acad Sci U S A 2001; 98(8): 4746-4751.

International Preliminary Report on Patentability received for PCT Patent Application No. PCT/US2016/036985, dated Dec. 21, 2017, 12 pages.

International Preliminary Report on Patentability received for PCT Patent Application No. PCT/US2018/032540, dated Nov. 21, 2019, 9 pages.

International Search Report and Written Opinion received for PCT Patent Application No. PCT/US2016/036985, dated Sep. 9, 2016, 12 pages.

International Search Report and Written Opinion received for PCT Patent Application No. PCT/US2018/032540, dated Sep. 14, 2018, 11 pages.

Karege F, Perroud N, Burkhardt S, Fernandez R, Ballmann E, La Harpe R et al. Alterations in phosphatidylinositol 3-kinase activity and PTEN phosphatase in the prefrontal cortex of depressed suicide victims. Neuropsychobiology 2011; 63(4): 224-231.

Karege F. et al., Alteration in kinase activity but not in protein levels of protein kinase B and glycogen synthase kinase-3beta in ventral prefrontal cortex of depressed suicide victims. Biol Psychiatry 61, 240-245, doi:10.1016/j.biopsych.2006.04.036 (2007).

Kelleher, I., F. Lynch, et al. (2012). "Psychotic Symptoms in Adolescence Index Risk for Suicidal Behavior: Findings From 2 Population-Based Case-Control Clinical Interview Studies." Arch Gen Psychiatry: 1-7.

Kim, S., K. H. Choi, et al. (2007). "Suicide candidate genes associated with bipolar disorder and schizophrenia: an exploratory gene expression profiling analysis of post-mortem prefrontal cortex." BMC Genomics 8: 413.

Klempan, T. A., A. Sequeira, et al. (2009). "Altered expression of genes involved in ATP biosynthesis and GABAergic neurotransmission in the ventral prefrontal cortex of suicides with and without major depression." Mol Psychiatry 14(2): 175-189.

Klempan, T. A., D. Rujescu, et al. (2008). "Profiling brain expression of the spermidine/spermine N1-acetyltransferase 1 (SAT1) gene in suicide." Am J Med Genet B Neuropsychiatr Genet 150B(7): 934-943.

Kurian S.M. et al., "Identification of blood biomarkers for psychosis using convergent functional genomics," Molecular Psychiatry 16, 37-58, doi:10.1038/mp.2009.117 (2011).

Lalovic, A., T. Klempan, et al. (2010). "Altered expression of lipid metabolism and immune response genes in the frontal cortex of suicide completers." J Affect Disord 120(1-3): 24-31.

Le-Niculescu H. et al., "Discovery and validation of blood biomarkers for suicidality", Molecular Psychiatry (2013), pp. 1-16.

Le-Niculescu H. et al., "Identifying blood biomarkers for mood disorders using convergent functional genomics," Molecular Psychiatry 14, 156-174, doi:10.1111/ele.12064 (2009).

Le-Niculescu H. et al., "Phenomic, convergent functional genomic, and biomarker studies in a stress-reactive genetic animal model of bipolar disorder and co-morbid alcoholism," American Journal of Medical Genetics, Part B, Neuropsychiatric genetics: the official publication of the International Society of Psychiatric Genetics 147B, 134-166, doi:10.1002/ajmg.b.30707 (2008).

Le-Niculescu, H., N. J. Case, et al. (2011). "Convergent functional genomic studies of omega-3 fatty acids in stress reactivity, bipolar disorder and alcoholism." Translational Psychiatry 1: e4.

Le-Niculescu, H., S. D. Patel, et al. (2009). "Convergent functional genomics of genome-wide association data for bipolar disorder: comprehensive identification of candidate genes, pathways and mechanisms." American journal of medical genetics. Part B, Neuropsychiatric genetics : the official publication of the International Society of Psychiatric Genetics 150B(2): 155-181.

Le-Niculescu, H., S. D. Patel, et at. (2010). "Convergent integration of animal model and human studies of bipolar disorder (manic-depressive illness)." Curr Opin Pharmacol 10(5): 594-600.

Le-Niculescu, H., Y. Balaraman, et al. (2007). "Towards understanding the schizophrenia code: an expanded convergent functional genomics approach." American journal of medical genetics. Part B, Neuropsychiatric genetics : the official publication of the International Society of Psychiatric Genetics 144B(2): 129-158.

Levey et al., "Towards understanding and predicting suicidality in women: biomarkers and clinical risk assessment", Molecular Psychiatry, vol. 21, No. 6, Apr. 5, 2016, pp. 768-785.

Lewis M.D. et al., "Suicide deaths of active-duty US military and omega-3 fatty-acid status: a case-control comparison," J Clin Psychiatry 72, 1585-1590, doi:10.4088/JCP.11m06879 (2011).

Lowthert et al., Increased ratio of anti-apoptotic to pro-apoptotic Bcl2 gene-family members in lithium-responders one month after treatment initiation. Biology of Mood & Anxiety Disorders 2, 15, doi:10.1186/2045-5380-2-15 (2012).

Malkesman et al. Targeting the BH3-interacting domain death agonist to develop mechanistically unique antidepressants. Mol. Psychiatry 17, 770-780, doi:10.1038/mp.2011.77 (2012).

Margoob et al. (2004) "Serum Cholesterol Level and Suicidal Attempts—Kashmir Scenario" JK—Practitioner 11 (3):171-177.

Menke, A., K. Domschke, et al. (2012). "Genome-wide association study of antidepressant treatment-emergent suicidal ideation." Neuropsychopharmacology 37(3): 797-807.

Miller BH, Zeier Z, Xi L, Lanz TA, Deng S, Strathmann Jet al. MicroRNA-132 dysregulation in schizophrenia has implications for both neurodevelopment and adult brain function. Proc Natl Acad Sci US A 2012; 109(8): 3125-3130.

Min et al., Altered levels of growth-related and novel gene transcripts in reproductive and other tissues of female mice overexpressing spermidien/spermine N1-actyltransferase (SSAT). J. Biol. Chem. 277, 3647-3657, doi: 10.1074/jbc.M100751200 (2002).

Mudge et al., Genomic Convergence Analysis of Schizophrenia: mRNA Sequencing Reveals Altered Synaptic Vesicular Transport in Post-Mortem Cerebellum, PLoS ONE, (2008) 11(3):e3625.

Niculescu et al., "Dissecting Suicidality Using a Combined Genomic and Clinical Approach," Neuropsychopharmacology, (2017), 42:360-378.

\* cited by examiner

SI Sate Predictions

| Universal Biomarkers | Genes | All (52/544) | High Anxiety (5/52) | Low Mood (10/103) | Combined Subtype (31/123) | Non-Affective (6/263) | Male BP (12/130) | Female BP (3/42) | Male MDD (10/57) | Male SZ (5/104) | Male SZA (10/103) | MaleSZSZA (15/207) | Male PTSD (9/30) |
|---|---|---|---|---|---|---|---|---|---|---|---|---|---|
| Top Dozen | ERG | | | 0.68/2.77E-02 | | 0.75/1.93E-02 | | | | | | | |
| Top Dozen | GAB1 | | | | | | | 0.68/1.49E-02 | | | | | |
| Top Dozen | HIST1H2BO | | | | | | | | | | 0.66/4.96E-02 | | |
| Top Dozen | HTR2A | | | 0.66/4.74E-02 | | | 0.67/2.78E-02 | | | 0.79/1.55E-02 | | 0.65/2.52E-02 | |
| Top Dozen | IFNG | | | | 0.61/3.03E-02 | | 0.65/4.45E-02 | | | | 0.68/3.14E-02 | 0.66/1.75E-02 | 0.72/2.72E-02 |
| Top Dozen | PPAP2B | | | 0.75/4.15E-03 | | | 0.71/9.22E-03 | | | | | | |
| Top Dozen | PSME4 | | | 0.68/3.47E-02 | | | 0.65/4.56E-02 | | | | | | |
| Top Dozen | SKA2 | 0.61/3.35E-03 | | 0.74/5.91E-03 | | | 0.69/1.41E-02 | | | | 0.73/8.07E-03 | 0.75/5.97E-04 | 0.79/6.82E-03 |
| Top Dozen | SLC4A4 | 0.64/3.83E-04 | | | 0.69/6.13E-04 | | 0.77/9.27E-04 | | | | | 0.66/1.85E-02 | |
| Bonferroni | ATP6V0E1 | | | | | | | | | | 0.76/3.76E-03 | 0.68/9.28E-03 | |
| Bonferroni | CD109 | | | | | | | | | | | | |
| Bonferroni | CLNS | 0.65/1.66E-04 | | 0.75/4.43E-03 | 0.66/1.27E-03 | | 0.65/3.91E-02 | | | | 0.66/3.47E-02 | 0.68/9.51E-03 | |
| Bonferroni | DUSP13 | | | | | | | | | | 0.72/9.96E-03 | 0.71/3.67E-03 | |
| Bonferroni | IGHG1 | | | | | | | | 0.79/2.47E-03 | | | | |
| Bonferroni | IL13 | | | 0.76/3.51E-03 | | | | | | | | | |
| Bonferroni | LHFP | | 0.78/1.95E-02 | | | | | 0.79/4.60E-02 | 0.69/3.32E-02 | | | | |
| Bonferroni | LRRN3 | | | | | | | 0.84/2.69E-02 | 0.68/3.56E-02 | | | | |
| Bonferroni | NGFR | | | | 0.66/4.27E-03 | | 0.66/3.55E-02 | | | | | | |
| Bonferroni | PRKAR2B | | | | | | | | 0.69/3.24E-02 | | 0.72/4.96E-02 | 0.72/1.92E-03 | |
| Bonferroni | PRKCI | 0.61/4.53E-03 | 0.81/1.55E-02 | | | | | | | | | | |
| Bonferroni | PTK2 | | | | 0.64/1.04E-02 | | 0.66/3.64E-02 | | | | | | 0.77/1.11E-02 |
| Bonferroni | TUBGCP3 | | | | 0.61/3.28E-02 | | 0.78/7.44E-04 | | | | | | |

| Male BP Biomarkers | GENES | | | | | | Male BP (12/130) | | | | | | |
|---|---|---|---|---|---|---|---|---|---|---|---|---|---|
| Bonferroni | C7orf73 | | | | | | 0.75/2.38E-03 | | | | | | |
| Top Dozen | SPTBN1 | | | | | | 0.72/6.82E-03 | | | | | | |
| Top Dozen | ICAM4 | | | | | | 0.67/2.83E-02 | | | | | | |
| Top Dozen | BE674182 | | | | | | 0.66/3.33E-02 | | | | | | |
| Top Dozen | HTR2A | | | | | | 0.65/4.45E-02 | | | | | | |

FIG. 3E

Future Hospitalizations Predictions

| Universal Biomarkers | Genes | All (38/471) | High Anxiety (7/46) | Low Mood (5/79) | Combined Subtype (18/111) | Non-Affective (8/229) | Male BP (4/120) | Female BP (na) | Male MDD (5/54) | Male SZ (11/99) | Male SZA (9/94) | MaleSZSZA (20/193) | Male PTSD (4/23) |
|---|---|---|---|---|---|---|---|---|---|---|---|---|---|
| Top Dozen | HIST1H2BO | 0.71/4.20E-02 | | | | | | | | | | | |
| Top Dozen | HTR2A | | | | | | | | | | 0.72/1.47E-02 | 0.65/1.67E-02 | |
| Top Dozen | PPAP2B | | | | | | | | | | | | 0.83/2.13E-02 |
| Top Dozen | PSME4 | | | 0.72/4.73E-02 | | | | | | | | | |
| Top Dozen | AK2 | | | | 0.68/6.72E-03 | | | | | | 0.78/2.70E-03 | 0.64/2.34E-02 | |
| Bonferroni | ALDH3AE | | | | 0.63/4.65E-02 | | 0.77/3.38E-02 | | | | 0.72/1.47E-02 | | 0.83/2.13E-02 |
| Bonferroni | ALDH7A1 | | | | | | | | | | 0.73/1.21E-02 | 0.67/6.53E-03 | |
| Bonferroni | ATP6VDE1 | | 0.76/1.55E-02 | | | | | | | | | | |
| Bonferroni | BF114768 | | | 0.84/5.28E-03 | | | | | | | | | |
| Bonferroni | CDC42EP4 | | | | | 0.69/3.36E-02 | | | 0.84/5.84E-03 | 0.67/3.15E-02 | | | |
| Bonferroni | CLN5 | | | | | | | | 0.91/1.64E-03 | | | | |
| Bonferroni | IGHG1 | | | | | | | | 0.96/2.54E-04 | | | | 0.87/1.16E-02 |
| Bonferroni | LHFP | | | | | | | | | | | | |
| Bonferroni | LPAR1 | | 0.77/1.33E-02 | | | | | | | | 0.7/2.22E-02 | | |
| Bonferroni | RIMS3 | | | | 0.66/1.88E-02 | 0.73/1.37E-02 | | | | | | | |
| Male BP Biomarkers | GENES | | | | | | Male BP (12/130) | | | | | | |
| Bonferroni | PTEN | | | | | | 0.90/3.27E-03 | | | | | | |
| Bonferroni | RNF6 | | | | | | 0.81/1.58E-02 | | | | | | |

FIG. 3E cont.

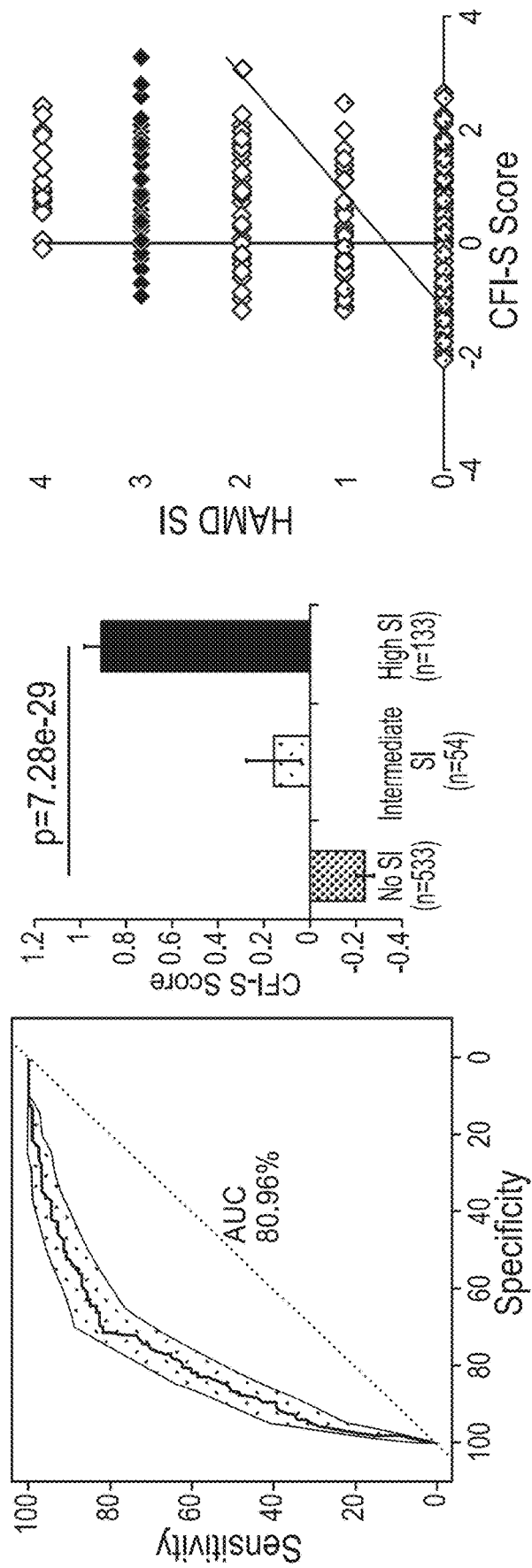

| | | | |
|---|---|---|---|
| 10 | Dissatisfaction with present life | Y | 3.10E-14 |
| 18 | Lack of coping skills (cracks under pressure) | Y | 1.41E-10 |
| 8 | Chronic stress: perceived uselessness, not feeling needed, burden to extended kin | Y | 2.71E-06 |
| 20 | History of command hallucinations of self-directed violence | Y | 5.56E-06 |
| 9 | History of excessive introversion, conscientiousness | Y | 7.23E-06 |
| 15 | Acute stress: rejection | Y | 7.46E-06 |
| 12 | Current substance abuse | Y | 8.57E-06 |
| 7 | Acute stress: losses, grief | Y | 9.52E-06 |
| 11 | Lack of hope for the future | Y | 2.65E-04 |
| 17 | History of excessive extroversion and impulsive behaviors (including rage, anger, physical fights, seeking revenge) | Y | 2.70E-04 |
| 14 | Lack of religious beliefs | Y | 3.77E-04 |
| 3 | Family history of suicide in blood relatives | Y | 7.51E-04 |
| 6 | Acute/severe medical illness, pain | Y | 7.76E-04 |
| 2 | With poor treatment compliance | Y | 8.58E-04 |
| 4 | Personally knowing somebody who committed suicide | Y | 0.005188 |
| 5 | History of abuse: physical, sexual, emotional, neglect | Y | 0.042144 |
| 19 | Lack of children | Y | 0.196639 |
| 21 | Age: Older >60 or Younger <25 | N | 0.055867 |
| 22 | Gender: Male | N | 0.496484 |
| 1 | Psychiatric illness diagnosed and treated | All have dx | All have dx |

FIG. 4A cont.

| | | | |
|---|---|---|---|
| 16 | Chronic stress: lack of positive relationships, social isolation | Y | 1.42E-04 |
| 15 | Acute stress: rejection | Y | 4.09E-04 |
| 6 | Acute/severe medical illness, pain | Y | 3.78E-03 |
| 9 | History of excessive introversion, conscientiousness | Y | 6.47E-03 |
| 10 | Dissatisfaction with present life | Y | 8.63E-03 |
| 11 | Lack of hope for the future | Y | 0.010596577 |
| 7 | Acute stress: losses, grief | Y | 0.011549309 |
| 18 | Lack of coping skills (cracks under pressure) | Y | 0.014967478 |
| 2 | With poor treatment compliance | Y | 0.025120503 |
| 3 | Family history of suicide in blood relatives | Y | 0.042731464 |
| 22 | Gender: Male | Y | 0.047852304 |
| 12 | Current substance abuse | Y | 0.069034807 |
| 5 | History of abuse: physical, sexual, emotional, neglect | Y | 0.104299343 |
| 4 | Personally knowing somebody who committed suicide | Y | 0.153942173 |
| 8 | Chronic stress: perceived uselessness, not feeling needed, burden to extended kin | Y | 0.156594082 |
| 21 | Age: Older >60 or Younger <25 | Y | 0.168685211 |
| 14 | Lack of religious beliefs | Y | 0.236253954 |
| 17 | History of excessive extroversion and impulsive behaviors (including rage, anger, physical fights, seeking revenge) | Y | 0.288722724 |
| 19 | Lack of children | N | 0.489134681 |
| 1 | Psychiatric illness diagnosed and treated | All have dx | All have dx |

FIG. 4B cont.

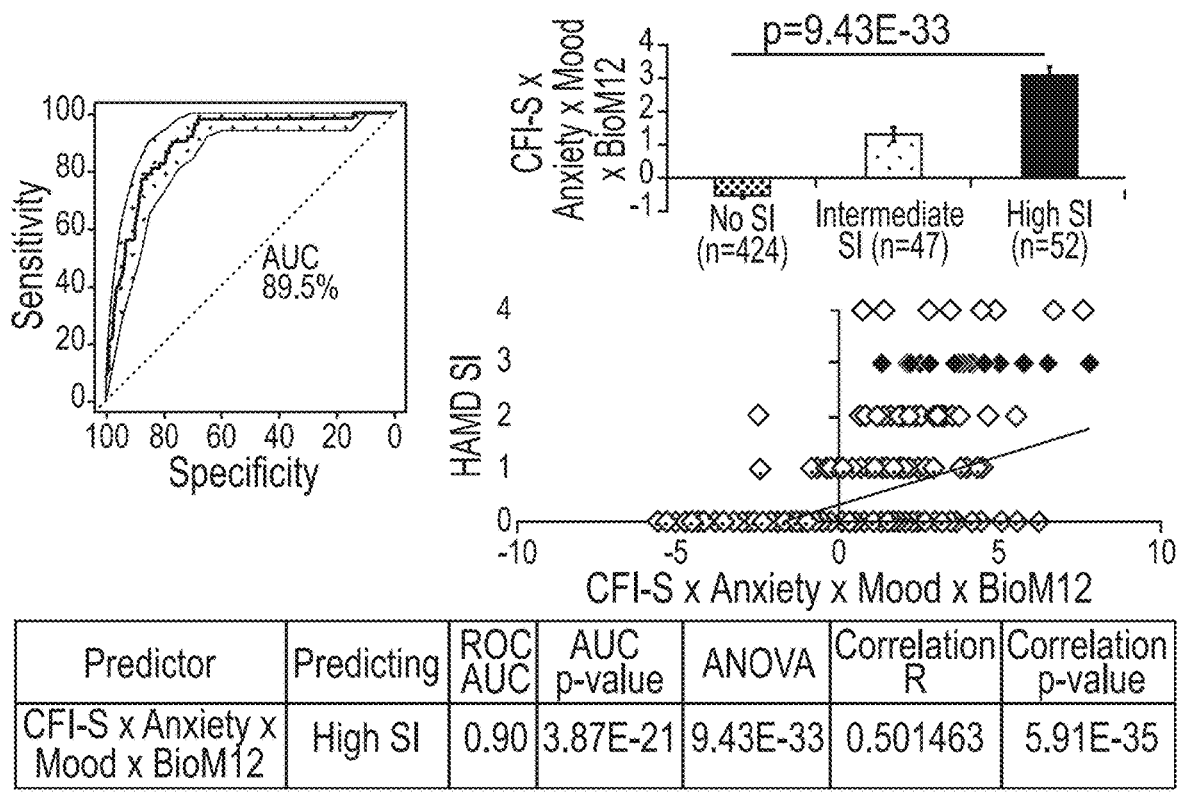
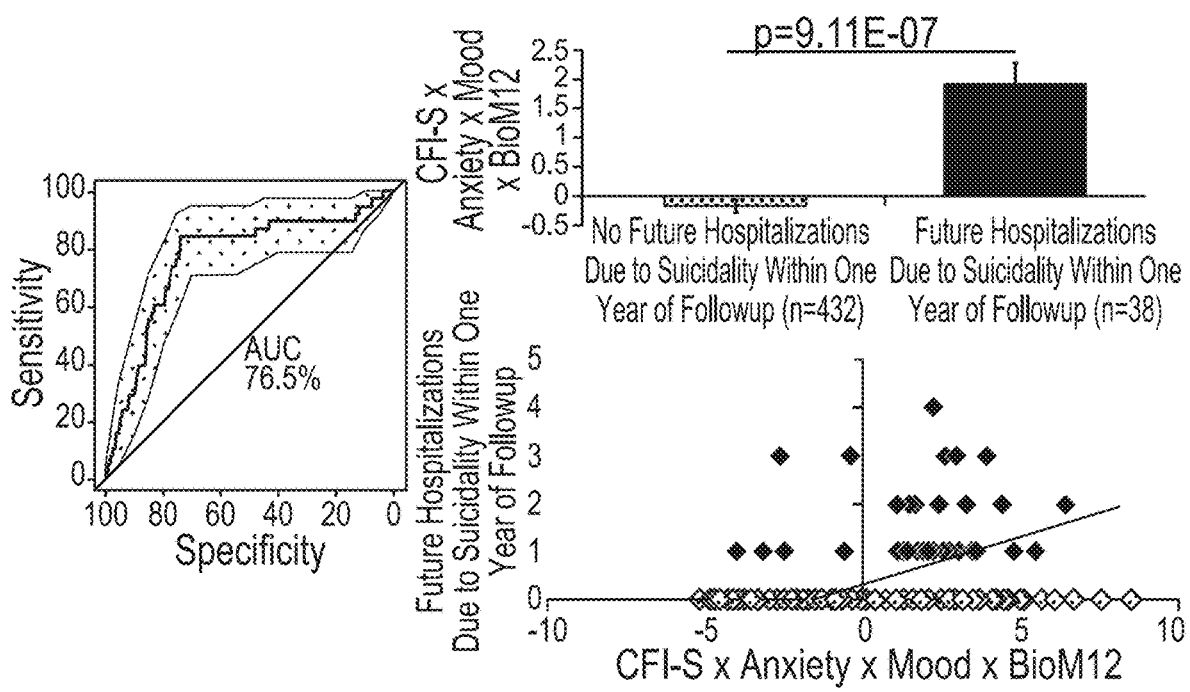
FIG. 5B

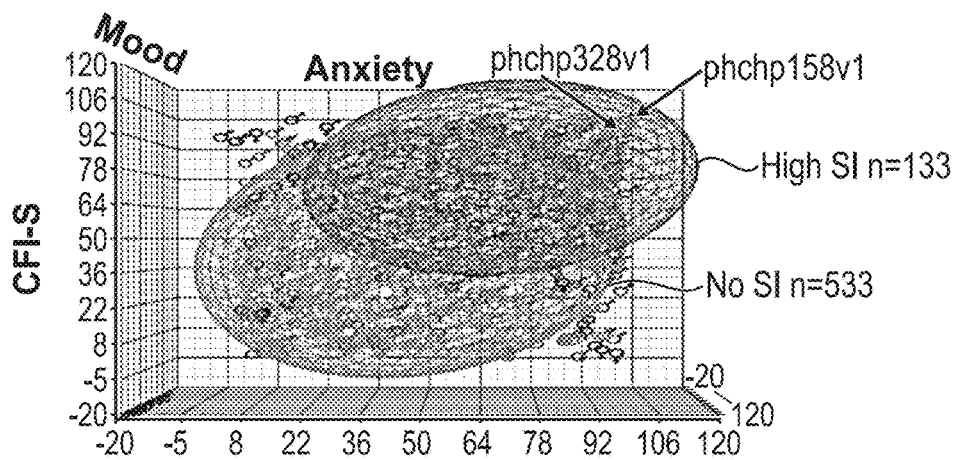

| Dimensions | Test Results Variable(s) | ROC AUC | Std. Error | AUC p-value | Asymptotic 95% Confidence Interval | |
|---|---|---|---|---|---|---|
| | | | | | Lower Bound | Upper Bound |
| 1D | CFIS | 0.81 | 0.019 | 6.42E-29 | 0.772 | 0.847 |
| 2D | CFIS x Anxiety | 0.833 | 0.019 | 4.16E-33 | 0.796 | 0.869 |
| 3D | CFIS x Anxiety x Mood | 0.841 | 0.018 | 8.01E-35 | 0.807 | 0.876 |
| 4D | CFIS x Anxiety x Mood x BioM12 | 0.849 | 0.019 | 2.37E-36 | 0.812 | 0.886 |

| | Participant 15B | | Participant 32 | | | | | | |
|---|---|---|---|---|---|---|---|---|---|
| Predictors | Visit 1 High SI HAMD-SI 4 | +2 H | Visit 1 High SI HAMD-SI 3 (T-14 months)% | +1 H | Visit 2 High SI HAMD-SI 2 (T-10 months)% | +1 H | Visit 3 No SI HAMD-SI 0 (T-5 months)% | +4 H | T Suicide |
| ARRB1 | 34.4 | | 59.5 | | 56.7 | | 93.1 | | |
| LDLRAP1 | 21.4 | | 99.8 | | 59.3 | | 29.8 | | |
| IFNG | 91.4 | | 88.5 | | 76.6 | | 18.2 | | |
| ERG | 36.8 | | 30.7 | | 16.3 | | 45.9 | | |
| CCL28 | 40.6 | | 76.5 | | 70.8 | | 39.4 | | |
| SKA2 | 64.8 | | 99.9 | | 59.5 | | 29.7 | | |
| SLC4A4 | 92.3 | | 92.7 | | 89.7 | | 42.5 | | |
| PPAP2B | 62.9 | | 89.2 | | 36.7 | | 83.9 | | |
| HIST1H2BO | 87.6 | | 97.5 | | 44.2 | | 39 | | |
| PSME4 | 67.8 | | 35.1 | | 83.5 | | 56.7 | | |
| GAB1 | 53.1 | | 89.6 | | 98.1 | | 11.4 | | |
| HTR2A | 8.6 | | 62.7 | | 43.6 | | 57.4 | | |
| BioM12 | 70.3 | | 99.4 | | 90.3 | | 46.1 | | |
| Mood | 100 | | 91.3 | | 47.8 | | 10.2 | | |
| CFIS | 99 | | 94.9 | | 90.9 | | 79.4 | | |
| Anxiety | 99.1 | | 99 | | 94.1 | | 73.1 | | |
| CFIS x Anxiety x Mood | 100 | | 99.4 | | 87.7 | | 56.6 | | |
| CFIS x Anxiety x Mood x BioM12 | 99.3 | | 100 | | 94.1 | | 56.8 | | |

FIG. 5C

| Predictors | Visit 1 High SI HAMD-SI 3 (T- 14 months) % | +1H | Visit 2 High SI HAMD-SI 2 (T- 10 months) % | +1H | Visit 3 No SI HAMD-SI 0 (T- 5 months) % | +4H | Y Suicide |
|---|---|---|---|---|---|---|---|
| *EPB41L5* | 39.03 | | 19.68 | | 100 | | |
| HAVCR2 | 62.85 | | 34.2 | | 17.67 | | |
| ARHGAP15 | 28.17 | | 33.26 | | 25.67 | | |
| HTRA1 | 100 | | 40.46 | | 20.6 | | |
| PER1 | 69.72 | | 26.62 | | 20.98 | | |
| *PDXDC1* | 17.75 | | 62.26 | | 100 | | |
| PIK3C3 | 81.07 | | 65.73 | | 56.85 | | |
| *GTF3C2* | 42.63 | | 51.89 | | 81.08 | | |
| ALDH3A2 | 81.47 | | 66.03 | | 55.81 | | |
| *BCL2* | 71.02 | | 40.43 | | 61.61 | | |
| MOB3B | 86.13 | | 65.50 | | 23.66 | | |
| *DPCD* | 33.51 | | 46.59 | | 44.6 | | |
| GTF3C3 | 23.14 | | 62.60 | | 17.21 | | |
| ASPH | 57.87 | | 16.57 | | 7.95 | | |
| KLHL28 | 59.17 | | 86.01 | | 37.19 | | |
| UIMC1 | 46.25 | | 60.38 | | 13.84 | | |
| SNX27 | 40.27 | | 100 | | 20.41 | | |
| *ACTR3* | 78.33 | | 80.32 | | 61.09 | | |
| *NUDT6* | 65.18 | | 80.59 | | 73.34 | | |
| *LRRC8B* | 86.34 | | 89.48 | | 70.00 | | |
| *CSNK1A1* | 93.4 | | 93.83 | | 78.25 | | |
| *LARP4* | 90.63 | | 91.63 | | 71.60 | | |
| ZNF548 | 83.18 | | 69.06 | | 34.55 | | |
| BioM18 | 82.99 | | 32.54 | | 17.85 | | |
| BioM32 | 95.40 | | 85.90 | | 29.51 | | |
| BioM50 | 100 | | 62.49 | | 21.16 | | |
| Anxiety | 96.00 | | 84.18 | | 59.80 | | |
| CFI-S | 87.15 | | 79.83 | | 65.19 | | |
| Mood | 83.61 | | 50.86 | | 21.43 | | |
| SASS | 97.13 | | 72.27 | | 42.75 | | |
| CFI-S +SASS | 100 | | 72.24 | | 40.62 | | |
| UP-Suicide | 100 | | 72.14 | | 36.80 | | |

Figure 5D

| | Subjects Total/ High SI | High SI prediction ROC AUC ROC p-value | t-test (High SI vs. No SI) | Correlation R P-value | Subjects Total/ First year hospitalized for suicidality/All future hospitalized for suicidality | Predictions First year hospitalized for suicidality ROC AUC ROC p-value | T-test First year hospitalized for suicidality | Correlation R p-value First Year hospitalized for suicidality | Correlation R p-value All future hospitalized for suicidality |
|---|---|---|---|---|---|---|---|---|---|
| All | 544/52 | 0.8954 3.87E-21 | 3.42E-19 | 0.5015 5.91E-35 | 470/38/98 | 0.7654 2.87E-08 | 9.11E-07 | 0.2284 2.81E-07 | 0.2803 1.72E-10 |
| High Anxiety Subtype | 50/5 | 0.8222 9.53E-03 | 1.22E-02 | 0.3457 6.97E-03 | 46/7/13 | 0.7912 7.52E-03 | 4.14E-03 | 0.2933 2.40E-02 | 0.1685 1.24E-01 |
| Low Mood Subtype | 99/10 | 0.9191 7.42E-06 | 3.61E-06 | 0.4268 5.28E-05 | 78/5/13 | 0.8 1.27E-02 | 1.15E-02 | 0.2756 7.29E-03 | 0.1808 4.99E-02 |
| Combined Subtype | 119/31 | 0.7548 1.29E-05 | 1.89E-05 | 0.4672 4.25E-08 | 111/18/38 | 0.6511 2.15E-02 | 1.87E-02 | 0.1712 3.62E-02 | 0.2077 1.33E-02 |
| Non-Affective Subtype | 252/6 | 0.9004 4.04E-04 | 3.94E-02 | 0.3319 3.39E-08 | 229/8/34 | 0.4242 7.67E-01 | 6.72E-01 | -0.0139 5.83E-01 | 0.0322 3.12E-01 |
| Male Bipolar | 128/12 | 0.9605 8.03E-08 | 4.79E-07 | 0.6322 6.05E-16 | 120/4/9 | 0.7888 2.51E-02 | 6.30E-02 | 0.1927 1.75E-02 | 0.2765 1.07E-03 |
| Female Bipolar | 31/3 | 0.8095 4.12E-02 | 5.03E-02 | 0.4005 1.28E-02 | NA/NA/NA | NA NA | NA | NA NA | NA NA |
| Male Depression | 57/10 | 0.9404 7.02E-06 | 4.35E-05 | 0.6067 2.83E-07 | 54/5/6 | 0.951 4.88E-04 | 1.83E-07 | 0.363 3.49E-03 | 0.3059 1.16E-02 |
| Male PTSD | 28/9 | 0.8596 1.24E-03 | 1.29E-03 | 0.6643 5.78E-05 | 23/4/14 | 0.8158 2.58E-02 | 2.72E-03 | 0.3493 5.12E-02 | 0.5951 5.30E-04 |
| Male Schizophrenia/ Schizoaffective | 206/15 | 0.8918 2.22E-07 | 5.80E-08 | 0.4356 3.01E-11 | 193/20/52 | 0.7598 7.20E-05 | 9.50E-04 | 0.315 4.05E-06 | 0.3345 7.79E-07 |
| Male Schizophrenia | 103/5 | 0.9204 7.86E-04 | 5.21E-04 | 0.389 2.44E-05 | 99/11/21 | 0.6612 4.12E-02 | 1.03E-01 | 0.2334 1.00E-02 | 0.3595 1.03E-04 |
| Male Schizoaffective | 103/10 | 0.8763 4.84E-05 | 3.01E-05 | 0.4714 2.50E-07 | 94/9/31 | 0.8719 1.28E-04 | 7.79E-05 | 0.3939 4.28E-05 | 0.3788 7.67E-05 |

FIG. 6 cont.

| | | | | | | |
|---|---|---|---|---|---|---|
| CD164 CD164 molecule, sialomucin | 208654_s_at | (D) DE/2 | 4 | 3.01E-08/4 | All: 0.59/1.80E-02 M-BP: 0.68/1.94E-02 | M-PTSD 0.86/1.43E-02 | PTSD, Sleep, Stress, SZ BP, Cocaine Dependence, Stress | Clozapine | 18 |
| CD47 CD47 molecule | 211075_s_at | (D) DE/2 | 4 | 1.62E-17/4 | All: 0.6/9.71E-03 Depressed Subtype: 0.68/2.99E-02 M-SZA: 0.69/2.19E-02 | M-PTSD 0.79/3.72E-02 | MDD, Stress, SZ | Clozapine Omega-3 | 18 |
| HTR2A 5-hydroxy-tryptamine (serotonin) receptor 2A, G protein-coupled | 244130_at | (I) DE/2 | 8 | NS | Depressed Subtype: 0.66/4.74E-02 M-SZ: 0.79/1.58E-02 | M-SZA 0.72/1.47E-02 | Alcohol, Anxiety, BP, MDD, SZ, OCD Response to Antidepressants | Clozapine, Lithium, Valproate, Antipsychotics, Antidepressants | 18 |
| PGK1 phosphoglycerate kinase 1 | 217383_at | (D) DE/2 | 4 | 4.07E-07/4 | M-SZA: 0.73/8.31E-03 | M-SZA 0.71/1.84E-02 | Alcohol, BP, MDD, SZ, SZA | Clozapine Diazepam | 18 |
| PKP4 plakophilin 4 | 201929_s_at | (D) DE/2 | 5 | 3.82E-08/4 | Combined Subtype: 0.62/2.59E-02 M-SZ: 0.75/2.93E-02 | Combined Subtype: 0.68/8.75E-03 | Alcohol, BP, MDD, SZ/SZA, SZ | Valproate | 18 |
| ACP1 acid phosphatase 1, soluble | 1554808_at | (D) DE/1 | 6 | 3.82E-11/4 | | M-MDD 0.74/3.79E-02 | BP, SZ | Omega-3, SSRIs, Olanzapine | 17 |
| DYRK2 dual-specificity tyrosine-(Y)-phosphoryla- | 202969_at | (D) DE/1 | 4 | 1.67E-13/4 | All: 0.58/3.37E-02 Combined Subtype: 0.61/3.00E-02 M-SZ/SZA: 0.68/9.85E-03 | M-PTSD 0.82/2.58E-02 | Aging, BP, MDD, Sleep | Clozapine | 17 |

FIG. 7 cont.

| Gene | Probe | Direction | # | p-value/n | Subtype | Meta | Associated Conditions | Drugs | Ref |
|---|---|---|---|---|---|---|---|---|---|
| tion regulated kinase 2 | | | | | | | | | |
| GATM L-arginine: glycine amidino-transferase | 1566861_at | (I) DE/1 | 4 | 1.80E-12/4 | Combined Subtype: 0.6/4.84E-02 M-BP: 0.68/1.94E-02 | M-PTSD 0.78/4.43E-02 | Alzheimer's Disease, BP, MDD, PTSD | Omega-3 | 17 |
| GSK3B glycogen synthase kinase 3 beta | 226183_at | (D) DE/1 | 6 | 2.19E-36/4 | M-SZA: 0.68/3.47E-02 | | Aging, Alcohol, BP, Dementia, Depression, Mood Stabilizers, Lithium response, MDD, SZ | Lithium, SSRI, Antipsychotics | 17 |
| IFNG interferon, gamma | 210354_at | (D) AP/1 | 8 | NS | All: 0.6/1.01E-02 Combined Subtype: 0.61/3.03E-02 M-PTSD: 0.73/2.72E-02 | M-PTSD 0.82/2.58E-02 | SZ, MDD, PTSD, Anxiety, SZ/SZA | Antipsychotics | 17 |
| ITGB1BP1 integrin beta 1 binding protein 1 | 203337_x_at | (D) DE/1 | 4 | 1.11E-08/4 | Depressed Subtype: 0.67/4.21E-02 M-SZ: 0.78/1.64E-02 | Non-Affective Subtype 0.7/2.59E-02 | Alzheimer's Disease, BP, Mood, SZ | Lithium | 17 |
| LHFP lipoma HMGIC fusion partner | 218656_s_at | (I) DE/1 | 4 | 3.97E-10/4 | All: 0.57/5.00E-02 Anxious Subtype: 0.78/1.95E-02 F-BP: 0.79/4.60E-02 | M-MDD 0.98/2.54E-04 | SZ | Omega-3 | 17 |
| LPAR1 lysophos-phatidic acid receptor 1 | 204036_at | (D) AP and DE/1 | 4 | 1.35E-23/4 | M-BP: 0.68/2.13E-02 | Anxious Subtype 0.77/1.33E-02 | Aging, BP, Longevity, MDD, Mood, PTSD, SZ | Clozapine, Omega-3, Antidepressants | 17 |

FIG. 7 cont.

| Gene | Probe | Dir | n | p-val | Subtype | Combined Subtype | Diseases | Drug | Ref |
|---|---|---|---|---|---|---|---|---|---|
| PRKCI protein kinase C, iota | 209677_at | (D) DE/1 | 4 | 2.71E-05/4 | Anxious Subtype: 0.8/1.55E-02 | Combined Subtype: 0.64/2.64E-02 | BP, Circadian abnormalities, Cocaine Dependence, MDD, SZ | Ingenol mebutate | 17 |
| SKA2 spindle and kinetochore associated complex subunit 2 | 225686_at | (D) DE/1 | 8 | 4.55E-03/2 | All: 0.61/3.35E-03 Depressed Subtype: 0.74/5.91E-03 M-SZ: 0.79/1.35E-02 | M-PTSD 0.84/1.75E-02 | PTSD, Stress | | 17 |
| SLC4A4 sodium bicarbonate cotransporter | 210739_x_at | (I) AP/1 | 6 | 7.74E-05/4 | All: 0.64/3.83E-04 Combined Subtype: 0.69/6.13E-04 M-BP: 0.77/9.27E-04 | | Circadian abnormalities, Longevity, MDD, SZ | Valproate | 17 |

Male Bipolar Biomarkers
Red – Increased in expression in suicidal participants
Blue – decreased in expression in suicidal participants
Significant predictions for: State *, Trait , Both *

CFE SCORE

HTR2A* — 16
SAT1 — 16
CRYAB* PIK3R1** PTK2* SPTBN1* — 15
AKT1S1 ARHGAP26 B2M PSME4* — 14
ACSM3* ADORA1 FAAH MARCKS MBP PAFAH1B2 PCDH9 PIK3R1 PTEN RNF6 SLC5A3 — 13

| Gene Symbol/ Gene name | Probesets | Step 1 Discovery in Blood (Direction of Change) Method/ Score | Step 2 Convergent Functional Genomics (CFG) Evidence For Involvement in Suicide Score | Step 3 Validation in Blood ANOVA p-value/ Score | Step 4 Significant Prediction of Suicidal Ideation in Male Bipolars ROC AUC/p-value | Step 4 Significant Prediction of First Year Hospitalizations for Suicidality in Male Bipolars ROC AUC/p-value | Step 5 Other Psychiatric and Related Disorders Evidence | Step 6 Drugs that Modulate the Biomarker in Opposite Direction to Suicide | CFE Poly-evidence Score |
|---|---|---|---|---|---|---|---|---|---|
| HTR2A 5-Hydroxytryptamine Receptor 2A | 244130_at | (I) DE/2 | 8.00 | NS | 0.65/4.45E-02 | NA | Alcohol, Anxiety, BP, MDD, SZ, OCD | Clozapine, Lithium, Valproate, Antipsychotics, Antidepressants | 16 |
| SAT1 spermidine/ spermine N1-acetyl-transferase 1 | 210592_s_at | (I) DE/2 | 6.00 | 4.00E-33/4 | NA | NA | MDD, Anxiety, Mood Disorders, NOS | Omega-3 | 16 |

| Gene | Probe | Direction | Score | p-value | p/q | Disorders | Drugs | Total |
|---|---|---|---|---|---|---|---|---|
| CRYAB crystallin, alpha B | 209283_at | (I) DE/1 | 4.00 | 3.49E-05 | 0.65/4.41E-02 | NA | Autism, Alchohol, PTSD, SZA, BP, SZ, Insomnia, Social Isolation, Stress, MDD | Lithium, Clozapine, Methamphet-amine | 15 |
| PIK3R1 Phosphoinositide-3-Kinase Regulatory Subunit 1 | 239476_at | (I) DE/1 | 4.00 | 2.79E-12 | NA | 0.81/1.64E-02 | Schizophrenia, MDD, Relaxation Response, PTSD, BP, Longevity, Stress, Insomnia, Anxiety | Mood Stabilizers | 15 |
| PTK2 Protein Tyrosine Kinase 2 | 241453_at | (I) DE/2 | 4.00 | 4.29E-16/4 | 0.66/3.64E-02 | NA | Alcohol, ASD, BP, Circadian abnormalities, MDD, Neurological, SZ/SZA, Stress, SZ | CT-707 | 15 |
| SAT1 spermidine/ spermine N1-acetyl-transferase 1 | 203455_s_at | (I) DE/1 | 6.00 | 9.99E-29/4 | NA | NA | MDD, Anxiety, Mood Disorders, NOS | Omega-3 | 15 |
| SAT1 spermidine/ spermine N1-acetyl-transferase 1 | 213988_s_at | (I) DE/2 | 6.00 | 4.06E-34 | NA | NA | MDD, Anxiety, Mood Disorders, NOS | Omega-3 | 15 |
| SPTBN1 spectrin, beta, non-erythrocytic 1 | 215918_s_at | (I) AP/1 | 4.00 | 6.7E-32 | 0.72/6.62E-03 | NA | Aging, BP, Longevity, MDD, SZ | Clozapine Omega-3, Diazepam | 15 |
| AKT1S1 AKT1 substrate 1 (proline-rich) | 1555821_a_at | (D) DE/2 | 4.00 | 8.69E-09/4 | NA | NA | Circadian abnormalities, Aging | Omega-3 fatty acids | 14 |
| AKT1S1 AKT1 substrate 1 (proline-rich) | 224982_at | (D) AP/1 and DE/2 | 4.00 | 8.04E-11/4 | NA | NA | Circadian abnormalities, Longevity | Omega-3 fatty acids | 14 |
| ARHGAP26 Rho GTPase activating protein 26 | 205068_s_at | (I) DE/1 | 5.00 | 7.99E-08/4 | NA | NA | BP, MDD, Panic Disorder, SZ | Clozapine | 14 |

FIG. 9 cont.

| Gene | Probe | Direction/Type | Score | p-value/n | | Conditions | Drugs | Ref |
|---|---|---|---|---|---|---|---|---|
| B2M beta-2-microglobulin | 232311_at | (I) DE/2 | 4.00 | 5.43E-06/4 | NA | Alcohol Effect of valproate, MDD, SZ | Omega-3 | 14 |
| PSME4 Proteasome Activator Subunit 4 | 237180_at | (I) DE/2 | 4.00 | 2.02E-16/4 | 0.69/1.41E-02 | ASD, MDD | | 14 |
| ACSM3 acyl-CoA synthetase medium-chain family member 3 | 210377_at | (D) DE/1 | 4.00 | 2.31E-10/4 | 0.69/1.35E-02 | MDD, Mood | | 13 |
| ADORA1 adenosine A1 receptor | 205481_at | (D) DE/1 | 4.00 | 1.19E-07/4 | NA | Alcohol, SZ, BP, Mood, Stimulants, Depression | Clozapine | 13 |
| FAAH fatty acid amide hydrolase | 204231_s_at | (D) DE/1 | 4.00 | 7.47E-12/4 | NA | Alcohol, SZ, BP, MDD, Pain, Placebo, PTSD, Stress, Hallucinogens, Social Isolation | | 13 |
| MARCKS Myristoylated alanine-rich protein kinase C substrate | 213002_at | (I) DE/1 | 4.00 | 7.35E-08/4 | NA | BP, SZ, MDD, Yohimbine, Alcohol, Pain Disorder | Lithium | 13 |
| MBP myelin basic protein | 225408_at | (D) AP/1 | 4.00 | 3.26E-06/4 | NA | Alcohol, Alzheimer's Disease, BP, MDD, Mood, Neurological, SZ | Clozapine Omega-3, Lithium | 13 |
| PAFAH1B2 platelet-activating factor acetylhydrolase 1b, catalytic subunit 2 (30kDa) | 210160_at | (D) DE/1 | 4.00 | 4.85E-09/4 | NA | MDD | Lithium, PCP, Clozapine | 13 |
| PCDH9 Protocadherin 9 | 238919_at | (D) AP/1 | 4.00 | 4.52E-05/4 | NA | Aging, MDD, SZ/SZA, SZ | Clozapine Omega-3 | 13 |

FIG. 9 cont.

| | | | | | | | |
|---|---|---|---|---|---|---|---|
| PIK3R1<br>phosphoinositide-3-kinase, regulatory subunit 1 (alpha) | 212240_s_at | (I)<br>DE/1 | 4.00 | 7.11E-14/4 | NA | NA | SZ, MDD, Relaxation Response, PTSD, BP, Longevity, Stress, Alchol, Insomnia, Anxiety | Amygdala mood stabilizers | 13 |
| PTEN<br>phosphatase and tensin homolog | 222176_at | (I)<br>DE/1 | 4.00 | 4.88E-05/4 | NA | 09/3.27E-03 | SZ, MDD, BP, PTSD, Longevity, Stress | | 13 |
| RNF6<br>ring finger protein (C3H2C3 type) 6 | 210932_s_at | (D)<br>DE/1 | 4.00 | 1.25E-05/4 | NA | 0.82/1.58E-02 | BP, Social Isolation | | 13 |
| SLC5A3<br>sodium/myo-inositol cotransporter | 213167_s_at | (D)<br>DE/1 | 4.00 | 4.89E-14/4 | NA | NA | Chronic Stress, MDD, Alcohol | Lithium | 13 |

FIG. 9 cont.

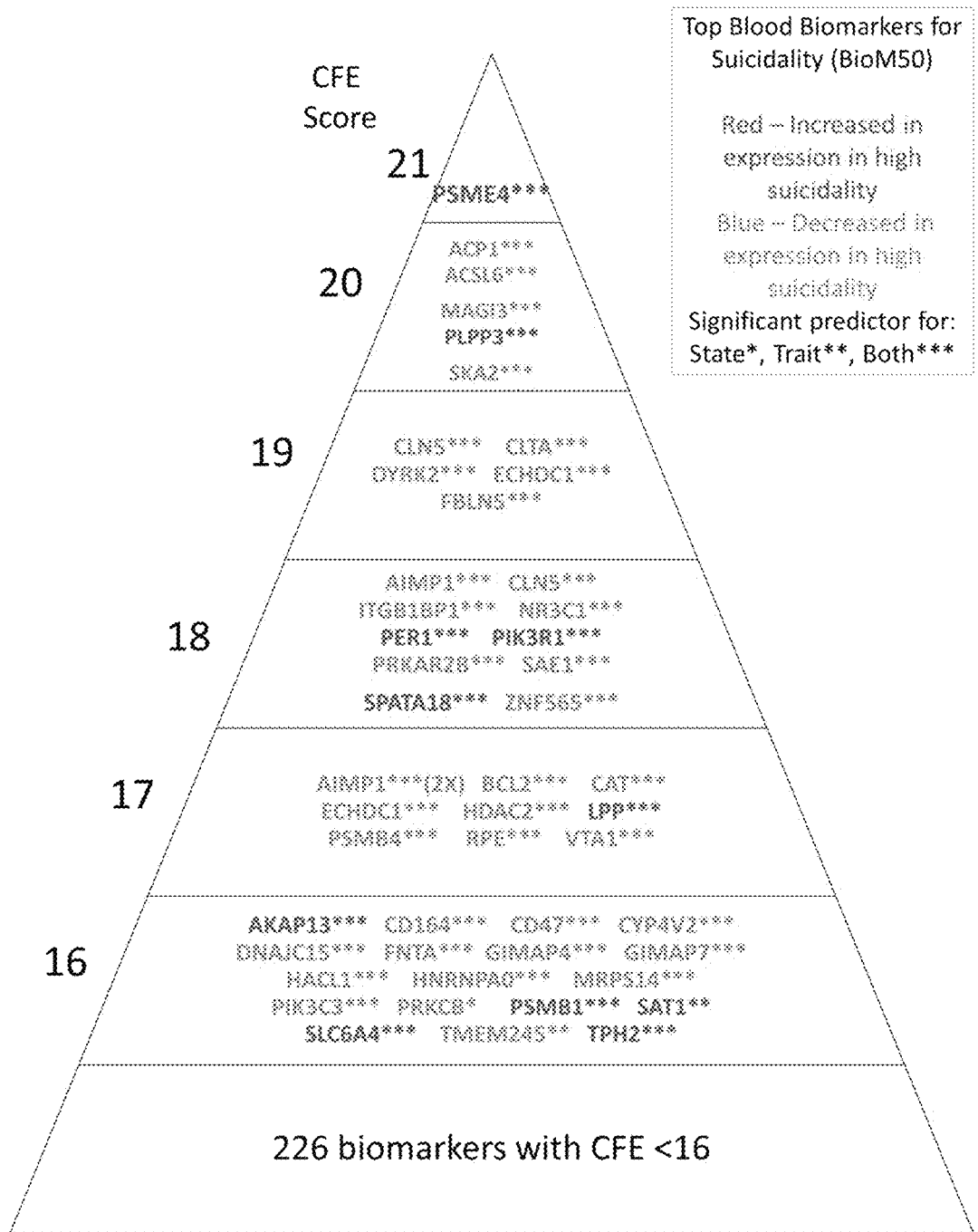
FIG. 10 CFE Pyramid for Top BioM 50

PRECISION MEDICINE FOR TREATING AND PREVENTING SUICIDALITY

CROSS-REFERENCE TO RELATED APPLICATION

This application is a continuation-in-part of and claims priority to PCT Application serial number PCT/US2018/032540, filed May 14, 2018, which claims priority to U.S. Provisional Application No. 62/505,197 filed on May 12, 2017, the contents of both of which are incorporated herein by reference in their entirety.

STATEMENT OF GOVERNMENT SUPPORT

This invention was made with government support under OD007363 awarded by the National Institutes of Health and 2IO1CX000139 merit award by the Veterans Administration. The government has certain rights in the invention.

BACKGROUND OF THE DISCLOSURE

Suicide is a leading cause of death in psychiatric patients, and in society at large. Particularly, suicide accounts for one million deaths worldwide each year. Worldwide, one person dies every 40 seconds through suicide, a potentially preventable cause of death. Further, although women have a lower rate of suicide completion as compared to men, due in part to the less-violent methods used, women have a higher rate of suicide attempts. A limiting step in the ability to intervene is the lack of objective, reliable predictors. One cannot just ask individuals if they are suicidal, as the desire to not be stopped or future impulsive changes of mind may make their self-report of feelings, thoughts and plans unreliable.

There are currently no objective tools to assess and track changes in suicidal risk without asking the subjects directly. Such tools, however, could prove substantially advantageous as the subjects at risk often choose not to share their suicidal ideation or intent with others, for fear of stigma, hospitalization, or that their plans will be thwarted. The ability to assess and track changes in suicidal risk without asking a subject directly would further allow for intervening prior to suicide attempt and suicide completion by the subject.

SUMMARY

Based on the foregoing, objective and precise identification of individuals at risk, ways of monitoring response to treatments, and novel preventive therapeutics need to be discovered, employed, and widely deployed. Particularly, objective and quantitative markers would permit better and more precise assessment, tracking, and prediction of suicidal risk, which would enable preventive therapeutic interventions. Accordingly, the present disclosure is directed to identifying universal predictors, and in some embodiments, personalized predictors for suicidality. The present disclosure is generally directed at methods for assessing suicidality and early identification of risk for future suicidality, as well as methods for matching patients and drugs for prevention and mitigation of suicidality, and for monitoring response to treatment. Further, the present disclosure describes new methods of use for drugs and natural compounds repurposed for treating suicidality. All the above-mentioned methods are computer-assisted methods analyzing the expression of panels of genes, clinical measures, and drug databases. A universal approach in everybody, as well as a personalized approach by gender, and by diagnosis, are disclosed.

The present disclosure relates generally to compounds for mitigating suicidality. Particularly, novel drugs and natural compounds for treating and preventing suicidality (e.g., suicide ideation and actions, future hospitalization due to suicidality, and suicide completion) have now been identified through bioinformatics drug repurposing methods using novel gene expression biomarkers. The disclosure describes compounds for use in everybody (universal), as well as personalized by gender (males, females), diagnosis (bipolar, depression), and gender and diagnosis combined (male bipolar, male depression). Further, the present disclosure relates to gene expression biomarkers and their use for deciding in a particular person which drug or natural compound to use (precision medicine) for treating and preventing suicidality (e.g., suicide ideation and actions, future hospitalization due to suicidality, and suicide completion), as well as for tracking response to the drug or natural compound (pharmacogenomics). More particularly, the present disclosure relates to an algorithm composed of clinical measures and biomarkers for identifying subjects who are at risk of committing suicide, as well as for monitoring response to treatment. In some embodiments, the biomarkers used herein have been found to be more universal in nature, working across psychiatric diagnoses and genders. Such biomarkers may reflect and/or be a proxy for the core biology of suicide. In other embodiments, the present disclosure relates to biomarkers identified using a personalized approach; that is, by psychiatric diagnosis and/or gender, with a focus on bipolar males, the highest risk group. Such a personalized approach may be more sensitive to gender differences and to the impact of psychiatric co-morbidities and medications.

The present disclosure further relates to determining subtypes of suicidality using an app (SASS), based on mental state at the time of high suicidal ideation, and identified four subtypes: high anxiety, low mood, combined, and non-affective (psychotic). Such subtypes may delineate groups of individuals that are more homogenous in terms of biology and behavior.

The present disclosure further relates to a checklist of socio-demographic and psychological factors that influence the likelihood of becoming suicidal (CFI-S), with contributions from six domains (life events, mental health, physical health, environmental factors, cultural factors, and addictions). It can provide a likelihood score for an individual attempting that behavior (suicide) in the future. The items that are positive on the checklist can have differences in importance embodied as weight coefficients, based on specificity for suicide (Table 1), and based on empirical data, such as rank order in predictive datasets (FIGS. 4A & 4B). They also vary from individual to individual. As such, there is an individualized profile that can be affected by targeted interventions to prevent that behavior (suicide).

TABLE 1

Convergent Functional Information for Suicidality (CFI-S 30) Scale
Items are scored 1 for Yes, 0 for No. Total Score has a maximum possible of 30. Final Score is Total Score divided by number of items that were scored (as for some items information might not be available (NA) so they are not scored), and multiplied by 100.

| Items | Yes = 1 | No = 0 | NA | Domain | Weights for sensitivity/Importance to behavior 3 is most important, 2 intermediate, 1 less important | Type Increased Reasons (IR) Decreased Barriers (DB) | Weights for specificity 2 is Specific for Suicidality, 1 is non-specific | Weighted Score |
|---|---|---|---|---|---|---|---|---|
| 1. Psychiatric illness diagnosed and treated | | | | Mental Health | x2 | IR | x1 | |
| 2. With poor treatment compliance | | | | Mental Health | x2 | DB | 1 | |
| 3. Family history of suicide in blood relatives | | | | Mental Health | x2 | IR | x2 | |
| 4. Personally knowing somebody who committed suicide | | | | Cultural Factors | x2 | DB | x2 | |
| 5. History of abuse growing up: physical, sexual, emotional, neglect | | | | Life Satisfaction | x3 | IR | x1 | |
| 6. Acute/severe medical illness, including acute pain ("I just can't stand this pain anymore.") (within last 3 months) | | | | Physical Health | x1 | IR | x1 | |
| 7. Acute stress: Losses, grief (within last 3 months) | | | | Environmental Stress | x1 | IR | x1 | |
| 8. Chronic stress: perceived uselessness, not feeling needed, burden to extended kin. | | | | Environmental Stress | x1 | IR | x1 | |
| 9. History of excessive introversion, conscientiousness (including planned suicide attempts) | | | | Mental Health | x2 | IR | x1 | |
| 10. Dissatisfaction with life at this moment in time | | | | Life Satisfaction | x3 | IR | x1 | |
| 11. Lack of hope for the future | | | | Life Satisfaction | x3 | IR | x1 | |
| 12. Current substance abuse | | | | Addictions | x3 | DB | x1 | |
| 13. Past history of suicidal acts/gestures | | | | Life Satisfaction | x3 | DB | x2 | |
| 14. Lack of religious beliefs | | | | Cultural Factors | x2 | DB | x1 | |
| 15. Acute stress: Rejection (within last 3 months) | | | | Environmental Stress | x1 | IR | x1 | |
| 16. Chronic stress: lack of positive relationships, social isolation | | | | Environmental Stress | x1 | DB | x1 | |
| 17. History of excessive extroversion and impulsive behaviors (including rage, anger, physical fights) | | | | Mental Health | x2 | DB | x1 | |
| 18. Lack of coping skills when faced with stress (cracks under pressure) | | | | Mental Health | x2 | DB | x1 | |
| 19. Lack of children. If has children, not in touch/not helping take care of them. | | | | Life Satisfaction | x3 | DB | x1 | |
| 20. History of command hallucinations of self-directed violence | | | | Mental Health | x2 | IR | x2 | |
| 21. Age: Older >60 or Younger <25 | | | | Age | x1 | IR | x1 | |

TABLE 1-continued

Convergent Functional Information for Suicidality (CFI-S 30) Scale
Items are scored 1 for Yes, 0 for No. Total Score has a maximum possible of 30. Final Score is Total
Score divided by number of items that were scored (as for some items information might not be
available (NA) so they are not scored), and multiplied by 100.

| Items | Yes = 1 | No = 0 | NA | Domain | Weights for sensitivity/Importance to behavior 3 is most important, 2 intermediate, 1 less important | Type Increased Reasons (IR) Decreased Barriers (DB) | Weights for specificity2 is Specific for Suicidality, 1 is non-specific | Weighted Score |
|---|---|---|---|---|---|---|---|---|
| 22. Gender: Male or Transgender | | | | Gender | 1 | DB | 1 | |
| 23. Persistent reduced (<5 hrs/night), excessive (>11 hrs/night) or fragmented sleep (within the last 3 months) | | | | Mental Health | x2 | IR | x1 | |
| 24. History of head trauma/traumatic brain injury | | | | Physical Health | x1 | DB | x1 | |
| 25. Owns/has easy access to guns or to multiple medications | | | | Cultural Factors | x2 | DB | x2 | |
| 26. History of exposure to trauma as an adult: combat, accidents, violence, rape | | | | Life Satisfaction/Environmental Stress | x3 | IR | x1 | |
| 27. Is an artist or entertainer, or works in the healthcare field as a provider of clinical care | | | | Cultural Factors | x2 | DB | x1 | |
| 28. History of revenge behaviors | | | | Mental Health | x2 | DB | x1 | |
| 29. History of feeling very guilty | | | | Mental Health | x2 | DB | x1 | |
| 30. Does not easily confide or seek help from others | | | | Cultural Factors | x2 | DB | x1 | |

Total score = (Sum of Weighted score/Number of items scored) × 100

Biomarkers underlying propensity to behaviors can also be identified, as described in the present disclosure. They can be viewed as a checklist of biological measures. Again, the items/biomarkers that are positive/changed in levels on the checklist can have different weights of importance embodied as weight coefficients, based on specificity for suicide as reflected in a convergent functional genomics (CFG) score obtained during their discovery, prioritization and validation, (Table 1), and also based on other empirical data, such as strength in predictive datasets (FIGS. 2 and 3A-3D). They also vary from individual to individual. There is an individualized profile that can be affected by targeted interventions, such as matched nutraceuticals and medications, as described in our invention.

Besides the checklists of factors that influence behavior (such as CFI-S in the case of suicide), and the checklist of biomarkers that indicate propensity to a behavior, such as panels of predictive biomarkers, the state of mind of an individual is a major factor influencing whether a behavior will happen or not. So a checklist of measures of the mind domains (anxiety and mood (for example measured with SASS), psychosis (for example measured with PANSS Positive Scale), and a direct assessment of the severity of suicidal ideation (for example measured with the suicide item in HAMD (HAMD-SI), would be informative to include in the overall algorithm to predict suicidality, and as targets for intervention to facilitate or prevent behaviors.

BRIEF DESCRIPTION OF THE DISCLOSURE

The present disclosure is generally directed at methods for assessing suicidality and early identification of risk for future suicidality, as well as methods for matching patients and drugs for prevention and mitigation of suicidality, and for monitoring response to treatment. The present disclosure is further related to drugs for mitigating suicidality in subjects. Particular drugs have been found that can mitigate suicidality in subjects universally; that is, drugs that can be used for mitigating suicidality across psychiatric diagnoses, genders and subtypes of suicidality. Some drugs, however, have been found that can be used more effectively for mitigating suicidality dependent on gender, psychiatric diagnoses, subtypes and combinations thereof.

Additionally, the present disclosure relates to biomarkers and their use for predicting a subject's risk of suicidality. In some embodiments, the biomarkers used herein have been found to be more universal in nature, working across psychiatric diagnoses, genders and subtypes. In other embodiments, the present disclosure relates to biomarkers identified using a personalized approach; that is, by psychiatric diagnosis, gender and subtype.

The present disclosure further relates to determining subtypes of suicidality based on mental state at the time of high suicidal ideation, and identified four subtypes: high anxiety, low mood, combined, and psychotic (non-affective)

such to delineate groups of individuals that are more homogenous in terms of biology and behavior.

BRIEF DESCRIPTION OF THE DRAWINGS

The patent or application file contains at least one drawing executed in color. Copies of this patent or patent application publication with color drawings will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

(FIG. 1A) Cohorts used in the Examples, depicting flow of discovery, prioritization, and validation, and testing of biomarkers from each step. (FIG. 1B) Discovery cohort longitudinal within-participant analysis. Phchp ### is study ID for each participant. V # denotes visit number (1, 2, 3, 4, 5, or 6). (FIG. 1C) Discovery of subtypes of suicidality based on high suicidal ideation visits in the discovery cohort. Subjects were clustered using measures of mood and anxiety (SASS), as well as psychosis (PANS S Positive). (FIG. 1D) Differential gene expression in the Discovery cohort-number of genes identified with DE and AP methods with an internal score of 1 and above. Underlined-increased in expression in High SI, no underline—decreased in expression in High SI. At the discovery step probesets were identified based on their score for tracking suicidal ideation with a maximum of internal points of 4 (33% (1 pt), 50% (2 pt) and 80% (4 pt)). (FIG. 1E) Prioritization with CFG for prior evidence of involvement in suicide. In the prioritization step probesets were converted to their associated genes using Affymetrix annotation and GeneCards. Genes were prioritized and scored using CFG for Suicide evidence with a maximum of 8 external points. Genes scoring at least 4 points out of a maximum possible of 12 total internal and external score point were carried to the validation step. (FIG. 1F) Validation in an independent suicide completers cohort from the coroner's office. In the validation step biomarkers were assessed for stepwise change from the discovery groups of participants with no SI, to high SI, to suicide completion, using ANOVA. Stringent Bonferroni correction is calculated for the total number of probesets analyzed. (FIG. 1G) Discovery, Prioritization and Validation scores for the cohorts in the Examples.

FIG. 3A is a circos plot depicting the best individual biomarker predictions for suicidal ideation state in the independent cohort (across all subjects, in subtypes, and personalized by gender and diagnosis), using universal biomarkers. FIG. 3B is a circos plot depicting the best individual biomarker predictions for future hospitalizations for suicidality in the first year following testing in the independent cohort (across all subjects, in subtypes, and personalized by gender and diagnosis), using universal biomarkers. FIG. 3C is a circos plot depicting the best individual biomarker predictions for suicidal ideation state in the independent male bipolar sub-cohort, using universal biomarkers and male bipolar biomarkers. FIG. 3D is a circos plot depicting the best individual biomarker predictions for future hospitalizations for suicidality in the first year following testing in the independent male bipolar sub-cohort, using universal biomarkers and male bipolar biomarkers. The circumference bands represent and are proportional to the number of participants in each cohort. The ribbons represent and are proportional to the AUC of the predictions. Table underneath the figures displays the actual numerical results. Only biomarkers whose AUC p-values are at least nominally significant are shown.

FIG. 3E The predictive ability of the biomarkers from FIGS. 3A-3D, shown in numerical fashion (AUC, p-value), in all (universal), by subtypes, and by gender and diagnosis.

FIGS. 4A & 4B depict Convergent Functional Information for Suicide (CFI-S) Testing. Testing in a large cohort that combines the discovery and test cohorts used for biomarker work. CFI-S was developed independently of any data from the Examples, by compiling known socio-demographic and clinical risk factors for suicide. It is composed of a short version with 22 items, and a longer version with 30 items (Table 1), that assess the influence of mental health factors, as well as of life satisfaction, physical health, environmental stress, addictions, and cultural factors known to influence suicidal behavior, as well as two demographic factors, age and gender. FIG. 4A depicts prediction of high suicidal ideation (HAMD SI>=2). FIG. 4B depicts prediction of future hospitalizations due to suicidality within one year of follow up. Table under FIG. 4A depicts individual items and their ability to differentiate between No SI and High SI. Table under FIG. 4B depicts participants with and without future hospitalizations due to suicidality.

FIGS. 5A-5C depict predicting suicidality using a broad-spectrum predictor (UP-Suicide), combining phenomic measures and the top dozen biomarkers. FIG. 5D-5E depict broad-spectrum predictor (UP-Suicide), combining phenomic measures and the top dozen biomarkers in a single research participant (phchp328). FIG. 5A depicts the UP-Suicide model. FIG. 5B depicts UP-Suicide predicting suicidal ideation in the independent test cohort, and predicting future hospitalizations due to suicidality in the first year following testing. UP-Suicide is composed of the top increased and decreased biomarkers from each step of discovery, prioritization, and validation, for a total of 12, along with CFI-S scores and SASS (Mood and Anxiety scores). n=number of testing visits. Top left Receiver operating curve identifying participants with suicidal ideation against participants with No SI or intermediate SI. Top right Y axis contains the average UP-Suicide scores with standard error of mean for no SI, intermediate SI, and high SI. Scatter plot depicting HAMD-SI score on the Y-axis and UP-Suicide score on the X axis with linear trend line. The table below FIG. 5B top left receiver operating curve and top right summarizes descriptive statistics. Bottom left Receiver operating curve identifying participants with future hospitalizations due to suicidality against participants without future hospitalizations due to suicidality. Top right Y axis contains the average UP-Suicide scores with standard error of mean for no future hospitalizations due to suicidality and participants with future hospitalizations due to suicidality. Scatter plot depicting frequency of future hospitalizations due to suicidality on the Y-axis and UP-Suicide score on the X axis with linear trend line. The table below FIG. 5B bottom left receiver operating curve and bottom right summarizes descriptive statistics. FIG. 5C is a dimensional view of risk stratification using clinical information measures, and example of two high risk participants. A tri-dimensional scatter plot was created using Partek. Tri-dimensional 95% confidence intervals were inserted as ellipsoids, color coded blue and red, for No SI and High SI, respectively. Euclidian D (distance from origin) is depicted for the 2 subjects, as indicated by the arrows. Percentiles for scores on top predictors in all the subjects' visits in this Example are depicted in the table underneath the plot. Participant phchp158 was a divorced African American male in his late 20s with a long history of schizoaffective disorder, bipolar type, and *Cannabis* abuse. He was tested once (v1) while hospitalized for a suicide attempt by hanging. In the five years following testing, he had two additional hospitalizations for suicidality: one for suicidal ideation, one for attempt by overdose. He also had two hospitalizations for psychosis exacerbation without suicidality during this time span. Moved out of state, lost to follow-up since December 2015. Participant phchp328 (FIGS. 5D and 5E) was a Caucasian female in her late 30s with a long history of depression, PTSD, borderline personality disorder, and polysubstance abuse/dependence. She was first tested while in-patient for suicidal ideation. Over the next year, she subsequently had six psychiatric hospitalizations for suicidality: five due to suicidal ideation and one due to a suicidal attempt by overdose. She also had one hospitalization for opioid withdrawal and depression during this time span. She committed suicide by overdose with pills, leaving behind a suicide note addressed to her mother. Her UP-Suicide score at Visit 1, composed of the panel of top dozen biomarkers (BioM12) scores and phenomic measures scores (CFI-S, SASS), was at the 100% of the scores of all the psychiatric participant visits in the Example. Of note, that testing was conducted during an in-patient hospitalization due to suicidal ideation. While her scores improved at subsequent outpatient testing visits (Visits 2 and 3), this high watermark score indicated her high risk. After the last testing visit for the Example, she had four subsequent psychiatric hospitalizations: three due to suicidal ideation, one for opioid withdrawal/detox (the last one), ending 2 weeks before date of committing suicide (T). FIG. 5D provides percentiles for scores on top predictors in the subjects' visits. FIG. 5E is a dimensional view of risk stratification using clinical information measures, and example of two high risk participants. A tri-dimensional scatter plot was created using Partek. Tri-dimensional 95% confidence intervals were inserted as ellipsoids, color coded blue and red, for No SI and High SI, respectively.

FIG. 9 depicts Male Bipolar Biomarkers—Convergent Functional Evidence for Involvement in Suicidality. Top Dozen and Bonferroni biomarkers. Post-hoc summation of all the evidence form discovery, validation, prioritization and testing, along with evidence for involvement in other psychiatric disorders and for being a target of drugs. This prioritization highlights, for future studies, biomarkers that may have broad applicability in the field, for diagnostics and therapeutics. BP—bipolar, MDD—major depressive disorder, SZ—schizophrenia, PTSD—post-traumatic stress disorder, ASD—autism spectrum disorder;

FIG. 10 is a schematic diagram depicting top blood biomarkers for suicidality (BioM50) in accordance with embodiments of the present disclosure;

FIG. 11A depicts state predictions-high suicidal ideation (HAMDSI>=2). FIG. 11B depicts trait predictions-first year hospitalizations for suicidality. FIG. 11C depicts trait predictions-all future years hospitalizations for suicidality. Bar graphs show the best predictive biomarkers in each group. * Nominally significant p<0.05. The tables underneath FIGS. 11A-11C display the actual number of biomarkers for each group whose ROC AUC p-values (FIGS. 11A-B) and Cox Odds Ratio p-values (FIG. 11C) are at least nominally significant. Some gender and diagnosis group are missing from the graph as they did not have any significant biomarkers. Cross-sectional is based on levels at one visit. Longitudinal is computed based on levels at multiple visits (integrates levels at most recent visit, maximum levels, slope into most recent visit, and maximum slope). Dividing lines represent the cutoffs for a test performing at chance levels (white), and at the same level as the best biomarkers for all subjects in cross-sectional (gray) and longitudinal (black) based predictions. All biomarkers performed better than chance. Biomarkers performed better when personalized by gender and diagnosis;

FIG. 12 depicts the top biomarkers, from the BioM 50 panel, with modulation capabilities by existing drugs in the opposite direction to suicidality. Such biomarkers can be used to target treatments to different patients, and to measure response to that treatment. The higher the proportion/percentile of biomarkers for a certain drug/class, the more indicated that drug would be for treatment. When biomarkers for multiple different drug/classes are changed in an individual, a prioritization based on the proportion/percentile of biomarkers for each class can be used to choose the drug or combination of drugs (targeted rational polypharmacy);

DETAILED DESCRIPTION

Figure 1A:
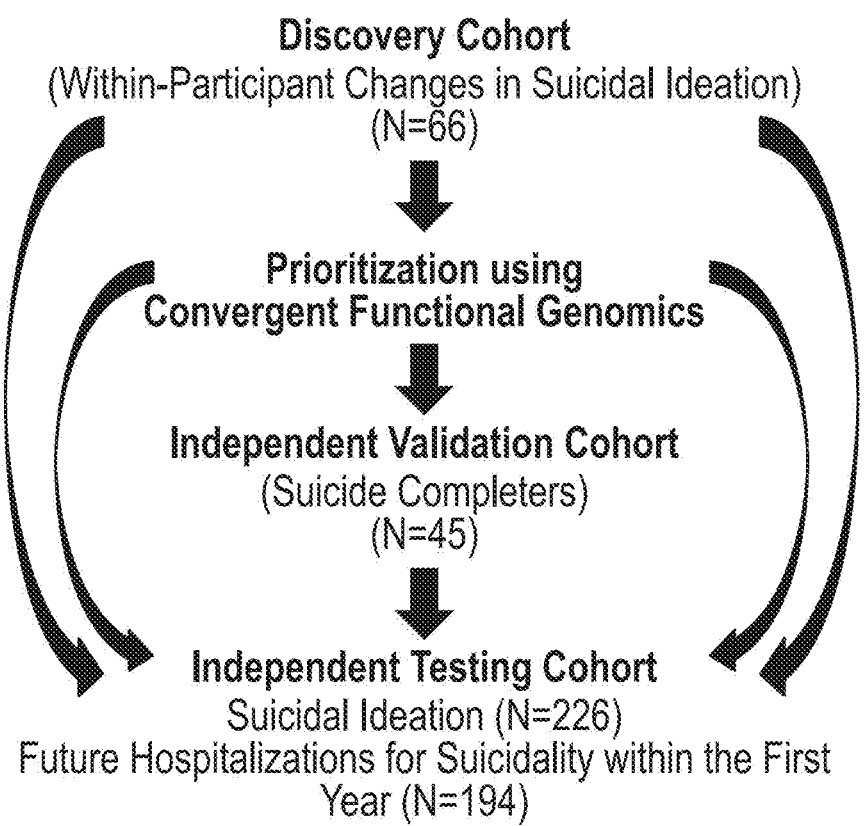
FIGS. 1A-1G depict Discovery, Prioritization and Validation methodology used in the Examples.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed at methods for assessing suicidality and early identification of risk for future suicidality, as well as methods for matching patients and drugs for prevention and mitigation of suicidality, and for monitoring response to treatment. The methods may further include the generation of a report providing a risk score and/or personalized treatment options. Further, the present disclosure generally is directed to drugs for mitigating suicidality in subjects. Particular drugs have been found that can mitigate suicidality in subjects universally; that is, drugs that can be used for mitigating suicidality across psychiatric diagnoses and genders. Some drugs, however, have been found that can be used more effectively for mitigating suicidality dependent on gender, psychiatric diagnoses, and combinations thereof.

In additional embodiments, the present disclosure is directed to blood gene expression biomarkers that are more universal in nature; that is, blood biomarkers that can be used for predicting suicidality across psychiatric diagnoses and genders. Accordingly, a longitudinal within-participant design and large cohorts were used.

Additionally, subtypes of suicidality were identified based on mental state (anxiety, mood, psychosis) at the time of high suicidal ideation.

Furthermore, the predictive ability of the biomarkers discovered were examined, in a completely independent cohort, in all the participants in it, as well as divided by subtypes, and personalized by gender and diagnosis.

The top biomarkers were combined with scores from a clinical information measure of suicide risk (CFI-S), as well as anxiety and mood (SASS), to obtain a broader spectrum predictor (UP-Suicide) that puts the biomarkers in the context of the person and his/her mental state. This list was then leveraged for therapeutics and drug discovery purposes to see if some of the biomarkers identified could be modulated by existing compounds used to treat suicidality, and also to conduct bioinformatics drug repurposing analyses to discover new drugs and natural compounds that may be useful for treating suicidality.

As disclosed herein, "patient psychiatric information" may include mood information, anxiety information, psychosis information and other psychiatric symptom information and combinations thereof.

As used herein, "predicting suicidality in a subject" is used herein to indicate in advance that a subject will attempt suicide and/or complete suicide.

As known by those skilled in the art, "suicidal ideation" refers to thoughts, feelings, intent, external actions and behaviors about completing suicide. Suicidal ideation can vary from fleeting thoughts to unsuccessful attempts. In some embodiments, the reference expression level of a biomarker can be obtained for a subject who has no suicidal ideation at the time the sample is obtained from the subject, but who later exhibits suicide ideation. As used herein, "suicidality" includes both suicide ideation and suicidal acts.

As used herein, "a reference expression level of a biomarker" refers to the expression level of a biomarker established for a subject with no suicidal ideation, expression level of a biomarker in a normal/healthy subject with no suicidal ideation as determined by one skilled in the art using established methods as described herein, and/or a known expression level of a biomarker obtained from literature. The reference expression level of the biomarker can further refer to the expression level of the biomarker established for a high suicide risk subject, including a population of high suicide risk subjects. The reference expression level of the biomarker can also refer to the expression level of the biomarker established for a low suicide risk subject, including a population of low suicide risk subjects. The reference expression level of the biomarker can also refer to the expression level of the biomarker established for any combination of subjects such as a subject with no suicidal ideation, expression level of the biomarker in a normal/healthy subject with no suicidal ideation, expression level of the biomarker for a subject who has no suicidal ideation at the time the sample is obtained from the subject, but who later exhibits suicide ideation, expression level of the biomarker as established for a high suicide risk subject, including a population of high suicide risk subjects, and expression level of the biomarker can also refer to the expression level of the biomarker established for a low suicide risk subject, including a population of low suicide risk subjects. The reference expression level of the biomarker can also refer to the expression level of the biomarker obtained from the subject to which the method is applied. As such, the change within a subject from visit to visit can indicate an increased or decreased risk for suicide. For example, a plurality of expression levels of a biomarker can be obtained from a plurality of samples obtained from the same subject and used to identify differences between the plurality of expression levels in each sample. Thus, in some embodiments, two or more samples obtained from the same subject can provide an expression level(s) of a blood biomarker and a reference expression level(s) of the blood biomarker.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), and combinations thereof.

As used herein, a "difference" in the expression level of the biomarker refers to an increase or a decrease in the expression of a blood biomarker when analyzed against a reference expression level of the biomarker. In some embodiments, the "difference" refers to an increase or a decrease by about 1.2-fold or greater in the expression level of the biomarker as identified between a sample obtained from the subject and the reference expression level of the biomarker. In one embodiment, the difference in expression level is an increase or decrease by about 1.2 fold. As used herein "a risk for suicide" can refer to an increased (greater) risk that a subject will attempt to commit suicide and/or complete suicide. For example, depending on the biomarker(s) selected, the difference in the expression level of the biomarker(s) can indicate an increased (greater) risk that a subject will attempt to commit suicide and/or complete suicide. Conversely, depending on the biomarker(s) selected, the difference in the expression level of the biomarker(s) can indicate a decreased (lower) risk that a subject will attempt to commit suicide and/or complete suicide.

In accordance with the present disclosure, biomarkers useful for objectively predicting, mitigating, and/or preventing suicidality in subjects have been discovered. In one aspect, the present disclosure is directed to a universal method for predicting suicidality in a subject; that is, a method for predicting suicidality across all psychiatric diagnoses and for either gender. The method includes obtaining a reference expression level of a blood biomarker; and determining an expression level of the blood biomarker in a sample obtained from the subject. A change in the expression level of the blood biomarker in the sample obtained from the subject as compared to the reference expression level indicates suicidality. In some embodiments, the methods further include obtaining clinical risk factor information and clinical scale data such as for anxiety, mood and/or psychosis from the subject in addition to obtaining blood biomarker expression level in a sample obtained from the subject.

In one embodiment, the expression level of the blood biomarker in the sample obtained from the subject is increased as compared to the reference expression level of the biomarker. It has been found that an increase in the expression level of particular blood biomarkers in the sample obtained from the subject as compared to the reference expression level of the biomarker indicates a risk for suicide. Suitable biomarkers that indicate a risk for suicide when the expression level increases can be, for example, one or more biomarkers as listed in Tables 3A-3G and combinations thereof.

In another embodiment, the expression level of the blood biomarker in the sample obtained from the subject is decreased as compared to the reference expression level of the biomarker. Suitable biomarkers that indicate a risk for suicide when the expression level decreases as compared to the reference expression level have been found to include, for example, one or more biomarkers as listed in Tables 3A-3G and combinations thereof.

Particularly suitable subjects are humans. Suitable subjects can also be experimental animals such as, for example, monkeys and rodents, that display a behavioral phenotype associated with suicide, for example, a mood disorder or psychosis. In one particular aspect, the subject is a female human. In another particular aspect, the subject is a male human, and in another particular aspect, the subject is a male bipolar human. In yet another particular aspect, the subject is a male depressed human.

A particularly suitable sample for which the expression level of a biomarker is determined can be, for example, blood, including whole blood, serum, plasma, leukocytes, and megakaryocytes.

The method can further include assessing mood, anxiety, psychosis and other like psychiatric symptoms, and combinations thereof in the subject using questionnaires and/or a computer-implemented method for assessing mood, anxiety, psychosis, other like psychiatric symptoms, and combinations thereof. In one aspect, the method is implemented using a first computer device coupled to a memory device, the method comprising: receiving mood information, anxiety information, psychosis information and combinations thereof into the first computer device; storing, by the first computer device, the mood information, anxiety information, psychosis information and combinations thereof in the memory device; computing, by the first computer device, of the mood information, anxiety information, psychosis and combinations thereof, a score that can be used to predict suicidality; presenting, by the first computer device, in visual form the mood information, anxiety information, psychosis information and combinations thereof to a second computer device; receiving a request from the second computer device for access to the mood information, anxiety information, psychosis information and combinations thereof; and transmitting, by the first computer device, the mood information, anxiety information, psychosis information and combinations thereof to the second computer device to assess mood, anxiety, psychosis and combinations thereof in the subject. Suitable mood and anxiety information is described herein in more detail below.

The method can further include assessing socio-demographic/psychological suicidal risk factors in the subject using a computer-implemented method for assessing socio-demographic/psychological suicidal risk factors in the subject, the method implemented using a first computer device coupled to a memory device, the method comprising: receiving socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to a second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject. Suitable socio-demographic/psychological suicidal risk factors are described herein in more detail below.

Figure 14:
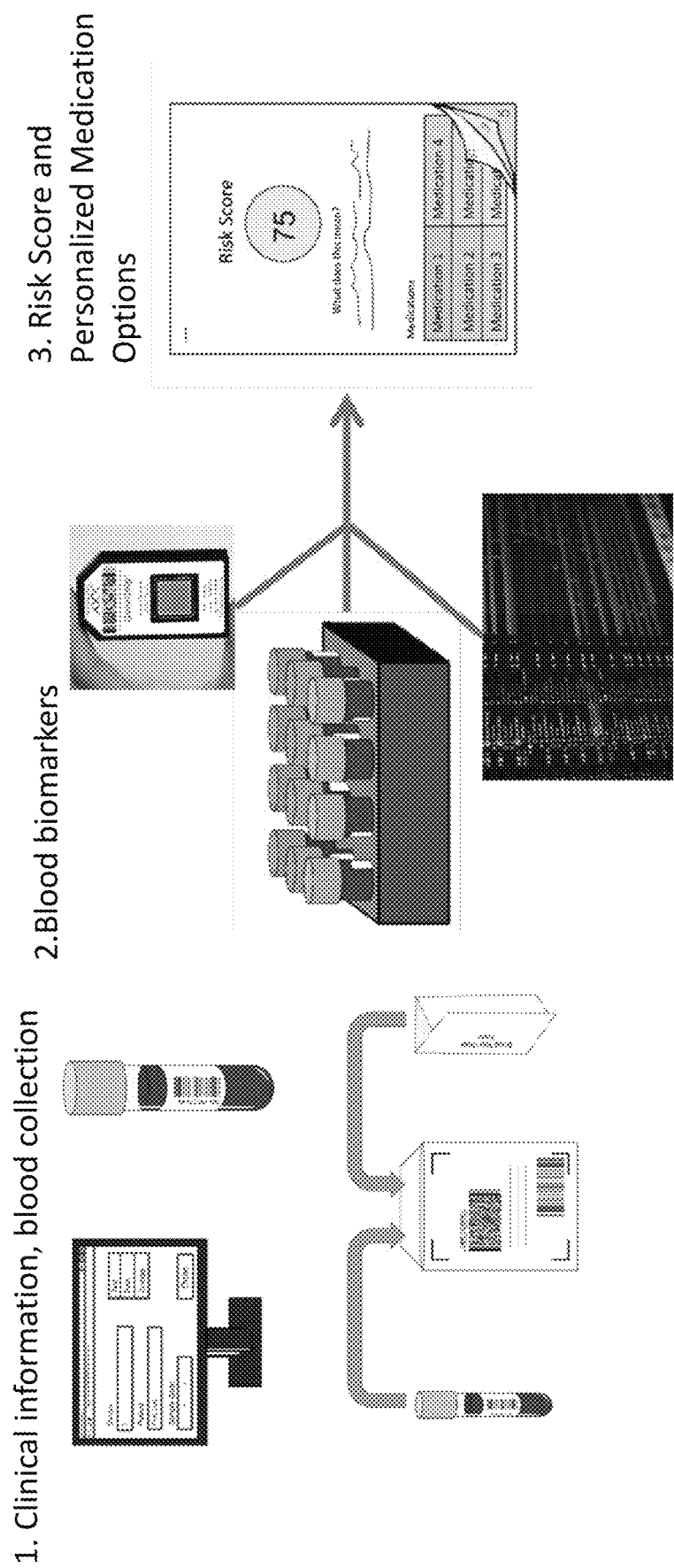
FIG. 14 depicts a schematic diagram of generating risk score and personalized medication options based on a panel of biomarkers, according to embodiments of the disclosed methods.
Figure 15:
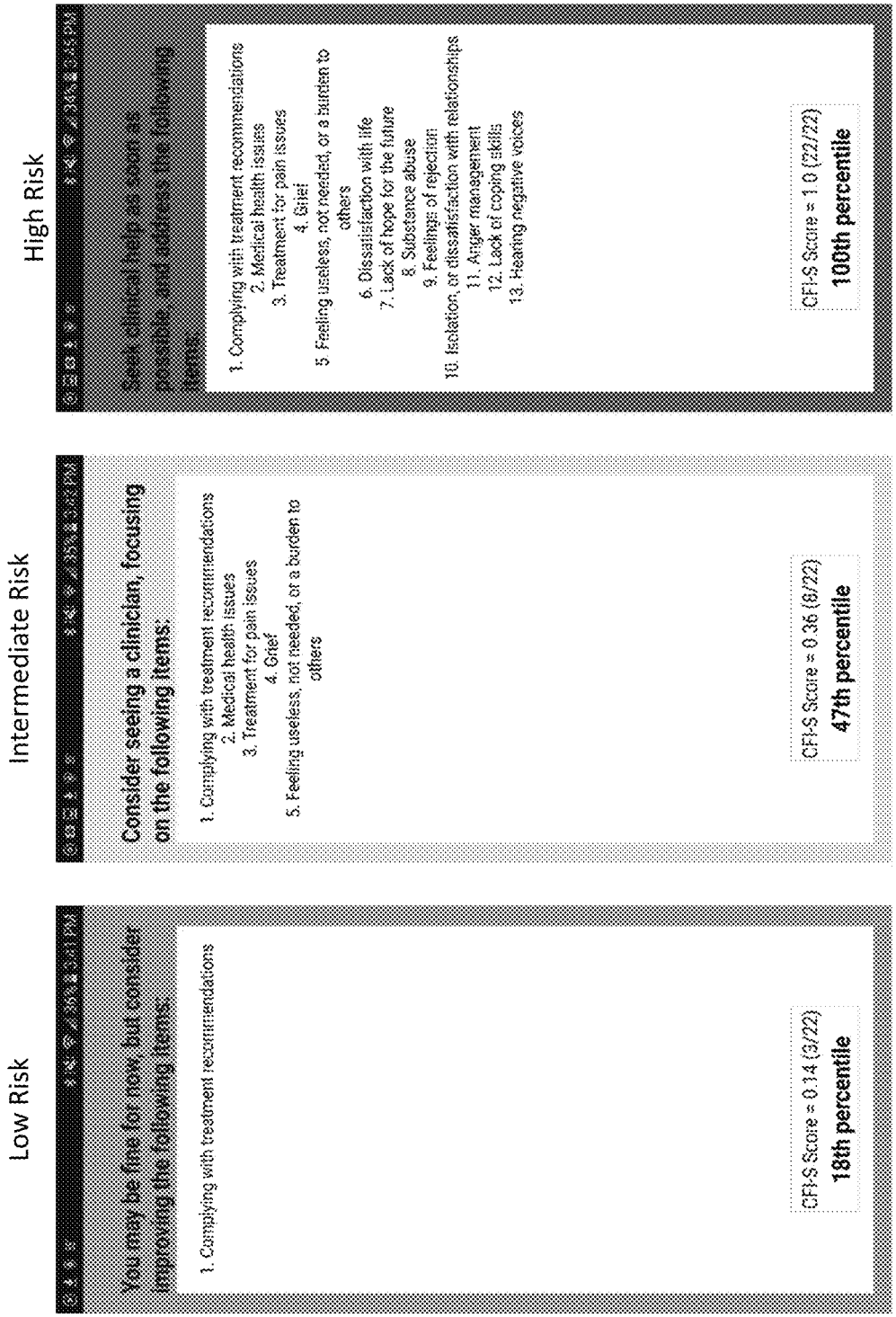
FIG. 15 depicts a representation of a report providing a risk score and personalized treatment options, according to embodiments of the disclosed methods.

In accordance with embodiments of the present disclosure, as specifically seen in FIG. 14, clinical information and blood may be collected, one or more blood biomarkers may be assessed, alone or in panel form, and a risk score and personalized medication options may be generated. In a variation, the risk score and/or personalized medication options may be presented in a report. As seen in FIG. 15, another report, based on clinical and socio-demographic data, may provide, a CFI-S score, percentile, a risk rating, and treatment recommendations. In an example, the reports are electronic, and processed via a computer device, system or an app. In another example, the reports are printed on paper.

Additionally, in accordance with another aspect of the present disclosure, biomarkers useful for objectively predicting future hospitalization due to suicidality in subjects have been discovered. In one aspect, the present disclosure is directed to a universal method for future hospitalization due to suicidality in a subject; that is, a method for predicting future hospitalization due to suicidality across all psychiatric diagnoses and genders. The method includes obtaining a first expression level of a blood biomarker in an initial sample obtained from the subject; and determining a second expression level of the blood biomarker in a subsequent sample obtained from the subject, wherein an increase in the expression level of the blood biomarker in the subsequent sample obtained from the subject as compared to the expression level of the initial sample indicates a higher risk of future hospitalizations due to suicidality. In some embodiments, the methods further include obtaining clinical risk factor information and clinical scale data such as for anxiety, mood and/or psychosis from the subject in addition to obtaining a blood biomarker expression level in a sample obtained from the subject.

In another aspect, the present disclosure is directed to further mitigating suicidality in the subject(s) identified above. The method includes: obtaining an expression level of a blood biomarker in a sample obtained from the subject; obtaining a reference expression level of the blood biomarker; identifying a difference in the expression level of the blood biomarker in the sample as compared to the reference expression level of the blood biomarker; and, upon identifying a difference between the expression level of the blood biomarker in the sample obtained from the subject and the reference expression level of the blood biomarker, administering a treatment, wherein the treatment reduces the difference between the expression level of the blood biomarker in the sample as compared to the reference expression level of the blood biomarker to mitigate suicidality in the subject. As used herein, "mitigate", "mitigating", and the like refer to making a condition less severe and/or preventing a condition. More particularly, the phrase "mitigate suicidality" refers to reducing suicide ideation in a subject and/or preventing suicide completion.

Suitable treatments can be a lifestyle modification, administering a therapy, and combinations thereof.

Suitable therapy can be a nutritional, a drug and psychotherapy.

Particularly suitable nutritionals can be omega-3 fatty acids, including, by way of example, docosahexaenoic acid (DHA).

In some embodiments, the therapies can include drugs and natural compounds that have now been found to be effective in mitigating suicidality either universally or for a specific gender and/or psychiatric diagnosis. Exemplary repurposed drugs and natural compounds are found in Tables 6-18.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

In this Example, blood biomarkers from three cohorts of subjects were analyzed.
Materials and Methods
Cohorts
Three independent cohorts were examined: discovery cohort (a live psychiatric participants cohort), validation cohort (a postmortem coroner's office cohort), and testing cohort (also referred to herein as "test cohort") (an independent live psychiatric participants test cohort for predicting suicidal ideation, and for predicting future hospitalizations for suicidality) (FIG. 1A).

Figure 1B:
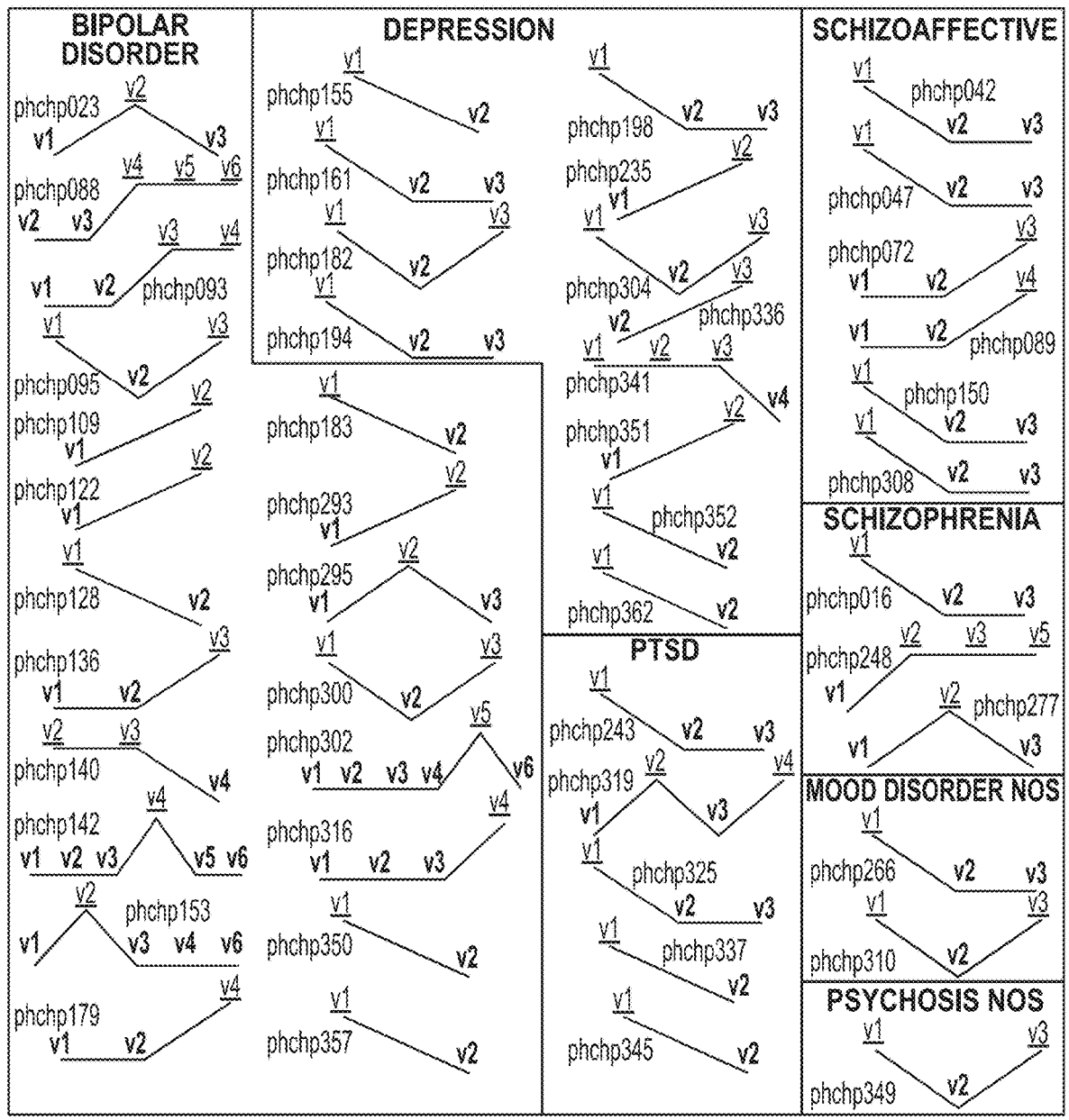
Figure 1B:
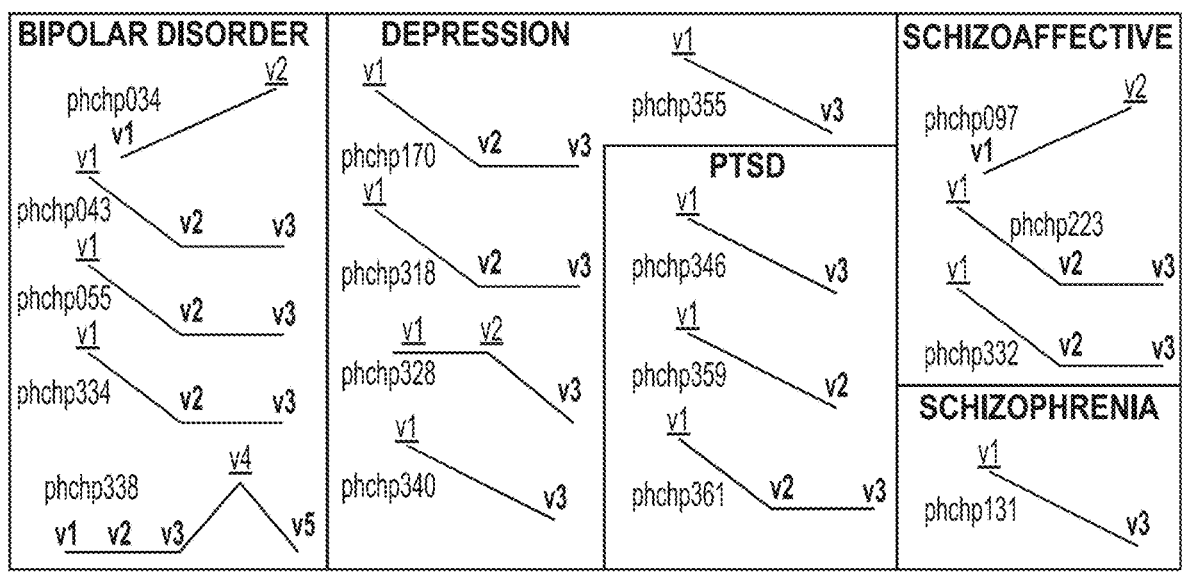

The live psychiatric participants are part of a larger longitudinal cohort of adults that are continuously being collected. Participants are recruited from the patient population at the Indianapolis VA Medical Center and Indiana University School of Medicine through referrals from care providers, the use of brochures left in plain sight in public places and mental health clinics, and through word of mouth. All participants understood and signed informed consent forms detailing the research goals, procedure, caveats and safeguards, per IRB approved protocol. Participants completed diagnostic assessments by an extensive structured clinical interview—Diagnostic Interview for Genetic Studies—at a baseline visit, followed by up to six testing visits, 3-6 months apart or whenever a new psychiatric hospitalization occurred. At each testing visit, they received a series of psychiatric rating scales, including the Hamilton Rating Scale for Depression-17, which includes a suicidal ideation (SI) rating item (FIG. 1B). Further, blood was drawn. Whole blood (10 ml) was collected in two RNA-stabilizing PAXgene tubes, labeled with an anonymized ID number, and stored at −80° C. in a locked freezer until the time of future processing. Whole-blood RNA was extracted for microarray gene expression studies from the PAXgene tubes, as detailed below.

The participant discovery cohort, from which the biomarker data were derived, consisted of 66 participants (49 males, 17 females) with psychiatric disorders and multiple testing visits, who each had at least one diametric change in SI scores from no SI to high SI from one testing visit to another. There were 2 participants with 6 visits each, 3 participants with 5 visits each, 5 participants with 4 visits each, 34 participants with 3 visits each, and 22 participants with 2 visits each resulting in a total of 193 blood samples for subsequent gene expression microarray studies (FIG. 1B and Table 2).

The postmortem validation cohort, in which the top biomarker findings were validated for behavior, consisted of 38 male and 7 female violent suicide completers obtained through the Marion County coroner's office (Table 2). A last observed alive postmortem interval of 24 h or less was required, and the cases selected had completed suicide by means other than overdose, which could affect gene expression. Thirty-one participants completed suicide by gunshot to head or chest, 12 by asphyxiation, 1 by slit wrist, and 1 by electrocution. Next of kin signed informed consent at the coroner's office for donation of blood for research.

The independent test cohort for predicting suicidal ideation (Table 2) consisted of 184 male and 42 female participants with psychiatric disorders, demographically matched with the discovery cohort, with one or multiple testing visits in the lab, with either no SI, intermediate SI, or high SI, resulting in a total of 226 blood samples in which whole-genome blood gene expression data were obtained (FIG. 1A and Table 2).

The test cohort for predicting future hospitalizations (FIG. 1A and Table 2) is a subset (170 males, 24 females) of the independent test cohort for which a longitudinal follow-up with electronic medical records was available. The participants' subsequent number of psychiatric hospitalizations, with or without suicidality (ideation or attempt), was tabulated from electronic medical records. Participants were evaluated for the presence of future hospitalizations for suicidality, and for the frequency of such hospitalizations. A hospitalization was deemed to be without suicidality if suicidality was not listed as a reason for admission, and no SI was described in the admission and discharge medical notes. Conversely, a hospitalization was deemed to be due to suicidality if suicidal acts or intent were listed as a reason for admission, and/or SI was described in the admission and discharge medical notes.

TABLE 2

Demographics

| Universal | Subjects | Gender | Diagnosis | Ethnicity | Age Mean (SD) |
|---|---|---|---|---|---|
| Discovery | | | | | |
| Discovery Cohort (Longitudinal Within-Subject Changes in Suicidal Ideation) | 66 | Male = 49 Female = 17 | BP = 25 MDD = 17 SZA = 9 SZ = 4 PTSD = 8 MOOD = 2 PSYCH = 1 | EA = 51 AA = 14 Asian = 1 | 47.94 (9.47) |
| Validation | | | | | |
| Independent Validation Cohort for Gene Expression (Suicide Completers) | 45 | Male = 38 Female = 7 | NP = 19 MDD = 19 BP = 2 SZ = 1 AX = 1 Alcoholism = 1 ADHD = 1 PTSD = 1 | EA = 37 AA = 7 Hispanic = 1 | 40.69 (16.93) |
| Testing All | | | | | |
| Independent Testing Cohort For Predicting State (Suicidal Ideation at Time of Assessment) | 226 | Male = 184 Female = 42 | BP = 68 MDD = 32 SZA = 53 SZ = 45 PTSD = 19 MOOD = 5 PSYCH = 4 | EA = 148 AA = 73 Asian = 1 Hispanic = 3 Mixed = 1 | All 50.26 (9.47) No SI 51.1 Intermediate SI 49 High SI 44.3 |
| Independent Testing Cohort For Predicting Trait (Hospitalizations for Suicidality in the Year Following Assessment) | 194 | Male = 170 Female = 24 | BP = 72 MDD = 44 SZA = 50 SZ = 46 PTSD = 24 MOOD = 8 PSYCH = 3 | EA = 167 AA = 76 Hispanic = 3 Mixed = 1 | All = 50.04 (9.11) No Hosp for SI = 50.52 Hosp for SI = 46.24 |
| Subtypes | | | | | |
| High Anxiety Subtype | 46 | Male = 40 Female = 6 | BP = 13 MDD = 10 SZA = 9 SZ = 11 PTSD = 2 MOOD = 1 | EA = 27 AA = 19 | All 50.96 (7.63) No SI 52.1 (n = 44) Intermediate SI 52.5 (n = 4) High SI 39.4 (n = 5) |
| Low Mood Subtype | 76 | Male = 57 Female = 19 | BP = 21 MDD = 17 SZA = 15 SZ = 15 PTSD = 6 MOOD = 1 PSYCH = 1 | EA = 53 AA = 20 Hispanic = 2 Asian = 1 | All 51.53 (10.04) No SI 51.44 (n = 58) Intermediate SI 51.81 (n = 14) High SI 51.9 (n = 8) |
| Combined Subtype | 86 | Male = 61 Female = 25 | BP = 30 MDD = 11 SZA = 21 SZ = 11 PTSD = 11 MOOD = 2 | EA = 63 AA = 21 Hispanic = 1 Mixed = 1 | All 47.95 (9.36) No SI 50.79(n = 56) Intermediate SI 45.43 (n = 18) High SI 43.06 (n = 25) |

TABLE 2-continued

| Demographics | | | | | |
|---|---|---|---|---|---|
| Non-Affective (Psychotic) Subtype | 141 | Male = 121<br>Female = 20 | BP = 40<br>MDD = 17<br>SZA = 35<br>SZ = 32<br>PTSD = 10<br>MOOD = 4<br>PSYCH = 3 | EA = 86<br>AA = 52<br>Hispanic = 2<br>Mixed = 1 | All<br>50.71<br>(9.49)<br>No SI<br>50.89 (n = 132)<br>Intermediate<br>SI 51.67 (n = 6)<br>High SI<br>42.33 (n = 6) |

| Male Bipolar | Subjects | Gender | Diagnosis | Ethnicity | Age Mean (SD) |
|---|---|---|---|---|---|
| Discovery | | | | | |
| Male Bipolar Discovery Cohort (Within-Subject Changes in Suicidal Ideation) | 20 | Male = 20 | BP = 20 | EA = 20 | 48.12 (9.10) |
| Validation | | | | | |
| Male Independent Validation Cohort for Gene Expression (Suicide Completers) | 38 | Male = 38 | NP = 18<br>MDD = 16<br>BP = 1<br>SZ = 1<br>AX = 1<br>Alcoholism = 1 | EA = 31<br>AA = 6<br>Hispanic = 1 | 40.82 (17.31) |
| Testing | | | | | |
| Male Bipolar Independent Testing Cohort For Predicting State (Suicidal Ideation at Time of Assessment | 49 | Male = 49 | BP = 49 | EA = 43<br>AA = 5<br>Hispanic = 1 | All<br>49.16<br>(10.01)<br>No SI<br>50.19<br>Intermediate<br>SI 48.73<br>High SI<br>40.42 |
| Male Bipolar Independent Testing Cohort For Predicting Trait (Hospitalizations for Suicidality in the Year Following Assessment) | 44 | Male = 44 | BP = 44 | EA = 39<br>AA = 4<br>Hispanic = 1 | All = 48.88 (10.23)<br>No Hosp for SI = 48.76<br>Hosp for SI = 52.25 |

Medications. The participants in the discovery cohort were all diagnosed with various psychiatric disorders (Table 2). Their psychiatric medications were listed in their electronic medical records, and documented at the time of each testing visit. The participants were on a variety of different psychiatric medications: mood stabilizers, antidepressants, antipsychotics, benzodiazepines and others (data not shown). Medications can have a strong influence on gene expression. However, the discovery of differentially expressed genes was based on within-participant analyses, which factor out not only genetic background effects but also minimizes medication effects, as the participants rarely had major medication changes between visits. Moreover, there was no consistent pattern in any particular type of medication, or between any change in medications and SI, in the rare instances where there were changes in medications between visits.

Blood Gene Expression Experiments

RNA extraction. Whole blood (2.5-5 ml) was collected into each PaxGene tube by routine venipuncture. PaxGene tubes contain proprietary reagents for the stabilization of RNA. RNA was extracted and processed as described in Le-Niculescu et al., Mol Psychiatry 2013; 18(12): 1249-1264.

Microarrays. Microarray work was carried out using methodology described in Niculescu et al., Mol Psychiatry 2015; 20(11): 1266-1285.

Biomarkers

Discovery Cohort

Figure 1C:
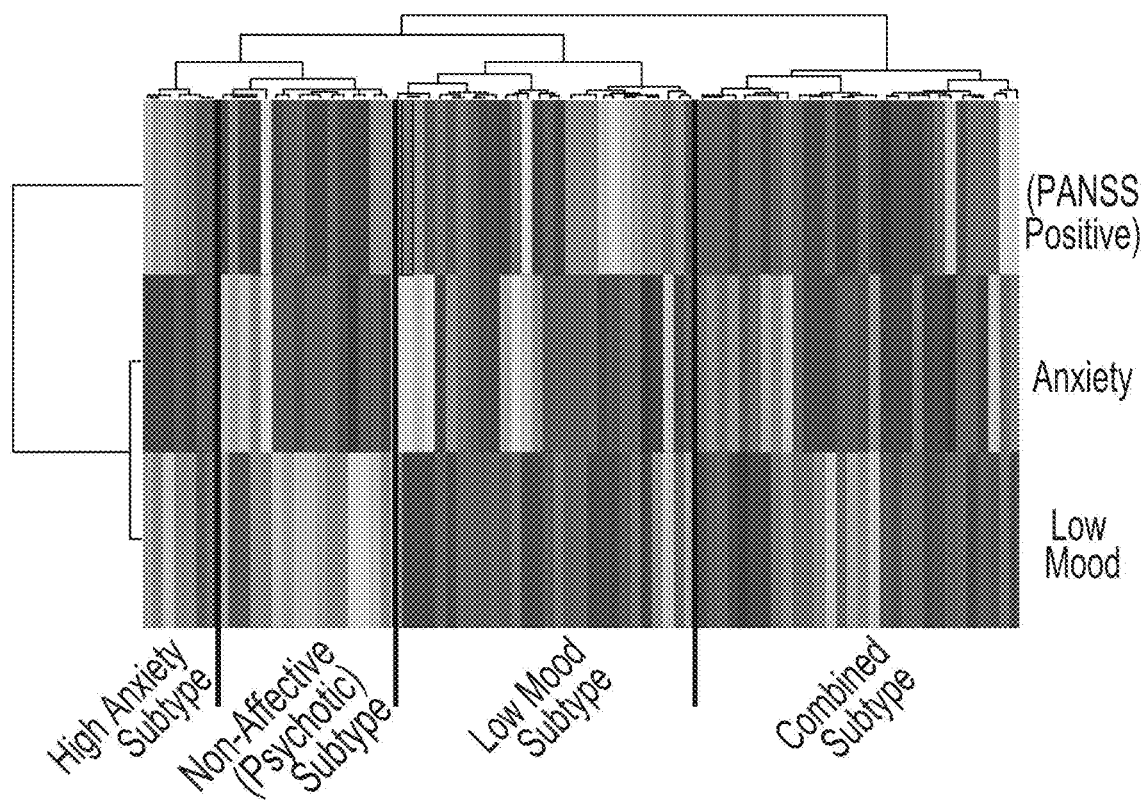
Figure 1D:
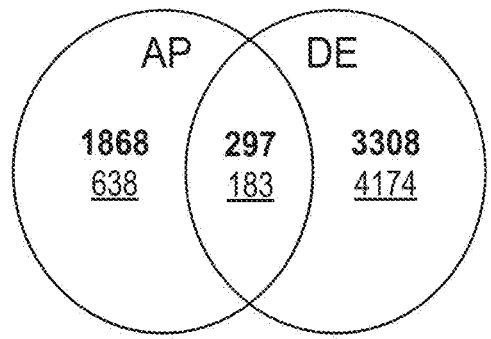
Figure 1E:
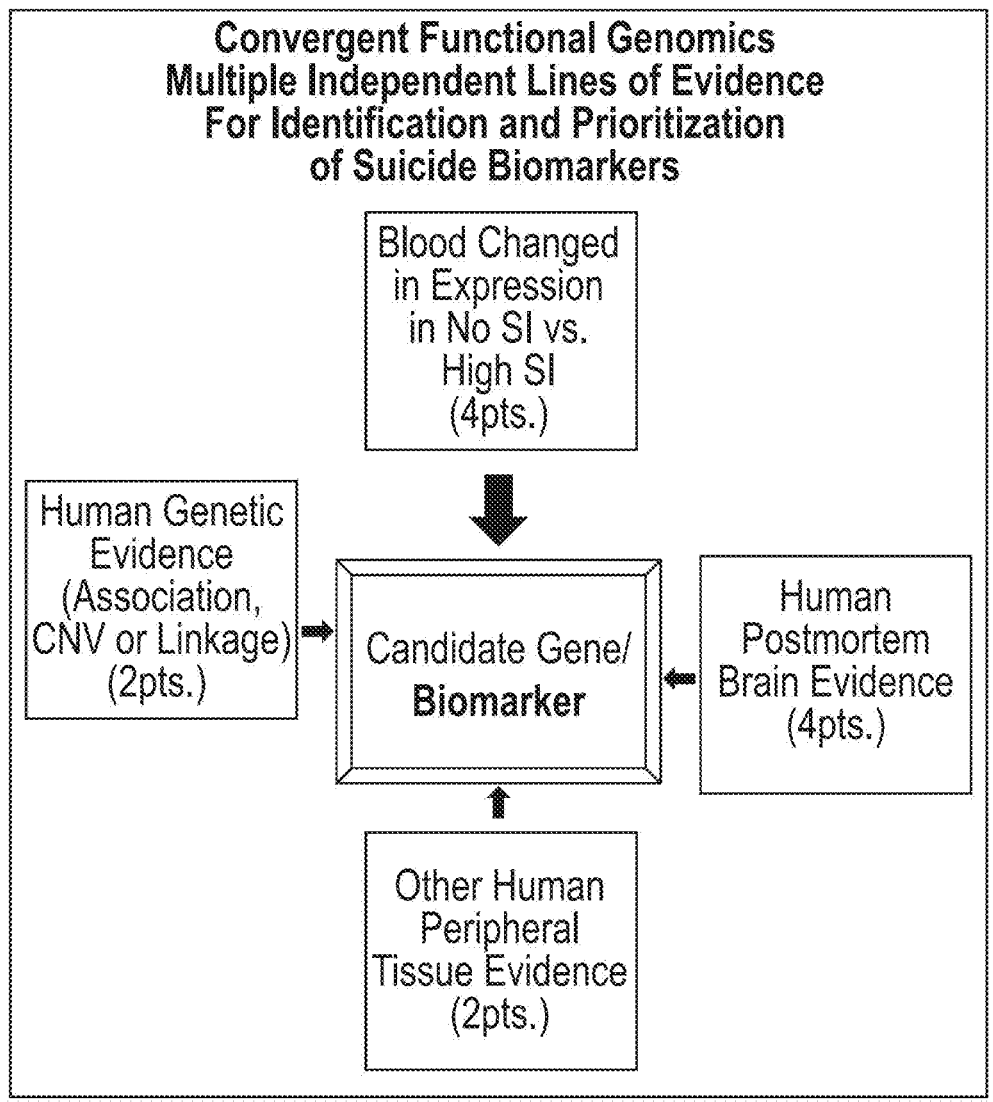
Figure 1F:
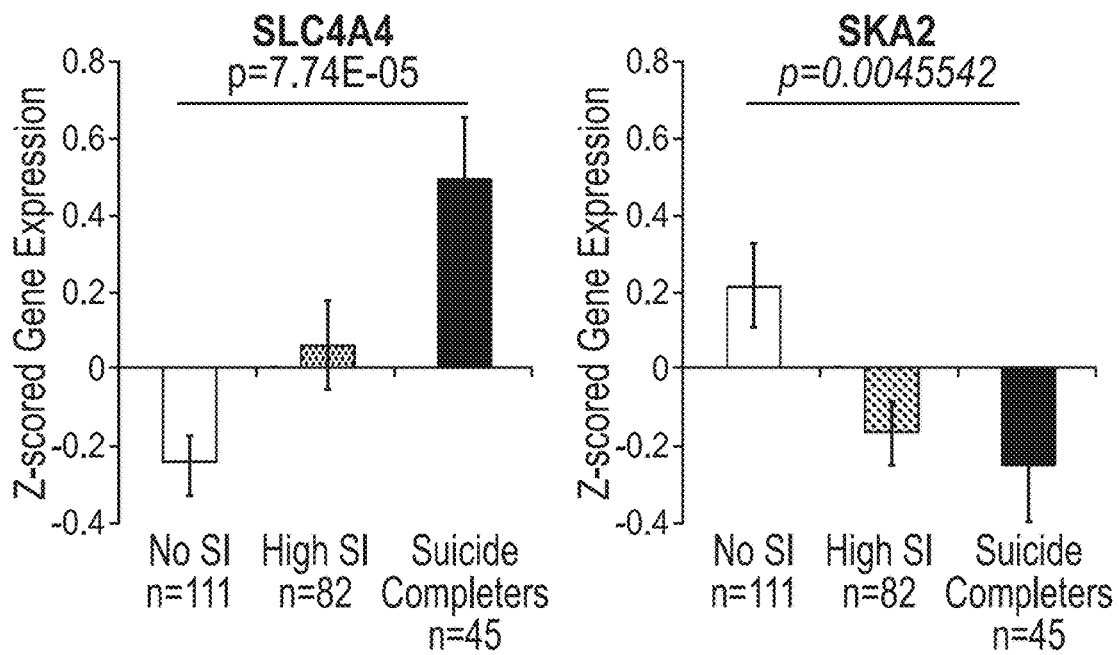
Figure 1G:
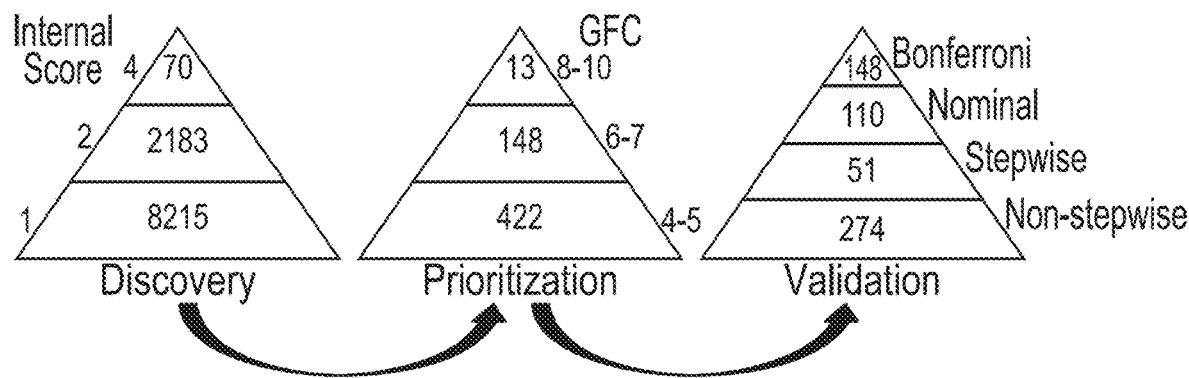
Figure 2:
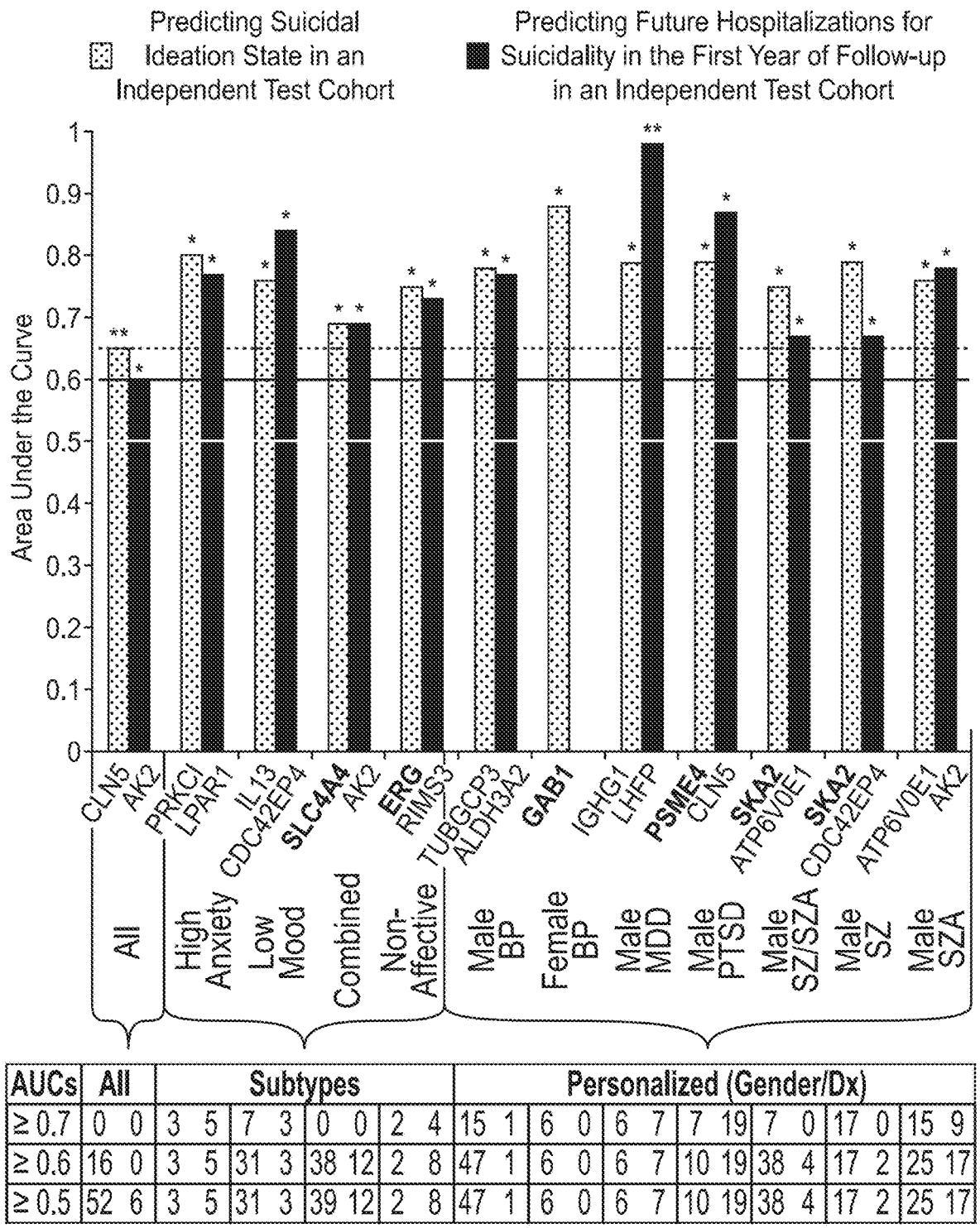
FIG. 2 depicts the best universal individual biomarkers for predicting suicidality out of the top dozen and Bonferroni validated biomarkers.

The participant's suicidality score from the item in the Hamilton Rating Scale for Depression (HAMD SI) assessed at the time of blood collection (FIG. 1G) was used. The gene expression differences were analyzed between the no SI (a score of 0) and the high SI (a score of 2 and above) visits, using a powerful within-participant design, then an across-participants summation (FIG. 1F).

The data was analyzed in two ways: an Absent-Present (AP) approach, and a differential expression (DE) approach. The AP approach may capture turning on and off of genes, and the DE approach may capture gradual changes in expression.

For the AP approach, Affymetrix Microarray Suite Version 5.0 (MASS) was used to generate Absent (A), Marginal (M), or Present (P) calls for each probeset on the chip (Affymetrix U133 Plus 2.0 GeneChips) for all participants in the discovery cohort (Affymetrix Inc., Santa Clara, Calif.). For the DE approach, all Affymetrix microarray data was imported as .cel files into Partek Genomic Suites 6.6 software package (Partek Incorporated, St Louis, Mich., USA). Using only the perfect match values, a robust multi-array analysis (RMA) was conducted, background corrected with quantile normalization and a median polish probeset summarization, to obtain the normalized expression levels of all probesets for each chip. RMA was performed independently for each gender and diagnosis subgroup used in the Example, to avoid potential artefacts due to different ranges of gene expression in different gender and diagnoses. Then the participants' normalized data was extracted from these gender and diagnosis RMAs and assembled for the different cohorts used in the Example.

A/P analysis. For the longitudinal within-participant AP analysis, comparisons were made within-participant between sequential visits to identify changes in gene expression from Absent to Present that track changes in phene expression (suicidal ideation) from No SI to High SI, as described in Niculescu et al., Mol Psychiatry 2015; 20(11): 1266-1285 and Levey et al., Mol Psychiatry 2016; 21(6): 768-785. For a comparison between two sequential visits, if there was a change from A to P tracking a change from No SI to High SI, or a change from P to A tracking a change from High SI to No SI, that was given a score of +1 (increased biomarker in High SI). If the change was in opposite direction in the gene versus the phene (which is SI), that was given a score of −1 (decreased biomarker in High SI). If there was no change in gene expression between visits despite a change of phene expression (SI levels), or a change in gene expression between visits despite no change in phene expression (SI levels), that was given a score of 0 (not tracking as a biomarker). If there was no change in gene expression and no change in suicidal ideation between visits, that was given a score of +1 if there was concordance (P-P with High SI-High SI, or A-A with No SI-No SI), or a score of −1 if there was the opposite (A-A with High SI-High SI, or P-P with No SI-No SI). If the changes were to M (moderate) instead of P, the values used were 0.5 or −0.5. These values were then summed up across the comparisons in each participant, resulting in an overall score for each gene/probeset in each participant. A perfection bonus was also used. If the gene expression perfectly tracked the suicidal ideation in a participant that had at least two comparisons (3 visits), that probeset was rewarded by a doubling of its overall score. Additionally, a non-tracking correction was used. If there was no change in gene expression in any of the comparisons for a particular participant, that overall score for that probeset in that participant was zero. An R script was developed to conduct the calculations, and the analysis was double-checked manually using formulas/macros in Excel.

DE analysis. For the longitudinal within-participant DE analysis, fold changes (FC) in gene expression were calculated between sequential visits within each participant, as described in Niculescu et al., Mol Psychiatry 2015; 20(11): 1266-1285 and Levey et al., Mol Psychiatry 2016; 21(6): 768-785. Scoring methodology was similar to that used above for AP. Probesets that had a FC≥1.2 were scored +1 (increased in High SI) or −1 (decreased in High SI). FC≥1.1 were scored +0.5 or −0.5. FC lower than 1.1 were considered no change. The only difference between the DE and the AP analyses was when scoring comparisons where there was no phene expression (SI) change between visits and no change in gene expression between visits (FC lower than 1.1). In that case, the comparison received the same score as the nearest preceding comparison where there was a change in SI from visit to visit. If no preceding comparison with a change in SI was available, then it was given the same score as the nearest subsequent comparison where there was a change in SI. A perfection bonus and a non-tracking correction were also used for the DE analysis. If the gene expression perfectly tracked the suicidal ideation in a participant that had at least two comparisons (3 visits), that probeset was rewarded by a doubling of its score. If there was no change in gene expression in any of the comparisons for a particular participant, that overall score for that probeset in that participant was zero. An R script was developed to conduct the calculations, and the analysis was double-checked manually using formulas/macros in Excel.

Internal score. Once scores within each participant were calculated, an algebraic sum across all participants was obtained, for each probeset. Probesets were then given internal points based upon these algebraic sum scores. Probesets with scores above the 33.3% of the maximum score (for increased probesets, respectively for decreased probesets) received 1 point, those above 50% received 2 points, and those above 80% received 4 points. For AP analyses, 35 probesets received 4 points, 754 probesets received 2 points, and 2197 probesets received 1 point, for a total of 2986 probesets. For DE analyses, 35 probesets received 4 points, 1477 probesets received 2 points, and 6450 probesets received 1 point, for a total of 9829 probesets. The overlap between the two discovery methods for probesets with an internal score of 1 is shown in FIG. 1D. Different probesets may be found by the two methods due to differences in scope (DE is also capturing genes that are present in both visits of a comparison, i.e. PP, but are changed in expression), thresholds (what makes the 33.3% change cutoff across participants varies between methods), and technical detection levels (what is considered in the noise range varies between the methods).

Gene Symbol for the probesets were identified using NetAffyx (Affymetrix) for Affymetrix HG-U133 Plus 2.0 GeneChips, followed by GeneCards to confirm the primary gene symbol. In addition, for those probesets that were not assigned a gene symbol by NetAffyx, GeneAnnot (https://genecards.weizmann.ac.il/geneannot/index.shtml) was used to obtain a gene symbol for these uncharacterized probesets, followed by GeneCard. Genes were then scored using manually curated CFG databases as described below (FIG. 1E).

Prioritization Using Convergent Functional Genomics (CFG)

Databases. Manually curated databases were established of the human gene expression/protein expression studies (postmortem brain, peripheral tissue/fluids: CSF, blood and cell cultures), human genetic studies (association, copy number variations and linkage), and animal model gene expression and genetic studies, published to date on psychiatric disorders. Only the findings deemed significant in the primary publication, using the particular experimental design and thresholds, are included in the databases. The databases include only primary literature data and do not include review papers or other secondary data integration analyses to avoid redundancy and circularity. These large and constantly updated databases have been used in the CFG cross validation and prioritization platform (FIG. 1E). For this Example, data from 454 papers on suicide were present in the databases at the time of the CFG analyses (genetic studies-170, brain studies-197, peripheral fluids-87).

Human postmortem brain gene expression/protein expression evidence. Converging evidence was scored for a gene if there were published reports of human postmortem data showing changes in expression of that gene or changes in protein levels in brains from participants who died from suicide.

Human blood, CSF, and other peripheral tissue gene expression/protein expression evidence. Converging evidence was scored for a gene if there were published reports of human blood, lymphoblastoid cell lines, cerebrospinal fluid, or other peripheral tissue data showing changes in expression of that gene or changes in protein levels in participants who had a history of suicidality or who died from suicide.

Human genetic evidence (association, linkage). To designate convergence for a particular gene, the gene had to have independent published evidence of association or linkage for suicide. For linkage, the physical positions (bp) of each gene were obtained through GeneCards (http://www.genecards.org), and the sex averaged cM location of the start of the gene was then obtained through http://compgen.rutgers.edu/map_interpolator.shtml. For linkage convergence, the start of the gene had to map within 5 cM of the location of a marker linked to the disorder.

CFG scoring. For CFG analysis (FIG. 1E), the external cross-validating lines of evidence were weighted such that findings in human postmortem brain tissue, the target organ, were prioritized over peripheral tissue/fluid findings and genetic findings, by giving them twice as many points. Human brain expression evidence was given 4 points, whereas human peripheral evidence was given 2 points, and human genetic evidence was given a maximum of 2 points for association, and 1 point for linkage. Each line of evidence was capped in such a way that any positive findings within that line of evidence resulted in maximum points, regardless of how many different studies support that single line of evidence, to avoid potential popularity biases. In addition to the external CFG score, genes were prioritized based upon the initial gene expression analyses used to identify them, giving them an internal score. Probesets identified by gene expression analyses could receive a maximum of 4 points. Thus, the maximum possible total CFG score for each gene was 12 points (4 points for the internal score and 8 points for the external CFG score) (Tables 3A-3F). The scoring system was decided upon before the analyses were carried out. Twice as much weight was given to the external score as compared to the internal score in order to increase generalizability and avoid fit to cohort of the prioritized genes. This scoring system provides a good separation of genes based on gene expression evidence and on independent cross-validating evidence in the field (FIG. 1E). In the future, with multiple large datasets, machine learning approaches could be used and validated to assign weights to CFG.

TABLE 3

| Affymetrix Probe Set ID | Gene Symbol | Direction of Change in Suicidality | Analysis | Top Dozen Biomarker from: | Top Predictor Biomarker for: |
|---|---|---|---|---|---|
| A: Universal Biomarkers for Suicidality - Top Dozen and Top Predictor Biomarkers. D—Decreased, I—Increased. AP—Absent/Present, DE—Differential Expression | | | | | |
| 224240_s_at | CCL28 | D | AP | Discovery | |
| 213541_s_at | ERG | D | DE | Discovery | |
| 242572_at | GAB1 | I | AP | Discovery | |
| 214540_at | HIST1H2BO | I | DE | Discovery | |
| 210354_at | IFNG | D | AP | Prioritization | |
| 225686_at | SKA2 | D | DE | Prioritization | |
| 210739_x_at | SLC4A4 | I | AP | Prioritization | Suicidal ideation state - cross-sectional |
| 218832_x_at | ARRB1 | D | AP | Validation | |
| 57082_at | LDLRAP1 | D | DE | Validation | |
| 212226_s_at | PPAP2B | I | AP | Validation | |
| 2215078_at | SOD2 | I | | | Future hospitalizations for suicidality - all future years - cross-sectional |
| 203680_at | PRKAR2B | D | | | Future hospitalizations for suicidality - all future years - longitudinal |
| 209534_x_at | AKAP13 | I | | | Future hospitalizations for suicidality - all future years - longitudinal |
| 237180_at | PSME4 | I | DE | Validation | Future hospitalizations for suicidality - in the first year - cross-sectional |
| 209000_s_at | SEPT8 | I | | | Future hospitalizations for suicidality - in the first year - longitudinal |
| 218062_x_at | CDC42EP4 | D | | | Future hospitalizations for suicidality - in the first year - cross-sectional |
| 214252_s_at | CLN5 | D | | | Suicidal ideation state - cross-sectional Future hospitalizations for suicidality - all future years - cross-sectional |
| 232526_at | ITPKB | I | | | Suicidal ideation state - longitudinal |
| 209677_at | PRKCI | D | | | Suicidal ideation state - longitudinal |
| 244130_at | HTR2A | I | DE | Prioritization | Suicidal ideation state - longitudinal |
| B. Biomarkers for Suicidality in Males - Top Dozen and Top Predictor Biomarkers. D—Decreased, I—Increased. AP—Absent/Present, DE—Differential Expression | | | | | |
| 227351_at | C16orf52 | D | AP | Discovery | |
| 203032_s_at | FH | D | DE | Discovery | |
| 214540_at | HIST1H2BO | I | DE | Discovery | |
| 242538_at | TFDP1 | I | AP | Discovery | |
| 225686_at | SKA2 | D | AP, DE | Prioritization | |
| 210739_x_at | SLC4A4 | I | AP | Prioritization | |
| 241811_x_at | SLC6A4 | I | DE | Prioritization | |
| 57082_at | LDLRAP1 | D | DE | Validation | |
| 210592_s_at | SAT1 | I | DE | Validation | |
| 209386_at | TM4SF1 | I | AP | Validation | |
| 239991_at | ZMYND8 | D | AP | Validation | |

TABLE 3-continued

| | | | | | |
|---|---|---|---|---|---|
| 218174_s_at | TMEM254 | D | | | Suicidal ideation state - longitudinal |
| 200009_at | GDI2 | D | | | Suicidal ideation state - cross-sectional |
| 207194_s_at | ICAM4 | D | | | Future hospitalizations for suicidality - in first year - cross-sectional |
| 203336_s_at | ITGB1BP1 | D | | | Future hospitalizations for suicidality - all future years - longitudinal |
| 201460_at | MAPKAPK2 | I | | | Suicidal ideation state - cross-sectional |
| | | | | | Future hospitalizations for suicidality - all future years - cross-sectional |
| 237180_at | PSME4 | I | | | Future hospitalizations for suicidality - in first year - cross-sectional |
| 224758_at | C7orf73 | D | | | Future hospitalizations for suicidality - in first year - longitudinal |
| 214252_s_at | CLN5 | D | | | Future hospitalizations for suicidality - all future years - cross-sectional |
| 244677_at | PER1 | I | | | Future hospitalizations for suicidality - all future years - longitudinal |

C. Biomarkers for Suicidality in Females - Top Dozen and Top Predictor Biomarkers.
D—Decreased, I—Increased. AP—Absent/Present, DE—Differential Expression

| | | | | | |
|---|---|---|---|---|---|
| 1566183_at | Hs.637764 | I | AP | Discovery | Suicidal ideation state |
| 243713_at | Hs.661328 | I | DE | Discovery | |
| 217369_at | IGHG1 | D | AP | Discovery | |
| 1556842_at | LOC286087 | D | DE | Discovery | |
| 244019_at | T89845 | I | AP | Discovery | |
| 219025_at | CD248 | I | AP | Prioritization | |
| 236804_at | COMT | I | AP | Prioritization | |
| 244130_at | HTR2A | I | DE | Prioritization | |
| 210354_at | IFNG | D | AP | Prioritization | |
| 210354_at | IFNG | D | DE | Prioritization | |
| 240226_at | AA828246 | I | DE | Validation | |
| 1568903_at | Hs.736359 | D | AP | Validation | |
| 201185_at | HTRA1 | I | AP | Validation | |
| 220005_at | P2RY13 | D | DE | Validation | |
| 210486_at | ANKMY1 | D | | | Suicidal ideation state - cross-sectional |
| 1569022_a_at | PIK3C2A | I | | | Future hospitalizations for suicidality - in first year - longitudinal |
| | | | | | Future hospitalizations for suicidality - all future years - longitudinal |
| 215078_at | SOD2 | I | | | Future hospitalizations for suicidality - all future years - longitudinal |

| Affymetrix Probe Set ID | Gene Symbol | Direction of Change in Suicidality | Analysis | Top Dozen Biomarker from: | Top Bonferroni Predictor Biomarker for: |
|---|---|---|---|---|---|

D. Biomarkers for Suicidality in Bipolar Disorder - Top Dozen and Top Bonferroni Predictor Biomarkers.
D—Decreased, I—Increased. A—Absent/Present, DE—Differential Expression

| | | | | | |
|---|---|---|---|---|---|
| 236879_at | BF114768 | I | DE | Discovery | |
| 1562416_at | FLNB | I | AP | Discovery | |
| 231262_at | Hs.147375 | D | DE | Discovery | |
| 1557984_s_at | RPAP3 | D | AP | Discovery | |
| 239683_at | CLYBL | D | AP | Prioritization | |
| 244130_at | HTR2A | I | DE | Prioritization | |
| 207519_at | SLC6A4 | D | DE | Prioritization | |
| 1563357_at | TNF | I | AP | Prioritization | |
| 218081_at | C20orf27 | D | DE | Validation | |
| 203394_s_at | HES1 | I | AP | Validation | |
| 214144_at | POLR2D | D | AP | Validation | |
| 213988_s_at | SAT1 | I | DE | Validation | |
| 232526_at | ITPKB | I | | | Suicidal ideation state - cross-sectional |
| 224758_at | C7orf73 | D | | | Suicidal ideation state - cross-sectional |
| 208889_s_at | NCOR2 | D | | | Suicidal ideation state - longitudinal |
| 214433_s_at | SELENBP1 | D | | | Future hospitalizations for suicidality - in first year - cross-sectional |
| | | | | | Future hospitalizations for suicidality - all future years - cross-sectional |
| 219862_s_at | NARF | I | | | Future hospitalizations for suicidality - in first year - cross-sectional |
| 201466_s_at | JUN | I | | | Future hospitalizations for suicidality - in first year - longitudinal |
| 237180_at | PSME4 | I | | | Future hospitalizations for suicidality - all future years - cross-sectional |

| Affymetrix Probe Set ID | Gene Symbol | Direction of Change in Suicidality | Analysis | Top Dozen Biomarker from: | Top Predictor Biomarker for: |
|---|---|---|---|---|---|

E. Biomarkers for Suicidality in Depression - Top Dozen and Top Predictor Biomarkers.
D—Decreased, I—Increased. AP—Absent/Present, DE—Differential Expression

| | | | | | |
|---|---|---|---|---|---|
| 35201_at | HNRNPL | D | DE | Discovery | |
| 1556828_at | MNAT1 | I | DE | Discovery | |
| 218509_at | PLPPR2 | I | AP, DE | Discovery | |
| 222351_at | PPP2R1B | D | AP | Discovery | |

TABLE 3-continued

| Affymetrix Probe Set ID | Gene Symbol | Direction of Change in Suicidality | Analysis | Top Dozen Biomarker from: | Top Bonferroni Predictor Biomarker for: |
|---|---|---|---|---|---|
| 219243_at | GIMAP4 | D | DE | Discovery and Validation | |
| 1554808_at | ACP1 | D | AP | Prioritization | |
| 239367_at | BDNF | I | DE | Prioritization | |
| 209560_s_at | DLK1 | I | AP, DE | Prioritization | |
| 206462_s_at | NTRK3 | I | AP, DE | Prioritization | |
| 225686_at | SKA2 | D | DE | Prioritization | |
| 236527_at | ATP6V0E1 | D | AP | Validation | |
| 1554264_at | CKAP2 | I | AP | Validation | Future hospitalizations for suicidality |
| 201465_s_at | JUN | I | DE | Validation | |
| 241453_at | PTK2 | I | | | Suicidal ideation state - cross-sectional<br>Future hospitalizations for suicidality - in first year - cross-sectional |
| 214085_x_at | GLIPR1 | D | | | Suicidal ideation state - cross-sectional |
| 232633_at | XRCC5 | D | | | Suicidal ideation state - longitudinal |
| 1554610_at | ANKMY1 | D | | | Future hospitalizations for suicidality - in first year - cross-sectional<br>Future hospitalizations for suicidality - all future years - cross-sectional |
| 204850_s_at | DCX | D | | | Future hospitalizations for suicidality - in first year - longitudinal |

F. Biomarkers for Suicidality in Males with Bipolar Disorder - Top Dozen and Top Predictor Biomarkers.
D—Decreased, I—Increased. AP—Absent/Present, DE—Differential Expression

| Affymetrix Probe Set ID | Gene Symbol | Direction of Change in Suicidality | Analysis | Top Dozen Biomarker from: | Top Bonferroni Predictor Biomarker for: |
|---|---|---|---|---|---|
| 239711_at | ADAL | D | AP | Discovery | Future hospitalizations for suicidality |
| 237259_at | BE674182 | I | DE | Discovery | |
| 208299_at | CACNA1I | I | AP | Discovery | |
| 207194_s_at | ICAM4 | D | DE | Discovery | |
| 239683_at | CLYBL | D | AP | Prioritization | |
| 214619_at | CRHR1 | D | DE | Prioritization | |
| 244130_at | HTR2A | I | DE | Prioritization | |
| 213769_at | KSR1 | I | AP | Prioritization | |
| 218081_at | C20orf27 | D | DE | Validation | |
| 214144_at | POLR2D | D | AP | Validation | |
| 213988_s_at | SAT1 | I | DE | Validation | |
| 215918_s_at | SPTBN1 | I | AP | Validation | Suicidal ideation state - cross-sectional |
| 224758_at | C7orf73 | D | | | Suicidal ideation state - cross-sectional |
| 234332_at | NUB1 | I | | | Suicidal ideation state - longitudinal |
| 205481_at | ADORA1 | D | | | Suicidal ideation state - longitudinal |
| 222176_at | PTEN | I | | | Future hospitalizations for suicidality - in first year - cross-sectional |
| 214433_s_at | SELENBP1 | D | | | Future hospitalizations for suicidality - in first year - cross-sectional |
| 237180_at | PSME4 | I | | | Future hospitalizations for suicidality - all future years - cross-sectional |
| 210377_at | ACSM3 | D | | | Future hospitalizations for suicidality - all future years - cross-sectional |

| Affymetrix Probe Set ID | Gene Symbol | Direction of Change in Suicidality | Analysis | Top Dozen Biomarker from: | Top Bonferroni Predictor Biomarker for: |
|---|---|---|---|---|---|

G. Biomarkers for Suicidality in Males with Depression - Top Dozen and Top Predictor Biomarkers.
D—Decreased, I—Increased. AP—Absent/Present, DE—Differential Expression

| Affymetrix Probe Set ID | Gene Symbol | Direction of Change in Suicidality | Analysis | Top Dozen Biomarker from: | Top Bonferroni Predictor Biomarker for: |
|---|---|---|---|---|---|
| 234681_s_at | CHD6 | I | AP | Discovery | |
| 223974_at | DLGAP1-AS2 | I | DE | Discovery | |
| 35201_at | HNRNPL | D | DE | Discovery | |
| 237951_at | R02328 | I | DE | Discovery | |
| 215263_at | ZXDA | D | AP | Discovery | |
| 209560_s_at | DLK1 | I | AP | Prioritization | |
| 214170_x_at | FH | D | DE | Prioritization | |
| 236587_at | LRRC6 | I | DE | Prioritization | |
| 217033_x_at | NTRK3 | D | AP | Prioritization | |
| 236527_at | ATP6V0E1 | D | AP | Validation | |
| 213524_s_at | G0S2 | I | DE | Validation | |
| 226687_at | PRPF40A | D | DE | Validation | |
| 209841_s_at | LRRN3 | D | | | Suicidal ideation state - cross-sectional |
| 241453_at | PTK2 | I | | | Suicidal ideation state - cross-sectional |
| 210192_at | ATP8A1 | I | | | Suicidal ideation state - longitudinal<br>Future hospitalizations for suicidality - all future years - longitudinal |
| 228305_at | ZNF565 | D | | | Suicidal ideation state - longitudinal |
| 1554610_at | ANKMY1 | D | | | Future hospitalizations for suicidality - in first year - cross-sectional<br>Future hospitalizations for suicidality - all future years - cross-sectional |

TABLE 3-continued

| Affymetrix Probe Set ID | Gene Symbol | Direction of Change in Suicidality | Top Predictor Biomarker for: |
|---|---|---|---|
| 205898_at | CX3CR1 | D | Future hospitalizations for suicidality - in first year - longitudinal |
| 213524_s_at | G0S2 | I | Future hospitalizations for suicidality - all future years - cross-sectional |

H. Biomarkers for Suicidality in Males with Post-Traumatic Stress Disorder (PTSD) - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 237180_at | PSME4 | I | Suicidal ideation state - cross-sectional |
|  |  |  | Future hospitalizations for suicidality - all future years - cross-sectional |
| 209841_s_at | LRRN3 | D | Suicidal ideation state - cross-sectional |
| 209677_at | PRKCI | D | Suicidal ideation state - longitudinal |
| 229331_at | SPATA18 | I | Suicidal ideation state - longitudinal |
|  |  |  | Future hospitalizations for suicidality - in first year - longitudinal |
|  |  |  | Future hospitalizations for suicidality - all future years - longitudinal |
| 214252_s_at | CLN5 | D | Future hospitalizations for suicidality - in first year - cross-sectional |
| 212226_s_at | PPAP2B | I | Future hospitalizations for suicidality - in first year - cross-sectional |
| 202259_s_at | N4BP2L2 | D | Future hospitalizations for suicidality - all future years - cross-sectional |
| 238919_at | PCDH9 | D | Future hospitalizations for suicidality - all future years - longitudinal |

I. Biomarkers for Suicidality in Males with Schizophrenia/Schizoaffective Disorder - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 205996_s_at | AK2 | D | Suicidal ideation state - cross-sectional |
| 205858_at | NGFR | I | Suicidal ideation state - cross-sectional |
|  |  |  | Suicidal ideation state - longitudinal |
| 236527_at | ATP6V0E1 | D | Suicidal ideation state - longitudinal |
|  |  |  | Future hospitalizations for suicidality - in first year - cross-sectional |
| 218062_x_at | CDC42EP4 | D | Future hospitalizations for suicidality - in first year - longitudinal |
| 229331_at | SPATA18 | I | Future hospitalizations for suicidality - in first year - longitudinal |
| 1557966_x_at | MTERF4 | D | Future hospitalizations for suicidality - all future years - cross-sectional |
| 212226_s_at | PPAP2B | I | Future hospitalizations for suicidality - all future years - cross-sectional |
| 213321_at | BCKDHB | D | Future hospitalizations for suicidality - all future years - longitudinal |

J. Biomarkers for Suicidality in High Anxiety Subtype - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 209677_at | PRKCI | D | Suicidal ideation state - cross-sectional |
|  |  |  | Future hospitalizations for suicidality - all future years - longitudinal |
| 218656_s_at | LHFP | I | Suicidal ideation state - longitudinal |
| 204036_at | LPAR1 | D | Future hospitalizations for suicidality - in first year - cross-sectional |
| 214540_at | HIST1H2BO | I | Future hospitalizations for suicidality - in first year - cross-sectional |
|  |  |  | Future hospitalizations for suicidality - all future years - cross-sectional |
| 236879_at | BF114768 | I | Future hospitalizations for suicidality - all future years - longitudinal |
| 216765_at | MAP2K5 | D | Future hospitalizations for suicidality - all future years - cross-sectional |

K. Biomarkers for Suicidality in Low Mood Subtype - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 209534_x_at | AKAP13 | I | Suicidal ideation state - longitudinal |
| 231772_x_at | CENPH | D | Suicidal ideation state - longitudinal |
| 207844_at | IL13 | I | Suicidal ideation state - cross-sectional |
| 214252_s_at | CLN5 | D | Suicidal ideation state - cross-sectional |
| 230191_at | TTBK1 | D | Future hospitalizations for suicidality - in first year - longitudinal |
| 237180_at | PSME4 | I | Future hospitalizations for suicidality - in first year - longitudinal |
|  |  |  | Future hospitalizations for suicidality - all future years - cross-sectional |
| 231854_at | PIK3CA | D | Future hospitalizations for suicidality - in first year - cross-sectional |
| 214782_at | CTTN | I | Future hospitalizations for suicidality - in first year - cross-sectional |
| 211633_x_at | IGHG1 | D | Future hospitalizations for suicidality - all future years - longitudinal |

L. Biomarkers for Suicidality in the High Psychosis (Non-Affective) Subtype - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 231854_at | PIK3CA | D | Suicidal ideation state - cross-sectional |
| 204730_at | RIMS3 | D | Future hospitalizations for suicidality - in first year - cross-sectional |
| 215078_at | SOD2 | I | Future hospitalizations for suicidality - in first year - cross-sectional |
| 229856_s_at | PITHD1 | D | Future hospitalizations for suicidality - all future years - longitudinal |
| 215078_at | SOD2 | I | Future hospitalizations for suicidality - all future years - longitudinal |
|  |  |  | Future hospitalizations for suicidality - all future years - cross-sectional |
| 203336_s_at | ITGB1BP1 | D | Future hospitalizations for suicidality - all future years - cross-sectional |

M. Biomarkers for Suicidality in the Combined (Affective) Subtype - Top Predictor Biomarkers.
D—Decreased, I—Increased.

| Affymetrix Probe Set ID | Gene Symbol | Direction of Change in Suicidality | Top Predictor Biomarker for: |
|---|---|---|---|
| 209677_at | PRKCI | D | Suicidal ideation state - longitudinal |
|  |  |  | Future hospitalizations for suicidality - all future years - longitudinal |
| 566861_at | GATM1 | I | Suicidal ideation state - longitudinal |
| 214782_at | CTTN | I | Future hospitalizations for suicidality - in first year - longitudinal |
| 228305_at | ZNF565 | D | Future hospitalizations for suicidality - in first year - longitudinal |
| 201929_s_at | PKP4 | D | Future hospitalizations for suicidality - in first year - cross-sectional |
| 236879_at | BF114768 | I | Future hospitalizations for suicidality - all future years - longitudinal |

TABLE 3-continued

| 1557966_x_at | MTERF4 | D | Future hospitalizations for suicidality - all future years - cross-sectional |
| 232526_at | ITPKB | I | Future hospitalizations for suicidality - all future years - cross-sectional |

Validation Analyses

For the AP analyses, the Affymetrix microarray .chp data files from the participants in the coroner validation cohort of suicide completers were imported into the MASS Affymetrix Expression Console, alongside the data files from the No SI and High SI groups in the live discovery cohort. The AP data was transferred to an Excel sheet and transformed: A into 0, M into 0.5, and P into 1. All data was then Z-scored together by gender. If a probeset would have showed no variance and thus gave a non-determined (0/0) value in Z-scoring in a gender, the values were excluded from that probeset for that gender from the analysis. All probesets, however, did show variance in this Example.

For the DE analyses, Affymetrix microarray .cel files were imported from the participants in the validation cohort of suicide completers into Partek Genomic Suites. An RMA was run by gender, background corrected with quantile normalization, and a median polish probeset summarization of the chips from the validation cohort was conducted to obtain the normalized expression levels of all probesets for each chip. The No SI and High SI groups from the discovery cohort were RMA by gender and diagnosis, as described above for Discovery. Partek normalizes expression data into a log base of 2 for visualization purposes. Expression data was non-log transformed by taking 2 to the power of the transformed expression value, and the non-log transformed coroner validation cohort expression data was transferred to an Excel sheet, alongside data from the No SI and High SI groups from the discovery cohort. All data was then Z-scored together by gender.

Validation analyses of the candidate biomarker genes were conducted separately for AP and for DE. The top candidate genes (total CFG score of 4 or above), were stepwise changed in expression from the No SI group to the High SI group to the suicide completers group. A CFG score of 4 or above reflects an empirical cutoff of 33.3% of the maximum possible CFG score of 12, which permits the inclusion of potentially novel genes with maximal internal score of 4, but no external evidence score. The Excel sheets with the Z-scored by gender expression data from AP were imported, respectively from DE, into Partek, and statistical analyses were performed using a one-way ANOVA for the stepwise changed probesets, and stringent Bonferroni corrections for all the probesets tested in AP and DE (stepwise and non-stepwise) (FIG. 1F).

Discovery and Validation in Male Bipolars

For male bipolar disorders, the discovery and validation were conducted as described above except that only male bipolar subjects from the discovery cohort (n=20 subjects, 65 visits) were used for discovery, and male suicide completers (n=38) were used for validation.

Phenotypic Measures

SASS. The Simplified Affective State Scale (SASS) is an 11-item scale for measuring mood state (SMS) and anxiety state (SAS), previously developed and described in Niculescu et al., Mol Psychiatry 2015; 20(11): 1266-1285 and Niculescu et al., American journal of medical genetics Part B, Neuropsychiatric genetics: the official publication of the International Society of Psychiatric Genetics 2006; 141B (6): 653-662. The SASS has a set of 11 visual analog scales (7 for mood, 4 for anxiety) each item ranging from 0 to 100 for mood state, and the same for anxiety state. The averaged 7 items for mood give the Mood score, and the averaged 4 items for anxiety give the Anxiety score.

CFI-S. Convergent Functional Information for Suicidality (CFI-S) (FIG. 4A) is a 22-item scale and Android app for suicide risk, which integrates, in a simple binary fashion (Yes-1, No-0), similar to a polygenic risk score, information about known life events, mental health, physical health, stress, addictions, and cultural factors that can influence suicide risk. The scale was administered at participant testing visits (263), or scored based on retrospective electronic medical record information and Diagnostic Interview for Genetic Testing (DIGS) information (457). When information was not available for an item, it was not scored (NA). The average of the score of the items for which there was information gives us the CFI-S score.

Subtypes

In order to identify possible subtypes of suicidality, a two-way unsupervised hierarchical clustering of the high SI visits in the discovery cohort, based on measures of anxiety and mood (from the SASS), as well as psychosis (PANS S Positive) was used. The mood item was inverted for the purposes of this analysis so that higher values indicate low mood. This clustering was used to identify four distinct subtypes of suicidality/high suicidal ideation: a high anxiety subtype, a low mood subtype, a combined affective subtype, and a non-affective (psychotic) subtype (FIG. 1C).

The insight from the discovery cohort was used to divide the independent test cohort into the four subtypes, using anxiety and mood measures from SASS, which are on a scale of 0 to 100. The high anxiety subtype participant visits had anxiety above 50 and low mood below 50, the low mood subtype had low mood below 50 and anxiety below 50, the combined affective subtype had low mood above 50 and anxiety above 50, and the non-affective subtype had low mood below 50 and anxiety below 50.

Combining Biomarkers and Phenotypic Measures

The Universal Predictor for Suicidality (UP-Suicide) construct, the primary endpoint, was decided upon as part of the apriori study design. It combines the top biomarkers with the phenomic (clinical) measures (CFI-S score, Mood and Anxiety scores from SASS). It is calculated as the simple algebraic summation of the components included (averaged panel of biomarkers (BioM), CFI-S, Mood, Anxiety). All individual biomarkers and clinical measure scores are Z-scored by gender and diagnosis, to normalize for different ranges of values and be able to combine them into a composite predictor (UP-Suicide). Decreased biomarkers, and Mood, have a minus sign in front of them.

Diagnostics

The test cohort for predicting suicidal ideation (state), and the subset of it that is a test cohort for predicting future hospitalizations for suicidality (trait), were assembled out of data that was RMA normalized by gender and diagnosis. The cohort was completely independent, there was no subject overlap with the discovery cohort. Phenomic (clinical) and gene expression markers used for predictions were Z-scored by gender and diagnosis, to be able to combine different markers into panels and to avoid potential artefacts due to different ranges of expression in different gender and diagnoses. Markers were combined by simple summation of the increased risk markers minus the decreased risk markers. Predictions were performed using R-studio. For cross-sectional analyses, marker expression levels were used, z-scored by gender and diagnosis. For longitudinal analyses, four measures were combined: marker expression levels, slope (defined as ratio of levels at current testing visit vs. previous visit, divided by time between visits), maximum levels (at any of the current or past visits), and maximum slope (between any adjacent current or past visits). For decreased markers, the minimum, rather than the maximum, was used for level calculations. All four measures were Z-scored then combined in an additive fashion into a single measure. The longitudinal analysis was carried out in a sub-cohort of the testing cohort consisting of participants that had at least two test visits.

Predicting High Suicidal Ideation State. Receiver-operating characteristic (ROC) analyses between genomic and phenomic marker levels and suicidal ideation (SI) were performed by assigning participants with a HAMD-SI score of 2 and greater into the high SI category. The pROC function of the R studio was used. The Z-scored biomarker and phene scores were used, running them in this ROC generating program against the "diagnostic" groups in the independent test cohort (high SI vs. the rest of subjects). Additionally, ANOVA was performed between no SI (HAMD-SI 0), intermediate (HAMD-SI 1), and high SI participants (HAMD-SI 2 and above) and Pearson R (one-tail) was calculated between HAMD-SI scores and marker levels (Tables 4A & 4B, FIGS. 5A-5C & FIG. 6).

TABLE 4

Diagnostics. Biomarkers, Phenes, and Combined Predictions.
Red - top increased biomarker predictor; Blue - top decreased biomarker predictor. Underlined are individual biomarkers from the Top Dozen list, the others are from the Bonferroni list. For Universal, the panel of Top Dozen biomarkers is called BioM 12, and the panel of Bonferroni biomarkers is called BioM148, reflecting the number of markers in the panel. For Male Bipolar, the panel of Top Dozen biomarkers is called BioM 12, and the panel of Bonferroni biomarkers is called BioM54, reflecting the number of markers in the panel. Italic - a priori primary endpoint (UP-Suicide).

A. Suicidal Ideation State
Bold - p-value of AUC survives correction for multiple testing for predictions. ROC AUC is apriori primary predictive tool.

| Predictors | Cohort | Participants with high SI/Participants total | ROC AUC/ p-value | Suicidality Severity (HAMD SI Score) Correlation R/ p-value | T-test p-value |
|---|---|---|---|---|---|
| | | Universal Best Biomarkers | | | |
| SLC4A4 | All | 52/544 | 0.64/3.83E−04 | 0.13/1.54E−03 | 1.50E−03 |
| CLN5 | All | 52/544 | 0.65/1.86E−04 | −0.11/6.13E−03 | 3.90E−04 |
| BioM 148 Panel (Bonferroni List) | All | 52/544 | 0.61/6.18E−03 | 0.069/5.33E−02 | 1.77E−02 |
| BioM 12 Panel (Top Dozen List) | All | 52/544 | 0.61/3.66E−03 | 0.12/3.02E−03 | 3.08E−03 |
| BioM 2 Panel (SLC4A4 and CLN5) | All | 52/544 | 0.66/4.92E−05 | 0.14/7.82E−04 | 1.90E−04 |
| | | Phenes | | | |
| Mood | All | 52/544 | 0.77/5.93E−11 | −0.38/3.17E−20 | 1.95E−10 |
| Anxiety | All | 52/544 | 0.77/3.43E−11 | 0.31/8.60E−14 | 2.03E−12 |
| Mood and Anxiety (SASS) | All | 52/544 | 0.81/5.55E−14 | 0.40/3.66E−22 | 3.57E−14 |
| CFI-S | All | 52/523 | 0.86/9.98E−18 | 0.43/1.03E−24 | 5.46E−16 |
| Mood and Anxiety and CFI-S | All | 52/523 | 0.89/2.59E−20 | 0.49/1.60E−33 | 1.08E−18 |
| | | Phenes and Biomarkers | | | |
| Mood and Anxiety and CFI-S and BioM 148 | All | 52/523 | 0.89/1.36E−20 | 0.49/2.84E−33 | 2.88E−18 |
| *Mood and Anxiety and CFI-S and BioM 12(UP-Suicide)* | *All* | *52/523* | *0.90/3.87E−21* | *0.50/5.91−35* | *3.42E−19* |
| Mood and Anxiety and CFI-S and BioM2 | All | 52/523 | 0.89/4.56E−21 | 0.50/4.07E−34 | 2.83E−18 |
| | | Male Bipolar Best Biomarkers | | | |
| SPTBN1 | M-BP | 12/130 | 0.72/6.62E−03 | 0.21/8.54E−03 | 9.05E−03 |
| C7orf73 | M-BP | 12/130 | 0.75/2.38E−03 | −0.17/2.76E−02 | 1.08E−04 |
| BioM 54 Panel (Bonferroni List) | M-BP | 12/130 | 0.49/5.29E−01 | 0/4.90E−01 | 7.12E−01 |
| BioM 12 Panel (Top Dozen List) | M-BP | 12/130 | 0.57/2.08E−01 | 0.08/1.78E−01 | 8.79E−02 |
| BioM 2 (SPTBN1 and C7orf73) | M-BP | 12/130 | 0.80/3.54E−04 | 0.23/4.77E−03 | 6.62E−05 |
| | | Phenes | | | |
| Mood | M-BP | 12/130 | 0.8/3.65E−04 | −0.47/6.83E−09 | 1.65E−03 |
| Anxiety | M-BP | 12/130 | 0.86/2.19E−05 | 0.41/7.09E−07 | 1.91E−05 |
| Mood and Anxiety (SASS) | M-BP | 12/130 | 0.86/1.66E−05 | 0.5/7.15E−10 | 5.66E−05 |
| CFI-S | M-BP | 12/128 | 0.92/1.10E−06 | 0.5/6.11E−10 | 1.31E−06 |
| Mood and Anxiety and CFI-S | M-BP | 12/128 | 0.94/2.82E−07 | 0.61/1.24E−14 | 3.01E−06 |

TABLE 4-continued

Diagnostics. Biomarkers, Phenes, and Combined Predictions.
Red - top increased biomarker predictor; Blue - top decreased biomarker predictor. Underlined are individual biomarkers from the
Top Dozen list, the others are from the Bonferroni list. For Universal, the panel of Top Dozen biomarkers is called BioM 12, and the
panel of Bonferroni biomarkers is called BioM148, reflecting the number of markers in the panel. For Male Bipolar, the panel of
Top Dozen biomarkers is called BioM 12, and the panel of Bonferroni biomarkers is called BioM54, reflecting the number of
markers in the panel. Italic - a priori primary endpoint (UP-Suicide).

Phenes and Biomarkers

| | | | | | |
|---|---|---|---|---|---|
| Mood and Anxiety and CFI-S and BioM 54 | M-BP | 12/128 | 0.93/5.30E−07 | 0.61/1.78E−14 | 5.54E−06 |
| *Mood and Anxiety and CFI-S and BioM 12* | *M-BP* | *12/128* | *0.95/1.62E−07* | *0.62/1.92E−15* | *8.31E−07* |
| Mood and Anxiety and CFI-S and BioM 2 | M-BP | 12/128 | 0.97/5.14E−08 | 0.64/2.29E−16 | 2.59E−07 |

B. Future Hospitalizations for Suicidality in the First Year Following Assessment in the Independent Test Cohort
Bold - p-value of AUC survives correction for multiple testing for predictions. ROC AUC is our apriori primary predictive tool.
HAMD SI is the suicide rating question from the Hamilton Rating Scale for Depression. *Smaller cohort, as not everybody had
HAMD SI information.

| Predictors | Cohort | Participants with future hospitalizations for suicidality within the first year/Particpants total | ROC AUC/ p-value | Frequency of future hospitalizations for suicidality within the first year Correlation R/p-value | T-test p-value | Cox Regression Hazard Ratio/ P-value |
|---|---|---|---|---|---|---|
| | | Universal Best Biomarkers | | | | |
| <u>PSME4</u> | All | 38/471 | 0.59/2.62E−02 | 0.08/4.12E−02 | 6.20E−02 | 1.23/1.56E−01 |
| AK2 | All | 38/471 | 0.60/2.31E−02 | −0.06/9.70E−02 | 9.39E−03 | 1.35/7.22E−02 |
| BioM 148 Panel (Bonferroni List) | All | 38/471 | 0.52/3.37E−01 | −0.02/6.67E−01 | 4.18E−01 | 1.09/8.27E−01 |
| BioM 12 Panel (Top Dozen List) | All | 38/471 | 0.58/4.20E−02 | 0.05/1.47E−01 | 5.02E−02 | 1.88/1.41E−01 |
| BioM 2 Panel (PSME4 and AK2) | All | 38/471 | 0.65/1.10E−03 | 0.10/1.29E−02 | 1.35E−03 | 1.68/0.018 |
| | | Phenes | | | | |
| Mood | All | 38/471 | 0.65/1.00E−03 | −0.16/3.63E−04 | 1.03E−03 | 1.69/1.47E−03 |
| Anxiety | All | 38/471 | 0.69/3.70E−05 | 0.16/3.43E−04 | 2.30E−04 | 1.82/2.62E−04 |
| Mood and Anxiety (SASS) | All | 38/471 | 0.71/9.78E−06 | 0.18/4.89E−05 | 7.73E−05 | 1.45/8.11E−05 |
| CFI-S | All | 38/470 | 0.75/1.79E−07 | 0.2/5.11E−06 | 1.40E−06 | 2.02/7.11E−07 |
| Mood and Anxiety and CFI-S | All | 38/470 | 0.76/6.34E−08 | 0.22/4.18E−07 | 2.22E−06 | 1.40/1.13E−07 |
| HAMD SI | All | 35/458* | 0.81/5.27E−10 | 0.40/1.57E−19 | 2.64E−06 | 2.10/1.11E−15 |
| Mood and Anxiety and CFI-S and HAMD SI | All | 35/458* | 0.82/9.96E−11 | 0.35/4.11E−15 | 4.34E−08 | 1.36/1.83E−13 |
| | | Phenes and Biomarkers | | | | |
| Mood and Anxiety and CFI-S and BioM 148 | All | 38/470 | 0.76/6.65E−08 | 0.21/1.29E−06 | 2.29E−06 | 1.37/2.01E−07 |
| *Mood and Anxiety and CFI-S and BioM 12 (UP-Suicide)* | *All* | *38/470* | *0.77/2.87E−08* | *0.23/2.81E−07* | *9.11E−07* | *1.40/5.31E−08* |
| Mood and Anxiety and CFI-S and BioM 2 | All | 38/470 | 0.76/3.87E−08 | 0.24/1.17E−07 | 1.02E−06 | 1.39/3.98E−08 |
| Mood and Anxiety and CFI-S and HAMD SI and BioM 2 | All | 35/458* | 0.82/9.38E−11 | 0.35/3.20E−15 | 3.39E−08 | 1.35/1.83E−13 |
| | | Male Bipolars Best Biomarkers | | | | |
| PTEN | M-BP | 4/120 | 0.9/3.27E−03 | 0.22/6.76E−03 | 3.12E−02 | 1.73/2.73E−02 |
| RNF6 | M-BP | 4/120 | 0.82/1.58E−02 | −0.14/5.89E−02 | 9.14E−03 | 6.24/7.19E−02 |
| BioM 54 Panel (Bonferroni List) | M-BP | 4/120 | 0.75/4.23E−02 | 0.11/1.23E−01 | 4.71E−02 | 4.58/2.52E−01 |
| BioM 12 Panel (Top Dozen List) | M-BP | 4/120 | 0.56/3.41E−01 | 0.05/2.85E−01 | 3.08E−01 | 2.57/5.73E−01 |
| BioM 2 (PTEN and RNF6) | M-BP | 4/120 | 0.94/1.50E−03 | 0.23/5.17E−03 | 3.06E−03 | 2.68/1.19E−02 |
| | | Phenes | | | | |
| Mood | M-BP | 4/120 | 0.69/1.04E−01 | −0.14/6.08E−02 | 1.75E−01 | 2.10/1.32E−01 |
| Anxiety | M-BP | 4/120 | 0.70/9.29E−02 | 0.12/9.74E−02 | 1.12E−01 | 1.87/2.09E−02 |
| Mood and Anxiety (SASS) | M-BP | 4/120 | 0.72/7.19E−02 | 0.15/5.27E−02 | 1.34E−01 | 1.52/1.18E−01 |
| CFI-S | MBP | 4/120 | 0.80/2.10E−02 | 0.15/5.22E−02 | 3.46E−03 | 1.95/1.21E−01 |
| Mood and Anxiety and CFI-S | M-BP | 4/120 | 0.78/2.77E−02 | 0.18/2.36E−02 | 6.78E−02 | 1.41/5.54E−02 |

TABLE 4-continued

Diagnostics. Biomarkers, Phenes, and Combined Predictions.
Red - top increased biomarker predictor; Blue - top decreased biomarker predictor. Underlined are individual biomarkers from the
Top Dozen list, the others are from the Bonferroni list. For Universal, the panel of Top Dozen biomarkers is called BioM 12, and the
panel of Bonferroni biomarkers is called BioM148, reflecting the number of markers in the panel. For Male Bipolar, the panel of
Top Dozen biomarkers is called BioM 12, and the panel of Bonferroni biomarkers is called BioM54, reflecting the number of
markers in the panel. Italic - a priori primary endpoint (UP-Suicide).

Phenes and Biomarkers

| | | | | | | |
|---|---|---|---|---|---|---|
| Mood and Anxiety and CFIS and BioM 54 | M-BP | 4/120 | 0.81/1.64E−02 | 0.2/1.61E−02 | 5.13E−02 | 1.45/4.04E−02 |
| *Mood and Anxiety and CFI-S and BioM 12 (UP-Suicide Male BP)* | *M-BP* | *4/120* | *0.79/2.59E−02* | *0.19/1.88E−02* | *7.92E−02* | *1.44/4.72E−02* |
| Mood and Anxiety and CFI-S and BioM 2 | M-BP | 4/120 | 0.86/7.02E−03 | 0.25/3.48E−03 | 2.22E−02 | 1.55/1.18E−2 |

Predicting Future Hospitalizations for Suicidality in First Year Following Testing. Analyses for predicting hospitalizations for suicidality in the first year following each testing visit were conducted in subjects that had at least one year of follow-up in the VA system, for which there was access to complete electronic medical records. ROC analyses between genomic and phenomic marker levels at a specific testing visit and future hospitalizations were performed as described above, based on assigning if participants had been hospitalized for suicidality (ideation, attempts) or not within one year following a testing visit. Additionally, a one tailed t-test with unequal variance was performed between groups of participant visits with and without future hospitalizations for suicidality. Pearson R (one-tail) correlation was performed between hospitalization frequency (number of hospitalizations for suicidality divided by duration of follow-up) and marker levels.

A correlation analyses for hospitalization frequency for all future hospitalizations due to suicidality was also conducted, including those occurring beyond one year of follow-up, in the years following testing (on average 4.90 years per participant, range 0.40 to 10.42 years), as this calculation, unlike the ROC and t-test, accounts for the actual length of follow-up, which varied from participant to participant. The ROC and t-test might in fact, if used, under-represent the power of the markers to predict, as the more severe psychiatric patients are more likely to move geographically and/or be lost to follow-up.

Therapeutics

The individual top biomarkers known to be modulated by existing drugs were analyzed using the CFG databases, and using Ingenuity Drugs analyses (Tables 5A-5G). Drugs and natural compounds which are an opposite match for the gene expression profile of panels of the top biomarkers (top dozen biomarkers, Bonferroni corrected) were also analyzed using the Connectivity Map (Broad Institute, MIT) (Tables 6-18). For the top dozen universal biomarker panel, 7 of 12 probesets were present of the array used for the Connectivity Map; for the Bonferroni universal biomarker panel, 102 out of 148 probesets; for the top dozen male bipolar panel, 8 out of 12 probesets; and for the Bonferroni male bipolar panel, 31 out of 56 probesets.

TABLE 5

| Gene Symbol Gene Name | (Direction of Change in Suicidality) Analysis/ Internal Score | Modulated by Omega-3 | Modulated by Lithium | Modulated by Clozapine | Modulated by other Antidepressants | Modulated by other Mood Stabilizers | Modulated by other Antipsychotics | Modulated by other Drugs |
|---|---|---|---|---|---|---|---|---|
| A. Top Universal Biomarkers for Suicidality - Pharmacogenomics for potential stratification and monitoring response to treatment. Biomarker genes that are targets of existing drugs and modulated by them in opposite direction to suicide. | | | | | | | | |
| CCL28 chemokine (C-C motif) ligand 28 | (D) AP/4 | | | | Paroxetine | | | |
| HTR2A 5-hydroxytryptamine (serotonin) receptor 2A, G protein-coupled | (I) DE/2 | | | Yes | Buspirone, mirtazapine, amitriptyline | Valproate | Haloperidol Paliperidone, Risperidone, Iloperidone, asenapine, cariprazine, thioproperazine, lurasidone, opipramol, quetiapine, olanzapine, | |
| IFNG interferon, gamma | (D) AP/1 | | | | | | Olanzapine, Risperidone, Quetiapine, Aripiprazole | |
| ITGB1BP1 integrin beta 1 binding protein 1 | (D) DE/1 | | Yes | | | | | |

TABLE 5-continued

| Gene Symbol / Gene Name | Direction of Change in Suicidality Analysis/ Internal Score | Modulated by Omega-3 | Modulated by Lithium | Modulated by Clozapine | Modulated by other Antidepressants | Modulated by other Mood Stabilizers | Modulated by other Antipsychotics | Modulated by other Drugs |
|---|---|---|---|---|---|---|---|---|
| LHFP lipoma HMGIC fusion partner | (I) DE/1 | Yes | | | | | | |
| PTK2 protein tyrosine kinase 2 | (I) DE/1 | | | | | | | CT-707 |
| SLC4A4 solute carrier family 4 (sodium bicarbonate cotransporter), member 4 | (I) AP/1 | | | | | Valproate | | |
| B. Top Biomarkers for Suicidality in Males - Pharmacogenomics for potential stratification and monitoring response to treatment. Biomarker genes that are targets of existing drugs and modulated by them in opposite direction to suicide | | | | | | | | |
| AGT Angiotensinogen | I AP/1 | | Yes | | | | | |
| GDI2 GDP Dissociation Inhibitor 2 | D DE/1 | | Yes | | | | | Benzodiazepines |
| IL6 Interleukin 6 | I AP/2 | | Yes | Yes | | Yes | | tocilizumab, siltuximab |
| ITGB1BP1 Integrin Subunit Beta 1 Binding Protein 1 | D DE/1 | Yes | | | | | | |
| PRKACB Protein Kinase CAMP-Activated Catalytic Subunit Beta | D AP/4 | | Yes | | | | | |
| SAT1 Spermidine/Spermine N1-Acetyltransferase 1 | I DE/1 | Yes | | | | | | |
| SLC4A4 Solute Carrier Family 4 Member 4 | I AP/2 | | | | | Valproate | | |
| SLC6A4 Solute Carrier Family 6 Member 4 | I DE/2 | Yes | | | Yes SSRIs SNRIs | | | bicifadine, DOV-102,677, SLV-314 |
| TM4SF1 Transmembrane 4 L Six Family Member 1 | I AP/1 | Yes | Yes | | | | | |
| ZMYND8 Zinc Finger MYND-Type Containing 8 | D AP/1 | Yes | | | | | | |
| C. Top Biomarkers for Suicidality in Females - Pharmacogenomics for potential stratification and monitoring response to treatment. Biomarker genes that are targets of existing drugs and modulated by them in opposite direction to suicide | | | | | | | | |
| BDNF Brain Derived Neurotrophic Factor | I DE/2 | Yes | | | Fluoxetine | | Haloperidol | Mifepristone |
| HS6ST2 Heparan Sulfate 6-O-Sulfotransferase 2 | I DE/1 | | Yes | | | | | |
| HTR2A 5-Hydroxytryptamine Receptor 2A | I DE/2 | | Yes | Yes | Buspirone, mirtazapine, amitriptyline | Valproate | Haloperidol Paliperidone, Risperidone, Iloperidone, asenapine, cariprazine, thioproperazine, lurasidone, opipramol, quetiapine, olanzapine, | |
| IFNG Interferon Gamma | D AP/1 | | Yes | | | | Yes | |
| NTRK3 Neurotrophic | I DE/2 | | Yes | | | | | TSR-011, entrectinib, |

TABLE 5-continued

| | | | | | | | | |
|---|---|---|---|---|---|---|---|---|
| Receptor Tyrosine Kinase 3 | | | | | | | | PLX7486, DS-6051b |
| TPR Translocated Promoter Region, Nuclear Basket Protein | D AP/4 | | | | Valproate | | | |

| Gene Symbol Gene Name | (Direction of Change in Suicidality) Analysis/ Internal Score | Modulated by Omega-3 | Modulated by Lithium | Modulated by Clozapine | Modulated by other Antidepressants | Modulated by other Mood Stabilizers | Modulated by other Antipsychotics | Modulated by other Drugs |
|---|---|---|---|---|---|---|---|---|
| D. Top Biomarkers for Suicidality in Bipolar Disorder - Pharmacogenomics for potential stratification and monitoring response to treatment. Biomarker genes that are targets of existing drugs and modulated by them in opposite direction to suicide | | | | | | | | |
| HTR2A 5-Hydroxytryptamine Receptor 2A | (I) DE/2 | | Yes | Yes | Buspirone, mirtazapine, amitriptyline | Valproate | Haloperidol Paliperidone, Risperidone, Iloperidone, asenapine, cariprazine, thioproperazine, lurasidone, opipramol, quetiapine, olanzapine, | |
| ITPKB Inositol-Trisphosphate 3-Kinase B | (I) AP/2 | Yes | | | | | | |
| PIK3R1 Phosphoinositide-3-Kinase Regulatory Subunit 1 | (I) DE/1 | | Yes | | | | | |
| SAT1 Spermidine/Spermine N1-Acetyltransferase 1 | (I) DE/1 | | Yes | | | | | |
| SLC6A4 Solute Carrier Family 6 Member 4 | (D) DE/1 | | Yes | Yes | Fluoxetine | | | bicifadine, DOV-102,677, SLV-314 |
| TM4SF1 Transmembrane 4 L Six Family Member 1 | (I) AP/1 | Yes | Yes | | | | | |
| TNF Tumor Necrosis Factor | (I) DE/1 (I) AP/1 | | | | Sertraline Venlafaxine | | | , etanercept, infliximab, certolizumab, golimumab, thalidomide |
| E. Top Biomarkers for Suicidality in Depression - Pharmacogenomics for potential stratification and monitoring response to treatment. Biomarker genes that are targets of existing drugs and modulated by them in opposite direction to suicide | | | | | | | | |
| BDNF Brain Derived Neurotrophic Factor | (I) DE/1 | Yes | | | Fluoxetine | | Haloperidol | Mifepristone |
| DLK1 Delta Like Non-Canonical Notch Ligand 1 | (I) AP/2 (I) DE/1 | Yes | | | | | | |
| NTRK3 Neurotrophic Receptor Tyrosine Kinase 3 | (I) AP/2 (I) DE/1 | | | Yes | | | | TSR-011, entrectinib, PLX7486, DS-6051b |
| ACP1 Acid Phosphatase 1, Soluble | (D) AP/1 | Yes | | | Fluoxetine | | Olanzapine | |
| TSPYL1 TSPY Like 1 | (D) AP/1 | Yes | | | | Valproate | | |
| CD47 CD47 Molecule | (D) AP/2 (D) DE/1 | Yes | Yes | | | | | |
| GLIPR1 GLI Pathogenesis Related 1 | (D) DE/1 | | | | | Valproate | | |

TABLE 5-continued

| | | | | | | |
|---|---|---|---|---|---|---|
| GEM<br>GTP Binding Protein<br>Overexpressed In<br>Skeletal Muscle | (I)<br>AP/1 | | Yes | | | |
| JUN<br>Jun Proto-Oncogene, AP-1<br>Transcription Factor<br>Subunit | (I)<br>DE/1 | Yes | Yes | Fluoxetine | | |
| GIMAP4<br>GTPase, IMAP Family<br>Member 4 | (D)<br>DE/4 | | | | | Benzodiazepines |
| HNRNPL<br>Heterogeneous Nuclear<br>Ribonucleoprotein L | (D)<br>DE/4 | | Yes | | | |

F. Top Biomarkers for Suicidality in Males with Bipolar Disorder - Pharmacogenomics for potential stratification and monitoring response to treatment. Biomarker genes that are targets of existing drugs and modulated by them in opposite direction to suicide

| | | | | | | |
|---|---|---|---|---|---|---|
| HTR2A<br>5-hydroxytryptamine<br>(serotonin) receptor<br>2A, G protein-coupled | (I)<br>DE/2 | Yes | Yes | Buspirone,<br>mirtazapine,<br>amitriptyline | Valproate | Haloperidol<br>Paliperidone,<br>Risperidone,<br>Iloperidone,<br>asenapine,<br>cariprazine,<br>thioproperazine,<br>lurasidone,<br>opipramol,<br>quetiapine,<br>olanzapine, |
| SPTBN1<br>spectrin, beta,<br>non-erythrocytic 1 | (I)<br>AP/1 | Yes | | | | |

G. Top Biomarkers for Suicidality in Males with Depression - Pharmacogenomics for potential stratification and monitoring response to treatment. Biomarker genes that are targets of existing drugs and modulated by them in opposite direction to suicide

| | | | | | | |
|---|---|---|---|---|---|---|
| DLK1<br>Delta Like Non-<br>Canonical Notch<br>Ligand 1 | (I)<br>AP/2 | Yes | | | | |
| NTRK3<br>Neurotrophic<br>Receptor<br>Tyrosine Kinase 3 | (D)<br>AP/2 | | | Fluoxetine | | TSR-011,<br>entrectinib,<br>PLX7486,<br>DS-6051b |
| CD47<br>CD47 Molecule | D<br>AP/2 | Yes | Yes | | | |
| PTK2<br>Protein Tyrosine<br>Kinase 2 | I<br>DE/1 | | | | | CT-707 |
| TSPYL1<br>TSPY Like 1 | D<br>AP/1 | Yes | | | Valproate | |
| HNRNPL<br>Heterogeneous<br>Nuclear<br>Ribonucleoprotein L | (D)<br>DE/4 | | Yes | | | |

TABLE 6

Repurposed Drugs for Suicidality Treatment in Everybody (Universal)

| compound name | dose | cell | score | gene expression signature |
|---|---|---|---|---|
| dapsone | 16 µM | HL60 | −1 | Top Predictor Biomarkers |
| ebselen | 15 µM | PC3 | −1 | Top Dozen Biomarkers |
| *chlorogenic acid* | 11 µM | HL60 | −1 | Bonferroni Biomarkers |
| clemastine | 9 µM | HL60 | −0.983 | Top Predictor Biomarkers |
| metformin | 24 µM | HL60 | −0.983 | Bonferroni Biomarkers |
| *piracetam* | 28 µM | MCF7 | −0.973 | Top Dozen Biomarkers |
| *dihydroergocristine* | 6 µM | MCF7 | −0.946 | Top Dozen Biomarkers |
| amoxapine | 13 µM | MCF7 | −0.927 | Top Dozen Biomarkers |
| metformin | 24 µM | HL60 | −0.925 | Top Predictor Biomarkers |
| lisuride | 12 µM | PC3 | −0.922 | Top Dozen Biomarkers |
| homatropine | 11 µM | HL60 | −0.917 | Top Predictor Biomarkers |
| ritodrine | 12 µM | HL60 | −0.916 | Top Predictor Biomarkers |
| merbromin | 5 µM | HL60 | −0.904 | Top Predictor Biomarkers |
| naproxen | 16 µM | MCF7 | −0.903 | Top Dozen Biomarkers |
| *dl-alpha tocopherol* | 9 µM | HL60 | −0.885 | Top Predictor Biomarkers |
| chlorpromazine | 11 µM | HL60 | −0.877 | Top Predictor Biomarkers |
| diphenhydramine | 14 µM | HL60 | −0.873 | Bonferroni Biomarkers |

TABLE 6-continued

Repurposed Drugs for Suicidality Treatment in Everybody (Universal)

| compound name | dose | cell | score | gene expression signature |
|---|---|---|---|---|
| *genistein* | 10 μM | PC3 | −0.869 | Top Dozen Biomarkers |
| fluoxetine | 12 μM | HL60 | −0.851 | Top Predictor Biomarkers |
| adiphenine | 11 μM | HL60 | −0.847 | Top Predictor Biomarkers |
| *chlorogenic acid* | 11 μM | HL60 | −0.842 | Top Predictor Biomarkers |
| *yohimbine* | 10 μM | MCF7 | −0.842 | Top Predictor Biomarkers |
| prazosin | 10 μM | PC3 | −0.838 | Top Predictor Biomarkers |
| amitriptyline | 13 μM | HL60 | −0.827 | Top Predictor Biomarkers |
| *calcium folinate* | 8 μM | MCF7 | −0.825 | Bonferroni Biomarkers |

Using Universal Biomarker Signatures, as identified herein, Matching to the Connectivity Map (Cmap) to identify compounds that have opposite gene expression effects to suicide.
A score of −1 means perfect opposite effect.
Bold—known antidepressant/psychotropic.
Italic—natural compound

TABLE 7

Repurposed Drugs for Suicidality Treatment in Males

| compound name | dose | cell | score | gene expression signature |
|---|---|---|---|---|
| clemastine | 9 μM | HL60 | −1 | Top Predictor Biomarkers |
| metformin | 24 μM | HL60 | −1 | Bonferroni Biomarkers |
| chlorpromazine | 11 μM | HL60 | −0.997 | Top Predictor Biomarkers |
| *thiamine* | 12 μM | MCF7 | −0.989 | Top Dozen Biomarkers |
| hydrochlorothiazide | 13 μM | MCF7 | −0.984 | Top Dozen Biomarkers |
| LY-294002 | 100 nM | MCF7 | −0.981 | Top Predictor Biomarkers |
| *naringin* | 7 μM | MCF7 | −0.963 | Top Dozen Biomarkers |
| *betulin* | 9 μM | HL60 | −0.952 | Top Dozen Biomarkers |
| ritodrine | 12 μM | HL60 | −0.941 | Top Predictor Biomarkers |
| fluvastatin | 9 μM | PC3 | −0.935 | Top Predictor Biomarkers |
| dapsone | 16 μM | HL60 | −0.913 | Top Predictor Biomarkers |
| ranitidine | 11 μM | MCF7 | −0.908 | Top Dozen Biomarkers |
| diphenhydramine | 14 μM | MCF7 | −0.906 | Top Dozen Biomarkers |
| mephenesin | 22 μM | MCF7 | −0.905 | Top Predictor Biomarkers |
| thiamphenicol | 11 μM | HL60 | −0.904 | Top Predictor Biomarkers |
| dizocilpine | 12 μM | MCF7 | −0.9 | Top Predictor Biomarkers |
| metformin | 24 μM | HL60 | −0.885 | Top Predictor Biomarkers |
| droperidol | 11 μM | HL60 | −0.85 | Top Predictor Biomarkers |
| lisuride | 12 μM | MCF7 | −0.85 | Top Predictor Biomarkers |
| *vitexin* | 9 μM | PC3 | −0.842 | Top Predictor Biomarkers |
| risperidone | 10 μM | MCF7 | −0.841 | Top Predictor Biomarkers |
| fluoxetine | 12 μM | HL60 | −0.831 | Bonferroni Biomarkers |

Using the identified Male Biomarker Signatures Matching to the Connectivity Map (Cmap) to identify compounds that have opposite gene expression effects to suicide.
A score of −1 means perfect opposite effect.
Bold—known antidepressant/psychotropic.
Italic—natural compound

TABLE 8

Repurposed Drugs for Suicidality Treatment in Females

| compound name | dose | cell | score | gene expression signature |
|---|---|---|---|---|
| estradiol | 100 nM | HL60 | −1 | Bonferroni Biomarkers |
| pizotifen | 9 μM | HL60 | −1 | Top Dozen Biomarkers |
| rosiglitazone | 10 μM | HL60 | −1 | Top Dozen Biomarkers |
| orlistat | 10 μM | MCF7 | −0.972 | Top Dozen Biomarkers |
| nefopam | 14 μM | MCF7 | −0.953 | Bonferroni Biomarkers |
| biperiden | 11 μM | MCF7 | −0.941 | Bonferroni Biomarkers |
| fluoxetine | 12 μM | HL60 | −0.927 | Bonferroni Biomarkers |
| *cyanocobalamin* | 3 μM | MCF7 | −0.896 | Top Dozen Biomarkers |
| *vitexin* | 9 μM | MCF7 | −0.895 | Top Dozen Biomarkers |
| *hesperetin* | 13 μM | PC3 | −0.883 | Top Dozen Biomarkers |
| *kawain* | 17 μM | MCF7 | −0.883 | Bonferroni Biomarkers |
| *ergocalciferol* | 10 μM | HL60 | −0.832 | Bonferroni Biomarkers |

Using the identified Female Biomarkers Signatures Matching to the Connectivity Map (Cmap) to identify compounds that have opposite gene expression effects to suicide.
A score of −1 means perfect opposite effect.
Bold—known antidepressant/psychotropic.
Italic—natural compound

TABLE 9

Repurposed Drugs for Suicidality Treatment in Bipolar Disorder

| compound name | dose | cell | score | gene expression signature |
|---|---|---|---|---|
| phenelzine | 17 μM | MCF7 | −1 | Top Predictor Biomarkers |
| methocarbamol | 17 μM | PC3 | −1 | Top Dozen Biomarkers |
| baclofen | 19 μM | PC3 | −1 | Bonferroni Biomarkers |
| mepenzolate bromide | 10 μM | PC3 | −0.993 | Top Predictor Biomarkers |
| lobelanidine | 11 μM | MCF7 | −0.992 | Top Predictor Biomarkers |
| *genistein* | 10 μM | MCF7 | −0.985 | Top Dozen Biomarkers |
| lactobionic acid | 11 μM | MCF7 | −0.974 | Top Dozen Biomarkers |
| fluocinonide | 8 μM | PC3 | −0.968 | Top Predictor Biomarkers |
| *apigenin* | 15 μM | PC3 | −0.957 | Top Predictor Biomarkers |
| betahistine | 17 μM | MCF7 | −0.948 | Top Dozen Biomarkers |
| levonorgestrel | 13 μM | PC3 | −0.933 | Top Predictor Biomarkers |
| amoxapine | 13 μM | PC3 | −0.932 | Top Dozen Biomarkers |
| (+/−)-catechin | 14 μM | MCF7 | −0.931 | Top Predictor Biomarkers |
| *apigenin* | 15 μM | PC3 | −0.93 | Bonferroni Biomarkers |
| fenoprofen | 7 μM | PC3 | −0.923 | Top Predictor Biomarkers |
| carisoprodol | 15 μM | MCF7 | −0.919 | Bonferroni Biomarkers |
| *benfotiamine* | 9 μM | PC3 | −0.918 | Top Predictor Biomarkers |
| felodipine | 10 μM | MCF7 | −0.917 | Bonferroni Biomarkers |
| nifedipine | 12 μM | MCF7 | −0.914 | Bonferroni Biomarkers |
| 0175029-0000 | 10 μM | PC3 | −0.913 | Top Predictor Biomarkers |
| nifuroxazide | 15 μM | HL60 | −0.91 | Top Predictor Biomarkers |
| *cotinine* | 23 μM | MCF7 | −0.862 | Top Dozen Biomarkers |
| *ergocalciferol* | 10 μM | MCF7 | −0.86 | Top Dozen Biomarkers |
| *resveratrol* | 18 μM | MCF7 | −0.857 | Top Predictor Biomarkers |
| *hesperetin* | 13 μM | PC3 | −0.854 | Top Dozen Biomarkers |

Using the identified Bipolar Biomarkers Signatures Matching to the Connectivity Map (Cmap) to identify compounds that have opposite gene expression effects to suicide.
A score of −1 means perfect opposite effect.
Bold—known antidepressant/psychotropic.
Italic—natural compound

TABLE 10

Repurposed Drugs for Suicidality Treatment in Depression

| compound name | dose | cell | score | gene expression signature |
|---|---|---|---|---|
| *hyoscyamine* | 14 μM | HL60 | −1 | Top Dozen Biomarkers |
| metrizamide | 5 μM | HL60 | −1 | Top Dozen Biomarkers |
| nadolol | 13 μM | MCF7 | −1 | Bonferroni Biomarkers |
| mebhydrolin | 5 μM | HL60 | −0.969 | Top Dozen Biomarkers |
| rofecoxib | 10 μM | MCF7 | −0.966 | Top Dozen Biomarkers |
| gabapentin | 23 μM | MCF7 | −0.958 | Top Dozen Biomarkers |
| thiamazole | 35 μM | MCF7 | −0.953 | Top Dozen Biomarkers |
| celecoxib | 10 μM | MCF7 | −0.952 | Top Dozen Biomarkers |
| nimodipine | 10 μM | MCF7 | −0.951 | Bonferroni Biomarkers |
| estradiol | 10 nM | MCF7 | −0.949 | Top Dozen Biomarkers |
| *ginkgolide A* | 10 μM | PC3 | −0.946 | Top Dozen Biomarkers |
| *harmine* | 16 μM | HL60 | −0.931 | Top Dozen Biomarkers |
| nifedipine | 12 μM | PC3 | −0.929 | Top Dozen Biomarkers |
| SC-58125 | 10 μM | MCF7 | −0.929 | Top Dozen Biomarkers |
| *noscapine* | 10 μM | MCF7 | −0.924 | Top Dozen Biomarkers |
| *thiamine* | 12 μM | MCF7 | −0.922 | Top Dozen Biomarkers |
| diphenhydramine | 14 μM | HL60 | −0.861 | Bonferroni Biomarkers |
| metformin | 24 μM | HL60 | −0.84 | Bonferroni Biomarkers |

Using the identified Depression Biomarkers Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 11

Repurposed Drugs for Suicidality Treatment in Males with Bipolar Disorder

| compound name | dose | cell | score | gene expression signature |
|---|---|---|---|---|
| betonicine | 25 μM | MCF7 | −1 | Top Predictor Biomarkers |
| *betulin* | 9 μM | HL60 | −1 | Top Dozen Biomarkers |
| Prestwick-692 | 7 μM | MCF7 | −1 | Top Dozen Biomarkers |
| chlorphenesin | 16 μM | HL60 | −1 | Bonferroni Biomarkers |
| naproxen | 16 μM | PC3 | −0.96 | Bonferroni Biomarkers |
| biperiden | 11 μM | PC3 | −0.948 | Top Dozen Biomarkers |
| carteolol | 12 μM | HL60 | −0.946 | Top Dozen Biomarkers |
| baclofen | 19 μM | PC3 | −0.94 | Bonferroni Biomarkers |
| *harmaline* | 14 μM | MCF7 | −0.932 | Top Dozen Biomarkers |
| carteolol | 12 μM | HL60 | −0.907 | Top Dozen Biomarkers |
| amylocaine | 15 μM | MCF7 | −0.9 | Top Predictor Biomarkers |
| estradiol | 10 nM | MCF7 | −0.894 | Top Dozen Biomarkers |
| *acacetin* | 14 μM | PC3 | −0.882 | Bonferroni Biomarkers |
| *alpha-ergocryptine* | 7 μM | MCF7 | −0.862 | Top Dozen Biomarkers |
| *myosmine* | 27 μM | MCF7 | −0.846 | Top Predictor Biomarkers |
| zuclopenthixol | 9 μM | MCF7 | −0.839 | Top Predictor Biomarkers |
| *benfotiamine* | 9 μM | PC3 | −0.839 | Bonferroni Biomarkers |

TABLE 11-continued

Repurposed Drugs for Suicidality Treatment in Males with Bipolar Disorder

| compound name | dose | cell | score | gene expression signature |
|---|---|---|---|---|
| valproic acid | 500 μM | PC3 | −0.832 | Top Predictor Biomarkers |
| *resveratrol* | 18 μM | HL60 | −0.826 | Top Dozen Biomarkers |
| azacyclonol | 15 μM | MCF7 | −0.814 | Top Predictor Biomarkers |
| *allantoin* | 25 μM | PC3 | −0.811 | Top Dozen Biomarkers |

Using the identified Bipolar Males Biomarker Signatures Matching to the Connectivity Map (Cmap) to identify compounds that have opposite gene expression effects to suicide.

A score of −1 means perfect opposite effect.

Bold - known antidepressant/psychotropic.

Italic - natural compound

TABLE 12

Repurposed Drugs for Suicidality Treatment in Males with Depression

| compound name | dose | cell | score | gene expression signature |
|---|---|---|---|---|
| suloctidil | 12 μM | PC3 | −1 | Top Predictor Biomarkers |
| *vincamine* | 11 μM | MCF7 | −1 | Top Dozen Biomarkers |
| ciprofibrate | 14 μM | HL60 | −1 | Bonferroni Biomarkers |
| methanthelinium bromide | 10 μM | HL60 | −0.996 | Bonferroni Biomarkers |
| amantadine | 10 μM | MCF7 | −0.967 | Bonferroni Biomarkers |
| estradiol | 10 nM | ssMCF7 | −0.956 | Top Dozen Biomarkers |
| fenspiride | 13 μM | PC3 | −0.945 | Top Dozen Biomarkers |
| nimodipine | 10 μM | PC3 | −0.939 | Top Dozen Biomarkers |
| lansoprazole | 11 μM | HL60 | −0.931 | Bonferroni Biomarkers |
| famotidine | 12 μM | MCF7 | −0.923 | Top Dozen Biomarkers |
| cyclopenthiazide | 11 μM | HL60 | −0.917 | Top Predictor Biomarkers |
| cyclopenthiazide | 11 μM | HL60 | −0.91 | Top Dozen Biomarkers |
| fluvoxamine | 9 μM | MCF7 | −0.903 | Top Dozen Biomarkers |
| adipiodone | 4 μM | HL60 | −0.902 | Top Predictor Biomarkers |
| *calcium folinate* | 8 μM | HL60 | −0.902 | Bonferroni Biomarkers |
| trichostatin A | 1 μM | MCF7 | −0.892 | Top Predictor Biomarkers |
| *docosahexaenoic acid ethyl ester* | 100 μM | PC3 | −0.889 | Top Dozen Biomarkers |
| metformin | 10 μM | MCF7 | −0.882 | Top Dozen Biomarkers |
| *calcium folinate* | 8 μM | HL60 | −0.869 | Top Predictor Biomarkers |
| *chlorogenic acid* | 11 μM | HL60 | −0.864 | Bonferroni Biomarkers |
| dosulepin | 12 μM | HL60 | −0.831 | Top Predictor Biomarkers |
| thioproperazine | 6 μM | HL60 | −0.831 | Top Predictor Biomarkers |
| rolipram | 15 μM | PC3 | −0.811 | Top Predictor Biomarkers |
| citalopram | 1 μM | MCF7 | −0.787 | Top Predictor Biomarkers |

Using Our Depression Males Biomarker Signatures Matching to the Connectivity Map (Cmap) to identify compounds that have opposite gene expression effects to suicide.

A score of −1 means perfect opposite effect.

Bold - known antidepressant/psychotropic.

Italic - natural compound

TABLE 13

Repurposed Drugs for Suicidality Treatment in Males with Post-Traumatic Stress Disorder (PTSD)

| compound name | dose | cell | score | gene expression signature |
|---|---|---|---|---|
| hemicholinium | 7 μM | PC3 | −1 | Top Predictor Biomarkers |
| epitiostanol | 13 μM | PC3 | −0.974 | Top Predictor Biomarkers |
| pirenperone | 10 μM | HL60 | −0.913 | Top Predictor Biomarkers |
| tretinoin | 13 μM | PC3 | −0.901 | Top Predictor Biomarkers |
| betamethasone | 10 μM | PC3 | −0.901 | Top Predictor Biomarkers |
| tolnaftate | 13 μM | MCF7 | −0.895 | Top Predictor Biomarkers |
| atractyloside | 5 μM | HL60 | −0.884 | Top Predictor Biomarkers |
| prochlorperazine | 7 μM | HL60 | −0.878 | Top Predictor Biomarkers |
| tolazoline | 20 μM | MCF7 | −0.866 | Top Predictor Biomarkers |
| fulvestrant | 10 nM | HL60 | −0.858 | Top Predictor Biomarkers |
| procainamide | 15 μM | HL60 | −0.844 | Top Predictor Biomarkers |
| pioglitazone | 10 μM | PC3 | −0.839 | Top Predictor Biomarkers |
| *calcium folinate* | 8 μM | MCF7 | −0.838 | Top Predictor Biomarkers |
| merbromin | 5 μM | HL60 | −0.831 | Top Predictor Biomarkers |
| adipiodone | 4 μM | HL60 | −0.831 | Top Predictor Biomarkers |

TABLE 13-continued

Repurposed Drugs for Suicidality Treatment in Males
with Post-Traumatic Stress Disorder (PTSD)

| compound name | dose | cell | score | gene expression signature |
|---|---|---|---|---|
| benzbromarone | 9 μM | HL60 | −0.83 | Top Predictor Biomarkers |
| prazosin | 10 μM | PC3 | −0.828 | Top Predictor Biomarkers |

Using the identified PTSD Males Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 14

Repurposed Drugs for Suicidality Treatment in Males with
Schizophrenia and Schizoaffective Disorder (SZ/SZA)

| compound name | dose | cell | score | gene expression signature |
|---|---|---|---|---|
| *asiaticoside* | 4 μM | HL60 | −1 | Top Predictor Biomarkers |
| procainamide | 15 μM | HL60 | −0.959 | Top Predictor Biomarkers |
| 3-hydroxy-DL-kynurenine | 18 μM | HL60 | −0.946 | Top Predictor Biomarkers |
| mafenide | 18 μM | HL60 | −0.913 | Top Predictor Biomarkers |
| metformin | 24 μM | HL60 | −0.899 | Top Predictor Biomarkers |
| trimipramine | 10 μM | HL60 | −0.895 | Top Predictor Biomarkers |
| ramifenazone | 14 μM | HL60 | −0.885 | Top Predictor Biomarkers |
| lithocholic acid | 11 μM | HL60 | −0.881 | Top Predictor Biomarkers |
| *chlorogenic acid* | 11 μM | HL60 | −0.878 | Top Predictor Biomarkers |
| hydrastinine | 16 μM | HL60 | −0.875 | Top Predictor Biomarkers |
| diphenhydramine | 14 μM | HL60 | −0.874 | Top Predictor Biomarkers |
| clozapine | 12 μM | HL60 | −0.868 | Top Predictor Biomarkers |

Using the identified SZ/SZA Males Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 15

Repurposed Drugs for Suicidality Treatment in the High Anxiety Subtype

| compound name | dose | cell | score | gene expression signature |
|---|---|---|---|---|
| ethaverine | 9 μM | PC3 | −1 | Top Predictor Biomarkers |
| moracizine | 9 μM | HL60 | −0.969 | Top Predictor Biomarkers |
| *dl-alpha tocopherol* | 9 μM | HL60 | −0.944 | Top Predictor Biomarkers |
| cefalotin | 10 μM | PC3 | −0.933 | Top Predictor Biomarkers |
| *calcium folinate* | 8 μM | PC3 | −0.855 | Top Predictor Biomarkers |
| indoprofen | 14 μM | PC3 | −0.854 | Top Predictor Biomarkers |
| ethoxyquin | 18 μM | PC3 | −0.825 | Top Predictor Biomarkers |
| mesalazine | 26 μM | MCF7 | −0.824 | Top Predictor Biomarkers |
| valproic acid | 500 μM | MCF7 | −0.822 | Top Predictor Biomarkers |
| orphenadrine | 13 μM | PC3 | −0.82 | Top Predictor Biomarkers |
| thioridazine | 10 μM | HL60 | −0.819 | Top Predictor Biomarkers |
| risperidone | 10 μM | HL60 | −0.812 | Top Predictor Biomarkers |
| trifluoperazine | 10 μM | HL60 | −0.811 | Top Predictor Biomarkers |
| thioproperazine | 6 μM | PC3 | −0.804 | Top Predictor Biomarkers |
| chlorpromazine | 11 μM | HL60 | −0.791 | Top Predictor Biomarkers |

Using the Top Predictor Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 16

Repurposed Drugs for Suicidality Treatment in the Low Mood Subtype

| compound name | dose | cell | score | gene expression signature |
|---|---|---|---|---|
| streptomycin | 3 μM | MCF7 | −1 | Top Predictor Biomarkers |
| isoetarine | 12 μM | MCF7 | −0.988 | Top Predictor Biomarkers |
| carbimazole | 21 μM | HL60 | −0.947 | Top Predictor Biomarkers |

TABLE 16-continued

Repurposed Drugs for Suicidality Treatment in the Low Mood Subtype

| compound name | dose | cell | score | gene expression signature |
| --- | --- | --- | --- | --- |
| IC-86621 | 1 μM | PC3 | −0.944 | Top Predictor Biomarkers |
| dapsone | 16 μM | HL60 | −0.94 | Top Predictor Biomarkers |
| bumetanide | 11 μM | MCF7 | −0.909 | Top Predictor Biomarkers |
| pergolide | 10 μM | PC3 | −0.906 | Top Predictor Biomarkers |
| sulindac | 11 μM | PC3 | −0.905 | Top Predictor Biomarkers |
| bemegride | 26 μM | MCF7 | −0.904 | Top Predictor Biomarkers |
| *yohimbine* | 10 μM | MCF7 | −0.894 | Top Predictor Biomarkers |
| *cotinine* | 23 μM | MCF7 | −0.892 | Top Predictor Biomarkers |
| prochlorperazine | 7 μM | HL60 | −0.891 | Top Predictor Biomarkers |
| chlorprothixene | 11 μM | MCF7 | −0.885 | Top Predictor Biomarkers |
| sulindac | 11 μM | PC3 | −0.88 | Top Predictor Biomarkers |
| ramifenazone | 14 μM | HL60 | −0.874 | Top Predictor Biomarkers |
| *boldine* | 12 μM | HL60 | −0.874 | Top Predictor Biomarkers |
| *dl-alpha tocopherol* | 9 μM | HL60 | −0.87 | Top Predictor Biomarkers |
| nordihydroguaiaretic acid | 1 μM | ssMCF7 | −0.858 | Top Predictor Biomarkers |
| serotonin | 19 μM | PC3 | −0.854 | Top Predictor Biomarkers |
| diphenhydramine | 14 μM | HL60 | −0.852 | Top Predictor Biomarkers |

Using the Top Predictor Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 17

Repurposed Drugs for Suicidality Treatment in the High Psychosis (Non-Affective) Subtype

| compound name | dose | cell | score | gene expression signature |
| --- | --- | --- | --- | --- |
| PF-01378883-00 | 10 μM | MCF7 | −0.975 | Top Predictor Biomarkers |
| ketotifen | 9 μM | MCF7 | −0.959 | Top Predictor Biomarkers |
| levamisole | 17 μM | MCF7 | −0.938 | Top Predictor Biomarkers |
| tenoxicam | 12 μM | HL60 | −0.934 | Top Predictor Biomarkers |
| ifosfamide | 15 μM | MCF7 | −0.933 | Top Predictor Biomarkers |
| naloxone | 11 μM | MCF7 | −0.931 | Top Predictor Biomarkers |
| timolol | 9 μM | MCF7 | −0.928 | Top Predictor Biomarkers |
| metformin | 24 μM | HL60 | −0.926 | Top Predictor Biomarkers |
| iocetamic acid | 7 μM | HL60 | −0.922 | Top Predictor Biomarkers |
| rofecoxib | 10 μM | MCF7 | −0.921 | Top Predictor Biomarkers |
| pepstatin | 6 μM | MCF7 | −0.913 | Top Predictor Biomarkers |
| isocarboxazid | 17 μM | PC3 | −0.909 | Top Predictor Biomarkers |
| tinidazole | 16 μM | MCF7 | −0.908 | Top Predictor Biomarkers |
| mefexamide | 13 μM | PC3 | −0.907 | Top Predictor Biomarkers |
| etodolac | 14 μM | MCF7 | −0.907 | Top Predictor Biomarkers |
| *myricetin* | 13 μM | MCF7 | −0.899 | Top Predictor Biomarkers |
| promazine | 12 μM | MCF7 | −0.897 | Top Predictor Biomarkers |
| nomegestrol | 11 μM | MCF7 | −0.884 | Top Predictor Biomarkers |
| *lobelanidine* | 11 μM | MCF7 | −0.881 | Top Predictor Biomarkers |
| diphenhydramine | 14 μM | HL60 | −0.878 | Top Predictor Biomarkers |

Using the Top Predictor Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound

TABLE 18

Repurposed Drugs for Suicidality Treatment in the Combined (Affective) Subtype

| compound name | dose | cell | score | gene expression signature |
| --- | --- | --- | --- | --- |
| trimipramine | 10 μM | HL60 | −1 | Top Predictor Biomarkers |
| proguanil | 14 μM | HL60 | −1 | Top Predictor Biomarkers |
| cyclopenthiazide | 11 μM | HL60 | −0.961 | Top Predictor Biomarkers |
| lansoprazole | 11 μM | HL60 | −0.941 | Top Predictor Biomarkers |
| ozagrel | 15 μM | HL60 | −0.939 | Top Predictor Biomarkers |
| *asiaticoside* | 4 μM | HL60 | −0.928 | Top Predictor Biomarkers |
| metformin | 24 μM | HL60 | −0.92 | Top Predictor Biomarkers |
| corticosterone | 12 μM | HL60 | −0.907 | Top Predictor Biomarkers |
| *chlorogenic acid* | 11 μM | HL60 | −0.904 | Top Predictor Biomarkers |
| ondansetron | 12 μM | HL60 | −0.876 | Top Predictor Biomarkers |
| *betulin* | 9 μM | HL60 | −0.875 | Top Predictor Biomarkers |

TABLE 18-continued

Repurposed Drugs for Suicidality Treatment in the Combined (Affective) Subtype

| compound name | dose | cell | score | gene expression signature |
|---|---|---|---|---|
| pirenperone | 10 μM | HL60 | −0.872 | Top Predictor Biomarkers |
| adiphenine | 11 μM | HL60 | −0.855 | Top Predictor Biomarkers |
| felbinac | 19 μM | MCF7 | −0.853 | Top Predictor Biomarkers |
| finasteride | 11 μM | HL60 | −0.843 | Top Predictor Biomarkers |
| rilmenidine | 8 μM | HL60 | −0.833 | Top Predictor Biomarkers |
| ritodrine | 12 μM | HL60 | −0.826 | Top Predictor Biomarkers |
| dexamethasone | 9 μM | PC3 | −0.819 | Top Predictor Biomarkers |
| cyclic adenosine monophosphate | 12 μM | HL60 | −0.806 | Top Predictor Biomarkers |
| fluoxetine | 12 μM | HL60 | −0.805 | Top Predictor Biomarkers |

Using the Top Predictor Biomarker Signatures Matching to the Connectivity Map (Cmap) to identify compounds that have opposite gene expression effects to suicide.
A score of −1 means perfect opposite effect.
Bold - known antidepressant/psychotropic.
Italic - natural compound Understanding
Pathway Analyses IPA (Ingenuity Pathway Analyses, version 24390178, Qiagen), David Functional Annotation Bioinformatics Microarray Analysis (National Institute of Allergy and Infectious Diseases), and Kyoto Encyclopedia of Genes and Genomes (KEGG) (through DAVID) were used to analyze the biological roles, including top canonical pathways, and diseases, of the candidate genes, as well as to identify genes in that dataset that are the targets of existing drugs (Table 19). The pathway analyses were conducted for the combined AP and DE probesets with a total internal and external CFG prioritization score >4 that showed stepwise change in the suicide completers validation cohort and survived Bonferroni correction (130 genes, 148 probesets) (Table 4). For male bipolars, there were 50 genes, 54 probesets.

TABLE 19

Biological Pathways and Diseases
A. Universal biomarkers

| Universal Pathways | DAVID GO Functional Annotation Biological Processes | | | | | KEGG Pathways | | | |
|---|---|---|---|---|---|---|---|---|---|
| | # | Term | Count | % | P-Value | Term | Count | % | P-Value |
| Validation Bonferroni Significant in Suicide Completers (n = 130 genes) | 1 | Regulation of neurogenesis | 8 | 6.6 | 2.10E−04 | Tryptophan metabolism | 4 | 0.2 | 1.10E−02 |
| | 2 | Negative regulation of apoptosis | 11 | 9 | 2.60E−04 | Neurotrophin signaling pathway | 6 | 0.3 | 1.40E−02 |
| | 3 | Negative regulation of programmed cell death | 11 | 9 | 2.90E−04 | Insulin signaling pathway | 6 | 0.3 | 1.90E−02 |
| | 4 | Negative regulation of cell death | 11 | 9 | 3.00E−04 | Butanoate metabolism | 3 | 0.2 | 5.90E−02 |
| | 5 | Regulation of cell morphogenesis | 7 | 5.7 | 3.90E−04 | Endocytosis | 6 | 0.3 | 6.10E−02 |

| Universal Pathways | Ingenuity Pathways | | |
|---|---|---|---|
| | Top Canonical Pathways | P-Value | Overlap |
| Validation Bonferroni Significant in Suicide Completers (n = 130 genes) | Protein Kinase A Signaling | 4.36E−06 | 0.03112/386 |
| | IGF-1 Signaling | 2.86E−05 | 0.06235/582 |
| | Gap Junction Signaling | 4.66E−05 | 0.0457/155 |
| | Renin-Angiotensin Signaling | 5.52E−05 | 0.0556/109 |
| | Hepatic Cholestasis | 5.93E−05 | 0.0437/161 |

TABLE 19-continued

Biological Pathways and Diseases
A. Universal biomarkers

| Universal Diseases | DAVID | | | | Ingenuity Diseases and Disorders | P-Value | # Molecules |
|---|---|---|---|---|---|---|---|
| | # | Term | Count | % | P-Value | | |
| Validation Bonferroni Significant in Suicide Completers (n = 130 genes) | 1 | diabetes, type 1 | 9 | 7.4 | 1.40E−03 | 1 Infectious Diseases | 1.01E−03-1.31E−07 | 35 |
| | 2 | breast cancer | 9 | 7.4 | 1.40E−02 | 2 Organismal Injury and Abnormalities | 1.66E−03-7.72E−07 | 89 |
| | 3 | hypertension | 7 | 5.7 | 1.60E−02 | 3 Developmental Disorder | 1.10E−03-9.64E−07 | 28 |
| | 4 | oxidized LDL | 2 | 1.6 | 2.30E−02 | 4 Cancer | 1.66E−03-1.38E−06 | 83 |
| | 5 | brain aging | 2 | 1.6 | 2.30E−02 | 5 Cardiovascular Disease | 1.66E−03-1.70E−06 | 18 |

B. Male Bipolar biomarkers

| Male Bipolar Pathways | DAVID GO Functional Annotation Biological Processes | | | | | KEGG Pathways | | | |
|---|---|---|---|---|---|---|---|---|---|
| | # | Term | Count | % | P-Value | Term | Count | % | P-Value |
| Validation Bonferroni significant in Suicide Completers (n = 50 genes) | 1 | negative regulation of neuron differentiation | 7 | 14.6 | 9.30E−06 | mTOR signaling pathway | 3 | 6.2 | 1.60E−02 |
| | 2 | negative regulation of neurogenesis | 7 | 14.6 | 3.60E−05 | Small cell lung cancer | 3 | 6.2 | 3.20E−02 |
| | 3 | negative regulation of nervous system development | 7 | 14.6 | 5.50E−05 | Leukocyte transendothelial migration | 3 | 6.2 | 5.80E−02 |
| | 4 | positive regulation of protein localization to plasma membrane | 4 | 8.3 | 1.10E−04 | Sphingolipid signaling pathway | 3 | 6.2 | 6.00E−02 |
| | 5 | positive regulation of protein localization to cell periphery | 4 | 8.3 | 1.10E−04 | NA | NA | NA | NA |

B. Male Bipolar biomarkers

| Male Bipolar Pathways | Ingenuity Pathways | | |
|---|---|---|---|
| | Top Canonical Pathways | P-Value | Overlap |
| Validation Bonferroni significant in Suicide Completers (n = 50 genes) | G-Protein Coupled Receptor Signaling | 1.14E−14 | 0.11329/256 |
| | CREB Signaling in Neurons | 1.98E−14 | 0.1424/171 |
| | Neuropathic Pain Signaling In Dorsal Horn Neurons | 4.82E−13 | 0.1818/100 |
| | 14-3-3-mediated Signaling | 7.79E−12 | 0.15418/117 |
| | Gap Junction Signaling | 1.50E−11 | 0.12920/155 |

| Male Bipolar Diseases | DAVID | | | | | Ingenuity Diseases and Disorders | P-Value | # Molecules |
|---|---|---|---|---|---|---|---|---|
| | # | Term | Count | % | P-Value | | | |
| Validation Bonferroni significant | 1 | plasma HDL cholesterol (HDL-C) levels | 5 | 10.4 | 4.80E−03 | 1 Cancer | 6.89E−03-1.18E−05 | 46 |

TABLE 19-continued

Biological Pathways and Diseases
A. Universal biomarkers

| | | | | | | | | | |
|---|---|---|---|---|---|---|---|---|---|
| in Suicide Completers (n = 50 genes) | 2 | Type 2 Diabetes \| edema \| rosiglitazone | 13 | 27.1 | 1.30E−02 | 2 | Gastrointestinal Disease | 6.89E−03-1.18E−05 | 41 |
| | 3 | Eczema | 2 | 4.2 | 2.70E−02 | 3 | Organismal Injury and Abnormalities | 6.89E−03-1.18E−05 | 46 |
| | 4 | Neoplasms | 3 | 6.2 | 6.00E−02 | 4 | Reproductive System Disease | 6.89E−03-1.57E−05 | 20 |
| | 5 | healthy oldest-old | 2 | 4.2 | 6.50E−02 | 5 | Hematological Disease | 5.30E−03-2.55E−05 | 20 |

STRING Analysis

Figure 8:
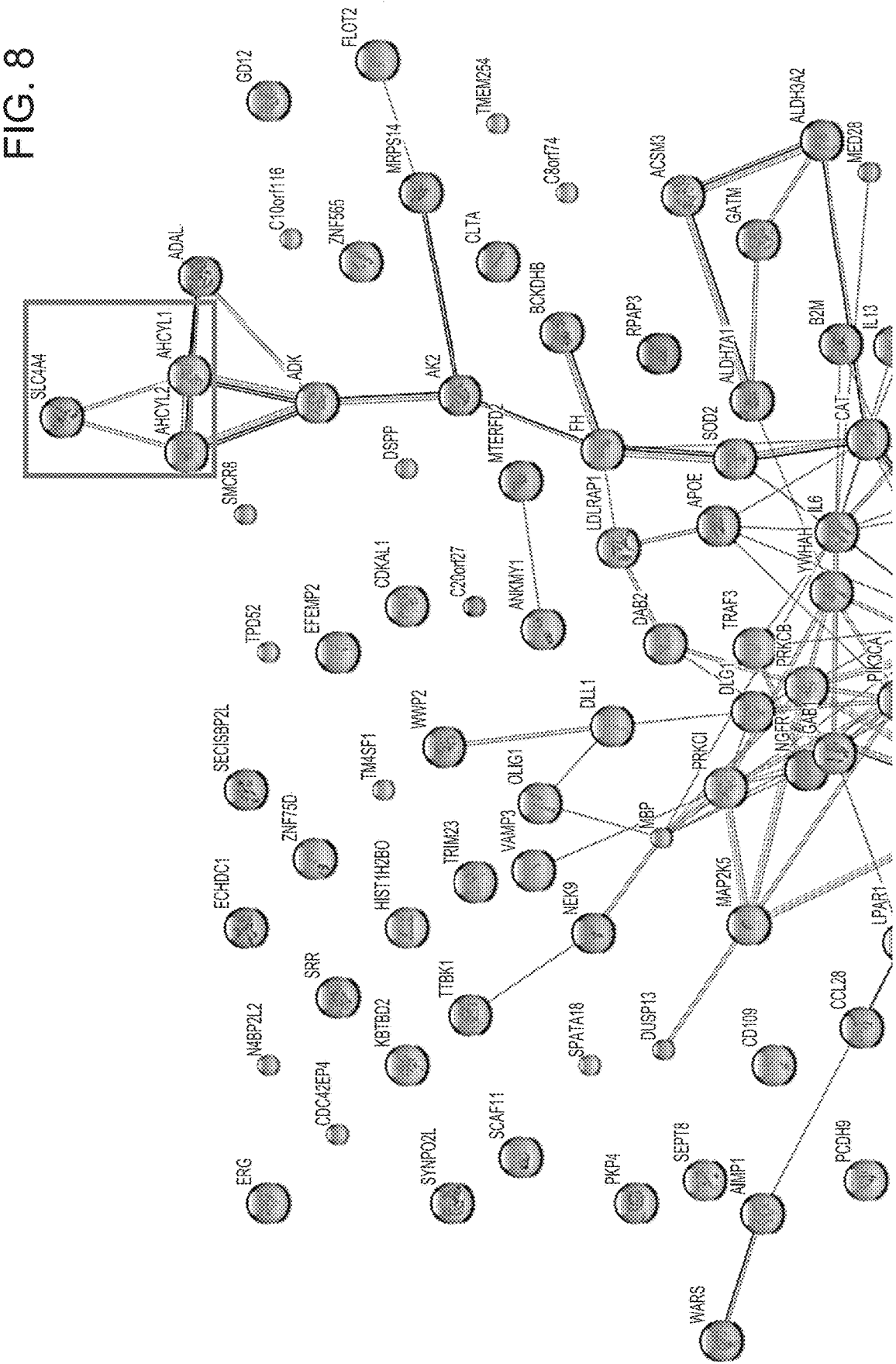
FIG. 8 depicts a STRING analysis depicting interactions between universal biomarkers. Top Dozen and Bonferroni combined lists.
Figure 8:
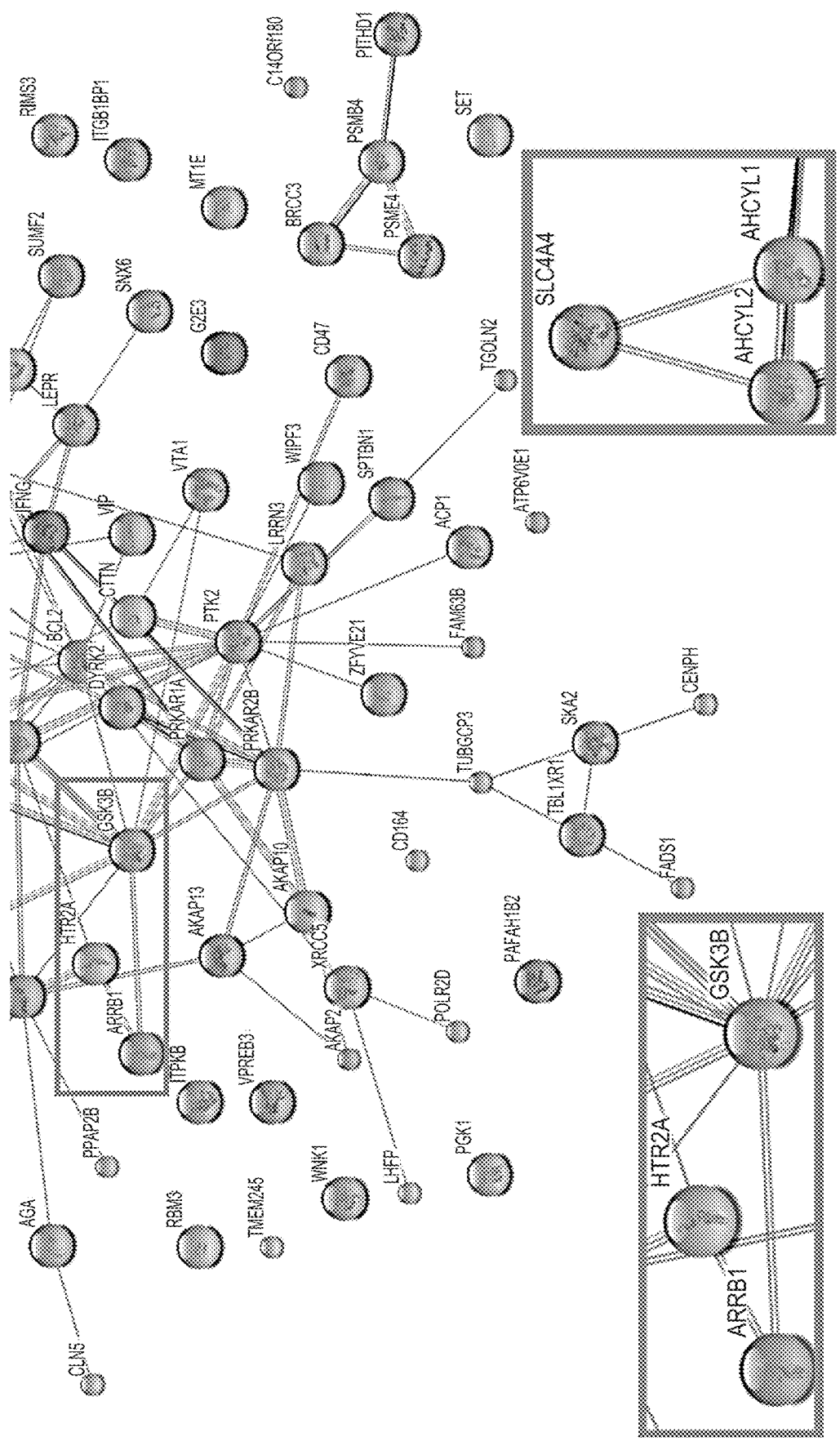

In order to examine potential network interactions between the biomarkers, the Search Tool for the Retrieval of Interacting Genes (STRING v10, string-db.org) was used. To run the analyses, the lists of genes were entered into the search box and *Homo Sapiens* was selected as the organism. The default (medium confidence) setting was used. (FIGS. 8 & 9).

CFG Beyond Suicide

A CFG approach was also used to examine evidence from other psychiatric and related disorders, for the top dozen biomarker genes and Bonferroni validated biomarker genes.

Clock Gene Database

For informational non-CFG scoring purposes, the suicide biomarker genes for involvement in the circadian clock were annotated. A database of genes associated with circadian function were compiled by using a combination of review papers (Zhang et al. 2009, McCarthy and Welsh 20129, 10) and searches of existing databases CircaDB (circadb.hogeneschlab.org), GeneCards (www.genecards.org), and GenAtlas (genatlas.medecine.univ-paris5.fr). Using the data compiled from these sources, a total of 1468 genes were identified that show circadian functioning. Genes were further classified into "core" clock genes, i.e., those genes that are the main engine driving circadian function (n=18), "immediate" clock genes, i.e., the genes that directly input or output to the core clock (n=331), and "distant" clock genes, i.e., genes that directly input or output to the immediate clock genes (n=1,119).

Convergent Functional Evidence (CFE)

A convergent functional evidence (CFE) score tabulated all the evidence from discovery (up to 4 points), prioritization (up to 8 points), validation (up to 4 points), testing (2 points for SI predictions, 2 points for hospitalizations predictions), other psychiatric and related disorders (2 points), and drug evidence (2 points). The goal was to highlight, based on the totality of the data and of the evidence in the field to date, biomarkers that have all around evidence: track suicidality, predict suicidality, are reflective of psychiatric pathology, and are potential drug targets. Such biomarkers merit priority evaluation in future clinical trials.

Additionally, a convergent functional evidence (CFE) score was computed with all the evidence from discovery (up to 4 points), prioritization (up to 8 points), testing (High Suicide State and Trait Suicide Hospitalization Future (up to 4 points each if significantly predicts in all subjects, 2 points if predicts by gender, 1 points if predicts in gender/diagnosis subgroups). The goal was to highlight, based on the totality of the data and of the evidence in the field to date, biomarkers that have all-around evidence for tracking suicidality in discovery and validation steps, as well as to permit an objective assessment of state, and predict future clinical events (hospitalizations for suicidality) in the clinical utility testing step.

Results

From Universal to Subtypes and Personalized

Discovery

A powerful within-participant discovery approach to identify genes that: 1. change in expression in blood between no suicidal ideation (no SI) and high suicidal ideation (high SI) states, 2. track the SI state across visits in a participant, and 3. track the SI state in multiple participants. A longitudinally followed cohort of participants was used that showed diametric changes in SI between at least two testing visits (n=66 participants out of a cohort of 293 men and women psychiatric disorder participants followed longitudinally, with diagnoses of bipolar disorder, depression, mood disorder nos, schizophrenia, schizoaffective disorder, psychosis nos, and PTSD). Using a 33% of maximum raw score threshold (internal score of 1 pt), 10,468 unique probesets from AP and DE were found. (FIG. 1D). These were carried forward to the prioritization step. This represents approximately a 5-fold enrichment of the 54,625 probesets on the Affymetrix array.

It was then examined in the discovery cohort whether subtypes of suicidality can be identified based on mental state at the time of high suicidal ideation visits, using two way hierarchical clustering with anxiety, mood, and psychosis measures. The SI state self-report may be more reliable in this cohort, as the subjects demonstrated the aptitude and willingness to report different, and diametric, SI states. Four potential subtypes of suicidality were found: high anxiety, low mood, co-morbid, and non-affective (psychotic) (FIG. 1C). These subtypes need to be tested in independent cohorts for practical utility, diagnostic and therapeutic.

Prioritization

A Convergent Functional Genomics (CFG) approach was used to prioritize the candidate biomarkers identified in the discovery step (internal score of >=1 pt.) by using all of the published prior independent evidence in the field (FIG. 1E). There were 583 probesets that had a CFG score (combined internal and external score) of 4 and above. These were carried forward to the validation step. This represents approximately a 100-fold enrichment of the probesets on the Affymetrix array.

Validation

Next, suicidal behavior was validated for these prioritized biomarkers in a demographically matched cohort of men and women suicide completers from the coroner's office (n=45), by assessing which markers were stepwise changed in expression from no SI to high SI to suicide completers (FIG. 1G). 274 probesets were non-stepwise changed, and 309 were stepwise changed. Of these, 148 survived Bonferroni correction for all the 583 probesets validated. This represents approximately a 500-fold enrichment of the probesets on the Affymetrix array.

Diagnostics

Diagnostic ability of the "universal" top dozen biomarkers (composed of the top increased and decreased biomarkers from AP and from DE from each step: discovery based on all participants, prioritization, and validation in all the coroner's cases) was tested, as well as all of the biomarkers that survived Bonferroni correction after the validation step (Table 3), in a completely independent test cohort of men and women psychiatric disorder participants (n=226), for prediction of suicidal ideation state, as well as for prediction of future psychiatric hospitalizations due to suicidality (FIGS. 3A-3D). Universal biomarkers that work across gender and diagnoses were successfully identified. Their predictive ability was also analyzed in participants in the independent cohort grouped by the subtypes described above, as well as grouped by a more personalized approach, by psychiatric diagnosis and gender. The universal approach was compared to the subtypes approach and the personalized approach, and it was shown that the subtype and personalized approaches permitted enhanced precision of predictions for different biomarkers (FIGS. 3A-3D). For example, for suicidal ideation prediction in the independent test cohort, SLC4A4, a top increased in expression biomarker, had an AUC of 64% (p=3.83E-04) across all subjects, 69% (6.13E-04) in the combined subtype, and 77% (9.72E-04) in male bipolars. SKA2, a top decreased in expression biomarker, had an AUC of 61% (p=3.35E-03) across all subjects, 74% (5.91E-03) in the low mood subtype, and 79% (1.35E-02) in male schizophrenics.

Additionally, two previously described clinical instruments in the form of apps, the Simplified Affective State Scale (SASS) that measures anxiety and mood, and the Convergent Functional Information for Suicidality (CFI-S) that measures risk for suicide indirectly, were used without asking about suicidal ideation. The scores from these apps showed good predictive ability for both state (suicidal ideation) and trait (future hospitalizations) (Table 4).

A panel of the dozen top biomarkers was combined with measures of anxiety and mood (SASS), and with the suicide risk scale (CFI-S), into a broad spectrum universal predictor (UP Suicide). The UP Suicide provides the biomarkers with mental state (SASS) and personal history context (CFI-S), enhancing precision of predictions (FIGS. 5A-5C and 6). Across all subjects in the independent test cohort, UP Suicide 12 had an AUC of 90% (3.87E-21) for state (suicidal ideation) prediction as well as an AUC of 77% (p=2.87E-08) for trait (future hospitalizations for suicidality) predictions. The results for predicting suicidal ideation were even stronger in the low mood subtype (AUC of 92%, p=7.42E-06) and in male bipolars, the highest risk group (AUC 96%, p=8.03E-08). For predicting future hospitalizations, the results were stronger in the high anxiety subtype (AUC 79%, p=7.52E-03), and in male depression (AUC 95%, p=4.88E-04).

Therapeutics

Figure 4B:
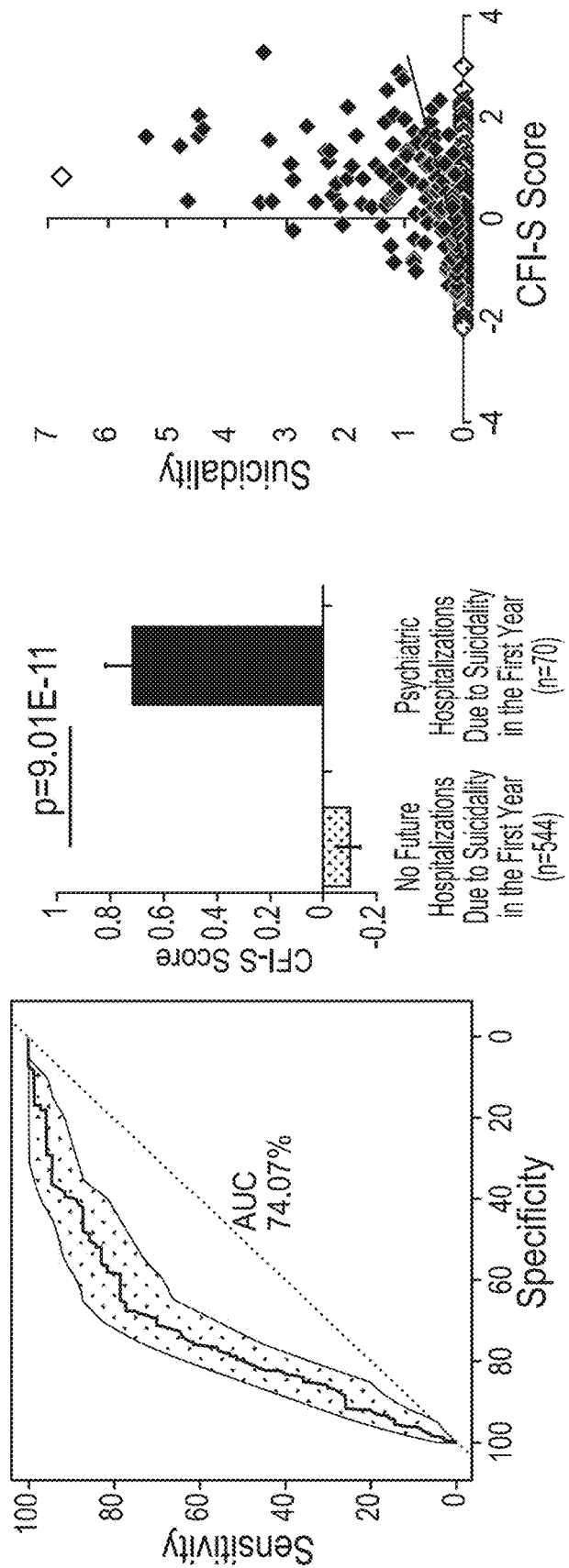
Figure 5A:
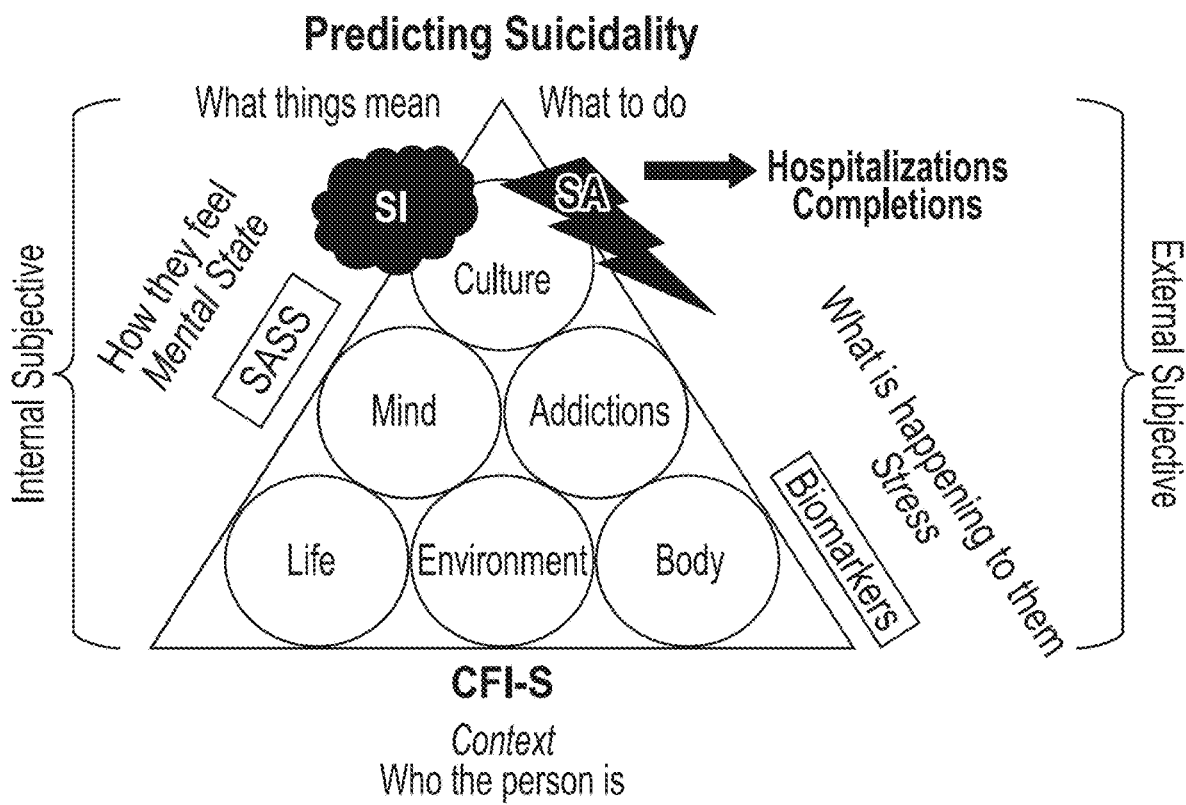
Figure 5E:
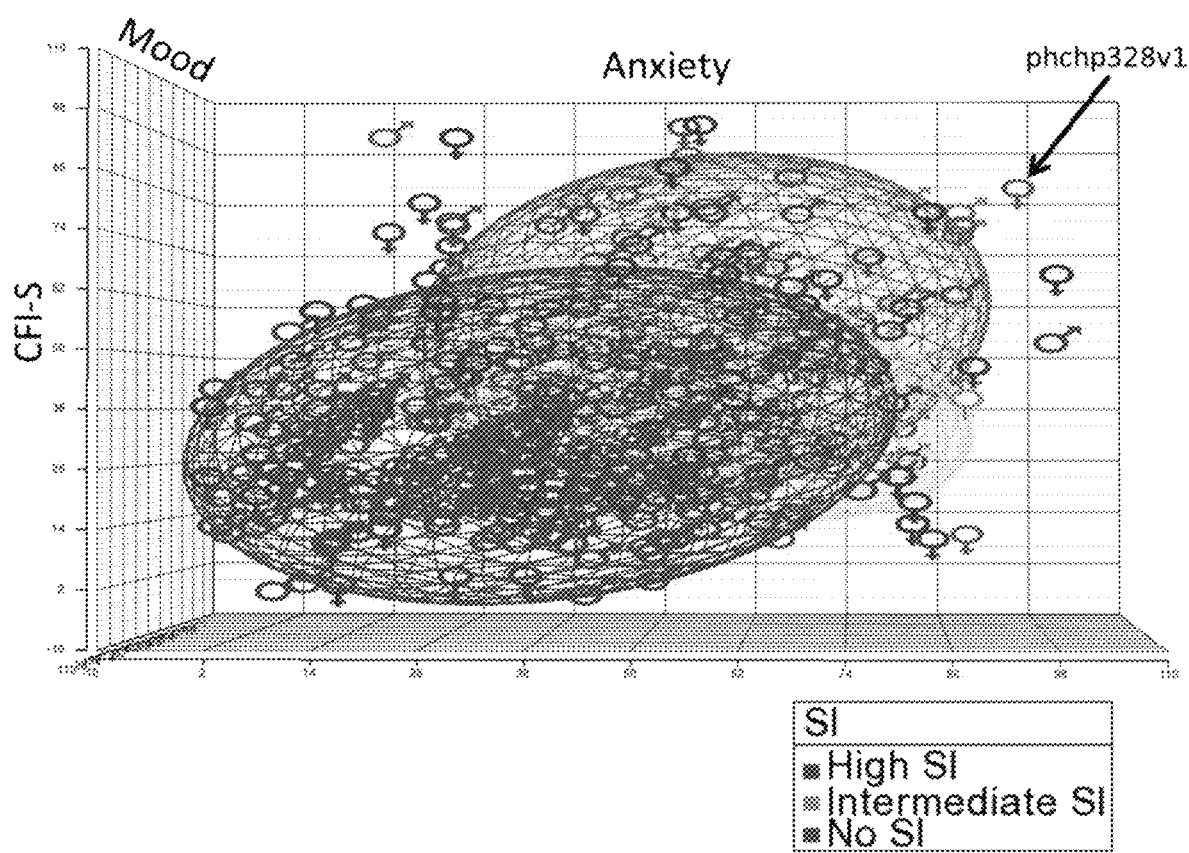
Figure 6:
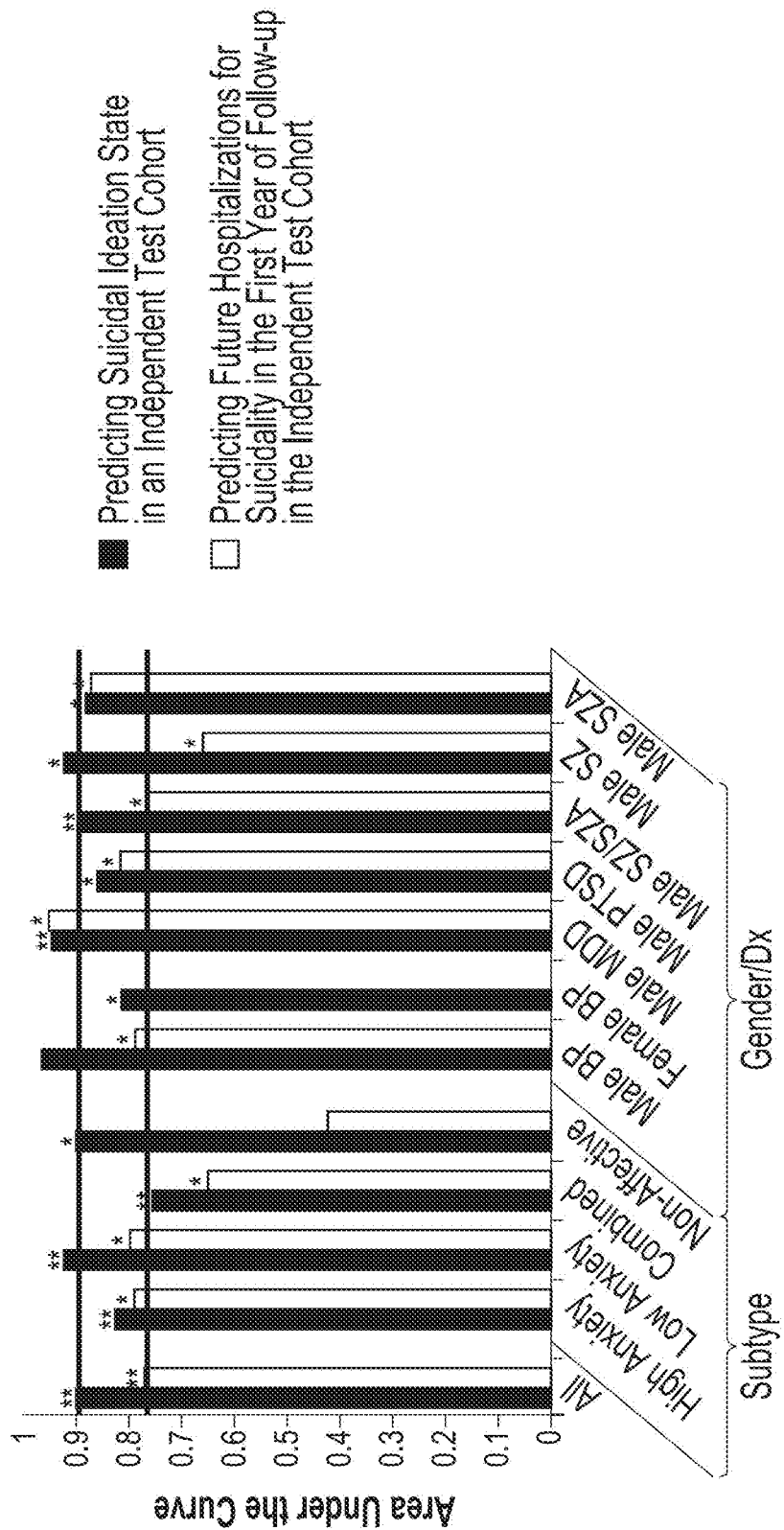
FIG. 6 depicts UP-Suicide across all, by subtypes, and personalized by gender/diagnosis. UP-Suicide is composed of the panel of the top dozen universal biomarkers, CFI-S, and SASS (Anxiety, Mood). Plot depicts Area Under the Curve (AUC) for the UP-Suicide predicting suicidal ideation and hospitalizations within the first year in all participants, as well as separately in subtypes, and by gender and diagnosis (Gender/Dx). Two asterisks indicate the comparison survived Bonferroni correction for all the multiple comparisons depicted. A single asterisk indicates nominal significance of p<0.05. Bold outline indicates that the UP-Suicide was synergistic to its components, i.e., performed better than the gene expression biomarkers or phenomic data individually. The table below contains descriptive statistics for all participants together, as well as separately by subtypes, and by gender/dx. Bold indicates the measure survived Bonferroni correction for all the multiple comparisons depicted. Pearson correlation data is also shown in the suicidal ideation test cohort for HAMD-SI vs. UP-Suicide, as well as Pearson correlation data in the hospitalization test cohort for frequency of hospitalizations for suicidality in the first year, and for frequency of hospitalizations for suicidality in all future available follow-up intervals (which varies among participants, from 0.40 to 10.42 years).

Pharmacogenomics. For phenomenology, the top CFI-S items distinguishing high SI from no SI states were past history of suicidality, social isolation, and dissatisfaction with one's life. The top CFI-S items distinguishing those that had future hospitalizations for suicidality vs. those that did not were past history of suicidality, command auditory hallucinations, and social isolation (FIGS. 4A & 4B). This provides empirical evidence that, in general, reducing social isolation is a good behavioral therapeutic intervention for preventing suicidality. In different individuals different CFI-S items are positive, providing avenues for tailored and targeted (psycho)therapeutic interventions.

A number of individual top biomarkers are targets of medications in current clinical use for treating suicidality, such as lithium (HTR2A, GSK3B, ITGB1BP1, BCL2), clozapine (IL6, CD164, CD47, HTR2A, PGK1, DYRK2, IFNG, LPAR1), and omega-3 fatty acids (APOE, CD47, ACP1, GATM, LHFP, LPAR1) (Tables 4A-4G). In particular, HTR2A and CRYAB are at the overlap of lithium and clozapine, and MBP is at the overlap of all three treatments. Omega-3 fatty acids may be a widely depoyable preventive treatment, with minimal side-effects, including in women who are or may become pregnant.

Bioinformatics drug repurposing analyses using the gene expression biosignature of panels of top biomarkers identified new potential therapeutics for suicidality, such as ebselen (a lithium mimetic), piracetam (a nootropic), chlorogenic acid (a polyphenol from coffee), and metformin (an antidiabetic and possible longevity promoting drug) (Tables 6-18).

Understanding

Biological Pathways. Biological pathway analyses using the Bonferroni validated biomarkers was conducted, which suggested that neurotrophic factors, programmed cell death, and insulin signaling are involved in the biology of suicide (Table 19).

Networks and Interactions. STING analyses revealed groups of directly interactive genes, in particular HTR2A/ARRB1/GSK3B, and SLC4A4/AHCYL1/AHCYL2 (FIG. 8), These networks may have biological significance and be targeted therapeutically.

A number of top biomarkers identified have biological roles that are related to the circadian clock (Table 20). To be able to ascertain all the genes in the dataset that were circadian and do estimates for enrichment, from the literature, a database was compiled of all the known genes that fall into these three categories, numbering a total of 1468 genes. Using an estimate of about 21,000 genes in the human genome, that gives about 7% of genes having some circadian pattern. Out of the 154 top biomarker genes, 18 had circadian evidence (11.7%) (Table 20), suggesting a 1.7 fold enrichment for circadian genes. Circadian clock abnormalities are related to mood disorders, and sleep abnormalities have been implicated in suicide.

Enrichment in suicide completers. Of the candidate biomarkers from the Prioritization step, 125/430 of the DE ones (29.1%) and 37/180 of the AP ones (20.6%) were Bonferroni validated in suicide completers. There is a 1.4 fold enrichment in DE vs. AP, which suggests that completion of suicide may be due more to an incremental change in expression of genes rather than the complete turning on and off of genes.

Figure 7:
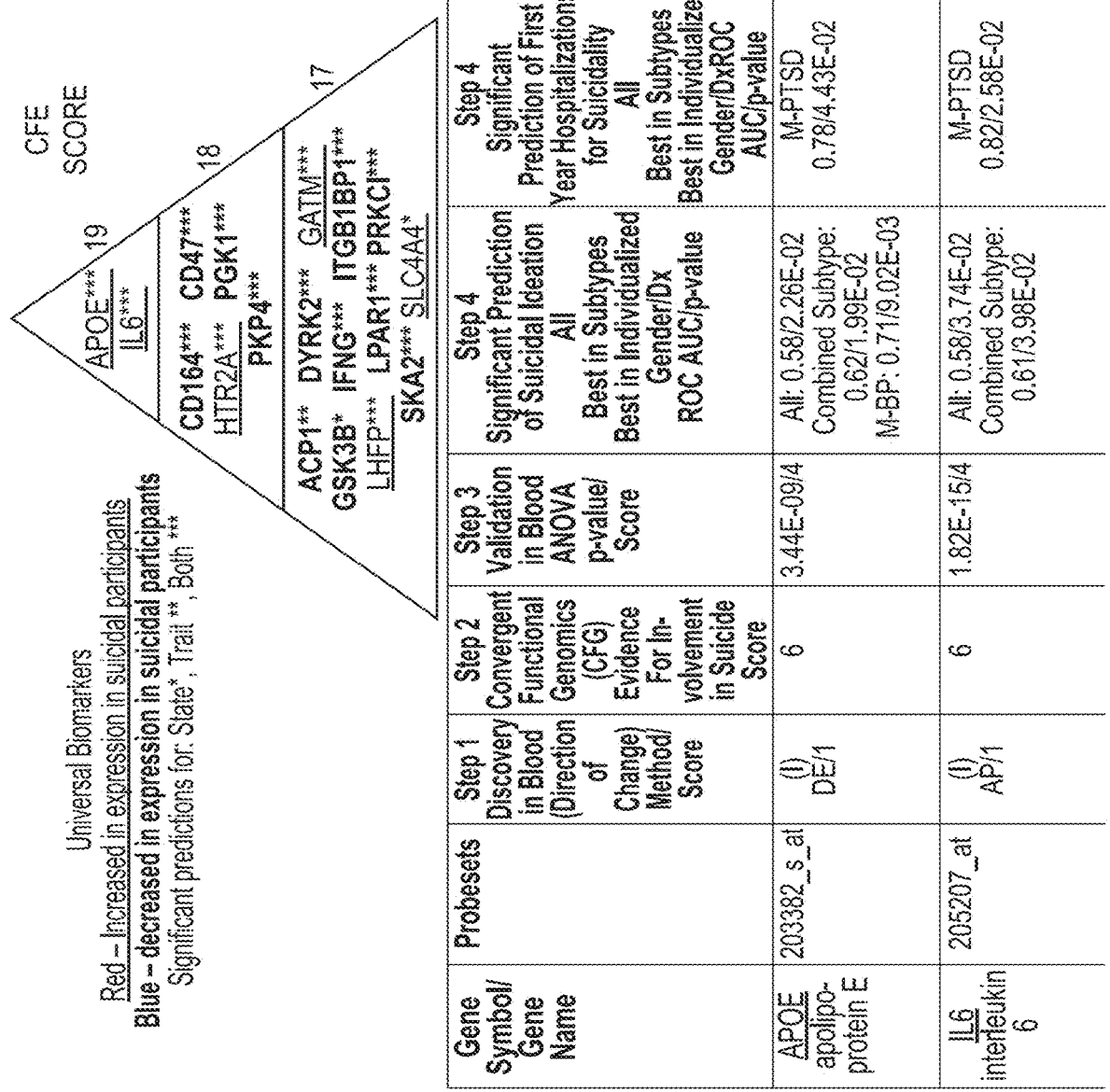
FIG. 7 depicts universal biomarkers—Convergent Functional Evidence for Involvement in Suicidality. Top dozen and Bonferroni validated biomarkers. Post-hoc summation of all the evidence form discovery, validation, prioritization and testing, along with evidence for being a target of drugs and for involvement in other psychiatric disorders. This prioritization highlights for future studies biomarkers that may have broad applicability in the field, for diagnostics and therapeutics.

Overall evidence. For the top biomarkers identified, combining all the available evidence from this Example and published literature into a convergent functional evidence (CFE) score (FIG. 7), leads to a prioritization of biomarkers for future studies in this field.

TABLE 20

Convergent Functional Evidence (CFE). Universal Top Dozen and Bonferroni biomarkers.
Only predictions with a significant p-value for the ROC AUC are tabulated and shown.

| Gene Symbol/ Gene Name | Probesets | Step 1 Discovery in Blood (Direction of Change) Method/ Score | Step 2 Convergent Functional Genomics (CFG) Evidence For Involvement in Suicide Score | Step 3 Validation in Blood ANOVA p-value/ Score | Step 4 Significant Prediction of Suicidal Ideation All Best in Subtypes Best in Individualized Gender/Dx ROC AUC/ p-value |
|---|---|---|---|---|---|
| APOE apolipoprotein E | 203382_s_at | (I) DE/1 | 6 | 3.44E−09/4 | All 0.58/2.26E−02 Combined Subtype 0.62/1.99E−02 M-BP 0.71/9.02E−03 |
| IL6 interleukin 6 | 205207_at | (I) AP/1 | 6 | 1.82E−15/4 | All 0.58/3.74E−02 Combined Subtype 0.61/3.98E−02 |
| CD164 CD164 molecule, sialomucin | 208654_s_at | (D) DE/2 | 4 | 3.01E−08/4 | All 0.59/1.80E−02 M-BP 0.68/1.94E−02 |
| CD47 CD47 molecule | 211075_s_at | (D) DE/2 | 4 | 1.62E−17/4 | All 0.6/9.71E−03 Low Mood Subtype 0.68/2.99E−02 M-SZA 0.69/2.19E−02 |
| HTR2A 5-hydroxytryptamine (serotonin) receptor 2A, G protein-coupled | 244130_at | (I) DE/2 | 8 | NS | Low Mood Subtype 0.66/4.74E−02 M-SZ 0.79/1.58E−02 |
| PGK1 phosphoglycerate kinase 1 | 217383_at | (D) DE/2 | 4 | 4.07E−07/4 | M-SZA 0.73/8.31E−03 |
| PKP4 plakophilin 4 | 201929_s_at | (D) DE/1 | 5 | 3.82E−08/4 | Combined Subtype 0.62/2.59E−02 M-SZ 0.75/2.93E−02 |
| ACP1 acid phosphatase 1, soluble | 1554808_at | (D) DE/1 | 6 | 3.82E−11/4 | |
| DYRK2 dual-specificity tyrosine-(Y)-phosphorylation regulated kinase 2 | 202969_at | (D) DE/1 | 4 | 1.67E−13/4 | All 0.58/3.37E−02 Combined Subtype 0.61/3.00E−02 M-SZ/SZA 0.68/9.85E−03 |
| GATM glycine amidinotransferase (L-arginine: glycine amidinotransferase) | 1566861_at | (I) DE/1 | 4 | 1.80E−12/4 | Combined Subtype 0.6/4.84E−02 M-BP 0.68/1.94E−02 |
| GSK3B glycogen synthase kinase 3 beta | 226183_at | (D) DE/1 | 6 | 2.19E−36/4 | M-SZA 0.68/3.47E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Direction | Score | p-value | Subtype/AUC |
|---|---|---|---|---|---|
| IFNG interferon, gamma | 210354_at | (D) AP/1 | 8 | NS | All 0.6/1.01E−02 Combined Subtype 0.61/3.03E−02 M-PTSD 0.73/2.72E−02 |
| ITGB1BP1 integrin beta 1 binding protein 1 | 203337_x_at | (D) DE/1 | 4 | 1.11E−08/4 | Low Mood Subtype 0.67/4.21E−02 M-SZ 0.78/1.64E−02 |
| LHFP lipoma HMGIC fusion partner | 218656_s_at | (I) DE/1 | 4 | 3.97E−10/4 | All 0.57/5.00E−02 Anxious Subtype 0.78/1.95E−02 F-BP 0.79/4.60E−02 |
| LPAR1 lysophosphatidic acid receptor 1 | 204036_at | (D) AP and DE/1 | 4 | 1.35E−23/4 | M-BP 0.68/2.13E−02 |
| PRKCI protein kinase C, iota | 209677_at | (D) DE/1 | 4 | 2.71E−05/4 | Anxious Subtype 0.8/1.55E−02 |
| SKA2 spindle and kinetochore associated complex subunit 2 | 225686_at | (D) DE/1 | 8 | 4.55E−03/2 | All 0.61/3.35E−03 Low Mood Subtype 0.74/5.91E−03 M-SZ 0.79/1.35E−02 |
| SLC4A4 solute carrier family 4 (sodium bicarbonate cotransporter), member 4 | 210739_x_at | (I) AP/1 | 6 | 7.74E−05/4 | All 0.64/3.83E−04 Combined Subtype 0.69/6.13E−04 M-BP 0.77/9.27E−04 |
| BCL2 B-cell CLL/lymphoma 2 | 203685_at | (D) DE/1 | 5 | 5.98E−11/4 | All 0.61/4.90E−03 M-SZ 0.76/2.73-02 Low Mood Subtype 0.67/4.02E−02 |
| ECHDC1 enoyl CoA hydratase domain containing 1 | 223087_at | (D) DE/2 | 4 | 3.35E−09/4 | All 0.6/9.14E−03 Combined Subtype 0.64/1.04E−02 M-SZA 0.68/3.14E−02 |
| GDI2 GDP dissociation inhibitor 2 | 200008_s_at | (D) DE/2 | 4 | 1.52E−11/4 | All 0.59/1.26E−02 M-BP 0.67/2.39E−02 |
| MTERF4 mitochondrial transcription termination factor 4 | 1557966_x_at | (D) DE/2 | 4 | 6.72E−06/4 | All 0.61/4.64E−03 Low Mood Subtype 0.67/4.21E−02 M-SZ 0.76/2.64E−02 |
| PCDH9 protocadherin 9 | 238919_at | (D) AP/2 | 4 | 6.61E−05/4 | Combined Subtype 0.6/4.45E−02 |
| TGOLN2 trans-golgi network protein 2 | 203834_s_at | (D) AP/1 | 5 | 1.37E−11/4 | |
| YWHAH tyrosine 3-monooxygenase/ tryptophan 5-monooxygenase activation protein, eta | 242325_at | (I) DE/2 | 4 | 6.65E−11/4 | All 0.57/4.92E−02 F-BP 0.79/4.60E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Dir | n | p-value | Subtype/AUC |
|---|---|---|---|---|---|
| ACSM3 acyl-CoA synthetase medium-chain family member 3 | 210377_at | (D) DE/1 | 4 | 9.67E−06/4 | All 0.58/2.90E−02 M-BP 0.69/1.35E−02 |
| AGA aspartylglucosaminidase | 204333_s_at | (D) DE/1 | 4 | 1.51E−06/4 | Combined Subtype 0.62/2.07E−02 |
| AKAP13 A kinase (PRKA) anchor protein 13 | 209534_x_at | (I) DE/1 | 4 | 2.06E−05/4 | Low Mood Subtype 0.68/3.14E−02 M-PTSD 0.78/8.75E−03 |
| AKAP2 A kinase (PRKA) anchor protein 2 | 202759_s_at | (D) DE/1 | 4 | 5.17E−07/4 | Combined Subtype 0.6/4.23E−02 |
| ALDH7A1 aldehyde dehydrogenase 7 family, member A1 | 208951_at | (I) DE/1 | 4 | 1.58E−07/4 | All 0.58/3.55E−02 M-BP 0.68/2.09E−02 |
| ATP6V0E1 ATPase, H+ transporting, lysosomal 9 kDa, V0 subunit e1 | 214244_s_at | (D) DE/1 | 4 | 7.84E−07/4 | M-SZA 0.76/3.76E−03 |
| ATP6V0E1 ATPase, H+ transporting, lysosomal 9 kDa, V0 subunit e1 | 236527_at | (D) AP/1 | 4 | 5.91E−13/4 | M-SZA 0.72/1.29E−02 |
| BRCC3 BRCA1/BRCA2-containing complex, subunit 3 | 216521_s_at | (D) DE/1 | 4 | 1.71E−12/4 | All 0.58/3.74E−02 M-BP 0.72/6.47E−03 |
| CAT catalase | 211922_s_at | (D) DE/1 | 4 | 1.28E−11/4 | All 0.57/3.84E−02 Low Mood Subtype 0.67/4.02E−02 M-BP 0.7/1.14E−02 |
| CTTN cortactin | 214782_at | (I) DE/1 | 4 | 1.04E−19/4 | Combined Subtype 0.61/3.33E−02 M-BP 0.76/1.54E−03 |
| DLG1 discs, large homolog 1 (*Drosophila*) | 202516_s_at | (D) DE/1 | 4 | 1.61E−12/4 | All 0.58/2.91E−02 Low Mood Subtype 0.7/2.02E−02 |
| DUSP13 dual specificity phosphatase 13 | 219963_at | (I) AP/1 | 4 | 5.27E−08/4 | M-SZA 0.73/9.96E−03 |
| ECHDC1 enoyl CoA hydratase domain containing 1 | 219974_x_at | (D) DE/1 | 4 | 4.00E−14/4 | All 0.59/1.38E−02 M-BP 0.65/4.48E−02 Combined Subtype 0.6/4.34E−02 |
| EFEMP2 EGF containing fibulin-like extracellular matrix protein 2 | 209356_x_at | (I) AP/1 | 4 | 2.38E−05/4 | Low Mood Subtype 0.66/4.96E−02 |
| G2E3 G2/M-phase specific E3 ubiquitin protein ligase | 223256_at | (D) DE/1 | 4 | 5.19E−09/4 | Low Mood Subtype 0.67/3.56E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Direction | Score | p-value | Subtype/AUC |
|---|---|---|---|---|---|
| GDI2 GDP dissociation inhibitor 2 | 200009_at | (D) DE/1 | 4 | 1.47E−05/4 | All 0.64/5.93E−04 M-BP 0.74/2.76E−03 Low Mood Subtype 0.69/2.43E−02 |
| IGHG1 | 211633_x_at | (D) AP and DE/1 | 4 | 6.55E−11/4 | M-MDD 0.79/2.47E−03 |
| IL13 interleukin 13 | 207844_at | (I) DE/1 | 4 | 3.38E−08/4 | Low Mood Subtype 0.76/3.51E−03 |
| ITGB1BP1 integrin beta 1 binding protein 1 | 203336_s_at | (D) DE/1 | 4 | 2.54E−08/4 | All 0.57/4.15E−02 |
| ITPKB inositol-trisphosphate 3-kinase B | 232526_at | (I) AP/1 | 4 | 4.46E−09/4 | All 0.62/1.90E−03 M-BP 0.76/1.31E−03 Combined Subtype 0.68/1.76E−03 |
| LRRN3 leucine rich repeat neuronal 3 | 209841_s_at | (D) DE/1 | 4 | 6.69E−10/4 | All 0.58/2.37E−02 M-PTSD 0.77/1.11E−02 |
| MRPS14 mitochondrial ribosomal protein S14 | 203800_s_at | (D) DE/1 | 4 | 3.95E−10/4 | M-SZA 0.72/1.15E−02 |
| MRPS14 mitochondrial ribosomal protein S14 | 203801_at | (D) DE/1 | 4 | 2.45E−17/4 | All 0.6/6.89E−03 M-SZ 0.72/4.66E−02 Low Mood Subtype 0.69/2.63E−02 |
| N4BP2L2 NEDD4 binding protein 2-like 2 | 202259_s_at | (D) DE/1 | 4 | 8.33E−10/4 | Low Mood Subtype 0.66/4.63E−02 |
| PIK3CA phosphatidylinositol-4,5-bisphosphate 3-kinase, catalytic subunit alpha | 231854_at | (D) DE/1 | 4 | 2.41E−37/4 | All 0.57/4.23E−02 M-BP 0.65/4.64E−02 Non-Affective Subtype 0.74/2.24E−02 |
| PPAP2B phosphatidic acid phosphatase type 2B | 212226_s_at | (I) AP/1 | 4 | 2.76E−17/4 | All 0.58/3.64E−02 M-BP 0.65/4.56E−02 Low Mood Subtype 0.75/4.15E−03 |
| PRKAR2B protein kinase, cAMP-dependent, regulatory, type II, beta | 203680_at | (D) DE/1 | 4 | 3.83E−09/4 | F-BP 0.84/2.69E−02 |
| PSMB4 proteasome (prosome, macropain) subunit, beta type, 4 | 202243_s_at | (D) DE/1 | 4 | 6.55E−14/4 | All 0.6/1.07E−02 M-SZA 0.71/1.67E−02 |
| PSME4 Proteasome Activator Subunit 4 | 237180_at | (I) DE/1 | 4 | 2.64E−36/4 | All 0.6/1.11E−02 M-PTSD 0.79/6.82E−03 Low Mood Subtype 0.68/3.47E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Type | | Score | Value | Groups |
|---|---|---|---|---|---|---|
| PTK2 protein tyrosine kinase 2 | 241453_at | (I) | DE/1 | 4 | 2.87E−32/4 | All 0.61/4.53E−03 M-MDD 0.69/3.24E−02 Combined Subtype 0.64/1.04E−02 |
| SECISBP2L SECIS binding protein 2-like | 212450_at | (D) | DE/1 | 4 | 6.30E−05/4 | All 0.59/2.05E−02 M-BP 0.71/7.49E−03 Low Mood Subtype 0.68/3.47E−02 |
| SEPT8 septin 8 | 209000_s_at | (I) | DE/1 | 4 | 4.56E−09/4 | All 0.58/2.31E−02 M-BP 0.69/1.52E−02 Combined Subtype 0.63/1.53E−02 |
| SNX6 sorting nexin 6 | 222410_s_at | (D) | DE/1 | 4 | 6.82E−06/4 | All 0.62/2.46E−03 M-PTSD 0.69/4.93E−02 Low Mood Subtype 0.72/1.15E−02 |
| SOD2 superoxide dismutase 2, mitochondrial | 215078_at | (I) | DE/2 | 5 | 2.27E−34/4 | |
| VTA1 vesicle (multivesicular body) trafficking 1 | 223021_x_at | (D) | DE/1 | 4 | 3.95E−08/4 | All 0.57/4.16E−02 M-SZ/SZA 0.64/3.26E−02 Combined Subtype 0.6/4.29E−02 |
| WIPF3 WAS/WASL interacting protein family, member 3 | 241600_at | (D) | DE/1 | 4 | 1.24E−07/4 | |
| ZNF565 zinc finger protein 565 | 228305_at | (D) | DE/1 | 4 | 4.20E−16/4 | All 0.59/1.31E−02 M-SZA 0.75/4.43E−03 Low Mood Subtype 0.69/2.50E−02 |
| ADK adenosine kinase | 204119_s_at | (D) | DE/4 | 0 | 1.99E−08/4 | All 0.62/2.58E−03 M-PTSD 0.69/4.93E−02 Combined Subtype 0.64/8.60E−03 |
| AIMP1 aminoacyl tRNA synthetase complex-interacting multifunctional protein 1 | 227605_at | (D) | AP/2 | 4 | 1.02E−05/4 | All 0.6/7.31E−03 M-SZA 0.72/1.06E−02 Combined Subtype 0.66/3.69E−03 |
| AK2 adenylate kinase 2 | 212174_at | (D) | DE/2 | 2 | 3.19E−06/4 | All 0.59/1.71E−02 M-SZ 0.76/2.64-02 Combined Subtype 0.62/2.35E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Dir | | | | |
|---|---|---|---|---|---|---|
| AK2 adenylate kinase 2 | 205996_s_at | (D) DE/2 | 2 | 1.15E−07/4 | All 0.64/5.39E−04 M-SZ 0.75/2.93E−02 Combined Subtype 0.62/2.04E−02 | |
| CD109 CD109 molecule | 226545_at | (I) DE/2 | 2 | 2.16E−09/4 | F-BP 0.81/3.73E−02 | |
| DSPP dentin sialophosphoprotein | 221681_s_at | (D) DE/2 | 4 | 7.04E−09/4 | All 0.57/4.26E−02 | |
| HIST1H2BO histone cluster 1, H2bo | 214540_at | (I) DE/4 | 0 | 5.37E−14/4 | M-BP 0.67/2.78E−02 | |
| LEPR leptin receptor | 211355_x_at | (D) DE/2 | 4 | 4.79E−05/4 | | |
| MAP2K5 mitogen-activated protein kinase 5 | 216765_at | (D) AP/2 | 4 | 1.74E−08/4 | M-SZA 0.67/3.56E−02 | |
| MBP myelin basic protein | 225408_at | (D) AP/2 | 4 | 8.34E−07/4 | | |
| MED28 mediator complex subunit 28 | 222636_at | (D) AP/2 | 4 | 1.30E−09/4 | | |
| PITHD1 PITH (C-terminal proteasome-interacting domain of thioredoxin-like) domain containing 1 | 229856_s_at | (D) AP/4 | 0 | 6.61E−08/4 | F-BP 0.83/3.00E−02 | |
| PRKAR1A protein kinase, cAMP-dependent, regulatory, type I, alpha | 200605_s_at | (D) DE/2 | 4 | 2.47E−06/4 | M-BP 0.72/5.84E−03 | |
| RBM3 RNA binding motif (RNP1, RRM) protein 3 | 222026_at | (D) DE/2 | 4 | 1.73E−05/4 | | |
| RIMS3 regulating synaptic membrane exocytosis 3 | 204730_at | (D) AP/4 | 0 | 6.47E−08/4 | | |
| SCAF11 SR-related CTD-associated factor 11 | 206989_s_at | (D) DE/2 | 4 | 1.71E−10/4 | All 0.6/8.62E−03 M-BP 0.77/8.78E−04 Combined Subtype 0.64/9.60E−03 | |
| TBL1XR1 transducin (beta)-like 1 X-linked receptor 1 | 235890_at | (D) AP/2 | 2 | 2.34E−08/4 | M-BP 0.66/3.36E−02 Combined Subtype 0.62/2.48E−02 | |
| ZFYVE21 zinc finger, FYVE domain containing 21 | 219929_s_at | (D) AP/2 | 4 | 5.96E−06/4 | All 0.58/2.56E−02 | |
| ADIRF adipogenesis regulatory factor | 203571_s_at | (I) DE/1 | 4 | 6.58E−14/4 | M-SZ/SZA 0.66/2.22E−02 Low Mood Subtype 0.71/1.58E−02 | |
| AGA aspartylglucosaminidase | 216064_s_at | (D) DE/1 | 4 | 2.41E−06/4 | | |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Direction | Score | p-value | Phenotype/AUC |
|---|---|---|---|---|---|
| AHCYL1 adenosylhomocysteinase-like 1 | 207464_at | (D) DE/1 | 4 | 3.53E−11/4 | |
| AKAP10 A kinase (PRKA) anchor protein 10 | 205045_at | (D) AP/1 | 4 | 4.05E−05/4 | All 0.58/3.79E−02 M-MDD 0.76/5.91E−03 |
| ALDH3A2 aldehyde dehydrogenase 3 family, member A2 | 202053_s_at | (D) DE/1 | 4 | 3.52E−06/4 | |
| ANKMY1 ankyrin repeat and MYND domain containing 1 | 1554610_at | (D) DE/1 | 4 | 6.19E−15/4 | M-PTSD 0.69/4.93E−02 |
| ARRB1 arrestin, beta 1 | 218832_x_at | (D) AP/1 | 4 | 5.26E−17/4 | |
| B2M beta-2-microglobulin | 232311_at | (I) DE/1 | 4 | 5.80E−12/4 | |
| BCKDHB branched chain keto acid dehydrogenase E1, beta polypeptide | 213321_at | (D) DE/1 | 4 | 1.72E−11/4 | |
| BRCC3 BRCA1/BRCA 2-containing complex, subunit 3 | 221196_x_at | (D) DE and AP/1 | 4 | 6.11E−12/4 | M-BP 0.73/4.69E−03 Low Mood Subtype 0.69/2.50E−02 |
| CAT catalase | 201432_at | (D) DE/1 | 4 | 3.39E−14/4 | M-BP 0.69/1.54E−02 Low Mood Subtype 0.7/1.97E−02 |
| CDC42EP4 CDC42 effector protein (Rho GTPase binding) 4 | 218062_x_at | (D) AP/1 | 4 | 1.48E−05/4 | |
| CLN5 ceroid-lipofuscinosis, neuronal 5 | 214252_s_at | (D) DE/1 | 4 | 1.79E−15/4 | All 0.65/1.86E−04 M-SZ/SZA 0.68/9.51E−03 Low Mood Subtype 0.75/4.43E−03 |
| CLTA clathrin, light chain A | 20405 0_s_at | (D) DE/1 | 4 | 7.07E−11/4 | All 0.6/7.10E−03 M-BP 0.68/2.18E−02 Combined Subtype 0.62/2.48E−02 |
| CLTA clathrin, light chain A | 216295_s_at | (D) DE/1 | 4 | 1.74E−15/4 | All 0.64/6.31E−04 M-SZ 0.77/2.20E−02 Combined Subtype 0.67/2.41E−03 |
| DAB2 Dab, mitogen-responsive phosphoprotein, homolog 2 (*Drosophila*) | 201279_s_at | (I) DE/1 | 4 | 6.28E−07/4 | All 0.59/1.99E−02 M-PTSD 0.72/3.02E−02 |
| FADS1 fatty acid desaturase 1 /// microRNA 1908 | 208964_s_at | (I) DE/1 | 4 | 3.12E−11/4 | M-PTSD 0.7/4.07E−02 |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Direction | Score | p-value | Subtype AUC |
|---|---|---|---|---|---|
| NGFR nerve growth factor receptor | 205858_at | (I) DE/1 | 4 | 2.24E−15/4 | All 0.59/1.81E−02 M-SZA 0.73/9.96E−03 Combined Subtype 0.66/4.27E−03 |
| OLIG1 oligodendrocyte transcription factor 1 | 228170_at | (D) DE/1 | 4 | 9.88E−16/4 | |
| PAFAH1B2 platelet-activating factor acetylhydrolase 1b, catalytic subunit 2 □Z | 210160_at | (D) DE/1 | 4 | 6.61E−18/4 | |
| POLR2D polymerase (RNA) II (DNA directed) polypeptide D | 214144_at | (D) AP/1 | 4 | 1.38E−13/4 | M-SZ/SZA 0.63/4.45E−02 Low Mood Subtype 0.66/4.42E−02 |
| PRKCB protein kinase C, beta | 227824_at | (D) DE and AP/1 | 4 | 2.40E−13/4 | |
| SMCR8 Smith-Magenis syndrome chromosome region, candidate 8 | 227304_at | (D) DE/1 | 4 | 1.37E−13/4 | All 0.58/2.35E−02 M-SZ 0.76/2.54E−02 Low Mood Subtype 0.69/2.37E−02 |
| SMCR8 Smith-Magenis syndrome chromosome region, candidate 8 | 227305_s_at | (D) DE/1 | 4 | 5.56E−12/4 | M-BP 0.67/2.53E−02 |
| SMCR8 Smith-Magenis syndrome chromosome region, candidate 8 | 238434_at | (D) DE/1 | 4 | 2.88E−10/4 | |
| SPTBN1 spectrin, beta, non-erythrocytic 1 | 200672_x_at | (D) DE/1 | 4 | 4.56E−07/4 | |
| TM4SF1 transmembrane 4 L six family member 1 | 209386_at | (I) DE/1 | 4 | 1.28E−12/4 | |
| TPD52 tumor protein D52 | 201691_s_at | (D) DE/1 | 4 | 5.67E−12/4 | Low Mood Subtype 0.73/7.59E−03 |
| TTBK1 tau tubulin kinase 1 | 230191_at | (D) DE/1 | 4 | 4.81E−07/4 | |
| VAMP3 vesicle-associated membrane protein 3 | 211749_s_at | (D) DE/1 | 4 | 7.97E−07/4 | |
| WARS tryptophanyl-tRNA synthetase | 200628_s_at | (D) AP/1 | 4 | 2.00E−05/4 | Anxious Subtype 0.73/4.84E−02 |
| WNK1 WNK lysine deficient protein kinase 1 | 202940_at | (D) AP/1 | 4 | 2.38E−12/4 | |

TABLE 20-continued

Convergent Functional Evidence (CFE). Universal Top Dozen and Bonferroni biomarkers.
Only predictions with a significant p-value for the ROC AUC are tabulated and shown.

| Gene | Probe | Type | | Value | Subtype |
|---|---|---|---|---|---|
| XRCC5 X-ray repair complementing defective repair in Chinese hamster cells 5 (double-strand-break rejoining) | 208643_s_at | (D) DE/1 | 4 | 3.71E−22/4 | Combined Subtype 0.61/4.03E−02 |
| ZNF75D zinc finger protein 75D | 1553225_s_at | (D) AP/4 | 1 | 5.40E−14/4 | All 0.58/2.79E−02 M-BP 0.73/4.80E−03 Combined Subtype 0.6/4.61E−02 |
| AIMP1 aminoacyl tRNA synthetase complex-interacting multifunctional protein 1 | 202542_s_at | (D) DE/4 | 4 | 1.48E−05/4 | All 0.59/1.31E−02 M-SZA 0.71/1.45E−02 Low Mood Subtype 0.69/2.25E−02 |
| FAM63B family with sequence similarity 63, member B | 214691_x_at | (D) DE/4 | 0 | 6.24E−11/4 | |
| FH fumarate hydratase | 203032_s_at | (D) DE/2 | 4 | 8.14E−20/4 | |
| TMEM254 transmembrane protein 254 | 218174_s_at | (D) DE/2 | 4 | 4.56E−15/4 | Combined Subtype 0.63/1.67E−02 |
| TUBGCP3 tubulin, gamma complex associated protein 3 | 215739_s_at | (D) DE/2 | 2 | 3.48E−24/4 | M-BP 0.78/7.44E−04 Combined Subtype 0.61/3.28E−02 |
| UQCC1 ubiquinol-cytochrome c reductase complex assembly factor 1 | 222470_s_at | (D) DE/4 | 0 | 6.99E−33/4 | All 0.57/4.27E−02 |
| VIP vasoactive intestinal peptide | 206577_at | (D) DE/1 | 5 | 3.76E−14/4 | |
| AHCYL2 adenosylhomocysteinase-like 2 | 212814_at | (D) AP/1 | 4 | 6.28E−05/4 | |
| C20orf27 chromosome 20 open reading frame 27 | 218081_at | (D) DE/1 | 4 | 3.56E−35/4 | |
| C8orf74 chromosome 8 open reading frame 74 | 1569245_at | (D) DE/1 | 6 | 6.63E−08/4 | |
| DLL1 delta-like 1 (Drosophila) | 227938_s_at | (D) DE/1 | 4 | 2.72E−10/4 | |
| FLOT2 flotillin 2 | 211299_s_at | (D) AP/1 | 4 | 1.17E−10/4 | |
| MAP2K5 mitogen-activated protein kinase kinase 5 | 211370_s_at | (D) DE/1 | 4 | 4.24E−05/4 | |
| MT1E metallothionein 1E | 212859_x_at | (I) DE/1 | 4 | 2.38E−09/4 | |

TABLE 20-continued

Convergent Functional Evidence (CFE). Universal Top Dozen and Bonferroni biomarkers.
Only predictions with a significant p-value for the ROC AUC are tabulated and shown.

| | | | | | |
|---|---|---|---|---|---|
| MTERF4 mitochondrial transcription termination factor 4 | 214364_at | (D) AP/1 | 4 | 3.38E−09/4 | |
| NEK9 NIMA-related kinase 9 | 212299_at | (D) DE/1 | 4 | 1.08E−09/4 | M-BP 0.69/1.75E−02 |
| SRR serine racemase | 222844_s_at | (D) DE/1 | 4 | 1.36E−18/4 | |
| SYNPO2L synaptopodin 2-like | 219804_at | (I) DE/1 | 4 | 1.12E−09/4 | Low Mood Subtype 0.69/2.50E−02 |
| TMEM245 transmembrane protein 245 | 223006_s_at | (D) DE/1 | 4 | 2.10E−08/4 | |
| TRAF3 TNF receptor-associated factor 3 | 221571_at | (D) DE/1 | 4 | 1.61E−25/4 | |
| TRIM23 tripartite motif containing 23 | 210995_s_at | (D) DE/1 | 4 | 3.24E−21/4 | |
| ADAL adenosine deaminase-like | 239711_at | (D) AP/4 | 0 | 1.23E−05/4 | |
| ANKMY1 ankyrin repeat and MYND domain containing 1 | 210486_at | (D) AP/2 | 4 | 6.98E−04/2 | M-SZ/SZA 0.67/1.66E−02 Combined Subtype 0.67/2.08E−03 |
| BF114768 — | 236879_at | (I) DE/4 | 0 | 1.61E−23/4 | |
| CDKAL1 CDK5 regulatory subunit associated protein 1-like 1 | 214877_at | (D) DE/4 | 0 | 3.66E−14/4 | |
| CENPH centromere protein H | 231772_x_at | (D) DE/4 | 0 | 4.47E−15/4 | M-SZ 0.72/4.96E−02 Low Mood Subtype 0.69/2.40E−02 |
| ERG V-Ets avian erythroblastosis virus E26 oncogene homolog | 213541_s_at | (D) DE/4 | 0 | NS | M-SZA 0.66/4.96E−02 Non-Affective Subtype 0.75/1.93E−02 |
| KBTBD2 kelch repeat and BTB (POZ) domain containing 2 | 223585_x_at | (D) DE/2 | 2 | 2.77E−06/4 | |
| LDLRAP1 low density lipoprotein receptor adaptor protein 1 | 221790_s_at | (D) DE/4 | 4 | 1.97E−32/4 | |
| RPAP3 RNA polymerase II associated protein 3 | 1557984_s_at | (D) AP/4 | 0 | 1.06E−05/4 | |
| SET SET nuclear proto-oncogene /// SET pseudogene 4 ///SET-like protein | 215780_s_at | (D) DE/4 | 0 | 1.19E−05/4 | |

TABLE 20-continued

Convergent Functional Evidence (CFE). Universal Top Dozen and Bonferroni biomarkers.
Only predictions with a significant p-value for the ROC AUC are tabulated and shown.

| | | | | | |
|---|---|---|---|---|---|
| WWP2<br>WW domain containing E3 ubiquitin protein ligase 2 | 1552737_s_at | (D)<br>AP/4 | 0 | 3.71E−06/4 | |
| C14orf180<br>chromosome 14 open reading frame 180 | 1558420_at | (I)<br>DE/1 | 4 | 3.21E−10/4 | |
| LDLRAP1<br>low density lipoprotein receptor adaptor protein 1 | 57082_at | (D)<br>DE/1 | 4 | 1.49E−38/4 | |
| SPATA18<br>spermatogenesis associated 18 | 229331_at | (I)<br>DE/1 | 4 | 1.10E−06/4 | |
| VPREB3<br>pre-B lymphocyte 3 | 220068_at | (D)<br>DE/1 | 4 | 1.79E−11/4 | |
| CCL28<br>chemokine (C-C motif) ligand 28 | 224240_s_at | (D)<br>AP/4 | 0 | NS | |
| GAB1<br>GRB2 Associated Binding Protein 1 | 242572_at | (I)<br>AP/4 | 0 | NS | F-BP<br>0.88/1.49E−02 |
| SUMF2<br>sulfatase modifying factor 2 | 225002_s_at | (D)<br>DE/4 | 0 | 1.69E−08/4 | |

| Gene Symbol/<br>Gene Name | Step 4<br>Significant<br>Prediction of<br>First Year<br>Hospitalizations<br>for Suicidality<br>All<br>Best in<br>Subtypes<br>Best in<br>Individualized<br>Gender/Dx<br>ROC AUC/<br>p-value | Step 5<br>Other<br>Psychiatric<br>and Related<br>Disorders<br>Evidence | Step 6<br>Drugs that<br>Modulate the<br>Biomarker in<br>Opposite<br>Direction to<br>Suicide | CFE<br>Polyevidence<br>Score |
|---|---|---|---|---|
| APOE<br>apolipoprotein E | M-PTSD<br>0.78/4.43E−02 | Aggression<br>Aging<br>Alcohol<br>Alzheimer's<br>Disease<br>ASD<br>Dementia<br>Depression-<br>related<br>Longevity<br>MDD<br>SZ/SZA<br>PTSD<br>SZ | Omega-3 | 19 |
| IL6<br>interleukin 6 | M-PTSD<br>0.82/2.58E−02 | Aggression<br>Antipsychotics<br>Anxiety<br>BP<br>Cognition<br>Dementia<br>Depression<br>Longevity<br>MDD<br>Mood | Antipsychotics<br>Antidepressants<br>Tocilizumab<br>Siltuximab | 19 |

TABLE 20-continued

Convergent Functional Evidence (CFE). Universal Top Dozen and Bonferroni biomarkers.
Only predictions with a significant p-value for the ROC AUC are tabulated and shown.

| | | Neurological Panic Personality SZ/SZA PTSD Sleep Stress SZ | | |
|---|---|---|---|---|
| CD164 CD164 molecule, sialomucin | M-PTSD 0.86/1.43E−02 | BP Cocaine Dependence Stress | Clozapine | 18 |
| CD47 CD47 molecule | M-PTSD 0.79/3.72E−02 | MDD Stress SZ | Clozapine Omega-3 | 18 |
| HTR2A 5-hydroxytryptamine (serotonin) receptor 2A, G protein-coupled | M-SZA 0.72/1.47E−02 | Alcohol Anxiety BP MDD SZ OCD Response to Antidepressants | Clozapine Lithium Valproate Paliperidone, Risperidone Loxapine, Quetiapine Olanzapine, Nefazodone Mirtazapine Ziprasidone Aripiprazole | 18 |
| PGK1 phosphoglycerate kinase 1 | M-SZA 0.71/1.84E−02 | Alcohol BP MDD SZ SZA | Clozapine Diazepam | 18 |
| PKP4 plakophilin 4 | Combined Subtype 0.68/8.75E−03 | Alcohol BP MDD SZ/SZA SZ | Valproate | 18 |
| ACP1 acid phosphatase 1, soluble | M-MDD 0.74/3.79E−02 | BP SZ | Omega-3 SSRIs Olanzapine | 17 |
| DYRK2 dual-specificity tyrosine-(Y)-phosphorylation regulated kinase 2 | M-PTSD 0.82/2.58E−02 | Aging BP MDD Sleep | Clozapine | 17 |
| GATM glycine amidinotransferase (L-arginine: glycine amidinotransferase) | M-PTSD 0.78/4.43E−02 | Alzheimer's Disease BP MDD PTSD | Omega-3 | 17 |
| GSK3B glycogen synthase kinase 3 beta | | Aging Alcohol BP Dementia Depression Mood Stabilizers Lithium response MDD SZ | Lithium SSRI Antipsychotics | 17 |
| IFNG interferon, gamma | M-PTSD 0.82/2.58E−02 | SZ MDD PTSD Anxiety SZ/SZA | Antipsychotics | 17 |
| ITGB1BP1 integrin beta 1 binding protein 1 | Non-Affective Subtype 0.7/2.59E−02 | Alzheimer's Disease BP Mood SZ | Lithium | 17 |
| LHFP lipoma HMGIC fusion partner | M-MDD 0.98/2.54E−04 | SZ | Omega-3 | 17 |

TABLE 20-continued

Convergent Functional Evidence (CFE). Universal Top Dozen and Bonferroni biomarkers.
Only predictions with a significant p-value for the ROC AUC are tabulated and shown.

| Gene | Subtype | Phenotype | Drug | Score |
|---|---|---|---|---|
| LPAR1 lysophosphatidic acid receptor 1 | Anxious Subtype 0.77/1.33E−02 | Aging BP Longevity MDD Mood PTSD SZ | Clozapine Omega-3 Antidepressants | 17 |
| PRKCI protein kinase C, iota | Combined Subtype 0.64/2.64E−02 | BP Circadian abnormalities Cocaine Dependence MDD SZ | Ingenol mebutate | 17 |
| SKA2 spindle and kinetochore associated complex subunit 2 | M-PTSD 0.84/1.75E−02 | PTSD Stress | | 17 |
| SLC4A4 solute carrier family 4 (sodium bicarbonate cotransporter), member 4 | | Circadian abnormalities Longevity MDD SZ | Valproate | 17 |
| BCL2 B-cell CLL/lymphoma 2 | | Aging Alcohol Anxiety BP Mood PTSD SZ | Lithium Oblimersen Paclitaxel | 16 |
| ECHDC1 enoyl CoA hydratase domain containing 1 | M-PTSD 0.84/1.75E−02 | Addictions BP PTSD | | 16 |
| GDI2 GDP dissociation inhibitor 2 | | BP MDD Mood SZ | Clozapine | 16 |
| MTERF4 mitochondrial transcription termination factor 4 | Non-Affective Subtype 0.67/4.71E−02 | Stress | | 16 |
| PCDH9 protocadherin 9 | | Aging MDD SZ/SZA SZ | Clozapine Omega-3 | 16 |
| TGOLN2 trans-golgi network protein 2 | Combined Subtype 0.64/3.41E−02 | BP Cocaine Dependence MDD Stress SZ | Clozapine | 16 |
| YWHAH tyrosine 3-monooxygenase/ tryptophan 5-monooxy genase activation protein, eta | | Alcohol BP Longevity MDD SZ | Omega-3 Clozapine | 16 |
| ACSM3 acyl-CoA synthetase medium-chain family member 3 | M-PTSD 0.79/3.72E−02 | MDD Mood | | 15 |
| AGA aspartylglucosaminidase | | MDD SZ | Haloperidol Antidepressants | 15 |
| AKAP13 A kinase (PRKA) anchor protein 13 | | Cocaine Dependence Other Substances/ Addictions | Clozapine Diazepam Haloperidol | 15 |

TABLE 20-continued

Convergent Functional Evidence (CFE). Universal Top Dozen and Bonferroni biomarkers.
Only predictions with a significant p-value for the ROC AUC are tabulated and shown.

| | | | | |
|---|---|---|---|---|
| AKAP2<br>A kinase<br>(PRKA) anchor<br>protein 2 | | Panic<br>Stress<br>MDD | Clozapine | 15 |
| ALDH7A1<br>aldehyde<br>dehydrogenase<br>7 family,<br>member A1 | M-SZA<br>0.72/1.47E−02 | BP<br>SZ<br>Stress | | 15 |
| ATP6V0E1<br>ATPase, H+<br>transporting,<br>lysosomal<br>9 kDa, V0<br>subunit e1 | Anxious<br>Subtype<br>0.76/1.55E−02<br>M-SZA<br>0.73/1.21E−02 | Alcohol<br>BP<br>MDD<br>Stress | | 15 |
| ATP6V0E1<br>ATPase, H+<br>transporting,<br>lysosomal<br>9 kDa, V0<br>subunit e1 | M-SZA<br>0.68/3.86E−02 | Alcohol<br>BP<br>MDD<br>Stress | | 15 |
| BRCC3<br>BRCA1/BRCA<br>2-containing<br>complex,<br>subunit 3 | Combined<br>Subtype<br>0.63/3.85E−02 | Sleep<br>BP | | 15 |
| CAT<br>catalase | M-SZA<br>0.70/2.29E−02 | BP<br>Longevity<br>MDD<br>Mood<br>PTSD<br>SZ | | 15 |
| CTTN<br>cortactin | | BP<br>Effect of<br>valproate<br>MDD<br>Stress | Clozapine<br>Omega-3<br>Valproate | 15 |
| DLG1<br>discs, large<br>homolog 1<br>(*Drosophila*) | | Alcohol<br>BP<br>MDD<br>SZ | Omega-3<br>Clozapine | 15 |
| DUSP13<br>dual specificity<br>phosphatase 13 | | SZ/SZA | Olanzapine | 15 |
| ECHDC1<br>enoyl CoA<br>hydratase<br>domain<br>containing 1 | M-PTSD<br>0.79/3.72E−02 | Addictions<br>BP<br>PTSD | | 15 |
| EFEMP2<br>EGF containing<br>fibulin-like<br>extracellular<br>matrix protein 2 | | Neurological | Clozapine | 15 |
| G2E3<br>G2/M-phase<br>specific E3<br>ubiquitin<br>protein ligase | | Cocaine<br>Dependence | Omega-3 | 15 |
| GDI2<br>GDP<br>dissociation<br>inhibitor 2 | | BP<br>MDD<br>Mood<br>SZ | Clozapine | 15 |
| IGHG1<br>— | M-MDD<br>0.9/1.64E−03 | ASD<br>BP<br>Mood<br>SZ/SZA<br>Stress<br>SZ<br>SZA | | 15 |
| IL13<br>interleukin 13 | | MDD<br>SZ | CAT-354 | 15 |
| ITGB1BP1<br>integrin beta 1<br>binding protein 1 | | Alzheimer's<br>Disease<br>BP | Lithium | 15 |

TABLE 20-continued

Convergent Functional Evidence (CFE). Universal Top Dozen and Bonferroni biomarkers.
Only predictions with a significant p-value for the ROC AUC are tabulated and shown.

| Gene | | | | |
|---|---|---|---|---|
| ITPKB<br>inositol-<br>trisphosphate 3-<br>kinase B | | Mood<br>SZ<br>Aging<br>Alcohol<br>Alzheimer's<br>Disease<br>ASD<br>BP<br>MDD<br>Multiple<br>Sclerosis<br>Stress<br>SZ<br>SZA | Omega-3 | 15 |
| LRRN3<br>leucine rich<br>repeat neuronal 3 | | Bipolar disorder<br>(Effect of Mood<br>Stibilizers) | Mood<br>stabilizers | 15 |
| MRPS14<br>mitochondrial<br>ribosomal<br>protein S14 | | SZ | Omega-3 | 15 |
| MRPS14<br>mitochondrial<br>ribosomal<br>protein S14 | | SZ | Omega-3 | 15 |
| N4BP2L2<br>NEDD4<br>binding protein<br>2-like 2 | M-PTSD<br>0.8/3.11E−02 | BP<br>MDD<br>SZ | | 15 |
| PIK3CA<br>phosphatidylinositol-<br>4,5-bisphosphate 3-<br>kinase, catalytic<br>subunit alpha | | Longevity<br>MDD<br>Stress<br>SZ | Lithium | 15 |
| PPAP2B<br>phosphatidic<br>acid<br>phosphatase<br>type 2B | M-PTSD<br>0.83/2.13E−02 | SZ/SZA<br>SZ | | 15 |
| PRKAR2B<br>protein kinase,<br>cAMP-<br>dependent,<br>regulatory, type<br>II, beta | | Alcohol<br>Antipsychotics<br>BP<br>MDD<br>PTSD<br>SZ | Clozapine<br>Valproate | 15 |
| PSMB4<br>proteasome<br>(prosome,<br>macropain)<br>subunit, beta<br>type, 4 | | BP<br>MDD<br>SZ<br>SZA | Diazepam | 15 |
| PSME4<br>Proteasome<br>Activator<br>Subunit 4 | All<br>0.59/2.62E−02<br>Low Mood<br>Subtype<br>0.72/4.73E−02 | ASD | | 15 |
| PTK2<br>protein tyrosine<br>kinase 2 | | Alcohol<br>ASD<br>BP<br>Circadian<br>abnormalities<br>MDD<br>Neurological<br>SZ/SZA<br>Stress<br>SZ | CT-707 | 15 |
| SECISBP2L<br>SECIS binding<br>protein 2-like | | Cocaine<br>Dependence<br>MDD<br>SZ | Clozapine | 15 |
| SEPT8<br>septin 8 | M-SZA<br>0.68/4.14E−02 | Alcohol<br>Epilepsy<br>Mood<br>SZ | | 15 |

TABLE 20-continued

Convergent Functional Evidence (CFE). Universal Top Dozen and Bonferroni biomarkers.
Only predictions with a significant p-value for the ROC AUC are tabulated and shown.

| Gene | | | | |
|---|---|---|---|---|
| SNX6 sorting nexin 6 | M-PTSD 0.83/2.13E−02 | Panic | | 15 |
| SOD2 superoxide dismutase 2, mitochondrial | | Longevity MDD methamphetamine SZ/SZA Mood SZ | Clozapine Antidepressants | 15 |
| VTA1 vesicle (multivesicular body) trafficking 1 | M-SZA 0.67/4.55E−02 | BP MDD SZ SZA | | 15 |
| WIPF3 WAS/WASL interacting protein family, member 3 | M-MDD 0.82/9.58E−03 | SZ | Clozapine | 15 |
| ZNF565 zinc finger protein 565 | All 0.6/2.36E−02 M-SZA 0.67/4.81E−02 Anxious Subtype 0.71/3.93E−02 | SZ | | 15 |
| ADK adenosine kinase | | Depression | Omega-3 | 14 |
| AIMP1 aminoacyl tRNA synthetase complex-interacting multifunctional protein 1 | M-PTSD 0.82/2.58E−02 Non-Affective Subtype 0.68/3.83E−02 | | | 14 |
| AK2 adenylate kinase 2 | All 0.59/3.29E−02 Non-Affective Subtype 0.71/2.05E−02 | BP SZ | | 14 |
| AK2 adenylate kinase 2 | All 0.6/2.31E−02 M-SZA 0.78/2.70E−03 Combined Subtype 0.68/6.72E−03 | BP SZ | | 14 |
| CD109 CD109 molecule | M-MDD 0.76/2.90E−02 | Response to paroxetine (SSRI) | | 14 |
| DSPP dentin sialophosphoprotein | | SZ Circadian abnormalities | | 14 |
| HIST1H2BO histone cluster 1, H2bo | Anxious Subtype 0.71/4.20E−02 | Stress | | 14 |
| LEPR leptin receptor | | Alcohol Cocaine Dependence MDD Mood Other Substances/ Addictions | Antidepressants Recombinant-methionyl human leptin | 14 |
| MAP2K5 mitogen-activated protein kinase kinase 5 | | Agoraphobia BP MDD Methamphetamine dependence Other Substances/ Addictions | | 14 |

TABLE 20-continued

Convergent Functional Evidence (CFE). Universal Top Dozen and Bonferroni biomarkers.
Only predictions with a significant p-value for the ROC AUC are tabulated and shown.

| Gene | | | | |
|---|---|---|---|---|
| MBP myelin basic protein | | Alcohol Alzheimer's Disease BP MDD Mood Neurological SZ | Clozapine Omega-3 Lithium | 14 |
| MED28 mediator complex subunit 28 | M-PTSD 0.83/2.13E−02 | Alcohol BP PTSD | | 14 |
| PITHD1 PITH (C-terminal proteasome-interacting domain of thioredoxin-like) domain containing 1 | M-PTSD 0.78/4.43E−02 | BP SZ/SZA SZ | | 14 |
| PRKAR1A protein kinase, cAMP-dependent, regulatory, type I, alpha | | Alcohol BP Epilepsy Mood Stress SZ | | 14 |
| RBM3 RNA binding motif (RNP1, RRM) protein 3 | | Epilepsy Response to Lithium (Bipolar) SZ | Omega-3 Valproate | 14 |
| RIMS3 regulating synaptic membrane exocytosis 3 | Non-Affective Subtype 0.73/1.37E−02 | Alcohol Antipsychotics BP SZ | Clozapine Haloperidol | 14 |
| SCAF11 SR-related CTD-associated factor 11 | | BP Mood | | 14 |
| TBL1XR1 transducin (beta)-like 1 X-linked receptor 1 | | Alcohol BP Longevity | Clozapine | 14 |
| ZFYVE21 zinc finger, FYVE domain containing 21 | | SZ | | 14 |
| ADIRF adipogenesis regulatory factor | | BP | | 13 |
| AGA aspartyl glucosaminidase | | MDD SZ | Haloperidol Antidepressants | 13 |
| AHCYL1 adenosylhomocysteinase-like 1 | | SZ | Omega-3 | 13 |
| AKAP10 A kinase (PRKA) anchor protein 10 | | BP | | 13 |
| ALDH3A2 aldehyde dehydrogenase 3 family, member A2 | M-PTSD 0.83/2.13E−02 Combined Subtype 0.63/4.65E−02 | BP | | 13 |
| ANKMY1 ankyrin repeat and MYND domain containing 1 | M-MDD 0.76/2.71E−02 | | | 13 |
| ARRB1 arrestin, beta 1 | M-SZA 0.69/3.35E−02 Combined | Alcohol MDD Personality | | 13 |

TABLE 20-continued

Convergent Functional Evidence (CFE). Universal Top Dozen and Bonferroni biomarkers.
Only predictions with a significant p-value for the ROC AUC are tabulated and shown.

| Gene | Subtype | Condition | Treatment | Score |
|---|---|---|---|---|
| | Subtype 0.65/2.19E−02 | Response to paroxetine (SSRI) | | |
| B2M beta-2-microglobulin | | Stress Alcohol Effect of valproate MDD SZ | Omega-3 | 13 |
| BCKDHB branched chain keto acid dehydrogenase E1, beta polypeptide | All 0.59/3.90E−02 M-SZ 0.67/3.74E−02 Non-Affective Subtype 0.7/2.53E−02 | MDD SZ/SZA | | 13 |
| BRCC3 BRCA1/BRCA 2-containing complex, subunit 3 | | Sleep BP | | 13 |
| CAT catalase | | BP Longevity MDD Mood PTSD SZ | | 13 |
| CDC42EP4 CDC42 effector protein (Rho GTPase binding) 4 | All 0.59/2.91E−02 M-MDD 0.85/5.84E−03 Low Mood Subtype 0.84/5.28E−03 | Aging Alcohol MDD | | 13 |
| CLN5 ceroid-lipofuscinosis, neuronal 5 | M-PTSD 0.87/1.16E−02 | | | 13 |
| CLTA clathrin, light chain A | | Alzheimer's Disease BP MDD | | 13 |
| CLTA clathrin, light chain A | | Alzheimer's Disease BP MDD | | 13 |
| DAB2 Dab, mitogen-responsive phosphoprotein, homolog 2 (*Drosophila*) | | SZ/SZA | | 13 |
| FADS1 fatty acid desaturase 1 /// microRNA 1908 | | Aging Antipsychotics SZ | | 13 |
| NGFR nerve growth factor receptor | | MDD OCD Panic Disorder SZ | | 13 |
| OLIG1 oligodendrocyte transcription factor 1 | Non-Affective Subtype 0.69/3.08E−02 | Agreeableness SZ | | 13 |
| PAFAH1B2 platelet-activating factor acetylhydrolase 1b, catalytic subunit 2 | | Lithium effect | Lithium | 13 |

TABLE 20-continued

Convergent Functional Evidence (CFE). Universal Top Dozen and Bonferroni biomarkers.
Only predictions with a significant p-value for the ROC AUC are tabulated and shown.

| | | | | |
|---|---|---|---|---|
| POLR2D polymerase (RNA) II (DNA directed) polypeptide D | | BP | | 13 |
| PRKCB protein kinase C, beta | | Aging ASD BP MDD PTSD Stress SZ | Lithium Ingenol mebutate | 13 |
| SMCR8 Smith-Magenis syndrome chromosome region, candidate 8 | | MDD Anxiety | | 13 |
| SMCR8 Smith-Magenis syndrome chromosome region, candidate 8 | | MDD Anxiety | | 13 |
| SMCR8 Smith-Magenis syndrome chromosome region, candidate 8 | Combined Subtype 0.63/4.42E−02 | MDD Anxiety | | 13 |
| SPTBN1 spectrin, beta, non-erythrocytic 1 | | Aging BP Longevity MDD SZ | Clozapine Omega-3 Diazepam | 13 |
| TM4SF1 transmembrane 4 L six family member 1 | | SZ BP | Lithium Omega-Antipschotic | 13 |
| TPD52 tumor protein D52 | | BP Mood Myalgic Encephalomyelitis/ Chronic Fatigue Syndrome SZ | | 13 |
| TTBK1 tau tubulin kinase 1 | | SZ | Clozapine | 13 |
| VAMP3 vesicle-associated membrane protein 3 | | Alcohol lithium effect MDD Stress valproate effect | Lithium | 13 |
| WARS tryptophanyl-tRNA synthetase | | Alcohol SZ | | 13 |
| WNK1 WNK lysine deficient protein kinase 1 | | Alcohol BP Cocaine Dependence MDD SZ | Omega-3 SSRI | 13 |
| XRCC5 X-ray repair complementing defective repair in Chinese hamster cells 5 (double-strand-break rejoining) | | Alcohol BP Longevity MDD | | 13 |

TABLE 20-continued

Convergent Functional Evidence (CFE). Universal Top Dozen and Bonferroni biomarkers.
Only predictions with a significant p-value for the ROC AUC are tabulated and shown.

| Gene | Condition | Drug | Score |
|---|---|---|---|
| ZNF75D zinc finger protein 75D | Circadian abnormalities Myalgic Encephalomyelitis/ Chronic Fatigue Syndrome | | 13 |
| AIMP1 aminoacyl tRNA synthetase complex-interacting multifunctional protein 1 | | | 12 |
| FAM63B family with sequence similarity 63, member B | BP Mood Sleep SZ | Clozapine | 12 |
| FH fumarate hydratase | BP MDD Stress | | 12 |
| TMEM254 transmembrane protein 254 | | | 12 |
| TUBGCP3 tubulin, gamma complex associated protein 3 | BP | | 12 |
| UQCC1 ubiquinol-cytochrome c reductase complex assembly factor 1 | BP | | 12 |
| VIP vasoactive intestinal peptide | Alcohol BP MDD SZ | | 12 |
| AHCYL2 adenosylhomocysteinase-like 2 | ASD | | 11 |
| C20orf27 chromosome 20 open reading frame 27 | BP MDD | | 11 |
| C8orf74 chromosome 8 open reading frame 74 | | | 11 |
| DLL1 delta-like 1 (*Drosophila*) | BP PTSD SZ | | 11 |
| FLOT2 flotillin 2 | SZ | | 11 |
| MAP2K5 mitogen-activated protein kinase kinase 5 | Agoraphobia BP MDD Methamphetamine dependence Other Substances/ Addictions | | 11 |
| MT1E metallothionein 1E | BP SZ SZ/SZA | | 11 |
| MTERF4 mitochondrial transcription termination factor 4 | Stress | | 11 |
| NEK9 NIMA-related kinase 9 | | | 11 |

TABLE 20-continued

Convergent Functional Evidence (CFE). Universal Top Dozen and Bonferroni biomarkers.
Only predictions with a significant p-value for the ROC AUC are tabulated and shown.

| | | | |
|---|---|---|---|
| SRR<br>serine racemase | | SZ | 11 |
| SYNPO2L<br>synaptopodin 2-like | | | 11 |
| TMEM245<br>transmembrane protein 245 | | BP<br>MDD<br>Stress | 11 |
| TRAF3<br>TNF receptor-associated factor 3 | | BP<br>MDD<br>Neurological<br>Stress<br>SZ<br>SZA | 11 |
| TRIM23<br>tripartite motif containing 23 | | BP<br>SZ | 11 |
| ADAL<br>adenosine deaminase-like | | Mood<br>Circardian abnormalities | 10 |
| ANKMY1<br>ankyrin repeat and MYND domain containing 1 | | | 10 |
| BF114768<br>— | Non-Affective<br>Subtype<br>0.69/3.36E−02 | | 10 |
| CDKAL1<br>CDK5 regulatory subunit associated protein 1-like 1 | | Alcohol<br>BP<br>SZ | 10 |
| CENPH<br>centromere protein H | | | 10 |
| ERG<br>V-Ets avian erythroblastosis virus E26 oncogene homolog | Low Mood<br>Subtype<br>0.82/8.29E−03 | Alcohol | 10 |
| KBTBD2<br>kelch repeat and BTB (POZ) domain containing 2 | M-SZA<br>0.7/2.43E−02 | | 10 |
| LDLRAP1<br>low density lipoprotein receptor adaptor protein 1 | | | 10 |
| RPAP3<br>RNA polymerase II associated protein 3 | | SZ/SZA | 10 |
| SET<br>SET nuclear proto-oncogene /// SET pseudogene 4 ///SET-like protein | | Alzheimer's<br>Epilepsy | 10 |
| WWP2<br>WW domain containing E3 ubiquitin protein ligase 2 | | Alcohol<br>SZ | 10 |
| C14orf180<br>chromosome 14 open reading frame 180 | | | 9 |

TABLE 20-continued

Convergent Functional Evidence (CFE). Universal Top Dozen and Bonferroni biomarkers.
Only predictions with a significant p-value for the ROC AUC are tabulated and shown.

| | | | |
|---|---|---|---|
| LDLRAP1 low density lipoprotein receptor adaptor protein 1 | | | 9 |
| SPATA18 spermatogenesis associated 18 | | | 9 |
| VPREB3 pre-B lymphocyte 3 | | | 9 |
| CCL28 chemokine (C-C motif) ligand 28 | Circadian abnormalities Mood | SSRI | 8 |
| GAB1 GRB2 Associated Binding Protein 1 | Alcohol BP Delusions Hallucinations | | 8 |
| SUMF2 sulfatase modifying factor 2 | | | 8 |

Biological pathway analyses were conducted using the top biomarkers, which suggest that neurotrophic factors, programmed cell death, and insulin signaling are involved in the biology of suicide (Table 19).

For the top biomarkers identified, combining all the available evidence from this current Example and the published literature, into a convergent functional evidence (CFE) score (FIG. 7), leads to a prioritization of biomarkers for future studies in the field.

Example 2

As a comparator to the universal approach across gender and diagnoses, in this Example, a within-participant longitudinal biomarker discovery analyses in male bipolars only, the largest subgroup (n=20 participants, 65 testing visits) in our discovery cohort, was conducted.

Figure 3A:
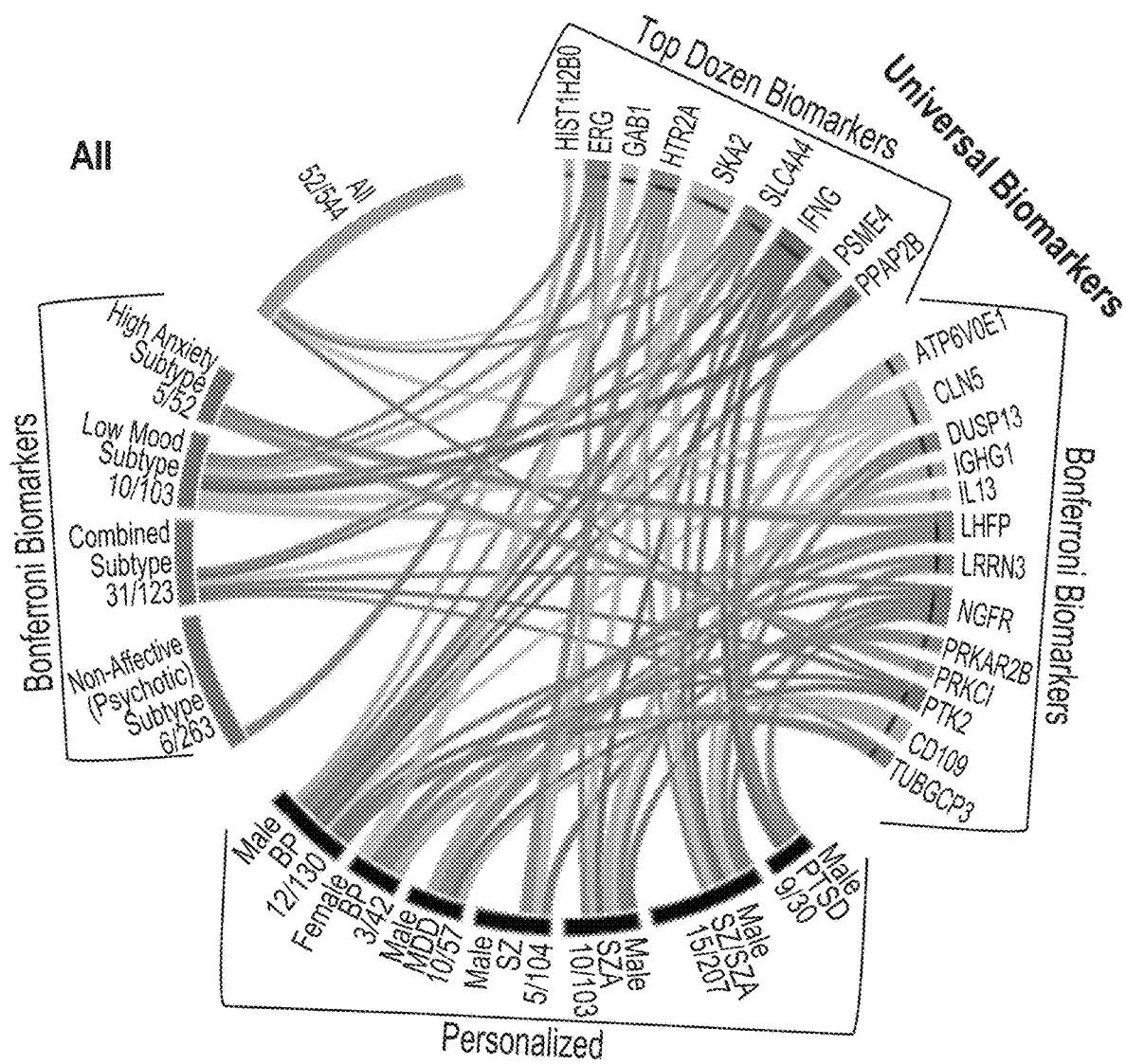
FIGS. 3A-3D depict the best biomarkers predicting suicidality as found in the Examples. Best individual biomarkers out of top dozen and Bonferroni validated.
Figure 3B:
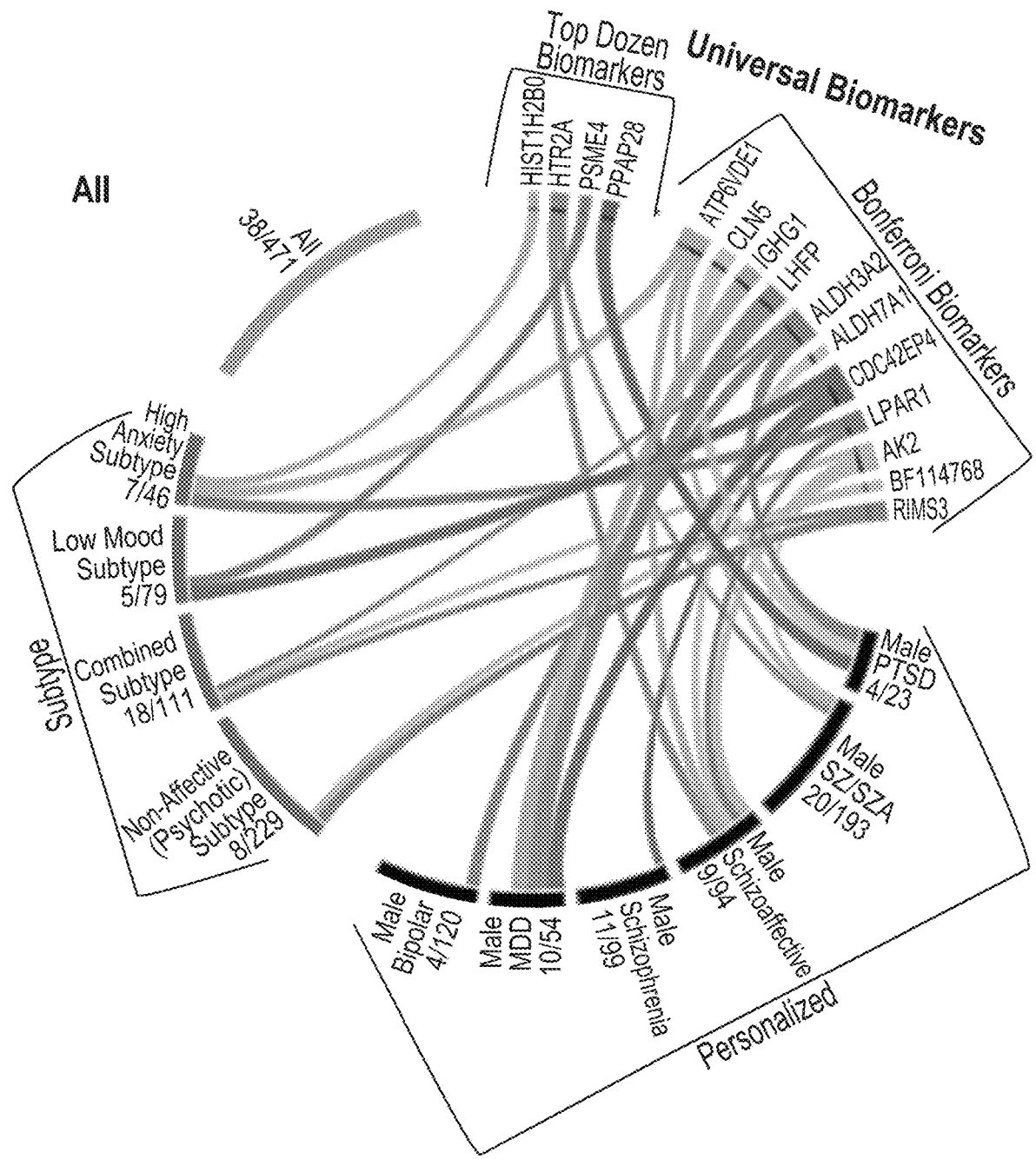
Figure 3C:
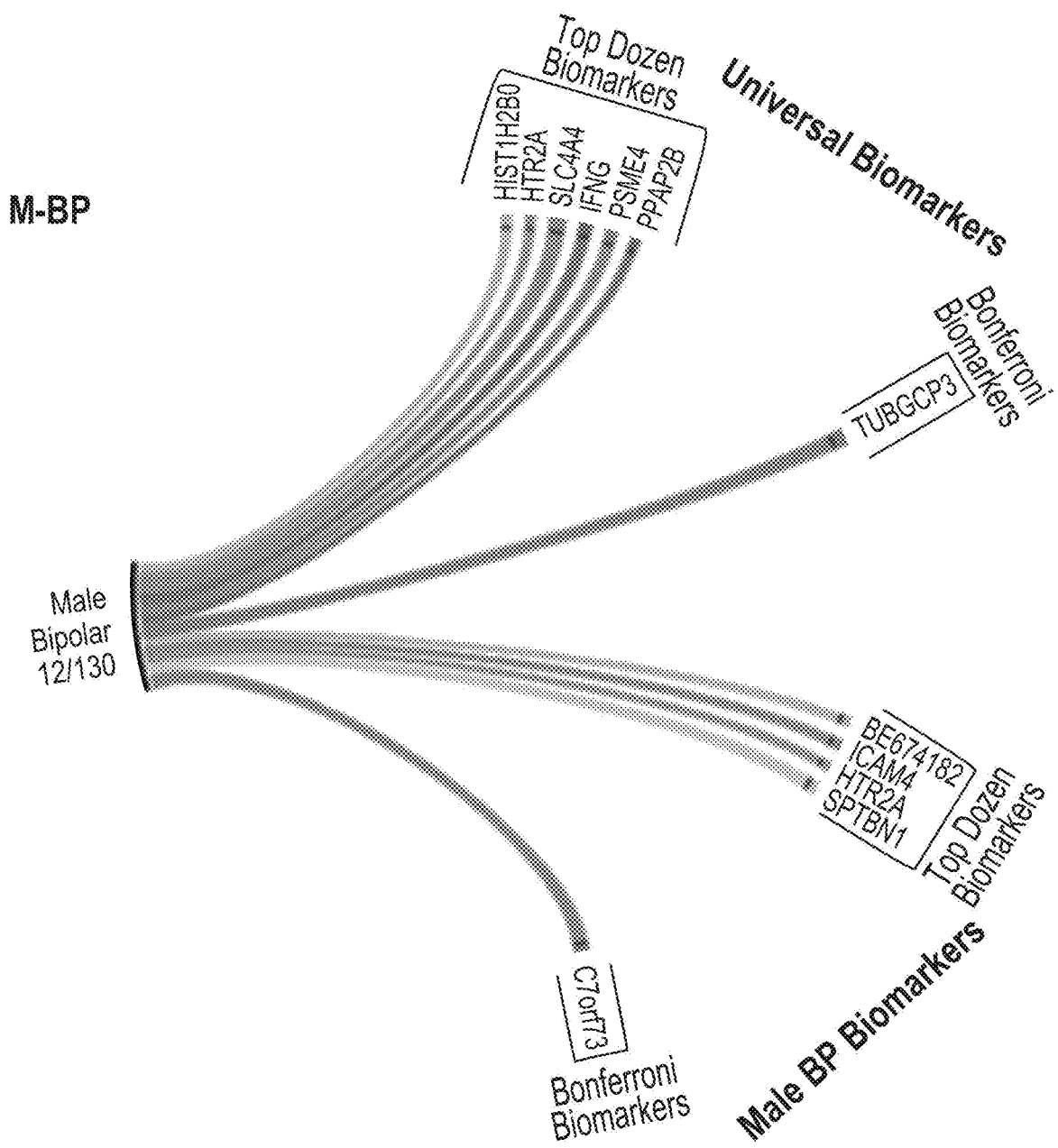
Figure 3D:
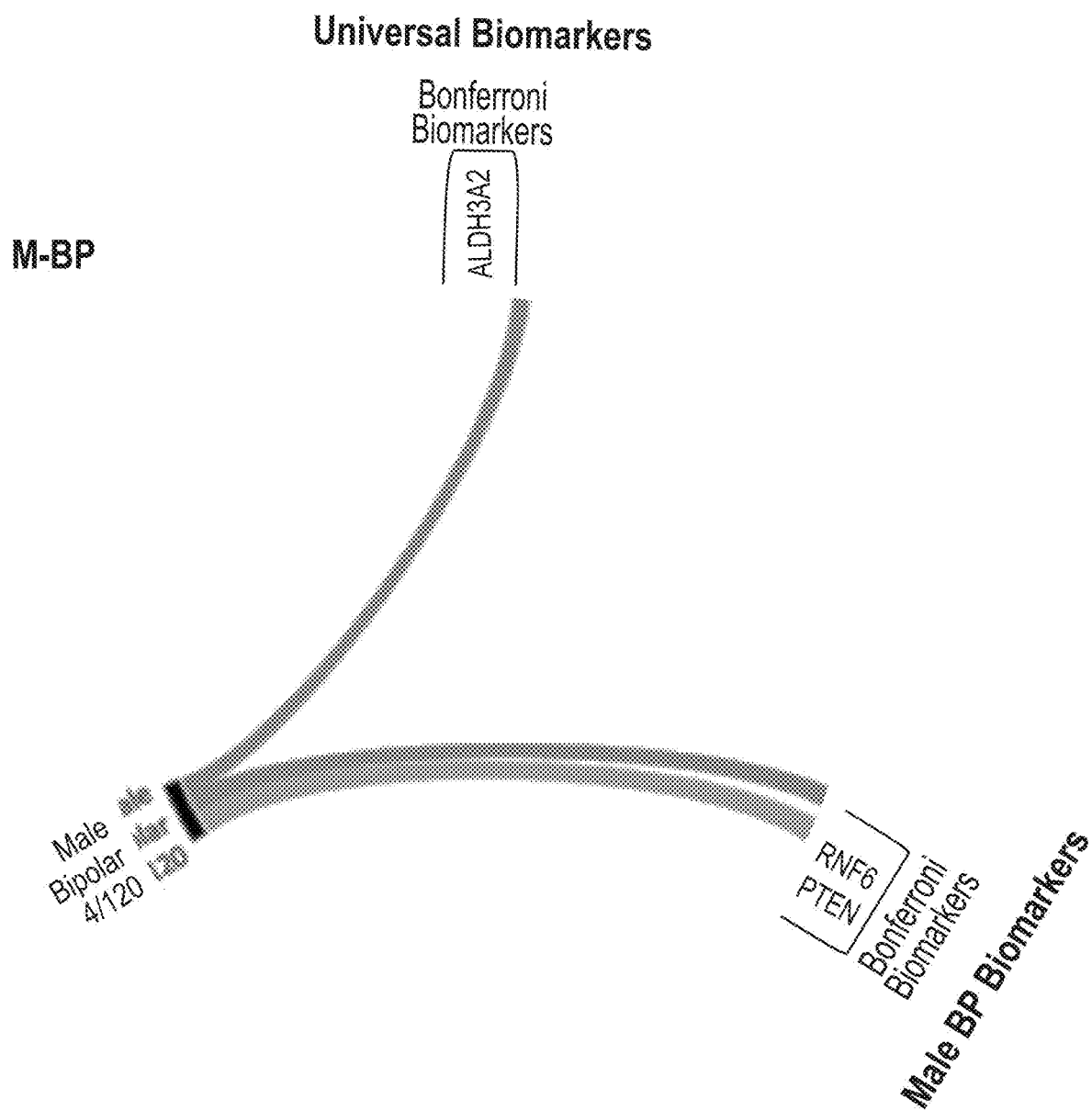

Male bipolars are the highest risk group for suicide clinically, and have been the focus of earlier suicide biomarker studies, with an N that was less than half of the current one (n=9). The discovery step was followed by prioritization, and by validation in male suicide completers. Some of the previous biomarker findings in bipolar disorder (Tables 3B and FIGS. 3C & 3D) were reproduced and examined in this Example. The top dozen biomarkers (Table 3B), and all the biomarkers that survived Bonferroni correction after the validation, for prediction of suicidal ideation and for prediction of future psychiatric hospitalizations due to suicidality in the male bipolar subgroup (n=49) in the independent test cohort (FIGS. 3C & 3D & 9).

TABLE 21

Universal Biomarkers - Predictions In Male Bipolars

A. Predicting Suicidal Ideation State In Independent Sub-Cohort Of Male Bipolars

| Markers | Cohort | Participants with high SI/ Participants total | ROC AUC/ p-value | Suicidality Severity (HAMD SI Score) Correlation R/ p-value | T-test p-value |
|---|---|---|---|---|---|
| Male Bipolar | | | | | |
| Best Biomarkers | | | | | |
| SLC4A4 | M-BP | 12/130 | 0.77/9.27E−04 | 0.24/3.20E−03 | 1.06E−03 |
| TUBGCP3 | M-BP | 12/130 | 0.78/7.44E−04 | −0.21/7.99E−03 | 1.46E−04 |
| BioM 148 Panel (Bonferroni List) | M-BP | 12/130 | 0.7/1.27E−02 | 0.17/2.81E−02 | 4.06E−03 |
| BIOM 12 (Top Dozen List) | M-BP | 12/130 | 0.73/4.07E−03 | 0.19/1.72E−02 | 5.48E−03 |
| BioM 2 (SLC4A4 and TUBGCP3) | M-BP | 12/130 | 0.80/2.97E−04 | 0.26/1.63E−03 | 8.59E−05 |
| Phenes | | | | | |
| Mood | M-BP | 12/130 | 0.8/3.65E−04 | −0.47/6.83E−09 | 1.65E−03 |
| Anxiety | M-BP | 12/130 | 0.86/2.19E−05 | 0.41/7.09E−07 | 1.91E−05 |
| Mood and Anxiety | M-BP | 12/130 | 0.86/1.66E−05 | 0.5/7.15E−10 | 5.66E−05 |

TABLE 21-continued

| Universal Biomarkers - Predictions In Male Bipolars | | | | | |
|---|---|---|---|---|---|
| CFI-S | M-BP | 12/128 | 0.92/1.10E−06 | 0.5/6.11E−10 | 1.31E−06 |
| Mood and Anxiety and CFI-S | M-BP | 12/128 | 0.94/2.82E−07 | 0.61/1.24E−14 | 3.01E−06 |
| Phenes and Biomarkers | | | | | |
| Mood and Anxiety and CFI-S and BioM 148 | M-BP | 12/128 | 0.95/1.55E−07 | 0.62/1.71E−15 | 1.21E−06 |
| Mood and Anxiety and CFI-S and BioM 12 | M-BP | 12/128 | 0.96/8.03E−08 | 0.63/6.05E−16 | 4.79E−07 |
| Mood and Anxiety and CFI-S and BioM 2 | M-BP | 12/128 | 0.96/9.58E−08 | 0.62/2.20E−15 | 3.91E−07 |

B. Prediction Of Future Hospitalizations For Suicidality Within First Year Of Testing Visit In Independent Sub-Cohort Of Male Bipolars

| Biomarker | Cohort | Participants with future hospitalizations for suicidality within the first year/Particpants total | ROC AUC/ p-value | Frequency of future hospitalizations for suicidality within the first year Correlation R/ p-value | T-test p-value | Cox Regression Hazard Ratio/ P-value |
|---|---|---|---|---|---|---|
| | | Male Bipolar | | | | |
| Best Biomarkers | | | | | | |
| PPAP2B | M-BP | 4/120 | 0.74/5.08E−02 | 0.11/1.15E−01 | 7.74E−02 | 1.52/2.28E−01 |
| ALDH3A2 | M-BP | 4/120 | 0.77/3.38E−02 | −0.15/5.25E−02 | 4.15E−02 | 2.43/1.02E−01 |
| BioM 148 Panel (Bonferroni List) | M-BP | 4/120 | 0.52/4.48E−01 | 0.01/4.56E−01 | 4.66E−01 | 1.13/9.18E−01 |
| BIOM 12 (Top Dozen List) | M-BP | 4/120 | 0.67/1.21E−01 | 0.08/1.95E−01 | 1.85E−01 | 2.65/3.76E−01 |
| BioM 2 (PPAP2B and ALDH3A2) | M-BP | 4/120 | 0.77/2.97E−02 | 0.15/5.50E−02 | 5.59E−02 | 6.29/6.95E−02 |
| Phenes | | | | | | |
| Mood | M-BP | 4/120 | 0.69/1.04E−01 | −0.14/6.08E−02 | 2.75E−01 | 2.10/1.32E−01 |
| Anxiety | M-BP | 4/120 | 0.7/9.29E−02 | 0.12/9.74E−02 | 1.12E−01 | 1.87/2.09E−01 |
| Mood and Anxiety | M-BP | 4/120 | 0.72/7.19E−02 | 0.15/5.27E−02 | 1.34E−01 | 1.52/1.18E−01 |
| CFIS | M-BP | 4/120 | 0.80/2.10E−02 | 0.15/5.22E−02 | 3.46E−03 | 1.95/1.21E−01 |
| Mood and Anxiety and CFIS | M-BP | 4/120 | 0.78/2.77E−02 | 0.18/2.36E−02 | 6.78E−02 | 1.41/5.54E−02 |
| Phenes and Biomarkers | | | | | | |
| Mood and Anxiety and CFI-S and BioM 148 | M-BP | 4/120 | 0.77/3.49E−02 | 0.18/2.56E−02 | 8.84E−02 | 1.38/6.06E−02 |
| Mood and Anxiety and CFI-S and BioM 12 | M-BP | 4/120 | 0.79/2.51E−02 | 0.19/1.75E−02 | 6.30E−02 | 1.42/4.35E−02 |
| Mood and Anxiety and CFI-S and BioM 2 | M-BP | 4/120 | 0.84/1.13E−02 | 0.22/7.95E−03 | 3.67E−02 | 0.96/8.38E−01 |

C. Prediction Of All Future Hospitalizations For Suicidality Following Testing In Independent Sub-Cohort Of Male Bipolars

| Predictors | Cohort | Participants with future hospitalizations for suicidality/ Participants total | Frequency of future hospitalizations for suicidality Correlation R/ p-value | Cox Regression/ P-value |
|---|---|---|---|---|
| Best Biomarkers | | | | |
| | | Male Bipolar | | |
| Best Biomarkers | | | | |
| TM4SF1 | Male Bipolar | 9/121 | 0.11/1.07E−01 | 1.41/2.78E−01 |
| ADAL | Male Bipolar | 9/121 | −0.17/3.14E−02 | 1.42/3.98E−01 |
| BioM 148 Panel (Bonferroni List) | Male Bipolar | 9/121 | −0.04/6.74E−01 | 1.15/8.61E−01 |
| BIOM 12 (Top Dozen List) | Male Bipolar | 9/121 | 0.04/3.43E−01 | 7.97/2.44E−01 |
| BioM 2 (TM4SF1 and ADAL) | Male Bipolar | 9/121 | 0.18/2.21E−02 | 1.32/5.25E−01 |

TABLE 21-continued

Universal Biomarkers - Predictions In Male Bipolars

Phenes

| | | | | |
|---|---|---|---|---|
| Mood | Male Bipolar | 9/121 | −0.07/2.30E−01 | 1.86/6.72E−02 |
| Anxiety | Male Bipolar | 9/121 | 0.31/3.27E−04 | 4.00/1.10E−03 |
| Mood and Anxiety | Male Bipolar | 9/121 | 0.21/9.74E−03 | 1.77/2.71E−03 |
| CFI-S | Male Bipolar | 9/121 | 0.25/2.91E−03 | 2.78/7.90E−04 |
| Mood and Anxiety and CFI-S | Male Bipolar | 9/121 | 0.27/1.17E−03 | 1.6/1.11E−04 |

Phenes and Biomarkers

| | | | | |
|---|---|---|---|---|
| Mood and Anxiety and CFI-S and BioM 148 | Male Bipolar | 9/121 | 0.26/2.04E−03 | 1.55/1.47E−04 |
| Mood and Anxiety and CFI-S and BioM 12 | Male Bipolar | 9/121 | 0.28/1.07E−03 | 0.96/7.12E−01 |
| Mood and Anxiety and CFI-S and BioM 2 | Male Bipolar | 9/121 | 0.32/1.55E−04 | 0.98/8.10E−01 |

Bold - p-value of Correlation survives correction for multiple testing.
Correlation is our apriori primary measure.
HAMD SI is the suicide rating question from the Hamilton Rating Scale for Depression.
* Smaller cohort, as not everybody had HAMD SI information.

This Example was successful in the identification of predictive biomarkers that might be more specific for suicidality in male bipolars. Also examined was whether biomarkers discovered using just male bipolar subjects yielded even better predictors for male bipolar subjects than using the universal biomarkers. It was found that to be the case for trait (hospitalizations) predictions (FIG. 3D). For the top male bipolar biomarkers identified, a number of individual top biomarkers are targets of medications in current clinical use for treating suicidality. Bioinformatics drug repurposing analyses using the gene expression biosignature of panels of top biomarkers identified new potential therapeutics for suicidality in male bipolars. The top compounds identified include betulin (a natural plant compound with anticancer properties), carteolol (a non-specific beta-blocker used for glaucoma), alpha-ergocryptine (an ergot alkaloid and non-specific serotonin agonist used for migraines), and baclofen (a derivative of GABA used as a muscle relaxant). Combining all the available evidence from this Example and the published literature, into a convergent functional evidence (CFE) score, leads to a prioritization of biomarkers for future studies in the field.

TABLE 22

Convergent Functional Evidence (CFE). Male bipolar Top Dozen and Bonferroni biomarkers. Only predictions with a significant p-value for the ROC AUC are shown. Those that do not have a significant p-value are marked NA.

| Gene Symbol/ Gene Name | Probesets | Step 1 Discovery in Blood (Direction of Change)/ Score | Step 2 Convergent Evidence For Involvement in Suicide | Step 3 Validation in Blood ANOVA p-value/ Score | Step 4 Significant Prediction of Suicidal Ideation in Male Bipolars ROC AUC/ p-value | Step 4 Significant Prediction of First Year Hospitalizations for Suicidality in Male Bipolars ROC AUC/p-value |
|---|---|---|---|---|---|---|
| HTR2A 5-Hydroxytryptamine Receptor 2A | 244130_at | (I) DE/2 | 8.00 | NS | 0.65/ 4.45E−02 | NA |
| SAT1 spermidine/ spermine N1-acetyltransferase 1 | 213988_s_at | (I) DE/2 | 6.00 | 4.06E−34/4 | NA | NA |
| SAT1 spermidine/ spermine N1-acetyltransferase 1 | 210592_s_at | (I) DE/2 | 6.00 | 4.00E−33/4 | NA | NA |
| CRYAB crystalline, alpha B | 209283_at | (I) DE/1 | 4.00 | 3.49E−05 | 0.65/ 4.41E−02 | NA |
| PIK3R1 Phosphoinositide-3-Kinase Regulatory Subunit 1 | 239476_at | (I) DE/1 | 4.00 | 2.97E−12 | NA | 0.81/ 1.64E−02 |
| PTK2 Protein Tyrosine Kinase 2 | 241453_at | (I) DE/2 | 4.00 | 4.29E−16/4 | 0.66/ 3.64E−02 | NA |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| | | | | | | |
|---|---|---|---|---|---|---|
| SAT1 spermidine/ spermine N1-acetyltransferase 1 | 203455_s_at | (I) DE/1 | 6.00 | 9.99E−29/4 | NA | NA |
| SPTBN1 spectrin, beta, non-erythrocytic 1 | 215918_s_at | (I) AP/1 | 4.00 | 6.7E−32/4 | 0.72/ 6.62E−03 | NA |
| AKT1S1 AKT1 substrate 1 (proline-rich) | 1555821_a_at | (D) DE/2 | 4.00 | 8.69E−09/4 | NA | NA |
| AKT1S1 AKT1 substrate 1 (proline-rich) | 224982_at | (D) AP/1 and DE/2 | 4.00 | 8.04E−11/4 | NA | NA |
| ARHGAP26 Rho GTPase activating protein 26 | 205068_s_at | (I) DE/1 | 5.00 | 7.99E−08/4 | NA | NA |
| B2M beta-2-microglobulin | 232311_at | (I) DE/2 | 4.00 | 5.43E−06/4 | NA | NA |
| PSME4 Proteasome Activator Subunit 4 | 237180_at | (I) DE/2 | 4.00 | 2.02E−16/4 | 0.69/ 1.41E−02 | NA |
| ACSM3 acyl-CoA synthetase medium-chain family member 3 | 210377_at | (D) DE/1 | 4.00 | 2.31E−10/4 | 0.69/ 1.35E−02 | NA |
| ADORA1 adenosine A1 receptor | 205481_at | (D) DE/1 | 4.00 | 1.19E−07/4 | NA | NA |
| FAAH fatty acid amide hydrolase | 204231_s_at | (D) DE/1 | 4.00 | 7.47E−12/4 | NA | NA |
| MARCKS Myristoylated alanine-rich protein kinase C substrate | 213002_at | (I) DE/1 | 4.00 | 7.35E−08/4 | NA | NA |
| MBP myelin basic protein | 225408_at | (D) AP/1 | 4.00 | 3.26E−06/4 | NA | NA |
| PAFAH1B2 platelet-activating factor acetylhydrolase 1b, catalytic subunit 2 (30 kDa) | 210160_at | (D) DE/1 | 4.00 | 4.85E−09/4 | NA | NA |
| PCDH9 Protocadherin 9 | 238919_at | (D) AP/1 | 4.00 | 4.52E−05/4 | NA | NA |
| PIK3R1 phosphoinositide-3-kinase, regulatory subunit 1 (alpha) | 212240_s_at | (I) DE/1 | 4.00 | 7.11E−14/4 | NA | NA |
| PTEN phosphatase and tensin homolog | 222176_at | (I) DE/1 | 4.00 | 4.88E−05/4 | NA | 0.9/ 3.27E−03 |
| RNF6 ring finger protein (C3H2C3 type) 6 | 210932_s_at | (D) DE/1 | 4.00 | 1.25E−05/4 | NA | 0.82/ 1.58E−02 |
| SLC5A3 solute carrier family 5 (sodium/myoinositol cotransporter), member 3 | 213167_s_at | (D) DE/1 | 4.00 | 4.89E−14/4 | NA | NA |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| | | | | | | |
|---|---|---|---|---|---|---|
| C20orf27 chromosome 20 open reading frame 27 | 218081_at | (D) DE/2 | 4.00 | 1.09E−34/4 | NA | NA |
| C7orf73 Chromosome 7 open reading frame 73 | 224758_at | (D) DE/2 | 4.00 | 4.72E−06/4 | 0.75/ 2.38E−03 | NA |
| CLYBL Citrate Lyase Beta Like | 239683_at | (D) AP/4 | 4.00 | 0.009/2 | NA | NA |
| EZR ezrin | 208623_s_at | (I) DE/1 | 5.00 | 3.92E−11/4 | NA | NA |
| ICAM4 intercellular adhesion molecule 4 (Landsteiner-Wiener blood group) | 207194_s_at | (D) DE/4 | 0.00 | 3.81E−08/4 | 0.67/ 2.83E−02 | NA |
| NEAT1 nuclear paraspeckle assembly transcript 1 (non-protein coding) | 224565_at | (I) DE/2 | 4.00 | 9.99E−20/4 | NA | NA |
| NUB1 Negative regulator of ubiquitin-like proteins 1 | 234332_at | (I) DE/4 | 0.00 | 8.11E−10/4 | NA | 0.75/ 4.78E−02 |
| PGBD2 PiggyBac Transposable Element Derived 2 | 238004_at | (D) AP/4 | 0.00 | 1.25E−05/4 | 0.72/ 6.77E−03 | NA |
| C8orf74 chromosome 8 open reading frame 74 | 1569245_at | (D) DE/1 | 6.00 | 3.82E−08/4 | NA | NA |
| CALR calreticulin | 212953_x_at | (I) DE/1 | 4.00 | 1.12E−10/4 | NA | NA |
| CRHR1 Corticotropin-Releasing Hormone Receptor 1 | 214619_at | (D) DE/1 | 6.00 | NS | NA | NA |
| DLL1 delta-like 1 (*Drosophila*) | 227938_s_at | (D) DE/1 | 4.00 | 1.17E−09/4 | NA | NA |
| FADS1 fatty acid desaturase 1 | 208963_x_at | (I) AP/1 | 4.00 | 1.58E−05/4 | NA | NA |
| KLK7 Kallikrein Related Peptidase 7 | 239381_at | (D) AP/1 | 4.00 | 2.79E−05/4 | NA | NA |
| MED28 mediator complex subunit 28 | 222635_s_at | (D) DE/1 | 4.00 | 1.63E−15/4 | NA | NA |
| NDUFS1 NADH:Ubiquinone Oxidoreductase Core Subunit S1 | 239268_at | (D) DE/1 | 4.00 | 3.72E−11/4 | NA | NA |
| POLR2D polymerase (RNA) II (DNA directed) polypeptide D | 214144_at | (D) AP/1 | 4.00 | 2.1E−08/4 | NA | NA |
| PPAP2B phosphatidic acid phosphatase type 2B | 212230_at | (I) DE/1 | 4.00 | 2.49E−06/4 | NA | NA |
| SELENBP1 selenium binding protein 1 | 214433_s_at | (D) DE/1 | 4.00 | 7.24E−05/4 | NA | NA |
| TRIM23 tripartite motif containing 23 | 210995_s_at | (D) DE/1 | 4.00 | 3.98E−19/4 | NA | NA |
| WARS tryptophanyl-tRNA synthetase | 200628_s_at | (D) AP/1 | 4.00 | 3.8E−06/4 | NA | NA |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| ADAL Adenosine Deaminase-Like | 239711_at | (D) AP/4 | 0.00 | 4.53E−08/4 | NA | NA |
|---|---|---|---|---|---|---|
| ATP13A2 ATPase type 13A2 | 218608_at | (D) DE/2 | 4.00 | 4.75E−08/4 | NA | NA |
| CNOT3 CCR4-NOT transcription complex, subunit 3 | 211141_s_at | (D) DE/4 | 0.00 | 4.05E−16/4 | NA | NA |
| JMJD1C jumonji domain containing 1C | 228793_at | (I) DE/4 | 0.00 | 3.6E−06/4 | NA | NA |
| KSR1 kinase suppressor of ras 1 | 213769_at | (I) AP/4 | 4.00 | NS | NA | NA |
| RPAP3 RNA polymerase II associated protein 3 | 1557984_s_at | (D) AP/4 | 0.00 | 4.34E−06/4 | NA | NA |
| SORBS1 sorbin and SH3 domain containing 1 | 211705_s_at | (D) DE/2 | 2.00 | 8.95E−11/4 | NA | NA |
| TDG thymine-DNA glycosylase | 203742_s_at | (I) DE/2 | 2.00 | 1.04E−16/4 | NA | NA |
| ZNF302 zinc finger protein 302 | 218490_s_at | (D) AP/4 | 0.00 | 3.87E−05/4 | NA | NA |
| AIMP1 aminoacyl tRNA synthetase complex-interacting multifunctional protein 1 | 202542_s_at | (D) DE/1 | 4.00 | 1.73E−05/4 | NA | NA |
| FIGNL1 fidgetin-like 1 | 222843_at | (D) AP/1 | 4.00 | 2.08E−05/4 | NA | NA |
| MRTO4 mRNA turnover 4 homolog (S. cerevisiae) | 235783_at | (D) DE/1 | 4.00 | 7.52E−16/4 | NA | NA |
| BF114768 | 236879_at | (I) DE/4 | 0.00 | 2.62E−12/4 | NA | NA |
| BE674182 | 237259_at | (I) DE/4 | 0.00 | NS | 0.66/ 3.33E−02 | NA |
| CACNA1I calcium channel, voltage-dependent, T type, alpha 1I subunit | 208299_at | (I) AP/4 | 0.00 | NS | NA | NA |

| Gene Symbol/ Gene Name | Step 5 Other Psychiatric and Related Disorders Evidence | Step 6 Drugs that Modulate the Biomarker in Opposite Direction to Suicide | CFE Polyevidence Score |
|---|---|---|---|
| HTR2A 5-Hydroxytryptamine Receptor 2A | Alcohol Anxiety BP MDD SZ OCD Response to Antidepressants | Clozapine Lithium Valproate Paliperidone, Risperidone, lurasidone, clozapine, doxepin, desipramine, , clomipramine, loxapine, quetiapine, olanzapine, nefazodone, mirtazapine, amitriptyline lisuride, sertindole, ziprasidone, mesoridazine, thioridazine, aripiprazole, methysergide, dihydroergotamine, apomorphine, ergotamine, azatadine | 16 |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| | | | |
|---|---|---|---|
| SAT1 spermidine/ spermine N1- acetyltransferase 1 | MDD Anxiety Mood Disorders NOS | Omega 3 | 16 |
| SAT1 spermidine/ spermine N1- acetyltransferase 1 | MDD Anxiety Mood Disorders NOS | Omega 3 | 16 |
| CRYAB crystalline, alpha B | Autism Alcohol PTSD SZA BP SZ Insomnia Social Isolation Stress MDD | Lithium Clozapine Methamphetamine | 15 |
| PIK3R1 Phosphoinositide- 3-Kinase Regulatory Subunit 1 | Schizophrenia MDD Relaxation Response PTSD BP Longevity Stress Alcohol Insomnia Anxiety | Mood Stabilizers | 15 |
| PTK2 Protein Tyrosine Kinase 2 | Alcohol ASD BP Circadian abnormalities MDD Neurological SZ/SZA Stress SZ | CT-707 | 15 |
| SAT1 spermidine/ spermine N1- acetyltransferase 1 | MDD Anxiety Mood Disorders NOS | Omega 3 | 15 |
| SPTBN1 spectrin, beta, non- erythrocytic 1 | Aging BP Longevity MDD SZ | Clozapine Omega-3 Diazepam | 15 |
| AKT1S1 AKT1 substrate 1 (proline-rich) | Circadian abnormalities Aging | Omega-3 fatty acids | 14 |
| AKT1S1 AKT1 substrate 1 (proline-rich) | Circadian abnormalities Longevity | (I) Brain Omega-3 fatty acids[195] | 14 |
| ARHGAP26 Rho GTPase activating protein 26 | BP MDD Panic Disorder SZ | Clozapine | 14 |
| B2M beta-2- microglobulin | Alcohol Effect of valproate MDD SZ | Omega-3 | 14 |
| PSME4 Proteasome Activator Subunit 4 | ASD MDD | | 14 |
| ACSM3 acyl-CoA synthetase medium-chain family member 3 | MDD Mood | | 13 |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| | | | |
|---|---|---|---|
| ADORA1 adenosine A1 receptor | Alcohol SZ BP Mood, Stimulants Depression | (I) Ventral tegmentum Clozapine[194] | 13 |
| FAAH fatty acid amide hydrolase | Alcohol SZ BP MDD Pain Placebo PTSD Stress Hallucinogens Social Isolation | (D)FAAH Hippocampus (males) Omega-3[193] | 13 |
| MARCKS Myristoylated alanine-rich protein kinase C substrate | BP SZ MDD Yohimbine Alcohol Panic Disorder | (D) Cerebral Cortex (right) Lithium[199] | 13 |
| MBP myelin basic protein | Alcohol Alzheimer's Disease BP MDD Mood Neurological SZ | Clozapine Omega-3 Lithium | 13 |
| PAFAH1B2 platelet-activating factor acetylhydrolase 1b, catalytic subunit 2 (30 kDa) | MDD | Lithium PCP Clozapine | 13 |
| PCDH9 Protocadherin 9 | Aging MDD SZ/SZA SZ | Clozapine Omega-3 | 13 |
| PIK3R1 phosphoinositide-3-kinase, regulatory subunit 1 (alpha) | SZ MDD Relaxation Response PTSD BP Longevity Hallucinogens Stress Alcohol Insomnia Anxiety | (D) Amygdala mood stabilizers[198] | 13 |
| PTEN phosphatase and tensin homolog | SZ MDD BP PTSD Longevity Hallucinogens Stress Yohimbine Alcohol Stimulants Anxiety | | 13 |
| RNF6 ring finger protein (C3H2C3 type) 6 | BP Social Isolation | | 13 |
| SLC5A3 solute carrier family 5 (sodium/myoinositol cotransporter), member 3 | Chronic Stress MDD Alcohol | frontal cortex Lithium[197] | 13 |
| C20orf27 chromosome 20 open reading frame 27 | BP MDD | | 12 |
| C7orf73 Chromosome 7 open reading frame 73 | | | 12 |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| Gene | Phenotype | Treatment/Region | Score |
|---|---|---|---|
| CLYBL<br>Citrate<br>Lyase<br>Beta Like | MDD<br>Delusions<br>Stimulants<br>ADHD<br>Longevity<br>Alcohol | | 12 |
| EZR<br>ezrin | SZ<br>Mood Disorders<br>NOS<br>Stimulants<br>Anxiety<br>Alcohol | | 12 |
| ICAM4<br>intercellular adhesion<br>molecule 4<br>(Landsteiner-Wiener<br>blood group) | MDD | | 12 |
| NEAT1<br>nuclear paraspeckle<br>assembly transcript 1<br>(non-protein coding) | | Clozapine | 12 |
| NUB1<br>Negative regulator of<br>ubiquitin-like<br>proteins 1 | | (D)<br>NUB1<br>Ventral tegmentum<br>Clozapine[194] | 12 |
| PGBD2<br>PiggyBac Transposable<br>Element Derived 2 | BP<br>Mood State | | 12 |
| C8orf74<br>chromosome 8<br>open reading<br>frame 74 | | | 11 |
| CALR<br>calreticulin | SZ<br>MDD<br>Relaxation Response<br>Pain<br>Longevity<br>Stimulants<br>SZA<br>Alcohol<br>Chronic Stress | | 11 |
| CRHR1<br>Corticotropin-<br>Releasing<br>Hormone<br>Receptor 1 | SZ<br>MDD<br>Pain<br>Panic Disorder<br>ASD<br>Depression<br>Alcohol<br>Substances/Addictions<br>SSRI<br>PTSD<br>Anxiolytics<br>BP<br>Aggression<br>SNRI<br>Longevity<br>Stress<br>Alcohol<br>Antipsychotics<br>Anxiety | "Ventral tegmentum<br>(D)<br>(Treatments,<br>Cognition,<br>Antipsychotics)[194]<br>Amygdala<br>(D)<br>(Addictions,<br>Alcohol,<br>Alcohol)[201]<br>Amygdala<br>(paradigm 3)<br>(I)<br>(Addictions,<br>Alcohol,<br>Alcohol)[202] | 11 |
| DLL1<br>delta-like 1<br>(Drosophila) | BP<br>PTSD<br>SZ | | 11 |
| FADS1<br>fatty acid<br>desaturase 1 | Aging<br>Antipsychotics<br>SZ | | 11 |
| KLK7<br>Kallikrein Related<br>Peptidase 7 | BP<br>Mood<br>State | | 11 |
| MED28<br>mediator complex<br>subunit 28 | Alcohol<br>BP<br>PTSD | | 11 |
| NDUFS1<br>NADH: Ubiquinone<br>Oxidoreductase<br>Core Subunit S1 | Alcohol<br>SZ<br>Circadian<br>abnormalities | | 11 |

TABLE 22-continued

Convergent Functional Evidence (CFE). Male bipolar Top Dozen and Bonferroni biomarkers. Only predictions with a significant p-value for the ROC AUC are shown. Those that do not have a significant p-value are marked NA.

| Gene | Conditions | Score |
|---|---|---|
| POLR2D polymerase (RNA) II (DNA directed) polypeptide D | BP | 11 |
| PPAP2B phosphatidic acid phosphatase type 2B | SZ/SZA SZ | 11 |
| SELENBP1 selenium binding protein 1 | SZ Psychosis Circadian abnormalities ASD | 11 |
| TRIM23 tripartite motif containing 23 | BP SZ | 11 |
| WARS tryptophanyl-tRNA synthetase | Alcohol SZ | 11 |
| ADAL Adenosine Deaminase-Like | Circadian abnormalities Mood | 10 |
| ATP13A2 ATPase type 13A2 | | 10 |
| CNOT3 CCR4-NOT transcription complex, subunit 3 | BP Hallucinogens | 10 |
| JMJD1C jumonji domain containing 1C | BP PTSD Anxiety Hallucinogens | 10 |
| KSR1 kinase suppressor of ras 1 | Hallucinogens MDD | 10 |
| RPAP3 RNA polymerase II associated protein 3 | SZ/SZA | 10 |
| SORBS1 sorbin and SH3 domain containing 1 | ASD SZ Longevity Mood Disorders NOS MDD BP | 10 |
| TDG thymine-DNA glycosylase | Alcohol Chronic Stress | 10 |
| ZNF302 zinc finger protein 302 | MDD SZ Post-Traumatic Stress Disorder | 10 |
| AIMP1 aminoacyl tRNA synthetase complex-interacting multifunctional protein 1 | | 9 |
| FIGNL1 fidgetin-like 1 | | 9 |
| MRTO4 mRNA turnover 4 homolog (*S. cerevisiae*) | | 9 |
| BF114768 | | 8 |
| BE674182 | | 6 |
| CACNA1I calcium channel, voltage-dependent, T type, alpha 1I subunit | MDD SZ | 6 |

Example 3

A list/panel of 50 biomarkers (BioM50) was generated from the biomarkers with the best evidence from discovery, prioritization, validation, and testing in independent cohorts, obtained with additional data, longer follow-up, and longitudinal analyses (Table 23, FIG. 10).

In this Example, the following abbreviations were utilized: validation: DE—differential expression, AP—Absent/Present. NS—Non-stepwise; Step 4 Predictions: C—cross-sectional (using levels from one visit), L—longitudinal (using levels, slope, as well as maximum levels and maximum slope from multiple prior visits); M—Males, F—Females. MDD—depression, BP—bipolar, SZ—schizophrenia, SZA—schizoaffective, PSYCHOSIS—schizophrenia and schizoaffective combined, PTSD-post-traumatic stress disorder. In ALL, by Gender, and personalized by Gender and Diagnosis. Score for predictions: 4 pts if in ALL, 2 pts Gender, 1 pts Gender/Dx. Bold name genes are also Bonferroni significant at Step 3 validation.

To generate the BioM50, the raw gene expression data was first Z-scored by gender and diagnosis, for normalization purposes. Then, each of the biomarkers in the panel was multiplied by a weight coefficient corresponding to their CFE (convergent functional evidence) score, and then an additive score of the 50 weighted biomarkers was obtained. This score can be used for (1) objective assessment of suicidality state and (2) predictive purposes for future clinical worsening, as reflected in hospitalizations for suicidality. Two types of analyses can be performed: cross-sectional, and longitudinal (Table 23, FIGS. 11A-11C).

Figure 11A:
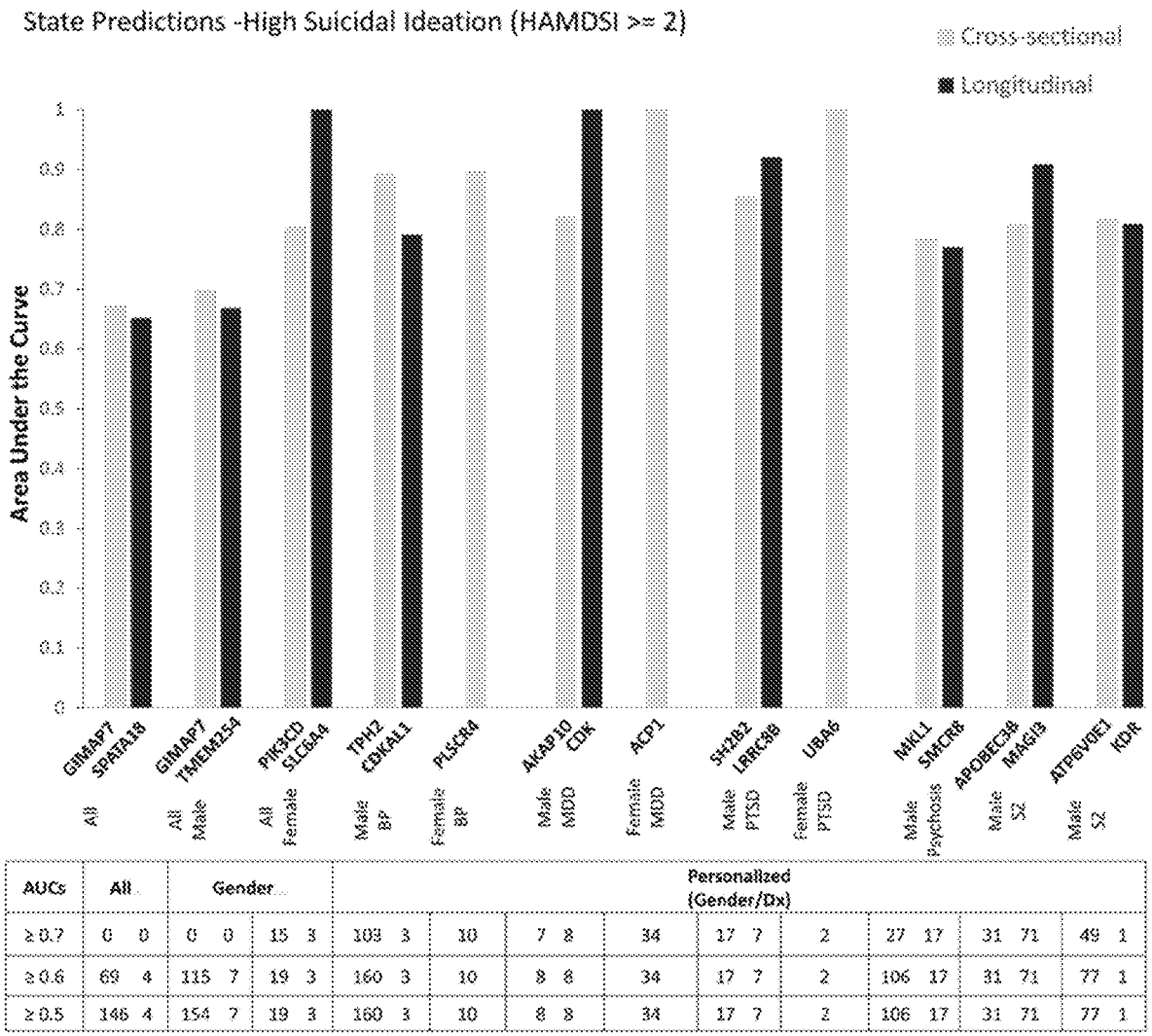
FIGS. 11A-11C depict the best Single Biomarkers Predictors for Suicidality State, and for Trait (Future Hospitalizations for Suicidality) from top candidate biomarkers from each of the Steps 1-3 (Discovery, Prioritization, Validation-Bold).
Figure 11B:
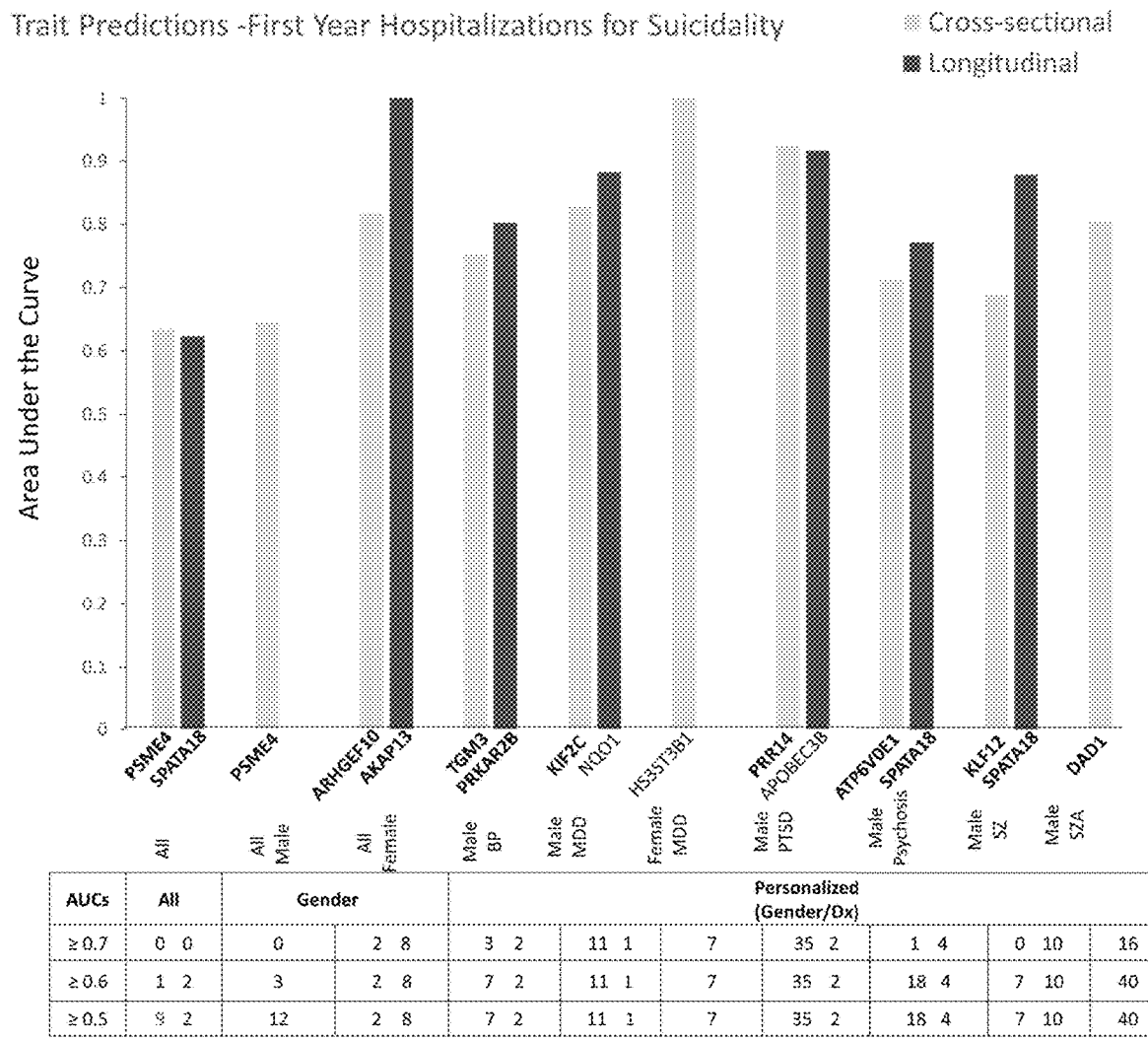
Figure 11C:
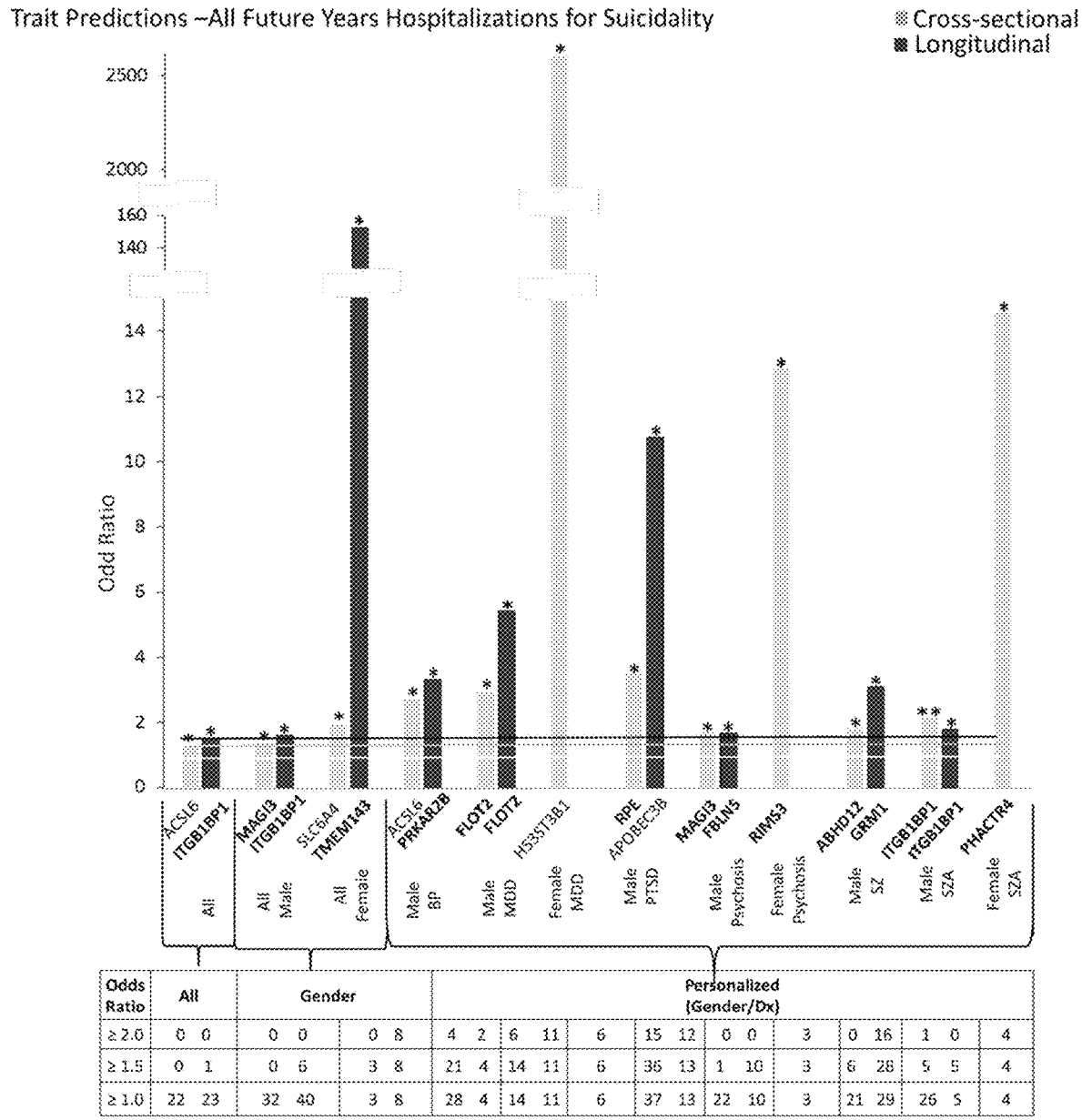

As depicted in FIGS. 11A-11C, for cross-sectional analyses, biomarker expression levels were used, z-scored by gender and diagnosis. For longitudinal analyses, four measures were combined: biomarker expression levels, slope (defined as ratio of levels at current testing visit vs. previous visit, divided by time between visits), maximum levels (at any of the current or past visits), and maximum slope (between any adjacent current or past visits). For decreased biomarkers, the minimum rather than the maximum was used for level calculations. All four measures were Z-scored, then combined in an additive fashion into a single measure. This type of longitudinal analysis can be carried out in patients that have at least two test visits.

The BioM-50 score of a new patient tested was compared against the scores of previously tested patients with known severity and outcomes. The thresholds were set based on averages of previous data, and on previous ROC AUC curves, choosing values for sensitivity and specificity. A report was generated with a raw score, a % score, and a risk classification (low, intermediate, high).

BioM50 scores can also be used in combination with quantitative phenotypic data from questionnaires/apps (such as CFI-S, SASS, others), in the UP-Suicide algorithm.

Figure 12:
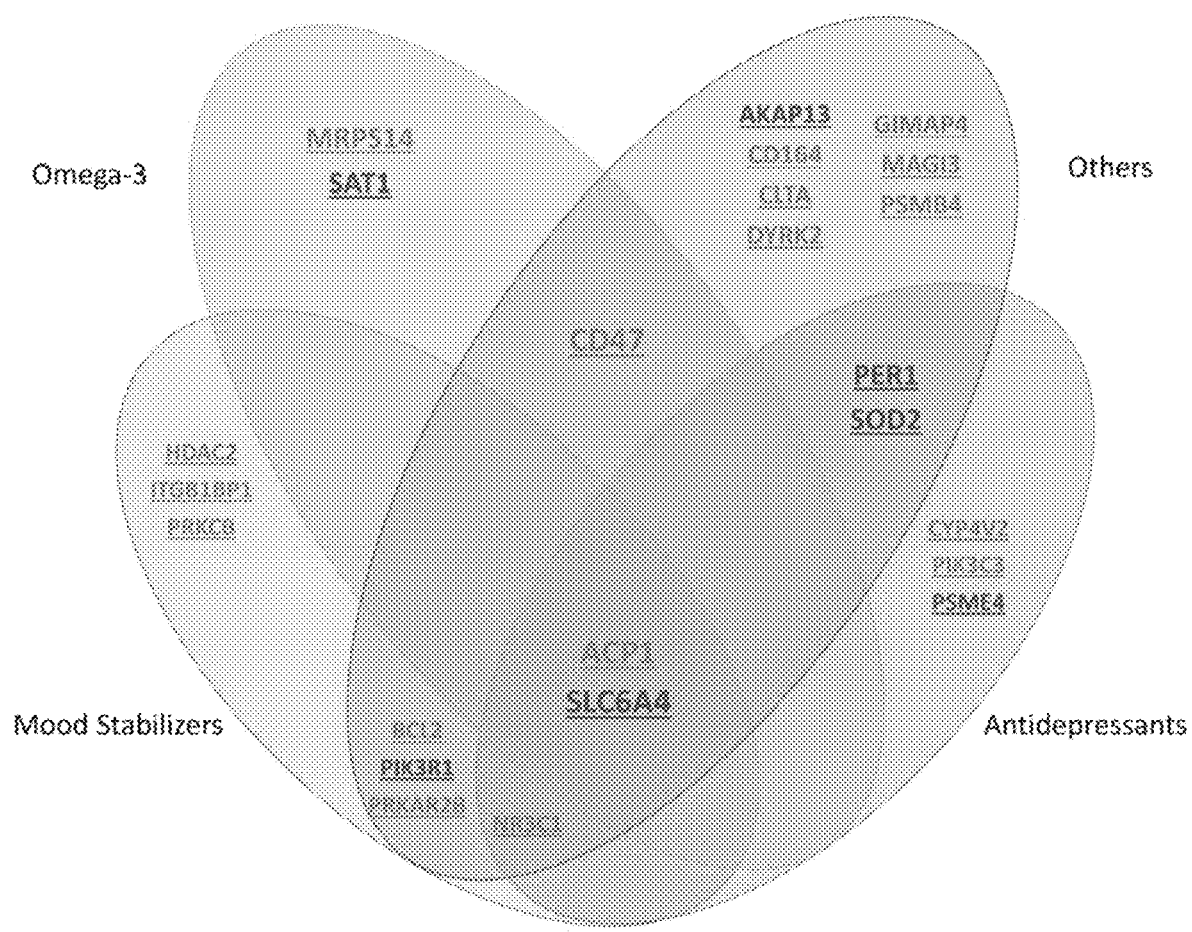
FIG. 12 is a schematic diagram depicting the matching of patients to drugs, the pharmacogenomics for suicidality.

The biomarkers from the BioM50 panel can be used to (3) match patients to medications (Table 23, FIG. 12). Some biomarkers have corresponding known drugs or classes of drugs, that have an opposite effect to suicidality on their direction of change (pharmacogenomics). Such biomarkers can be used to target treatments to different patients, and to (4) measure response to that treatment. The higher the proportion/percentile of biomarkers for a certain drug/class, the more indicated that drug would be for treatment. When biomarkers for multiple different drug/classes are changed in an individual, a prioritization based on the proportion/percentile of biomarkers for each class can be used to choose the drug or combination of drugs (targeted rational polypharmacy).

Figure 13:
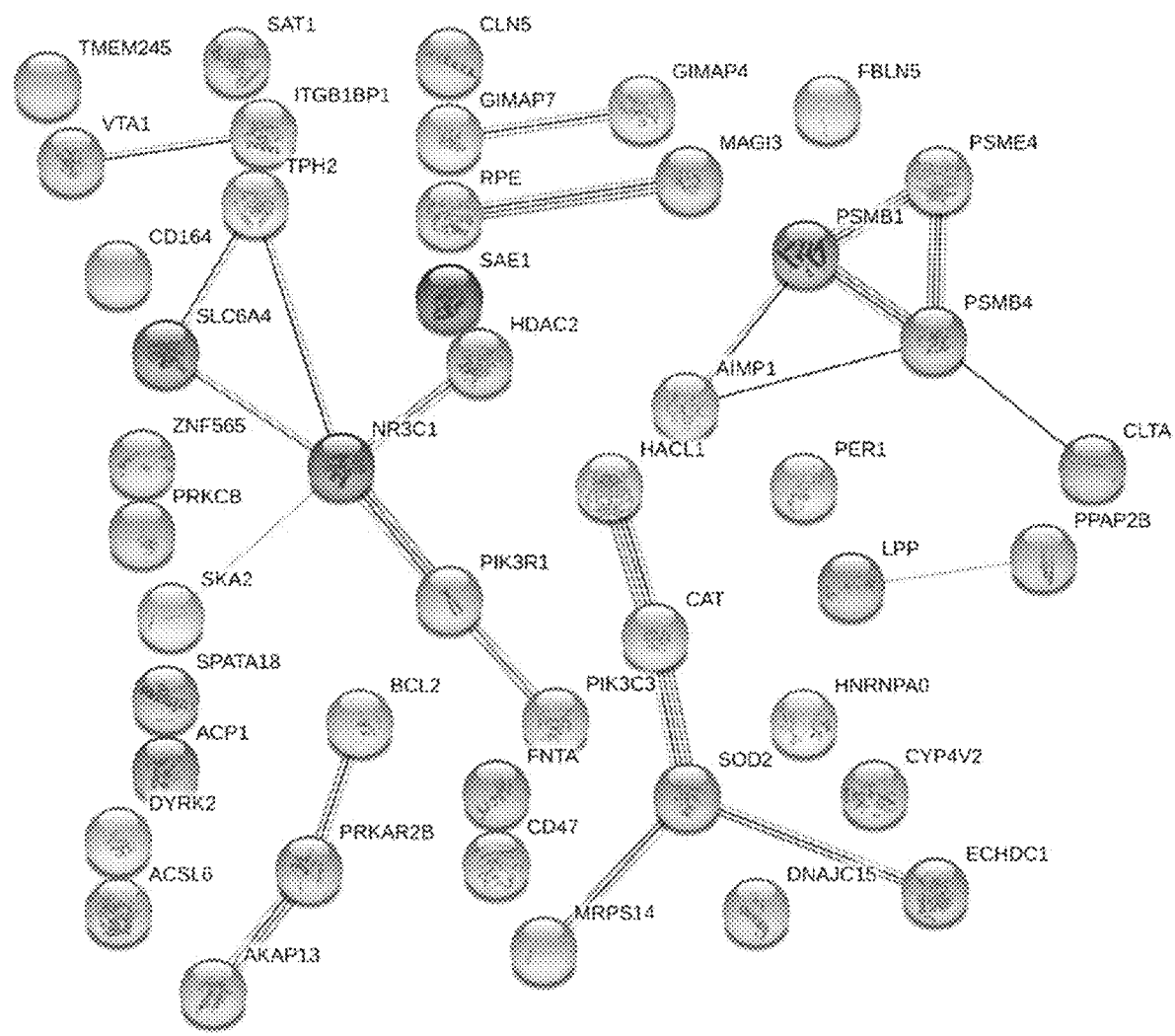
FIG. 13 depicts a STRING analysis depicting interactions between Top CFE BioM 50 Biomarkers (n=46 top genes, 50 probesets). The links between nodes depict various types of evidence of interaction (see (https://string-db.org). The STRING interaction analysis revealed at least 3 biological networks (centered on NR3C1, PSMB4, and SOD2), which represent biomarkers and networks/pathways which can be targets for new drug development.

The gene expression signature of the 50 biomarkers (BioM50) was used to identify repurposed drugs, for (5) new method of use in suicidality treatment and prevention (Table 24). The biological networks where these 50 biomarkers map offer additional targets for new drug development (FIG. 13).

For the top biomarkers identified, combining all the available evidence from this current Example and the published literature, into a convergent functional evidence (CFE) score (Table 23), leads to a prioritization of biomarkers for future studies in the field.

TABLE 23

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene Symbol/ Gene Name | Probeset | Discovery in Longitudinally Followed Patients Step 1 Discovery in Blood (Direction of Change tracking High Suicidal Ideation) Method/Score/% 4 pts | Step 2 Prioritization External CFG Evidence for Involvement in Suicide Score 8 pt | Validation in Suicide Completers Step 3 Validation Anova p-value 4 pts |
|---|---|---|---|---|
| PSME4 Proteasome Activator Subunit 4 | 237180_at | (I) DE/1 46.2% | 4.00 | 3.81E−12 Bonferroni/4 |
| ACP1 acid phosphatase 1, soluble | 201630_s_at | (D) DE/2 55.2% | 6.00 | 4.03E−05 Bonferroni/4 |
| ACSL6 acyl-CoA synthetase long-chain family member 6 | 211207_s_at | (D) DE/4 94.8% | 2.00 | 6.92E−02 Nominal/2 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| MAGI3 membrane associated guanylate kinase, WW and PDZ domain containing 3 | 226770_at | (D) AP/2 56% | 4.00 | 4.02E−12 Bonferroni/4 |
| PLPP3 phospholipid phosphatase 3 | 212226_s_at | (I) DE/1 36.9% (I) AP/2 53.1% | 4.00 | 1.65E−05 Bonferroni/4 |
| SKA2 spindle and kinetochore associated complex subunit 2 | 225686_at | (D) AP/1 34.5% | 8.00 | 4.74E−03 Nominal/2 |
| SOD2 superoxide dismutase 2, mitochondrial | 215078_at | (I) DE/2 73.8% | 4.00 | 6.26E−11 Bonferroni/4 |
| CLN5 ceroid-lipofuscinosis, neuronal 5 | 214252_s_at | (D) DE/2 60.4% | 4.00 | 1.66E−11 Bonferroni/4 |
| CLTA clathrin, light chain A | 204050_s_at | (D) DE/2 62.5% | 4.00 | 5.13E−07 Bonferroni/4 |
| DYRK2 dual specificity tyrosine-(Y)-phosphorylation regulated kinase 2 | 202969_at | (D) DE/2 56.3% | 4.00 | 2.29E−09 Bonferroni/4 |
| ECHDC1 ethylmalonyl-CoA decarboxylase 1 | 223087_at | (D) DE/2 74% | 4.00 | 2.12E−07 Bonferroni/4 |
| FBLN5 fibulin 5 | 203088_at | (D) DE/2 52.1% | 6.00 | 1.05E−11 Bonferroni/4 |
| AIMP1 aminoacyl tRNA synthetase complex-interacting multifunctional protein 1 | 227605_at | (D) DE/2 53.1% (D) AP/1 41.4% | 4.00 | 8.98E−13 Bonferroni/4 |
| CLN5 ceroid-lipofuscinosis, neuronal 5 | 204084_s_at | (D) DE/1 41.7% | 4.00 | 6.03E−15 Bonferroni/4 |
| ITGB1BP1 integrin beta 1 binding protein 1 | 203336_s_at | (D) DE/2 57.3% | 4.00 | 9.47E−06 Bonferroni/4 |
| NR3C1 nuclear receptor subfamily 3, group C, member 1 (glucocorticoid receptor) | 201866_s_at | (D) DE/2 53.1% | 6.00 | 2.83E−06 Bonferroni/4 |
| PER1 period circadian clock 1 | 244677_at | (I) DE/1 37.7% | 4.00 | 3.52E−18 Bonferroni/4 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| PIK3R1 Phosphoinositide-3-Kinase Regulatory Subunit 1 | 244181_at | (I) DE/1 36.2% | 4.00 | 7.33E−08 Bonferroni/4 |
| PRKAR2B protein kinase, cAMP-dependent, regulatory, type II, beta | 203680_at | (D) DE/2 66.7% | 6.00 | 7.27E−06 Bonferroni/4 |
| SAE1 SUMO1 activating enzyme subunit 1 | 1555618_s_at | (D) DE/4 86.5% | 0.00 | 3.33E−05 Bonferroni/4 |
| SPATA18 spermatogenesis associated 18 | 229331_at | (I) DE/2 54.6% | 4.00 | 1.39E−05 Bonferroni/4 |
| ZNF565 zinc finger protein 565 | 228305_at | (D) DE/1 49% | 4.00 | 3.43E−10 Bonferroni/4 |
| AIMP1 aminoacyl tRNA synthetase complex-interacting multifunctional protein 1 | 202542_s_at | (D) DE/2 78.1% | 4.00 | 3.55E−05 Bonferroni/4 |
| AIMP1 aminoacyl tRNA synthetase complex-interacting multifunctional protein 1 | 202541_at | (D) DE/1 34.4% | 4.00 | 4.06E−05 Bonferroni/4 |
| BCL2 B-cell CLL/lymphoma 2 | 203685_at | (D) DE/2 55.2% | 6.00 | 1.55E−07 Bonferroni/4 |
| CAT catalase | 211922_s_at | (D) DE/2 59.4% | 4.00 | 1.03E−08 Bonferroni/4 |
| ECHDC1 ethylmalonyl-CoA decarboxylase 1 | 219974_x_at | (D) DE/2 59.4% | 4.00 | 2.94E−09 Bonferroni/4 |
| HDAC2 histone deacetylase 2 | 201833_at | (D) DE/4 82.3% | 0.00 | 9.15E−08 Bonferroni/4 |
| LPP LIM domain containing preferred translocation partner in lipoma | 241879_at | (I) DE/1 36.2% | 4.00 | 8.45E−11 Bonferroni/4 |
| PSMB4 proteasome subunit beta 4 | 202243_s_at | (D) DE/2 51% | 6.00 | 5.97E−08 Bonferroni/4 |
| RPE ribulose-5-phosphate-3-epimerase | 221770_at | (D) DE/2 68.8% | 2.00 | 2.79E−09 Bonferroni/4 |
| VTA1 vesicle (multivesicular body) trafficking 1 | 223021_x_at | (D) DE/2 52.1% | 4.00 | 1.01E−06 Bonferroni/4 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| AKAP13 A kinase (PRKA) anchor protein 13 | 209534_x_at | (I) DE/1 46.2% | 4.00 | 1.61E−07 Bonferroni/4 |
| CD164 CD164 molecule, sialomucin | 208654_s_at | (D) DE/2 64.6% | 4.00 | 3.65E−07 Bonferroni/4 |
| CD47 CD47 molecule | 211075_s_at | (D) DE/2 62.5% | 4.00 | 6.65E−11 Bonferroni/4 |
| CYP4V2 cytochrome P450, family 4, subfamily V, polypeptide 2 | 226745_at | (D) DE/2 50% | 2.00 | 6.31E−07 Bonferroni/4 |
| DNAJC15 DnaJ (Hsp40) homolog, subfamily C, member 15 | 230305_at | (D) DE/2 63.5% | 4.00 | 3.94E−08 Bonferroni/4 |
| FNTA farnesyl-transferase, CAAX box, alpha | 209471_s_at | (D) DE/4 90.6% | 0.00 | 2.15E−09 Bonferroni/4 |
| GIMAP4 GTPase, IMAP family member 4 | 219243_at | (D) DE/2 77.1% | 2.00 | 1.90E−17 Bonferroni/4 |
| GIMAP7 GTPase, IMAP family member 7 | 228071_at | (D) DE/2 71.9% | 2.00 | 7.51E−08 Bonferroni/4 |
| HACL1 2-hydroxyacyl-CoA lyase 1 | 223211_at | (D) DE/1 46.9% | 4.00 | 8.93E−09 Bonferroni/4 |
| HNRNPA0 heterogeneous nuclear ribonucleo-protein A0 | 201054_at | (D) DE/2 53.1% | 2.00 | 2.83E−10 Bonferroni/4 |
| MRPS14 mitochondrial ribosomal protein S14 | 203801_at | (D) DE/2 50% | 4.00 | 1.18E−11 Bonferroni/4 |
| PIK3C3 phosphatidyl-inositol 3-kinase, catalytic subunit type 3 | 232086_at | (D) DE/2 63.5% | 3.00 | 1.43E−16 Bonferroni/4 |
| PRKCB protein kinase C, beta | 207957_s_at | (D) DE/2 51% | 6.00 | 1.04E−11 Bonferroni/4 |
| PSMB1 proteasome subunit beta 1 | 214289_at | (I) DE/1 39.2% (I) AP/2 54.7% | 6.00 | 2.51E−07 Bonferroni/4 |
| SAT1 spermidine/ spermine N1-acetyltransferase 1 | 213988_s_at | (I) DE/1 39.2% | 6.00 | 1.66E−20 Bonferroni/4 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| SLC6A4 solute carrier family 6 (neurotransmitter transporter), member 4 | 241811_x_at | (I) DE/2 70% | 8.00 | NS |
| TMEM245 transmembrane protein 245 | 223007_s_at | (D) DE/2 50% | 4.00 | 1.89E−09 Bonferroni/4 |
| TPH2 tryptophan hydroxylase 2 | 1555332_at | (I) DE/1 33.8% | 8.00 | 1.36E−01 Nominal/2 |

Clinical Utility of our Biomarkers
1. Assessment of State,
2. Prediction of Future Risk,
3. Matching to Treatments
Testing/Demonstration in Independent Clinical Cohorts

| Gene Symbol/ Gene Name | Step 4 Best Significant Predictions of State High Suicidal Ideation ROC AUC/ p-value 4 pts ALL 2 pts Gender 1 pts Gender/Dx | Step 4 Best Significant Predictions of Trait First Year Hosp with Suicidality OR/OR p-value 4 pts ALL 2 pts Gender 1 pts Gender/Dx | Step 4 Best Significant Predictions of Trait All Future Years Hosp with Suicidality OR/OR p-value 4 pts ALL 2 pts Gender 1 pts Gender/Dx | Matching to Treatments (Pharmaco genomics) Drugs that Modulate the Biomarker in opposite Direction to Suicide | CFE Score |
|---|---|---|---|---|---|
| PSME4 Proteasome Activator Subunit 4 | ALL C: (54/320) 0.61/6.46E−03 Gender Males C: (46/247) 0.61/7.56E−03 Gender Dx M-BP C: (12/82) 0.69/1.97E−02 M-PTSD C: (9/19) 0.79/1.69E−02 | ALL C: (51/359) 0.64/9.99E−04 Gender Males C: (45/307) 0.65/8.54E−04 Gender Dx M-MDD C: (7/41) 0.72/3.19E−02 M-PTSD C: (6/24) 0.85/5.65E−03 | ALL C: (140/477) 1.21/3.53E−03 L: (74/287) 1.31/3.89E−02 Gender Females L: (5/42) 6.08/4.17E−02 Gender Males C: (129/409) 1.2/5.01E−03 Gender Dx M-BP C: (23/108) 1.33/4.02E−02 M-MDD C: (13/52) 1.55/3.03E−02 M-PTSD C: (12/28) 2.01/1.12E−02 M-SZA C: (37/99) 1.24/4.48E−02 M-SZA L: (19/57) 1.6/3.56E−02 | Antidepressants | 21 |
| ACP1 acid phosphatase 1, soluble | ALL C: (54/320) 0.63/1.77E−03 Gender Males | | ALL L: (74/287) 1.36/4.24E−02 Gender Males | Omega-3 fatty acids Lithium Antidepressants Antipsychotics Psychotherapy | 20 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

|  |  |  |  |  |  |
|---|---|---|---|---|---|
|  | C:<br>(46/247)<br>0.65/6.92E−04<br>Gender Dx<br>M-BP<br>C:<br>(12/82)<br>0.74/4.69E−03<br>M-PSYCHOSIS<br>C:<br>(15/107)<br>0.69/8.50E−03<br>M-PTSD<br>C:<br>(9/19)<br>0.73/4.32E−02<br>M-PTSD<br>L:<br>(5/10)<br>0.92/1.41E−02<br>M-SZ<br>L:<br>(3/32)<br>0.79/4.96E−02<br>M-SZA<br>C:<br>(10/50)<br>0.69/3.45E−02 |  | L:<br>(69/245)<br>1.44/2.21E−02<br>Gender Dx<br>M-PTSD<br>C:<br>(12/28)<br>1.81/3.91E−02<br>M-SZ<br>L:<br>(17/62)<br>1.94/3.46E−02 |  |  |
| ACSL6<br>acyl-CoA<br>synthetase<br>long-chain<br>family<br>member 6 | ALL<br>C:<br>(54/320)<br>0.6/1.17E−02<br>Gender<br>Males<br>C:<br>(46/247)<br>0.65/1.04E−03<br>Gender Dx<br>M-BP<br>C:<br>(12/82)<br>0.79/6.84E−04<br>M-PSYCHOSIS<br>C:<br>(15/107)<br>0.63/4.94E−02<br>M-PTSD<br>C:<br>(9/19)<br>0.84/5.68E−03 | ALL<br>C:<br>(51/359)<br>0.59/2.50E−02<br>Gender<br>Males<br>C:<br>(45/307)<br>0.59/2.40E−02 | ALL<br>C:<br>(140/477)<br>1.26/1.28E−02<br>Gender<br>Males<br>C:<br>(129/409)<br>1.26/1.57E−02<br>Gender Dx<br>M-BP<br>C:<br>(23/108)<br>2.72/3.09E−02 |  | 20 |
| MAGI3<br>membrane<br>associated<br>guanylate<br>kinase, WW<br>and PDZ<br>domain<br>containing 3 | ALL<br>C:<br>(54/320)<br>0.6/1.30E−02<br>Gender<br>Males<br>C:<br>(46/247)<br>0.61/9.81E−03<br>L:<br>(16/133)<br>0.64/3.34E−02<br>Gender Dx<br>M-BP<br>C:<br>(12/82)<br>0.68/2.38E−02<br>M-PSYCHOSIS<br>C:<br>(15/107)<br>0.78/3.04E−04<br>M-PSYCHOSIS<br>L:<br>(6/56) | Gender<br>Males<br>C:<br>(45/307)<br>0.58/4.79E−02<br>Gender Dx<br>M-PSYCHOSIS<br>C:<br>(21/134)<br>0.65/1.39E−02<br>M-SZ<br>C:<br>(12/67)<br>0.66/3.87E−02 | ALL<br>C:<br>(140/477)<br>1.26/5.13E−03<br>L:<br>(74/287)<br>1.44/1.47E−02<br>Gender<br>Males<br>C:<br>(129/409)<br>1.35/1.04E−03<br>L:<br>(69/245)<br>1.52/7.94E−03<br>Gender Dx<br>M-PSYCHOSIS<br>C:<br>(68/200)<br>1.69/2.39E−04<br>M-PSYCHOSIS<br>L:<br>(36/119)<br>1.6/2.71E−02 | Antipsychotics | 20 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | Col 2 | Col 3 | Col 4 | Score |
|---|---|---|---|---|
| | 0.72/4.25E−02<br>M-SZ<br>C:<br>(5/57)<br>0.79/1.60E−02<br>M-SZ<br>L:<br>(3/32)<br>0.91/1.09E−02<br>M-SZA<br>C:<br>(10/50)<br>0.78/3.30E−03 | | M-SZ<br>C:<br>(31/101)<br>1.82/3.27E−03<br>M-SZ<br>L:<br>(17/62)<br>2.46/1.53E−02<br>M-SZA<br>C:<br>(37/99)<br>1.52/2.15E−02 | |
| PLPP3<br>phospholipid<br>phosphatase 3 | ALL<br>C:<br>(54/320)<br>0.58/3.75E−02<br>Gender<br>Males<br>C:<br>(46/247)<br>0.59/2.61E−02<br>Gender Dx<br>M-BP<br>C:<br>(12/82)<br>0.68/2.69E−02<br>M-PSYCHOSIS<br>C:<br>(15/107)<br>0.65/3.43E−02 | Gender<br>Males<br>C:<br>(45/307)<br>0.59/2.86E−02<br>Gender Dx<br>M-BP<br>C:<br>(8/92)<br>0.73/1.76E−02<br>M-<br>PSYCHOSIS<br>C:<br>(21/134)<br>0.61/4.83E−02<br>M-SZA<br>C:<br>(9/67)<br>0.69/3.73E−02 | ALL<br>C:<br>(140/477)<br>1.17/1.50E−02<br>Gender<br>Males<br>C:<br>(129/409)<br>1.22/2.90E−03<br>Gender Dx<br>M-BP<br>C:<br>(23/108)<br>1.4/1.85E−02<br>M-PSYCHOSIS<br>C:<br>(68/200)<br>1.18/4.01E−02<br>M-SZA<br>C:<br>(37/99)<br>1.28/1.73E−02 | 20 |
| SKA2<br>spindle and<br>kinetochore<br>associated<br>complex<br>subunit 2 | ALL<br>C:<br>(54/320)<br>0.61/6.70E−03<br>Gender<br>Males<br>C:<br>(46/247)<br>0.65/8.03E−04<br>Gender Dx<br>M-BP<br>C:<br>(12/82)<br>0.68/2.61E−02<br>M-MDD<br>L:<br>(2/14)<br>0.92/3.39E−02<br>M-PSYCHOSIS<br>C:<br>(15/107)<br>0.74/1.77E−03<br>M-PSYCHOSIS<br>L:<br>(6/56)<br>0.72/4.02E−02<br>M-SZ<br>C:<br>(5/57)<br>0.79/1.60E−02<br>M-SZ<br>L:<br>(3/32)<br>0.86/2.09E−02<br>M-SZA<br>C:<br>(10/50)<br>0.7/2.77E−02 | Gender Dx<br>M-SZA<br>C:<br>(9/67)<br>0.71/1.97E−02 | ALL<br>C:<br>(140/477)<br>1.17/4.49E−02<br>Gender<br>Males<br>C:<br>(129/409)<br>1.22/2.39E−02<br>Gender Dx<br>M-BP<br>C:<br>(23/108)<br>2.05/1.67E−02 | 20 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | Col2 | Col3 | Col4 | Col5 | Col6 |
|---|---|---|---|---|---|
| SOD2 superoxide dismutase 2, mitochondrial | Gender Males C: (46/247) 0.58/4.93E−02 Gender Dx M-PSYCHOSIS C: (15/107) 0.66/2.37E−02 | ALL C: (51/359) 0.6/1.43E−02 Gender Males C: (45/307) 0.61/8.62E−03 Gender Dx M-BP C: (8/92) 0.68/4.96E−02 M-PTSD C: (6/24) 0.75/3.59E−02 | ALL C: (140/477) 1.24/3.68E−03 Gender Females L: (5/42) 3.28/3.25E−02 Gender Males C: (129/409) 1.25/3.21E−03 Gender Dx M-BP C: (23/108) 1.47/1.95E−02 | Antidepressants Antipsychotics | 20 |
| CLN5 ceroid-lipofuscinosis, neuronal 5 | ALL C: (54/320) 0.64/4.17E−04 Gender Males C: (46/247) 0.66/2.71E−04 Gender Dx M-BP C: (12/82) 0.74/4.02E−03 M-PSYCHOSIS C: (15/107) 0.71/4.39E−03 M-PSYCHOSIS L: (6/56) 0.71/4.76E−02 M-SZ C: (5/57) 0.73/4.53E−02 M-SZ L: (3/32) 0.83/3.27E−02 M-SZA C: (10/50) 0.72/1.85E−02 | Gender Dx M-SZA C: (9/67) 0.68/4.03E−02 | ALL C: (140/477) 1.23/9.78E−03 L: (74/287) 1.4/2.71E−02 Gender Males C: (129/409) 1.27/5.59E−03 L: (69/245) 1.49/1.39E−02 Gender Dx M-BP C: (23/108) 1.65/2.60E−02 | | 19 |
| CLTA clathrin, light chain A | ALL C: (54/320) 0.59/2.08E−02 Gender Males C: (46/247) 0.6/1.77E−02 Gender Dx M-BP C: (12/82) 0.71/1.01E−02 | Gender Dx M-SZA C: (9/67) 0.68/4.54E−02 | ALL L: (74/287) 1.3/4.49E−02 Gender Males L: (69/245) 1.33/3.35E−02 | Antipsychotics | 19 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

|  |  |  |  |  |  |
|---|---|---|---|---|---|
|  | M-PSYCHOSIS<br>C:<br>(15/107)<br>0.68/1.40E−02<br>M-SZA<br>C:<br>(10/50)<br>0.69/3.45E−02 |  |  |  |  |
| DYRK2<br>dual<br>specificity<br>tyrosine-(Y)-<br>phosphorylation<br>regulated<br>kinase 2 | ALL<br>C:<br>(54/320)<br>0.6/7.73E−03<br>L:<br>(17/174)<br>0.62/4.85E−02<br>Gender<br>Males<br>C:<br>(46/247)<br>0.64/1.34E−03<br>L:<br>(16/133)<br>0.66/2.10E−02<br>Gender Dx<br>M-BP<br>C:<br>(12/82)<br>0.73/5.26E−03<br>M-PSYCHOSIS<br>C:<br>(15/107)<br>0.73/2.49E−03<br>L:<br>(6/56)<br>0.74/2.82E−02<br>M-SZ<br>C:<br>(5/57)<br>0.73/4.26E−02<br>Gender Dx<br>M-SZ<br>L:<br>(3/32)<br>0.89/1.52E−02<br>Gender Dx<br>M-SZA<br>C:<br>(10/50)<br>0.74/1.13E−02 | Gender Dx<br>M-PTSD<br>C:<br>(6/24)<br>0.78/2.28E−02 | ALL<br>L:<br>(74/287)<br>1.39/2.99E−02<br>Gender<br>Males<br>L:<br>(69/245)<br>1.46/1.67E−02<br>Gender Dx<br>M-PTSD<br>C:<br>(12/28)<br>2.08/2.36E−02<br>L:<br>(8/16)<br>2.73/3.54E−02<br>M-SZ<br>L:<br>(17/62)<br>1.81/4.16E−02 | Antipsychotics | 19 |
| ECHDC1<br>ethylmalonyl-<br>CoA<br>decarboxylase 1 | ALL<br>C:<br>(54/320)<br>0.62/2.09E−03<br>Gender<br>Males<br>C:<br>(46/247)<br>0.64/1.49E−03<br>Gender Dx<br>M-BP<br>C:<br>(12/82)<br>0.68/2.38E−02<br>M-PSYCHOSIS<br>C:<br>(15/107)<br>0.67/1.53E−02 | Gender Dx<br>M-PTSD<br>C:<br>(6/24)<br>0.76/3.10E−02 | ALL<br>C:<br>(140/477)<br>1.18/3.14E−02<br>Gender<br>Males<br>C:<br>(129/409)<br>1.18/3.75E−02<br>Gender Dx<br>M-PTSD<br>C:<br>(12/28)<br>2.14/2.62E−02 |  | 19 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| | M-SZ<br>L:<br>(3/32)<br>0.82/3.77E−02<br>M-SZA<br>C:<br>(10/50)<br>0.71/2.34E−02 | | | |
| FBLN5<br>fibulin 5 | Gender Dx<br>M-SZA<br>C:<br>(10/50)<br>0.69/3.45E−02 | ALL<br>C:<br>(51/359)<br>0.6/1.13E−02<br>Gender<br>Males<br>C:<br>(45/307)<br>0.64/1.50E−03<br>Gender Dx<br>M-PSYCHOSIS<br>C:<br>(21/134)<br>0.65/1.50E−02<br>M-PTSD<br>C:<br>(6/24)<br>0.73/4.78E−02<br>M-SZ<br>L:<br>(5/36)<br>0.74/4.31E−02 | Gender<br>Males<br>C:<br>(129/409)<br>1.21/1.96E−02<br>Gender<br>Males<br>L:<br>(69/245)<br>1.45/1.62E−02<br>Gender Dx<br>M-PSYCHOSIS<br>C:<br>(68/200)<br>1.36/1.00E−02<br>L:<br>(36/119)<br>1.68/1.04E−02<br>M-SZ<br>C:<br>(31/101)<br>1.46/3.22E−02<br>M-SZ<br>L:<br>(17/62)<br>2.17/1.36E−02 | 19 |
| AIMP1<br>aminoacyl tRNA<br>synthetase<br>complex-<br>interacting<br>multifunctional<br>protein 1 | ALL<br>C:<br>(54/320)<br>0.62/2.41E−03<br>L:<br>(17/174)<br>0.63/3.58E−02<br>Gender<br>Males<br>C:<br>(46/247)<br>0.67/2.25E−04<br>L:<br>(16/133)<br>0.65/2.36E−02<br>Gender Dx<br>M-BP<br>C:<br>(12/82)<br>0.73/5.06E−03<br>M-PSYCHOSIS<br>C:<br>(15/107)<br>0.71/5.55E−03<br>M-PTSD<br>L:<br>(5/10)<br>0.92/1.41E−02<br>M-SZA<br>C:<br>(10/50)<br>0.76/6.24E−03 | | ALL<br>C:<br>(140/477)<br>1.17/3.79E−02<br>Gender<br>Males<br>C:<br>(129/409)<br>1.22/1.86E−02<br>Gender Dx<br>M-BP<br>C:<br>(23/108)<br>1.44/5.00E−02<br>M-PSYCHOSIS<br>C:<br>(68/200)<br>1.3/2.48E−02<br>M-SZ<br>C:<br>(31/101)<br>1.46/4.63E−02 | 18 |
| CLN5<br>ceroid-<br>lipofuscinosis,<br>neuronal 5 | ALL<br>C:<br>(54/320)<br>0.62/3.63E−03<br>Gender<br>Males<br>C:<br>(46/247) | Gender Dx<br>M-PSYCHOSIS<br>C:<br>(21/134)<br>0.63/2.91E−02<br>M-SZA<br>C:<br>(9/67) | ALL<br>C:<br>(140/477)<br>1.22/1.37E−02<br>L:<br>(74/287)<br>1.36/3.95E−02<br>Gender | 18 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | | | | Drug | Score |
|---|---|---|---|---|---|
| | 0.63/2.17E−03<br>Gender Dx<br>M-BP<br>C:<br>(12/82)<br>0.72/7.61E−03<br>M-PSYCHOSIS<br>C:<br>(15/107)<br>0.7/6.31E−03<br>M-PSYCHOSIS<br>L:<br>(6/56)<br>0.71/4.76E−02<br>M-SZ<br>L:<br>(3/32)<br>0.84/2.82E−02<br>M-SZA<br>C:<br>(10/50)<br>0.75/7.65E−03 | 0.76/5.89E−03 | Males<br>C:<br>(129/409)<br>1.26/5.59E−03<br>L:<br>(69/245)<br>1.43/2.18E−02<br>Gender Dx<br>M-PSYCHOSIS<br>C:<br>(68/200)<br>1.34/9.29E−03<br>L:<br>(36/119)<br>1.63/2.07E−02<br>M-SZ<br>L:<br>(17/62)<br>2.14/1.66E−02<br>M-SZA<br>C:<br>(37/99)<br>1.43/1.72E−02 | | |
| ITGB1BP1<br>integrin<br>beta 1<br>binding<br>protein 1 | ALL<br>C:<br>(54/320)<br>0.57/4.27E−02<br>Gender<br>Males<br>C:<br>(46/247)<br>0.61/1.17E−02 | | ALL<br>C:<br>(140/477)<br>1.26/3.93E−03<br>L:<br>(74/287)<br>1.51/6.20E−03<br>Gender<br>Males<br>C:<br>(129/409)<br>1.31/1.49E−03<br>L:<br>(69/245)<br>1.61/3.09E−03<br>Gender Dx<br>M-PSYCHOSIS<br>C:<br>(68/200)<br>1.28/2.19E−02<br>M-SZA<br>C:<br>(37/99)<br>2.17/1.06E−04<br>L:<br>(19/57)<br>1.8/2.44E−02 | Lithium | 18 |
| NR3C1<br>nuclear<br>receptor<br>subfamily<br>3, group C,<br>member 1<br>(glucocorticoid<br>receptor) | ALL<br>C:<br>(54/320)<br>0.58/4.00E−02<br>Gender<br>Males<br>C:<br>(46/247)<br>0.58/4.91E−02<br>Gender Dx<br>F-MDD<br>C:<br>(2/11)<br>0.89/4.95E−02<br>M-BP<br>C:<br>(12/82)<br>0.69/1.91E−02 | | Gender<br>Males<br>L:<br>(69/245)<br>1.38/3.05E−02 | Valproate<br>Antidepressants<br>Antipsychotics | 18 |
| PER1<br>period<br>circadian<br>clock 1 | ALL<br>C:<br>(54/320)<br>0.62/3.51E−03<br>Gender<br>Females | Gender Dx<br>M-PSYCHOSIS<br>C:<br>(21/134)<br>0.64/1.94E−02 | ALL<br>C:<br>(140/477)<br>1.16/2.89E−02<br>L:<br>(74/287) | Antidepressants<br>Anxiolytics | 18 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | Col2 | Col3 | Col4 | Col5 | Treatment | Score |
|---|---|---|---|---|---|---|
| | C:<br>(8/73)<br>0.75/1.19E−02<br>Gender<br>Males<br>C:<br>(46/247)<br>0.6/2.19E−02<br>Gender Dx<br>F-MDD<br>C:<br>(2/11)<br>1/1.69E−02<br>M-BP<br>C:<br>(12/82)<br>0.68/2.24E−02<br>M-SZ<br>C:<br>(5/57)<br>0.73/4.80E−02 | | | 1.49/3.57E−03<br>Gender<br>Males<br>C:<br>(129/409)<br>1.15/4.75E−02<br>L:<br>(69/245)<br>1.53/3.28E−03<br>Gender Dx<br>M-PSYCHOSIS<br>C:<br>(68/200)<br>1.3/7.61E−03<br>L:<br>(36/119)<br>1.52/1.87E−02<br>Gender Dx<br>M-SZ<br>C:<br>(31/101)<br>1.43/1.26E−02 | | |
| PIK3R1<br>Phospho-<br>inositide-3-<br>Kinase<br>Regulatory<br>Subunit 1 | Gender Dx<br>M-PTSD<br>C:<br>(9/19)<br>0.76/3.02E−02 | ALL<br>C:<br>(51/359)<br>0.58/4.10E−02<br>Gender<br>Females<br>L:<br>(1/31)<br>1/4.68E−02<br>Gender Dx<br>F-MDD<br>C:<br>(3/17)<br>0.91/1.78E−02 | ALL<br>L:<br>(74/287)<br>1.27/4.23E−02<br>Gender Dx<br>F-MDD<br>C:<br>(3/17)<br>2.93/3.98E−02<br>M-PTSD<br>C:<br>(12/28)<br>1.7/2.41E−02<br>M-PTSD<br>L:<br>(8/16)<br>1.94/4.50E−02 | | Lithium<br>Psychotherapy | 18 |
| PRKAR2B<br>protein<br>kinase,<br>cAMP-<br>dependent,<br>regulatory,<br>type II,<br>beta | Gender Dx<br>F-BP<br>C:<br>(3/32)<br>0.84/2.82E−02 | Gender Dx<br>M-BP<br>C:<br>(8/92)<br>0.68/4.55E−02<br>Gender Dx<br>M-BP<br>L:<br>(3/57)<br>0.8/4.00E−02 | ALL<br>L:<br>(74/287)<br>1.44/2.15E−02<br>Gender<br>Males<br>L:<br>(69/245)<br>1.4/3.74E−02<br>Gender Dx<br>M-BP<br>C:<br>(23/108)<br>1.63/2.48E−02<br>L:<br>(11/68)<br>3.34/4.09E−02 | | Valproate<br>Antipsychotics | 18 |
| SAE1<br>SUMO1<br>activating<br>enzyme<br>subunit 1 | Gender<br>Females<br>C:<br>(8/73)<br>0.71/2.60E−02<br>Gender Dx<br>F-MDD<br>C:<br>(2/11)<br>0.89/4.95E−02 | ALL<br>C:<br>(51/359)<br>0.58/3.97E−02<br>Gender<br>Males<br>C:<br>(45/307)<br>0.58/4.26E−02<br>Gender Dx<br>M-BP<br>C:<br>(8/92)<br>0.68/4.29E−02<br>M-MDD<br>C:<br>(7/41)<br>0.7/4.81E−02 | ALL<br>C:<br>(140/477)<br>1.17/3.25E−02<br>Gender<br>Males<br>C:<br>(129/409)<br>1.2/1.82E−02<br>Gender Dx<br>M-MDD<br>C:<br>(13/52)<br>2.4/1.56E−03<br>M-MDD<br>L:<br>(6/29)<br>2.76/2.76E−02 | | | 18 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | |
|---|---|---|---|---|
| SPATA18<br>spermatogenesis<br>associated 18 | ALL<br>C:<br>(54/320)<br>0.59/2.23E−02<br>L:<br>(17/174)<br>0.65/2.04E−02<br>Gender<br>Males<br>C:<br>(46/247)<br>0.58/3.76E−02<br>L:<br>(16/133)<br>0.63/4.78E−02<br>Gender Dx<br>M-PSYCHOSIS<br>L:<br>(6/56)<br>0.72/4.25E−02<br>M-PTSD<br>L:<br>(5/10)<br>0.84/3.79E−02 | ALL<br>C:<br>(19/200)<br>0.62/3.92E−02<br>Gender Dx<br>M-PSYCHOSIS<br>L:<br>(7/70)<br>0.77/9.66E−03<br>M-SZ<br>L:<br>(5/36)<br>0.88/3.73E−03 | | 18 |
| ZNF565<br>zinc finger<br>protein 565 | ALL<br>C:<br>(54/320)<br>0.58/4.07E−02<br>Gender<br>Males<br>C:<br>(46/247)<br>0.61/1.04E−02<br>Gender Dx<br>M-PSYCHOSIS<br>C:<br>(15/107)<br>0.71/4.88E−03<br>M-SZA<br>C:<br>(10/50)<br>0.75/8.17E−03 | Gender Dx<br>M-SZA<br>C:<br>(9/67)<br>0.7/2.68E−02 | ALL<br>C:<br>(140/477)<br>1.18/2.99E−02<br>L:<br>(74/287)<br>1.34/4.22E−02<br>Gender<br>Males<br>C:<br>(129/409)<br>1.21/1.67E−02<br>L:<br>(69/245)<br>1.44/1.88E−02<br>Gender Dx<br>M-PSYCHOSIS<br>C:<br>(68/200)<br>1.23/4.28E−02<br>L:<br>(36/119)<br>1.51/3.57E−02<br>M-SZ<br>L:<br>(17/62)<br>1.91/2.16E−02<br>M-SZA<br>C:<br>(37/99)<br>1.46/2.62E−02 | 18 |
| AIMP1<br>aminoacyl tRNA<br>synthetase<br>complex-<br>interacting<br>multifunctional<br>protein 1 | ALL<br>C:<br>(54/320)<br>0.6/1.20E−02<br>Gender<br>Males<br>C:<br>(46/247)<br>0.63/2.43E−03<br>Gender Dx<br>M-PSYCHOSIS<br>C:<br>(15/107)<br>0.72/2.86E−03<br>M-SZ<br>L:<br>(3/32)<br>0.84/2.82E−02<br>M-SZA | Gender Dx<br>M-SZA<br>C:<br>(9/67)<br>0.69/3.17E−02 | Gender<br>Males<br>C:<br>(129/409)<br>1.19/3.60E−02<br>L:<br>(69/245)<br>1.36/4.76E−02<br>Gender Dx<br>M-BP<br>C:<br>(23/108)<br>1.77/2.21E−02<br>M-PTSD<br>C:<br>(12/28)<br>1.8/4.33E−02 | 17 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | | |
|---|---|---|---|---|---|
| | C:<br>(10/50)<br>0.74/9.32E−03 | | | | |
| AIMP1<br>aminoacyl tRNA<br>synthetase<br>complex-<br>interacting<br>multifunctional<br>protein 1 | ALL<br>C:<br>(54/320)<br>0.62/2.92E−03<br>Gender<br>Males<br>C:<br>(46/247)<br>0.65/6.19E−04<br>Gender Dx<br>M-BP<br>C:<br>(12/82)<br>0.68/2.10E−02<br>M-PSYCHOSIS<br>C:<br>(15/107)<br>0.69/1.03E−02<br>M-SZ<br>L:<br>(3/32)<br>0.82/3.77E−02<br>M-SZA<br>C:<br>(10/50)<br>0.7/2.47E−02 | | ALL<br>C:<br>(140/477)<br>1.2/2.64E−02<br>L:<br>(74/287)<br>1.36/4.65E−02<br>Gender<br>Males<br>C:<br>(129/409)<br>1.25/1.31E−02<br>L:<br>(69/245)<br>1.41/3.38E−02<br>Gender Dx<br>M-PSYCHOSIS<br>C:<br>(68/200)<br>1.38/1.31E−02<br>M-SZA<br>C:<br>(37/99)<br>1.51/1.70E−02 | | 17 |
| BCL2<br>B-cell<br>CLL/<br>lymphoma 2 | ALL<br>C:<br>(54/320)<br>0.64/7.17E−04<br>Gender<br>Males<br>C:<br>(46/247)<br>0.65/5.80E−04<br>Gender Dx<br>M-BP<br>C:<br>(12/82)<br>0.74/4.69E−03<br>M-PSYCHOSIS<br>C:<br>(15/107)<br>0.69/8.50E−03<br>M-SZ<br>C:<br>(5/57)<br>0.78/2.11E−02<br>L:<br>(3/32)<br>0.85/2.43E−02 | | Gender Dx<br>M-SZ<br>C:<br>(31/101)<br>1.37/4.28E−02 | Lithium<br>Valproate<br>Antipsychotics | 17 |
| CAT<br>catalase | ALL<br>C:<br>(54/320)<br>0.62/2.24E−03<br>Gender<br>Females<br>C:<br>(8/73)<br>0.73/1.70E−02<br>Gender<br>Males<br>C:<br>(46/247)<br>0.6/1.58E−02<br>Gender Dx<br>F-MDD<br>C:<br>(2/11)<br>0.94/2.97E−02<br>M-BP | Gender<br>Males<br>C:<br>(45/307)<br>0.58/4.90E−02<br>Gender Dx<br>M-MDD<br>C:<br>(7/41)<br>0.72/3.58E−02<br>M-SZA<br>C:<br>(9/67)<br>0.72/1.65E−02 | Gender Dx<br>M-MDD<br>C:<br>(13/52)<br>2.02/1.68E−02 | | 17 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

|  |  |  |  |  |  |
|---|---|---|---|---|---|
|  | C:<br>(12/82)<br>0.75/3.44E−03 |  |  |  |  |
| ECHDC1<br>ethylmalonyl-<br>CoA<br>decarboxylase 1 | ALL<br>C:<br>(54/320)<br>0.61/4.99E−03<br>Gender<br>Males<br>C:<br>(46/247)<br>0.61/9.52E−03<br>Gender Dx<br>M-BP<br>C:<br>(12/82)<br>0.67/2.94E−02<br>M-SZA<br>C:<br>(10/50)<br>0.67/4.95E−02 | Gender Dx<br>M-SZA<br>C:<br>(9/67)<br>0.7/2.91E−02 | Gender<br>Males<br>C:<br>(129/409)<br>1.18/3.76E−02<br>L:<br>(69/245)<br>1.41/2.93E−02 |  | 17 |
| HDAC2<br>histone<br>deacetylase 2 | ALL<br>C:<br>(54/320)<br>0.64/6.78E−04<br>Gender<br>Males<br>C:<br>(46/247)<br>0.64/1.10E−03<br>Gender Dx<br>M-BP<br>C:<br>(12/82)<br>0.71/9.10E−03<br>M-PSYCHOSIS<br>C:<br>(15/107)<br>0.68/1.13E−02<br>M-SZA<br>C:<br>(10/50)<br>0.67/4.71E−02 | Gender Dx<br>M-PTSD<br>C:<br>(6/24)<br>0.75/3.59E−02 | ALL<br>L:<br>(74/287)<br>1.38/2.95E−02<br>Gender<br>Males<br>L:<br>(69/245)<br>1.45/1.73E−02<br>Gender Dx<br>M-BP<br>C:<br>(23/108)<br>1.6/1.61E−02 | Lithium | 17 |
| LPP<br>LIM domain<br>containing<br>preferred<br>translocation<br>partner<br>in lipoma | ALL<br>C:<br>(54/320)<br>0.62/2.14E−03<br>Gender<br>Females<br>C:<br>(8/73)<br>0.72/2.20E−02<br>Gender<br>Males<br>C:<br>(46/247)<br>0.61/1.07E−02<br>Gender Dx<br>F-BP<br>C:<br>(3/32)<br>0.84/2.82E−02<br>M-PTSD<br>C:<br>(9/19)<br>0.74/3.62E−02 | Gender<br>Females<br>L:<br>(1/31)<br>1/4.68E−02<br>Gender Dx<br>M-PTSD<br>C:<br>(6/24)<br>0.82/9.82E−03 | Gender<br>Females<br>L:<br>(5/42)<br>3.02/3.56E−02<br>Gender Dx<br>F-MDD<br>C:<br>(3/17)<br>3.33/3.37E−02<br>M-MDD<br>L:<br>(6/29)<br>2.21/3.20E−02<br>M-PTSD<br>C:<br>(12/28)<br>1.92/7.27E−03 |  | 17 |
| PSMB4<br>proteasome<br>subunit<br>beta 4 | ALL<br>C:<br>(54/320)<br>0.59/1.87E−02<br>Gender<br>Males<br>C:<br>(46/247) | Gender Dx<br>M-SZA<br>C:<br>(9/67)<br>0.7/3.04E−02 |  | Benzodiazepines | 17 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | | |
|---|---|---|---|---|---|
| | 0.63/2.91E−03 | | | | |
| | Gender Dx | | | | |
| | M-BP | | | | |
| | C: | | | | |
| | (12/82) | | | | |
| | 0.7/1.50E−02 | | | | |
| | M-PSYCHOSIS | | | | |
| | C: | | | | |
| | (15/107) | | | | |
| | 0.71/4.63E−03 | | | | |
| | M-SZA | | | | |
| | C: | | | | |
| | (10/50) | | | | |
| | 0.76/5.44E−03 | | | | |
| RPE | ALL | Gender Dx | ALL | | 17 |
| ribulose-5- | C: | M-PTSD | L: | | |
| phosphate- | (54/320) | C: | (74/287) | | |
| 3-epimerase | 0.6/1.15E−02 | (6/24) | 1.4/3.01E−02 | | |
| | Gender | 0.91/1.68E−03 | Gender | | |
| | Males | Gender Dx | Males | | |
| | C: | M-PTSD | L: | | |
| | (46/247) | L: | (69/245) | | |
| | 0.62/5.61E−03 | (4/13) | 1.45/2.37E−02 | | |
| | Gender Dx | 0.89/1.54E−02 | Gender Dx | | |
| | M-BP | | M-PTSD | | |
| | C: | | C: | | |
| | (12/82) | | (12/28) | | |
| | 0.7/1.47E−02 | | 3.51/6.74E−03 | | |
| | M-PSYCHOSIS | | L: | | |
| | C: | | (8/16) | | |
| | (15/107) | | 3.93/8.53E−03 | | |
| | 0.66/2.50E−02 | | | | |
| | M-SZ | | | | |
| | L: | | | | |
| | (3/32) | | | | |
| | 0.84/2.82E−02 | | | | |
| VTA1 | ALL | Gender Dx | Gender | | 17 |
| vesicle | C: | M-SZA | Males | | |
| (multivesicular | (54/320) | C: | L: | | |
| body) | 0.6/1.26E−02 | (9/67) | (69/245) | | |
| trafficking 1 | Gender | 0.72/1.72E−02 | 1.43/3.26E−02 | | |
| | Males | | | | |
| | C: | | | | |
| | (46/247) | | | | |
| | 0.61/1.00E−02 | | | | |
| | Gender Dx | | | | |
| | M-BP | | | | |
| | C: | | | | |
| | (12/82) | | | | |
| | 0.68/2.31E−02 | | | | |
| | M-PSYCHOSIS | | | | |
| | C: | | | | |
| | (15/107) | | | | |
| | 0.68/1.19E−02 | | | | |
| | M-SZ | | | | |
| | L: | | | | |
| | (3/32) | | | | |
| | 0.84/2.82E−02 | | | | |
| | M-SZA | | | | |
| | C: | | | | |
| | (10/50) | | | | |
| | 0.72/1.74E−02 | | | | |
| AKAP13 | Gender Dx | Gender | ALL | Antipsychotics | 16 |
| A kinase | M-PTSD | Females | L: | | |
| (PRKA) | C: | L: | (74/287) | | |
| anchor | (9/19) | (1/31) | 1.3/2.13E−02 | | |
| protein 13 | 0.76/3.02E−02 | 1/4.68E−02 | Gender | | |
| | | Gender Dx | Females | | |
| | | M-PTSD | L: | | |
| | | C: | (5/42) | | |
| | | (6/24) | 3.36/2.31E−02 | | |
| | | 0.78/2.28E−02 | Gender | | |
| | | | Males | | |
| | | | L: | | |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | | |
|---|---|---|---|---|---|
| | | | (69/245)<br>1.26/4.34E−02<br>Gender Dx<br>M-PTSD<br>C:<br>(12/28)<br>1.67/3.09E−02 | | |
| CD164<br>CD164<br>molecule,<br>sialomucin | ALL<br>C:<br>(54/320)<br>0.61/3.94E−03<br>Gender<br>Males<br>C:<br>(46/247)<br>0.62/5.70E−03<br>Gender Dx<br>M-BP<br>C:<br>(12/82)<br>0.72/7.34E−03<br>M-SZ<br>L:<br>(3/32)<br>0.82/3.77E−02 | Gender Dx<br>M-PTSD<br>C:<br>(6/24)<br>0.81/1.39E−02 | Gender Dx<br>M-PTSD<br>C:<br>(12/28)<br>2.15/1.91E−02 | Antipsychotics | 16 |
| CD47<br>CD47<br>molecule | ALL<br>C:<br>(54/320)<br>0.6/1.03E−02<br>Gender<br>Males<br>C:<br>(46/247)<br>0.63/2.94E−03<br>M-BP<br>C:<br>(12/82)<br>0.67/3.22E−02<br>M-PSYCHOSIS<br>C:<br>(15/107)<br>0.69/7.89E−03<br>M-SZ<br>L:<br>(3/32)<br>0.8/4.33E−02<br>M-SZA<br>C:<br>(10/50)<br>0.74/9.32E−03 | Gender Dx<br>M-SZA<br>C:<br>(9/67)<br>0.68/4.54E−02 | Gender Dx<br>M-PTSD<br>C:<br>(12/28)<br>1.87/3.94E−02 | Omega-3<br>fatty acids<br>Antipsychotics | 16 |
| CYP4V2<br>cytochrome<br>P450,<br>family 4,<br>subfamily V,<br>polypeptide 2 | ALL<br>C:<br>(54/320)<br>0.57/4.20E−02<br>Gender<br>Males<br>C:<br>(46/247)<br>0.61/1.14E−02<br>Gender Dx<br>M-BP<br>C:<br>(12/82)<br>0.77/1.58E−03<br>M-PSYCHOSIS<br>C:<br>(15/107)<br>0.68/1.36E−02<br>M-SZA<br>C:<br>(10/50)<br>0.78/3.82E−03 | | ALL<br>C:<br>(140/477)<br>1.25/8.55E−03<br>Gender<br>Males<br>C:<br>(129/409)<br>1.26/7.94E−03<br>Gender Dx<br>M-BP<br>C:<br>(23/108)<br>1.68/2.19E−02<br>M-PSYCHOSIS<br>C:<br>(68/200)<br>1.32/2.05E−02<br>M-SZA<br>C:<br>(37/99)<br>1.42/2.59E−02 | Antidepressants | 16 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | Col 2 | Col 3 | Col 4 | Col 5 | Score |
|---|---|---|---|---|---|
| DNAJC15 DnaJ (Hsp40) homolog, subfamily C, member 15 | ALL C: (54/320) 0.57/4.69E−02 Gender Males C: (46/247) 0.59/2.93E−02 Gender Dx M-PTSD C: (9/19) 0.77/2.27E−02 | Gender Dx M-PTSD C: (6/24) 0.76/2.87E−02 | Gender Dx M-PTSD C: (12/28) 2.37/2.03E−02 | | 16 |
| FNTA farnesyltransferase, CAAX box, alpha | ALL C: (54/320) 0.6/9.25E−03 Gender Males C: (46/247) 0.63/3.64E−03 Gender Dx M-BP C: (12/82) 0.74/4.52E−03 M-PSYCHOSIS C: (15/107) 0.65/3.10E−02 M-SZ L: (3/32) 0.83/3.27E−02 | | ALL L: (74/287) 1.35/4.46E−02 Gender Males L: (69/245) 1.43/2.51E−02 | | 16 |
| GIMAP4 GTPase, IMAP family member 4 | ALL C: (54/320) 0.6/8.98E−03 Gender Males C: (46/247) 0.62/4.62E−0 Gender Dx M-BP C: (12/82) 0.73/5.67E−03 | | ALL C: (140/477) 1.19/1.94E−02 L: (74/287) 1.49/1.00E−02 Gender Males C: (129/409) 1.21/1.57E−02 L: (69/245) 1.55/5.93E−03 Gender Dx M-PTSD L: (8/16) 2.45/3.52E−02 | Benzodiazepines | 16 |
| GIMAP7 GTPase, IMAP family member 7 | ALL C: (54/320) 0.67/3.59E−05 Gender Males C: (46/247) 0.7/1.36E−05 Gender Dx M-BP C: (12/82) 0.78/1.22E−03 M-PSYCHOSIS C: (15/107) 0.66/2.08E−02 | | ALL C: (140/477) 1.22/1.48E−02 Gender Males C: (129/409) 1.23/1.55E−02 Gender Dx M-BP C: (23/108) 1.54/3.90E−02 M-PSYCHOSIS C: (68/200) 1.27/3.91E−02 | | 16 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | | |
|---|---|---|---|---|---|
| | M-PTSD<br>C:<br>(9/19)<br>0.84/5.68E−03<br>M-SZ<br>L:<br>(3/32)<br>0.86/2.09E−02 | | M-PTSD<br>L:<br>(8/16)<br>2.42/3.55E−02 | | |
| HACL1<br>2-hydroxyacyl-<br>CoA lyase 1 | Gender<br>Males<br>C:<br>(46/247)<br>0.62/6.04E−03<br>Gender Dx<br>M-BP<br>C:<br>(12/82)<br>0.66/3.83E−02<br>M-PSYCHOSIS<br>C:<br>(15/107)<br>0.72/2.70E−03<br>M-SZA<br>C:<br>(10/50)<br>0.76/6.68E−03 | Gender Dx<br>M-SZA<br>C:<br>(9/67)<br>0.68/3.88E−02 | ALL<br>C:<br>(140/477)<br>1.19/2.11E−02<br>L:<br>(74/287)<br>1.35/3.32E−02<br>Gender<br>Males<br>C:<br>(129/409)<br>1.24/8.47E−03<br>L:<br>(69/245)<br>1.42/1.71E−02<br>Gender Dx<br>M-PSYCHOSIS<br>C:<br>(68/200)<br>1.26/3.24E−02<br>M-SZ<br>L:<br>(17/62)<br>1.92/3.45E−02 | | 16 |
| HNRNPA0<br>heterogeneous<br>nuclear<br>ribonucleo-<br>protein A0 | ALL<br>C:<br>(54/320)<br>0.6/9.17E−03<br>Gender<br>Males<br>C:<br>(46/247)<br>0.61/9.34E−03<br>Gender Dx<br>M-BP<br>C:<br>(12/82)<br>0.75/3.18E−03<br>M-PSYCHOSIS<br>C:<br>(15/107)<br>0.71/5.55E−03<br>M-SZ<br>C:<br>(5/57)<br>0.75/3.34E−02<br>M-SZ<br>L:<br>(3/32)<br>0.79/4.96E−02<br>M-SZA<br>C:<br>(10/50)<br>0.69/3.45E−02 | | ALL<br>L:<br>(74/287)<br>1.35/4.70E−02<br>Gender<br>Males<br>L:<br>(69/245)<br>1.38/3.73E−02 | | 16 |
| MRPS14<br>mitochondrial<br>ribosomal<br>protein S14 | ALL<br>C:<br>(54/320)<br>0.61/6.26E−03<br>Gender<br>Males<br>C:<br>(46/247)<br>0.64/1.76E−03<br>Gender Dx<br>M-BP | | Gender<br>Males<br>C:<br>(129/409)<br>1.2/3.06E−02<br>Gender<br>Males<br>L:<br>(69/245)<br>1.41/2.99E−02<br>Gender Dx | Omega-3<br>fatty acids | 16 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| | | | | | |
|---|---|---|---|---|---|
| | C:<br>(12/82)<br>0.72/8.78E−03<br>M-PSYCHOSIS<br>C:<br>(15/107)<br>0.71/4.51E−03<br>M-SZ<br>C:<br>(5/57)<br>0.73/4.80E−02<br>L:<br>(3/32)<br>0.79/4.96E−02<br>M-SZA<br>C:<br>(10/50)<br>0.71/1.96E−02 | | M-BP<br>C:<br>(23/108)<br>1.51/4.23E−02 | | |
| PIK3C3<br>phosphatidyl-<br>inositol<br>3-kinase,<br>catalytic<br>subunit<br>type 3 | ALL<br>C:<br>(54/320)<br>0.58/3.62E−02<br>Gender Dx<br>F-MDD<br>C:<br>(2/11)<br>0.94/2.97E−02<br>M-BP<br>C:<br>(12/82)<br>0.65/4.92E−02 | Gender Dx<br>M-PTSD<br>C:<br>(6/24)<br>0.83/8.20E−03<br>Gender Dx<br>M-SZA<br>C:<br>(9/67)<br>0.7/2.79E−02 | Gender<br>Males<br>L:<br>(69/245)<br>1.38/3.36E−02<br>Gender Dx<br>M-PSYCHOSIS<br>L:<br>(36/119)<br>1.57/2.66E−02<br>M-PTSD<br>C:<br>(12/28)<br>1.94/3.19E−02 | Antidepressants | 16 |
| PRKCB<br>protein<br>kinase C,<br>beta | ALL<br>C:<br>(54/320)<br>0.61/3.96E−03<br>Gender<br>Males<br>C:<br>(46/247)<br>0.61/8.52E−03<br>Gender Dx<br>M-BP<br>C:<br>(12/82)<br>0.76/2.21E−03 | | | Lithium | 16 |
| PSMB1<br>proteasome<br>subunit<br>beta 1 | Gender<br>Females<br>C:<br>(8/73)<br>0.75/1.19E−02<br>Gender Dx<br>F-MDD<br>C:<br>(2/11)<br>1/1.69E−02<br>M-PTSD<br>C:<br>(9/19)<br>0.8/1.37E−02<br>L:<br>(5/10)<br>0.92/1.41E−02 | Gender Dx<br>F-MDD<br>C:<br>(3/17)<br>0.88/2.58E−02 | Gender Dx<br>M-BP<br>L:<br>(11/68)<br>1.94/2.90E−02<br>M-SZA<br>L:<br>(19/57)<br>1.56/3.41E−02 | | 16 |
| SAT1<br>spermidine/<br>spermine<br>N1-<br>acetyltransferase 1 | | ALL<br>C:<br>(51/359)<br>0.59/1.62E−02<br>Gender<br>Males<br>C:<br>(45/307)<br>0.59/3.02E−02<br>Gender Dx<br>M-SZ | Gender Dx<br>M-SZ<br>C:<br>(31/101)<br>1.43/2.42E−02 | Omega-3<br>fatty acids | 16 |

TABLE 23-continued

CFE. Convergent Functional Evidence (CFE) Score: Prioritization of Top Biomarkers for Suicidality (resulting in a panel of n = 50 biomarkers, from 46 genes). Some genes have more than one biomarker probeset. The CFE score for each biomarker is based on the totality of evidence from our studies (Discovery, Prioritization, Validation, and Clinical Utility Testing). These biomarkers may be a panel, with the score for 50 biomarkers panel (BioM 50) computed in an additive way, with each biomarker in the panel having the CFE score as a weight coefficient.

| Gene | Col2 | Col3 | Col4 | Col5 | Col6 | CFE |
|------|------|------|------|------|------|-----|
| | | C:<br>(12/67)<br>0.68/2.58E−02 | | | | |
| SLC6A4<br>solute carrier family 6 (neurotransmitter transporter), member 4 | ALL<br>C:<br>(54/320)<br>0.63/1.73E−03<br>Gender Males<br>C:<br>(46/247)<br>0.66/3.89E−04<br>M-BP<br>C:<br>(12/82)<br>0.7/1.57E−02<br>M-PSYCHOSIS<br>C:<br>(15/107)<br>0.67/1.56E−02<br>M-SZ<br>C:<br>(5/57)<br>0.77/2.42E−02 | | | Gender Females<br>C:<br>(11/68)<br>1.94/2.25E−02 | Omega-3 fatty acids<br>Lithium<br>Antidepressants<br>Remifentanil<br>Exposure therapy | 16 |
| TMEM245<br>transmembrane protein 245 | | | Gender Males<br>C:<br>(45/307)<br>0.58/4.98E−02<br>Gender Dx<br>M-BP<br>C:<br>(8/92)<br>0.72/2.08E−02 | ALL<br>C:<br>(140/477)<br>1.2/1.50E−02<br>Gender Males<br>C:<br>(129/409)<br>1.21/1.71E−02 | | 16 |
| TPH2<br>tryptophan hydroxylase 2 | ALL<br>C:<br>(54/320)<br>0.65/2.98E−04<br>Gender Males<br>C:<br>(46/247)<br>0.68/6.60E−05<br>Gender Dx<br>M-BP<br>C:<br>(12/82)<br>0.89/7.93E−06<br>M-PSYCHOSIS<br>C:<br>(15/107)<br>0.69/8.29E−03<br>M-SZA<br>C:<br>(10/50)<br>0.75/8.17E−03 | | | Gender Dx<br>M-BP<br>C:<br>(23/108)<br>1.36/4.64E−02 | Antipsychotics<br>Physical and Cognitive stimulation | 16 |

TABLE 24

New drug Discovery/Repurposing. A. Top CFE BioM 50 Connectivity Map (CMAP) database discovery. Query for signature was done using exact Affymetrix probesets and direction of change. Drugs that have opposite gene expression profile effects to suicidality biomarkers signatures. A score of −1 indicates the perfect match, i.e. the best potential therapeutic for treating suicide. B. Top CFE BioM 50 NIH LINCS database discovery. Using the L1000CDS2 (LINCS L1000 Characteristic Direction Signature Search Engine) tool. Query for signature was done using gene symbols and direction of change. Shown are compounds Reversing direction of change in suicidality.

A. Top CFE BioM 50 CMAP Discovery
(n = 46 unique genes; 5 increased and 25 decreased were present in HG-U133A array used by CMAP)

| Rank | CMAP name | Score |
|---|---|---|
| 1 | trimethoprim | −1 |
| 2 | ethoxyquin | −0.979 |
| 3 | haloperidol | −0.966 |
| 4 | terazosin | −0.947 |
| 5 | pepstatin | −0.921 |
| 6 | diethylstilbestrol | −0.919 |
| 7 | nifenazone | −0.905 |
| 8 | metrizamide | −0.902 |
| 9 | prazosin | −0.87 |
| 10 | baclofen | −0.864 |

B. Top CFE BioM 50 LINCS Discovery
(n = 46 unique genes; 12 increased and 34 decreased).

| Rank | Drug | Score |
|---|---|---|
| 1 | Daunorubicin hydrochloride | 0.1143 |
| 2 | BRD-K06666320 | 0.1143 |
| 3 | WZ-3105 | 0.1143 |
| 4 | Piretanide | 0.0857 |
| 5 | Syk Inhibitor | 0.0857 |
| 6 | vorinostat | 0.0857 |
| 7 | DACTINOMYCIN | 0.0857 |
| 8 | trichostatin A | 0.0857 |
| 9 | Tiotidine | 0.0857 |
| 10 | troglitazone | 0.0857 |

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for treating suicidality and mitigating suicidality risk in a subject in need thereof, comprising the steps of:
determining an expression level of at least a fist panel of blood biomarkers or a second panel of blood biomarkers in a sample from the subject;
wherein the first panel of biomarkers in the panel comprise; Apolipoprotein E (APOE), anchor protein 13 (AKAP13), aldehyde dehydrogenase 7 family, member A1 (ALDH7A1), adipogenesis regulatory factor (ADIRF), beta-2-microglobulin (B2M), Gene Accession No. BF114768, CD109 molecule (CD109), Cortactin (CTTN), chromosome 14 open reading frame 180 (C14ORF180), Dab, mitogen-responsive phosphoprotein, homolog 2 (Drosophila) (DAB2), dual specificity phosphatase 13 (DUSP13), EGF containing fibulin-like extracellular matrix protein 2 (EFEMP2), fatty acid desaturase 1 (FADS1), GRB2 Associated Binding Protein 1 (GAB1), glycine amidinotransferase (L-arginine: glycine amidinotransferase) (GATM), 5-Hydroxytryptamine Receptor 2A (HTR2A), Histone Cluster 1 H2B Family Member O (HIST1H2BO), Interleukin 6 (IL6), interleukin 13 (IL13), inositol-trisphosphate 3-kinase B (ITPKB), Lipoma HMGIC fusion partner (LHFP), LIM domain containing preferred translocation partner in lipoma (LPP), metallothionein 1E (MT1E), Nerve Growth Factor Receptor (NGFR), Proteasome Activator Subunit 4 (PSME4), proteasome subunit beta 1 (PSMB1), phospholipid phosphatase 3 (PLPP3), period circadian clock 1 (PER1), Phosphoinositide-3-Kinase Regulatory Subunit 1 (PIK3R1), phosphatidic acid phosphatase type 2B (PPAP2B), protein tyrosine kinase 2 (PTK2), spermidine/spermine N1-acetyltransferase 1 (SAT1), septin 8 SEPT8, solute carrier family 4 (sodium bicarbonate cotransporter), member (SLC4A4), superoxide dismutase 2, mitochondrial (SOD2), spermatogenesis associated 18 (SPATA18), synaptopodin 2-like (SYNPO2L), Transmembrane 4 L Six Family Member 1 (TM4SF1), tryptophan hydroxylase 2 (TPH2), and tyrosine 3-monooxygenase/tryptophan 5-monooxygenase activation protein (YWHAH),
wherein the second panel of biomarkers comprises acid phosphatase 1, soluble (ACP1), acyl-CoA synthetase long-chain family member 6 (ACSL6), adenylate kinase 2 (AK2), arrestin, beta (ARRB1), aminoacyl tRNA synthetase complex-interacting multifunctional protein 1 (AIMP1), acyl-CoA synthetase medium-chain family member 3 (ACSM3), aspartylglucosaminidase (AGA), A kinase (PRKA) anchor protein 2 (AKAP2), A kinase (PRKA) anchor protein 10 (AKAP10), ATPase, H+ transporting, lysosomal 9 kDa, V0 subunit e1 (ATP6VOE1), adenosine kinase (ADK), ankyrin repeat and MYND domain containing (ANKMY1), adenosylhomocysteinase-like 1 (AHCYL1), adenosylhomocysteinase-like 2 (AHCYL2), adenosine deaminase-like (ADAL), ceroid-lipofuscinosis, neuronal 5 (CLN5), chromosome 20 open reading frame 27 (C20ORF27), chromosome 8 open reading frame 74 (C8ORF74), CDK5 regulatory subunit associated protein 1-like 1 (CDKAL1), centromere protein H (CENPH), delta-like 1 (Drosophila) (DLL1), dual specificity tyrosine-(Y)-phosphorylation regulated kinase 2 (ECHDC1), ERG, fibulin 5 (FBLN5), farnesyltransferase, CAAX box, alpha (FNTA), family with sequence similarity 63, member B (FAM63B), fumarate hydratase (FH), flotillin 2 (FLOT2), GDP dissociation inhibitor 2 (GDI2), glycogen synthase kinase 3 beta (GSK3B), G2/M-phase specific E3 ubiquitin protein ligase (G2E3), histone deacetylase 2 (HDAC2), heterogeneous nuclear ribonucleoprotein A0 (HNRNPA0), 2-hydroxyacyl-CoA lyase 1 (HACL1), IGHG1, kelch repeat and BTB (POZ) domain containing 2 (KBTBD2) GTPase, IMAP family member 7 (GIMAP7), GTPase, IMAP family member 4 (GIMAP4), interferon, gamma (IFNG), Integrin beta-1-binding protein 1 (ITGB1BP1), low density lipoprotein receptor adaptor protein 1 (LDLRAP1), leptin receptor (LEPR), lysophosphatidic acid receptor 1 (LPAR1), leucine rich repeat neuronal 3 (LRRN3), membrane associated guanylate kinase, WW and PDZ domain containing 3 (MAGI3), mitogen-activated protein kinase 5 (MAP2K5), mediator complex subunit 28

(MED28), myelin basic protein (MBP), mitochondrial ribosomal protein S14 (MRPS14), mitochondrial transcription (MTERF4), nuclear receptor subfamily 3, group C, member 1 (glucocorticoid receptor (NR3C1), NEDD4 binding protein 2-like 2 (N4BP2L2), NIMA-related kinase 9 (NEK9), oligodendrocyte transcription factor 1 (OLIG1), proteasome subunit beta 4 (PSMB4), protein kinase C, beta (PRKCB), PIK3C3 phosphatidylinositol 3-kinase, catalytic subunit type 3, (PIK3CA), protein kinase, cAMP-dependent, regulatory, type II, beta (PRKAR2B), protein kinase, cAMP-dependent, regulatory, type I, alpha (PRKAR1A), phosphoglycerate kinase 1 (PGK1), plakophilin 4 (PKP4), protein kinase C, iota (PRKCI), protocadherin 9 (PCDH9), PITH (C-terminal proteasome-interacting domain of thioredoxin-like) domain containing 1 (PITHD1), platelet-activating factor acetylhydrolase 1b, catalytic subunit 2 (30 kDa (PAFAH1B2), polymerase (RNA) II (DNA directed) polypeptide D (POLR2D), ribulose-5-phosphate-3-epimerase (RPE), RNA binding motif (RNP1, RRM) protein 3 (RBM3), regulating synaptic membrane exocytosis 3 (RIMS3), RNA polymerase II associated protein 3 (RPAP3), spindle and kinetochore associated complex subunit 2 (SKA2), SUMO1 activating enzyme subunit 1 (SAE1,) SECIS binding protein 2-like (SECISBP2L), sorting nexin 6 (SNX6), SR-related CTD-associated factor 11 (SCAF11), SCMR8, spectrin, beta, non-erythrocytic 1 (SPTBN1), serine racemase (SRR), SET nuclear proto-oncogene///SET pseudogene 4///SET-like protein (SET), sulfatase modifying factor 2 (SUMF2), tumor protein D52 (TPD52), tau tubulin kinase 1 (TTBK1), transmembrane protein 245 (TMEM245), TMEM254, (TMEM254), tubulin, gamma complex associated protein 3 (TUBGCP3), TNF receptor-associated factor 3 (TRAF3), tripartite motif containing 23 (TRIM23), ubiquinol-cytochrome c reductase complex assembly factor 1 (UQCC1), vesicle (multivesicular body) trafficking 1 (VTA1), vesicle-associated membrane protein 3 (VAMP3), vasoactive intestinal peptide (VIP), tryptophanyl-tRNA synthetase (WARS), WAS/WASL interacting protein family, member 3 (WIPF3), WNK lysine deficient protein kinase 1 (WNK1), WWP2 WW [MMK1]domain containing E3 ubiquitin protein ligase 2 (WWP2), pre-B lymphocyte 3 (VPREB3), X-ray repair complementing defective repair in Chinese hamster cells 5 (double-strand-break rejoining) (XRCC5), zinc finger protein 565 (ZNF565), zinc finger, FYVE domain containing 21 (ZFYVE21), and zinc finger protein 75D (ZNF75D), identifying a subject as having suicidality risk wherein the expression level of the blood biomarkers in the first panel is increased relative to a reference expression level, or, wherein the expression level of the blood biomarkers in the second panel is decreased relative to a reference expression level; and, administering to the subject identified as having suicidality a drug to treat the suicidality.

2. The method of claim 1, wherein the biomarkers are quantified in samples taken on two or more occasions from the individual.

3. The method of claim 1, wherein the biological sample is selected from the group consisting of; a tissue or a bodily fluid, cerebrospinal fluid, whole blood, blood serum, plasma, and saliva, or an extract of the sample.

4. The method of claim 1, further including the step of treating the subject with at least one therapeutic agent selected from the group consisting of: dissociatives, mood stabilizers; antipsychotics; antidepressants; omega-3 fatty acids; and anxiolytics.

5. The method of claim 1,
further including the step of treating:
a subject who exhibits changes in ACP1, BCL2, CRYAB, GSK3B, HDAC2, HTR2A, ITGB1BP1, MBP, NR3C1, PIK3R1, PRKAR2B, PRKCB, and SLC6A4 with a mood stabilizer;
a subject who exhibits changes in ACP1, AKAPI13, BCL2, CD164, CD47, CLTA, CRYAB, DYRK2, HTR2A, IFNG, IL6, LPAR1, MAGI3, MBP, NR3CI1, PGK1, PRKAR2B, SOD2, and TPH2 with an antipsychotic;
a subject who exhibits changes in ACP1, CD47, ACP1, GATM, LPAR1, MBP, MRPS14, and SLC6A4, with omega-3 fatty acids;
a subject who exhibits changes in ACP1, CYP4V2, NR3C1, PER1, PIK3C3, PSME4, SLC6A4, and SOD2, are treated with an antidepressant;
a subject who exhibits changes in GIMAP4, PER1, and PSMB4 with an anxiolytics; and
a subject who exhibits changes in one or more of ACP1, PIK3R1, SLC6A4, and TPH2 with CBT.

6. The method of claim 1,
further including the step of: treating a subject who exhibits changes in ACP1, CD47, ACPI, GATM, LPAR1, MBP, MRPS14, and SLC6A4, with omega-3 fatty acids.

7. The method of claim 1, further including the step: of treating the subject with at least one therapeutic selected from the group consisting of: chlorogenic acid, ebselen, metformin, piracetam, oxybuprocaine, sertaconazole, fenbufen, alprostadil, tolmetin, tenoxicam, merbromin, adiphenine, ozagrel, procainamide, asiaticoside, carbimazole, ramifenazone, dl-alpha tocopherol, diphenhydramine, betulin, calcium folinate, dapsone, clemastine, dihydroergocristine, amoxapine, lisuride, homatropine, ritodrine, merbromin, naproxen, chlorpromazine, genistein, fluoxetine, yohimbine, prazosin, amitriptyline, trimethoprim, ethoxyquin, haloperidol, terazosin, pepstatin, diethylstilbestrol, nifenazone, metrizamide, baclofen, Daunorubicin hydrochloride, BRD-K06666320, WZ-3105, Piretanide, Syk Inhibitor, vorinostat, DACTINOMYCIN, trichostatin A, Tiotidine, and troglitazone.

* * * * *